US011602511B2

(12) United States Patent
Hamill et al.

(10) Patent No.: US 11,602,511 B2
(45) Date of Patent: *Mar. 14, 2023

(54) AMINO ACID COMPOSITIONS AND METHODS FOR THE TREATMENT OF LIVER DISEASES

(71) Applicant: AXCELLA HEALTH INC., Cambridge, MA (US)

(72) Inventors: Michael Hamill, Wellesley, MA (US); Raffi Afeyan, Cambridge, MA (US); Chung-Wei Lee, Waban, MA (US); Harry Luithardt, Cambridge, MA (US)

(73) Assignee: AXCELLA HEALTH INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/918,606

(22) Filed: Jul. 1, 2020

(65) Prior Publication Data

US 2020/0330417 A1    Oct. 22, 2020

Related U.S. Application Data

(63) Continuation of application No. 15/847,289, filed on Dec. 19, 2017, now Pat. No. 11,129,804.

(60) Provisional application No. 62/576,267, filed on Oct. 24, 2017, provisional application No. 62/545,322, filed on Aug. 14, 2017, provisional application No. 62/491,773, filed on Apr. 28, 2017, provisional application No. 62/443,205, filed on Jan. 6, 2017, provisional application No. 62/436,073, filed on Dec. 19, 2016.

(51) Int. Cl.
| | | |
|---|---|---|
| *A61K 31/198* | (2006.01) | |
| *A61P 1/16* | (2006.01) | |
| *A61K 9/14* | (2006.01) | |
| *A23L 33/175* | (2016.01) | |
| *A23L 33/18* | (2016.01) | |
| *A61K 38/05* | (2006.01) | |
| *A61K 38/06* | (2006.01) | |

(52) U.S. Cl.
CPC .......... *A61K 31/198* (2013.01); *A23L 33/175* (2016.08); *A23L 33/18* (2016.08); *A61K 9/14* (2013.01); *A61K 38/05* (2013.01); *A61K 38/06* (2013.01); *A61P 1/16* (2018.01); *A23V 2250/0634* (2013.01)

(58) Field of Classification Search
CPC ............ A61K 31/198; A23V 2250/036; A23V 2250/0628; A23V 2250/0606; A23V 2250/062; A23V 2250/0626; A23V 2250/0654; A23L 33/175; A23L 33/18
See application file for complete search history.

(56) References Cited

U.S. PATENT DOCUMENTS

| | | |
|---|---|---|
| 693,094 A | 2/1902 | Wilson |
| 2,457,820 A | 1/1949 | Howe et al. |
| 3,832,465 A | 8/1974 | Ghadimi |
| 3,950,529 A | 4/1976 | Fischer et al. |
| 3,988,466 A | 10/1976 | Takagi et al. |
| 4,496,703 A | 1/1985 | Steinmetzer |
| 4,871,550 A | 10/1989 | Millman |
| 4,898,879 A | 2/1990 | Madsen et al. |
| 4,908,214 A | 3/1990 | Bobee et al. |
| 5,028,622 A | 7/1991 | Plaitakis |
| 5,034,377 A | 7/1991 | Adibi et al. |
| 5,106,836 A | 4/1992 | Clemens et al. |
| 5,229,136 A | 7/1993 | Mark et al. |
| 5,276,018 A | 1/1994 | Wilmore |
| 5,348,979 A | 9/1994 | Nissen et al. |
| 5,356,873 A | 10/1994 | Mark et al. |
| 5,405,835 A | 4/1995 | Mendy |
| 5,438,042 A | 8/1995 | Schmidl et al. |
| 5,504,072 A | 4/1996 | Schmidl et al. |
| 5,520,948 A | 5/1996 | Kvamme |
| 5,571,783 A | 11/1996 | Montagne et al. |
| 5,576,351 A | 11/1996 | Yoshimura et al. |
| 5,712,309 A | 1/1998 | Finnin et al. |
| 5,719,133 A | 2/1998 | Schmidl et al. |
| 5,719,134 A | 2/1998 | Schmidl et al. |
| 5,723,446 A | 3/1998 | Gray et al. |
| 5,728,678 A | 3/1998 | Trimbo et al. |
| 5,731,290 A | 3/1998 | Schneider |
| 5,733,884 A | 3/1998 | Barbul et al. |
| 5,744,157 A | 4/1998 | Droge |
| 5,756,481 A | 5/1998 | Amal et al. |

(Continued)

FOREIGN PATENT DOCUMENTS

| | | |
|---|---|---|
| AU | 2014212003 | 9/2015 |
| CN | 1582912 A | 2/2005 |

(Continued)

OTHER PUBLICATIONS

Børsheim et al., "Amino acid supplementation decreases plasma and liver triglycerides in elderly," Nutrition (2009) vol. 25, No. 3, pp. 281-288.

Børsheim et al., "Effect of amino acid supplementation on muscle mass, strength and physical function in elderly," Clin Nutr (2008) vol. 27, pp. 189-195.

Calvey et al., "Controlled Trial of Nutritional Supplementation With and Without Branched Chain Amino Acid Enrichment, in Treatment of Acute Alcoholic Hepatitis," Journal of Hepatology (1985) vol. 1, pp. 141-151.

Campollo et al., "Protein tolerance to standard and high protein meals in patients with liver cirrhosis," World J Hepatol (2017) vol. 9, Issue 14, pp. 667-676.

(Continued)

*Primary Examiner* — Theodore R. Howell
(74) *Attorney, Agent, or Firm* — K&L Gates LLP

(57) ABSTRACT

This disclosure provides pharmaceutical compositions comprising amino acid entities and uses thereof. Methods for improving liver function and for treating liver diseases comprising administering an effective amount of the compositions to a subject in need thereof are also disclosed.

17 Claims, 21 Drawing Sheets

(56) References Cited

U.S. PATENT DOCUMENTS

| | | | |
|---|---|---|---|
| 5,780,039 A | 7/1998 | Greenberg et al. |
| 5,817,329 A | 10/1998 | Gardiner |
| 5,849,335 A | 12/1998 | Ballevre et al. |
| 5,863,906 A | 1/1999 | Amal et al. |
| 5,866,537 A | 2/1999 | Bianchi |
| 5,977,073 A | 11/1999 | Khaled |
| 6,013,273 A | 1/2000 | Schneider et al. |
| 6,031,000 A | 2/2000 | Nissen et al. |
| 6,051,236 A | 4/2000 | Portman |
| 6,087,398 A | 7/2000 | Goodman |
| 6,096,785 A | 8/2000 | Schneider |
| 6,143,786 A | 11/2000 | Gohman et al. |
| 6,218,420 B1 | 4/2001 | Dioguardi |
| 6,274,612 B1 | 8/2001 | Bryan |
| 6,281,244 B1 | 8/2001 | Schneider et al. |
| 6,328,998 B1 | 12/2001 | Cavazza |
| 6,346,264 B1 | 2/2002 | White |
| 6,376,544 B2 | 4/2002 | Lowry et al. |
| 6,391,332 B1 | 5/2002 | Somerville et al. |
| 6,458,338 B1 | 10/2002 | Adjei et al. |
| 6,521,591 B1 | 2/2003 | Smeets et al. |
| 6,833,350 B2 | 12/2004 | Ballevre et al. |
| 6,864,230 B2 | 3/2005 | Ostrom |
| 6,864,242 B2 | 3/2005 | Ernest |
| 7,300,665 B2 | 11/2007 | Mowrey et al. |
| 7,468,193 B2 | 12/2008 | Schiffrin et al. |
| 7,622,447 B2 | 11/2009 | Lautt et al. |
| 7,645,796 B2 | 1/2010 | Murakami et al. |
| 7,790,688 B2 | 9/2010 | Wolfe et al. |
| 7,794,744 B2 | 9/2010 | Ballevre et al. |
| 7,879,796 B2 | 2/2011 | Edens et al. |
| 7,973,077 B2 | 7/2011 | Dioguardi |
| 8,012,924 B2 | 9/2011 | Abe et al. |
| 8,012,926 B2 | 9/2011 | Abe et al. |
| 8,133,503 B2 | 3/2012 | Laflamme et al. |
| 8,148,356 B2 | 4/2012 | Pavliv |
| 8,173,706 B2 | 5/2012 | Anderson et al. |
| 8,211,944 B2 | 7/2012 | Dioguardi |
| 8,362,080 B2 | 1/2013 | Sekhar |
| 8,383,680 B2 | 2/2013 | Whippie et al. |
| 8,389,471 B2 | 3/2013 | Edens et al. |
| 8,389,576 B2 | 3/2013 | Jalan et al. |
| 8,399,445 B2 | 3/2013 | Pavliv |
| 8,409,592 B2 | 4/2013 | Vidal et al. |
| 8,455,531 B2 | 6/2013 | Kramer et al. |
| 8,466,187 B2 | 6/2013 | Kramer et al. |
| 8,492,439 B2 | 7/2013 | Anderson et al. |
| 8,501,676 B2 | 8/2013 | Hageman |
| 8,524,772 B2 | 9/2013 | Arad et al. |
| 8,536,216 B2 | 9/2013 | Dioguardi |
| 8,648,040 B2 | 2/2014 | Edens et al. |
| 8,653,061 B2 | 2/2014 | Pavliv |
| 8,697,630 B2 | 4/2014 | Hayes et al. |
| 8,703,719 B1 | 4/2014 | Abraham et al. |
| 8,703,725 B2 | 4/2014 | Troup |
| 8,716,249 B2 | 5/2014 | Wolfe et al. |
| 8,722,738 B2 | 5/2014 | Pavliv et al. |
| 8,734,316 B2 | 5/2014 | Schmidt |
| 8,785,498 B2 | 7/2014 | Anderson et al. |
| 8,840,950 B2 | 9/2014 | Hibbert et al. |
| 8,846,759 B2 | 9/2014 | Luiking et al. |
| 8,895,059 B2 | 11/2014 | Vrana et al. |
| 8,946,473 B2 | 2/2015 | Anderson et al. |
| 8,952,040 B2 | 2/2015 | Yue et al. |
| 8,952,045 B1 | 2/2015 | Kramer et al. |
| 8,952,046 B1 | 2/2015 | Kramer et al. |
| 8,952,065 B2 | 2/2015 | Pavliv |
| 8,957,101 B1 | 2/2015 | Kramer et al. |
| 9,017,727 B2 | 4/2015 | Buijsse |
| 9,034,925 B2 | 5/2015 | Anderson et al. |
| 9,066,537 B2 | 6/2015 | Hofman et al. |
| 9,066,953 B2 | 6/2015 | Heaton et al. |
| 9,192,593 B2 | 11/2015 | Hirabayashi et al. |
| 9,198,889 B2 | 12/2015 | Heaton et al. |
| 9,216,162 B2 | 12/2015 | Goldstein |
| 9,233,090 B2 | 1/2016 | Breuille et al. |
| 9,260,379 B2 | 2/2016 | Anderson et al. |
| 9,271,521 B2 | 3/2016 | Okita et al. |
| 9,314,444 B2 | 4/2016 | Szewczyk |
| 9,320,759 B2 | 4/2016 | Pan |
| 9,327,028 B2 | 5/2016 | Pavliv et al. |
| 9,364,463 B2 | 6/2016 | Ferrando et al. |
| 9,375,451 B2 | 6/2016 | Hibbert et al. |
| 9,408,410 B2 | 8/2016 | Zemel et al. |
| 9,408,834 B2 | 8/2016 | Zemel et al. |
| 9,410,963 B2 | 8/2016 | Martin et al. |
| 9,492,498 B2 | 11/2016 | Van Goudoever et al. |
| 9,539,226 B2 | 1/2017 | Lee et al. |
| 9,561,194 B2 | 2/2017 | Schiffrin et al. |
| 9,596,870 B2 | 3/2017 | Zanghi et al. |
| 9,604,909 B2 | 3/2017 | Anderson et al. |
| 9,867,391 B2 | 1/2018 | Dardevet et al. |
| 9,878,004 B2 | 1/2018 | Williams et al. |
| 9,913,818 B2 | 3/2018 | Moinard et al. |
| 10,039,735 B2 | 8/2018 | Jalan et al. |
| 10,045,999 B2 | 8/2018 | Jourdan et al. |
| 10,085,947 B2 | 10/2018 | Shah et al. |
| 10,123,985 B2 | 11/2018 | Sabatini et al. |
| 10,201,513 B2 | 2/2019 | Hamill et al. |
| 10,238,617 B2 | 3/2019 | Hamill et al. |
| 10,471,034 B2 | 11/2019 | Hamill et al. |
| 10,596,136 B2 | 3/2020 | Chakravarthy et al. |
| 10,660,870 B2 | 5/2020 | Comb et al. |
| 10,682,325 B2 | 6/2020 | Comb et al. |
| 10,973,793 B2 | 4/2021 | Comb et al. |
| 11,129,804 B2 * | 9/2021 | Hamill ............... A61K 31/198 |
| 2001/0018066 A1 | 8/2001 | Hahn |
| 2001/0041187 A1 | 11/2001 | Hastings et al. |
| 2002/0006907 A1 | 1/2002 | Gardiner et al. |
| 2003/0187049 A1 | 10/2003 | Dioguardi |
| 2004/0023889 A1 | 2/2004 | Gardiner et al. |
| 2004/0067224 A1 | 4/2004 | Ernest |
| 2004/0082659 A1 | 4/2004 | Cooke et al. |
| 2004/0087490 A1 | 5/2004 | Troup |
| 2004/0120983 A1 | 6/2004 | Connolly |
| 2004/0192751 A1 | 9/2004 | Abe et al. |
| 2004/0213838 A1 | 10/2004 | Mazer et al. |
| 2005/0020656 A1 | 1/2005 | Horie et al. |
| 2005/0032898 A1 | 2/2005 | Ohtani |
| 2005/0053679 A1 | 3/2005 | Lee et al. |
| 2005/0176827 A1 | 8/2005 | Lee et al. |
| 2005/0197398 A1 | 9/2005 | Sonaka et al. |
| 2006/0002913 A1 | 1/2006 | Gehlsen |
| 2006/0004101 A1 | 1/2006 | Okita et al. |
| 2006/0052455 A1 | 3/2006 | Koga et al. |
| 2006/0159746 A1 | 7/2006 | Troup |
| 2006/0198899 A1 | 9/2006 | Gardiner et al. |
| 2006/0205633 A1 | 9/2006 | Nishitani et al. |
| 2007/0060651 A1 | 3/2007 | Larson et al. |
| 2007/0142469 A1 | 6/2007 | Thomas et al. |
| 2007/0197647 A1 | 8/2007 | Kumada et al. |
| 2007/0212447 A1 | 9/2007 | Nogata et al. |
| 2007/0243211 A1 | 10/2007 | Jaffe |
| 2007/0270355 A1 | 11/2007 | Garcia et al. |
| 2007/0286909 A1 | 12/2007 | Smith et al. |
| 2008/0038321 A1 | 2/2008 | Tsuji et al. |
| 2008/0102137 A1 | 5/2008 | Guffey |
| 2008/0114065 A1 | 5/2008 | Pacioretty et al. |
| 2008/0114067 A1 | 5/2008 | Yamamoto |
| 2008/0161398 A1 | 7/2008 | Verlaan et al. |
| 2008/0182811 A1 | 7/2008 | Ohsu et al. |
| 2008/0268038 A1 | 10/2008 | Wolfe |
| 2009/0011077 A1 | 1/2009 | Schiffrin et al. |
| 2009/0018196 A1 | 1/2009 | Bjork et al. |
| 2009/0048153 A1 | 2/2009 | Varma et al. |
| 2009/0076110 A1 | 3/2009 | Kramer et al. |
| 2009/0105123 A1 | 4/2009 | Tisdale et al. |
| 2009/0170786 A1 | 7/2009 | Greenberg |
| 2009/0181903 A1 | 7/2009 | Wolfe et al. |
| 2009/0186098 A1 | 7/2009 | Briceno |
| 2009/0203606 A1 | 8/2009 | Wolfe et al. |
| 2009/0306209 A1 | 12/2009 | Daugherty et al. |
| 2010/0021573 A1 | 1/2010 | Gonzalez et al. |
| 2010/0092610 A1 | 4/2010 | Haschke et al. |

(56) References Cited

U.S. PATENT DOCUMENTS

| | | |
|---|---|---|
| 2010/0104548 A1 | 4/2010 | Rossetti et al. |
| 2010/0119692 A1 | 5/2010 | Hamman et al. |
| 2010/0152107 A1 | 6/2010 | Le-Henand et al. |
| 2010/0233304 A1 | 9/2010 | Pan |
| 2010/0267831 A1 | 10/2010 | Kobayashi et al. |
| 2010/0280119 A1 | 11/2010 | Anderson et al. |
| 2011/0077198 A1 | 3/2011 | Tisdale et al. |
| 2011/0081329 A1 | 4/2011 | Smith et al. |
| 2011/0229447 A1 | 9/2011 | Schiffrin et al. |
| 2011/0257236 A1 | 10/2011 | Koyama et al. |
| 2011/0269678 A1 | 11/2011 | Breuille et al. |
| 2011/0294727 A1 | 12/2011 | Hibbert et al. |
| 2012/0020947 A1 | 1/2012 | Shirazi et al. |
| 2012/0157526 A1 | 6/2012 | Jalan et al. |
| 2012/0178672 A1 | 7/2012 | Wolfe et al. |
| 2012/0195873 A1 | 8/2012 | Miller et al. |
| 2012/0208885 A1 | 8/2012 | Anderson et al. |
| 2012/0251512 A1 | 10/2012 | Farmer et al. |
| 2012/0270860 A1 | 10/2012 | Yoon et al. |
| 2012/0315354 A1 | 12/2012 | Palzer et al. |
| 2012/0329846 A1 | 12/2012 | Matsumoto et al. |
| 2013/0143836 A1 | 6/2013 | Yue et al. |
| 2013/0143968 A1 | 6/2013 | Nihara |
| 2013/0209433 A1 | 8/2013 | Rossetti et al. |
| 2013/0210715 A1 | 8/2013 | Greenberg et al. |
| 2013/0211135 A1 | 8/2013 | Anderson et al. |
| 2013/0225510 A1 | 8/2013 | Greenberg |
| 2013/0296429 A1 | 11/2013 | Anderson et al. |
| 2014/0004205 A1 | 1/2014 | Satyaraj |
| 2014/0037601 A1 | 2/2014 | Greenberg |
| 2014/0093609 A1 | 4/2014 | Roy et al. |
| 2014/0135396 A1 | 5/2014 | Goessling et al. |
| 2014/0147549 A1 | 5/2014 | Jeukendrup et al. |
| 2014/0155448 A1 | 6/2014 | Kato et al. |
| 2014/0249078 A1 | 9/2014 | Breuille et al. |
| 2014/0255511 A1 | 9/2014 | Dardevet et al. |
| 2014/0271984 A1 | 9/2014 | Pouteau et al. |
| 2014/0288327 A1 | 9/2014 | Anderson et al. |
| 2014/0294788 A1 | 10/2014 | Bailey et al. |
| 2014/0295002 A1 | 10/2014 | Heaton et al. |
| 2014/0303099 A1 | 10/2014 | Wolfe et al. |
| 2014/0342040 A1 | 11/2014 | Miller et al. |
| 2014/0343112 A1 | 11/2014 | Ferrando et al. |
| 2014/0356479 A1 | 12/2014 | Serrano |
| 2014/0357553 A1 | 12/2014 | Smola et al. |
| 2014/0357576 A1 | 12/2014 | Breuille et al. |
| 2015/0118351 A1 | 4/2015 | Haschke et al. |
| 2015/0133684 A1 | 5/2015 | Anderson et al. |
| 2015/0223501 A1 | 8/2015 | Huynh-Ba et al. |
| 2015/0246066 A1 | 9/2015 | Nelson |
| 2015/0251990 A1 | 9/2015 | Anderson et al. |
| 2015/0313262 A1 | 11/2015 | Zanghi et al. |
| 2016/0027657 A1 | 1/2016 | Shi et al. |
| 2016/0051814 A1 | 2/2016 | Arigoni et al. |
| 2016/0067201 A1 | 3/2016 | Zemel et al. |
| 2016/0128960 A1 | 5/2016 | Faure et al. |
| 2016/0158305 A1 | 6/2016 | Thomson |
| 2016/0243202 A1 | 8/2016 | Mincent |
| 2016/0302451 A1 | 10/2016 | Hudnall |
| 2016/0338982 A1 | 11/2016 | Ruettimann et al. |
| 2016/0339078 A1 | 11/2016 | Hamill et al. |
| 2016/0367509 A1 | 12/2016 | Pan |
| 2017/0014461 A1 | 1/2017 | Jia et al. |
| 2017/0027897 A1 | 2/2017 | Wang et al. |
| 2017/0042189 A1 | 2/2017 | Pibarot et al. |
| 2017/0079897 A1 | 3/2017 | Minus |
| 2017/0079935 A1 | 3/2017 | Schiffrin et al. |
| 2017/0135973 A1 | 5/2017 | Wang et al. |
| 2017/0196944 A1 | 7/2017 | Portman |
| 2017/0360734 A1 | 12/2017 | Blum |
| 2017/0368026 A1 | 12/2017 | Faure et al. |
| 2017/0368027 A1 | 12/2017 | Blum-Sperisen et al. |
| 2017/0370910 A1 | 12/2017 | Rezzi et al. |
| 2018/0015122 A1 | 1/2018 | Villamil Torres et al. |
| 2018/0021278 A1 | 1/2018 | Faure et al. |
| 2018/0036270 A1 | 2/2018 | Aw et al. |
| 2018/0042879 A1 | 2/2018 | Scott |
| 2018/0044281 A1 | 2/2018 | Anderson et al. |
| 2018/0125926 A1 | 5/2018 | Williams et al. |
| 2018/0161293 A1 | 6/2018 | Jalan et al. |
| 2018/0169044 A1 | 6/2018 | Hamill et al. |
| 2018/0169045 A1 | 6/2018 | Hamill et al. |
| 2018/0169046 A1 | 6/2018 | Hamill et al. |
| 2018/0169047 A1 | 6/2018 | Hamill et al. |
| 2018/0200192 A1 | 7/2018 | Gammans |
| 2018/0207118 A1 | 7/2018 | Hamill et al. |
| 2018/0207119 A1 | 7/2018 | Hamill et al. |
| 2018/0221320 A1 | 8/2018 | Rose et al. |
| 2019/0000866 A1 | 1/2019 | Siegel et al. |
| 2019/0046486 A1 | 2/2019 | De Rienzo et al. |
| 2019/0046487 A1 | 2/2019 | Comb et al. |
| 2019/0105294 A1 | 4/2019 | Hamill et al. |
| 2019/0192463 A1 | 6/2019 | Nihara |
| 2019/0247351 A1 | 8/2019 | Comb et al. |
| 2019/0388374 A1 | 12/2019 | Hanlon et al. |
| 2019/0388375 A1 | 12/2019 | Hanlon et al. |
| 2019/0388376 A1 | 12/2019 | Carroll et al. |
| 2019/0388377 A1 | 12/2019 | Hamill et al. |
| 2020/0016104 A1 | 1/2020 | Chakravarthy et al. |
| 2020/0163919 A1 | 5/2020 | Carroll et al. |
| 2020/0281882 A1 | 9/2020 | Chakravarthy et al. |
| 2020/0306214 A1 | 10/2020 | Comb et al. |
| 2020/0330417 A1 | 10/2020 | Hamill et al. |

FOREIGN PATENT DOCUMENTS

| | | |
|---|---|---|
| CN | 1679941 | 2/2005 |
| CN | 101049500 A | 10/2007 |
| CN | 101332209 B | 12/2010 |
| CN | 101214050 B | 8/2011 |
| CN | 101664384 | 9/2011 |
| CN | 102327259 A | 1/2012 |
| CN | 102961377 A | 3/2013 |
| CN | 105092753 A | 11/2015 |
| CN | 106632605 A | 5/2017 |
| CN | 107242552 A | 10/2017 |
| CN | 108041501 A | 5/2018 |
| CN | 108524453 A | 9/2018 |
| EP | 0147699 A2 | 7/1985 |
| EP | 0656178 | 7/1995 |
| EP | 0827744 A2 | 3/1998 |
| EP | 0882451 A1 | 12/1998 |
| EP | 0891719 A1 | 1/1999 |
| EP | 1004302 A2 | 5/2000 |
| EP | 1025844 A1 | 8/2000 |
| EP | 1083915 B1 | 3/2001 |
| EP | 1108429 A2 | 6/2001 |
| EP | 0764405 B1 | 11/2002 |
| EP | 1399139 B1 | 3/2004 |
| EP | 1541141 A1 | 6/2005 |
| EP | 1552826 A1 | 7/2005 |
| EP | 1637163 A1 | 3/2006 |
| EP | 0983726 B1 | 10/2006 |
| EP | 0674902 B1 | 4/2007 |
| EP | 1774966 A1 | 4/2007 |
| EP | 1774973 A1 | 4/2007 |
| EP | 1938813 A1 | 7/2008 |
| EP | 2060914 A2 | 5/2009 |
| EP | 1374863 B1 | 9/2009 |
| EP | 2095728 A2 | 9/2009 |
| EP | 2196203 A2 | 6/2010 |
| EP | 1085862 B1 | 1/2011 |
| EP | 2091526 B1 | 5/2011 |
| EP | 2340725 A1 | 7/2011 |
| EP | 2413924 B1 | 2/2012 |
| EP | 2440200 B1 | 4/2012 |
| EP | 2196203 B1 | 8/2012 |
| EP | 2601951 A1 | 6/2013 |
| EP | 2327315 B1 | 10/2013 |
| EP | 1549299 B1 | 8/2014 |
| EP | 2792354 A2 | 10/2014 |
| EP | 2799067 A1 | 11/2014 |
| EP | 2865382 A1 | 4/2015 |
| EP | 2968241 B1 | 1/2016 |

(56) References Cited

FOREIGN PATENT DOCUMENTS

| | | |
|---|---|---|
| EP | 2977418 A1 | 1/2016 |
| EP | 2786750 B1 | 6/2016 |
| EP | 2327316 B1 | 11/2016 |
| EP | 2574333 B1 | 1/2017 |
| EP | 2440217 B1 | 12/2017 |
| EP | 3263100 A1 | 1/2018 |
| EP | 3298908 A2 | 3/2018 |
| EP | 3437649 A1 | 2/2019 |
| EP | 2782588 B1 | 4/2020 |
| GB | 1034358 A | 6/1966 |
| GB | 2029220 B | 3/1983 |
| GB | 2113524 B | 7/1985 |
| JP | 61186320 | 8/1986 |
| JP | 2003238401 A | 8/2003 |
| JP | 2007055992 A | 3/2007 |
| JP | 2008050277 | 3/2008 |
| JP | 4280310 | 6/2009 |
| JP | 2011116775 A | 6/2011 |
| JP | 2011132174 A | 7/2011 |
| JP | 5067160 B2 | 11/2012 |
| JP | 5100033 B2 | 12/2012 |
| JP | 5516654 B2 | 6/2014 |
| JP | 6110444 B2 | 4/2017 |
| KR | 20060124732 A | 12/2006 |
| KR | 100970664 B1 | 7/2010 |
| WO | 1983000085 A1 | 1/1983 |
| WO | 9414458 A1 | 7/1994 |
| WO | 9804254 A1 | 2/1998 |
| WO | 9854985 A1 | 12/1998 |
| WO | 064283 A1 | 11/2000 |
| WO | 2001026642 A2 | 4/2001 |
| WO | 2001056402 A2 | 8/2001 |
| WO | 2002002092 A2 | 1/2002 |
| WO | 2003103582 A2 | 12/2003 |
| WO | 2004058242 A1 | 7/2004 |
| WO | 2005017094 A2 | 2/2005 |
| WO | 2005021596 A2 | 3/2005 |
| WO | 2005084323 A2 | 9/2005 |
| WO | 2005102301 A2 | 11/2005 |
| WO | 2005110124 A1 | 11/2005 |
| WO | 2006083381 A2 | 8/2006 |
| WO | 2006105112 A2 | 10/2006 |
| WO | 2007002365 A2 | 1/2007 |
| WO | 2007056176 A2 | 5/2007 |
| WO | 2007064618 A1 | 6/2007 |
| WO | 2009062910 A1 | 5/2009 |
| WO | 2009109460 A1 | 9/2009 |
| WO | 149196 A1 | 12/2009 |
| WO | 2010081079 A2 | 7/2010 |
| WO | 2010115055 A1 | 10/2010 |
| WO | 2010144498 A2 | 12/2010 |
| WO | 2011030104 A1 | 3/2011 |
| WO | 2011038014 A2 | 3/2011 |
| WO | 2011044230 A9 | 8/2011 |
| WO | 2011097273 A1 | 8/2011 |
| WO | 2012005582 A1 | 1/2012 |
| WO | 2012048043 A1 | 4/2012 |
| WO | 2012088075 A1 | 6/2012 |
| WO | 2012092035 A1 | 7/2012 |
| WO | 2012097061 A1 | 7/2012 |
| WO | 2012143402 A1 | 10/2012 |
| WO | 2013006658 A1 | 1/2013 |
| WO | 2013028547 A1 | 2/2013 |
| WO | 2013077893 A1 | 5/2013 |
| WO | 2013108871 A1 | 7/2013 |
| WO | 2013188258 A1 | 12/2013 |
| WO | 2014172341 A1 | 10/2014 |
| WO | 2015015149 A1 | 2/2015 |
| WO | 2015048333 A2 | 4/2015 |
| WO | 2015048340 A2 | 4/2015 |
| WO | 2015048342 A2 | 4/2015 |
| WO | 2015048345 A2 | 4/2015 |
| WO | 2015048346 A2 | 4/2015 |
| WO | 2015048348 A2 | 4/2015 |
| WO | 2015061607 A1 | 4/2015 |
| WO | 2015131152 A1 | 9/2015 |
| WO | 2015161448 A1 | 10/2015 |
| WO | 2016003263 A1 | 1/2016 |
| WO | 2016058919 A1 | 4/2016 |
| WO | 2016088078 A1 | 6/2016 |
| WO | 2016094316 A1 | 6/2016 |
| WO | 2016097299 A1 | 6/2016 |
| WO | 2016116580 A1 | 7/2016 |
| WO | 2016121829 A1 | 8/2016 |
| WO | 2016128576 A1 | 8/2016 |
| WO | 2016172112 A1 | 10/2016 |
| WO | 2017001590 A1 | 1/2017 |
| WO | 2017031131 A1 | 2/2017 |
| WO | 2017033272 A1 | 3/2017 |
| WO | 2017053613 A1 | 3/2017 |
| WO | 2017083758 A1 | 5/2017 |
| WO | 2017085138 A1 | 5/2017 |
| WO | 2017107863 A1 | 6/2017 |
| WO | 2017127333 A1 | 7/2017 |
| WO | 2017193154 A1 | 11/2017 |
| WO | 2017202939 A1 | 11/2017 |
| WO | 2018013873 A1 | 1/2018 |
| WO | 2018117954 A1 | 6/2018 |
| WO | 2018118941 A1 | 6/2018 |
| WO | 2018118957 A1 | 6/2018 |
| WO | 2019036442 A1 | 2/2019 |
| WO | 2019036471 A1 | 2/2019 |
| WO | 246298 A1 | 12/2019 |
| WO | 246299 A1 | 12/2019 |
| WO | 246310 A1 | 12/2019 |

OTHER PUBLICATIONS

Campos-Ferraz et al., "An overview of amine as nutritional supplements to counteract cancer cachexia," J Cachexia Sarcopenia Muscle (2014) vol. 5, No. 2, pp. 105-110.

Campos-Ferraz et al., "Distinct effects of leucine or a mixture of the branched-chain amino acids (leucine, isoleucine, and valine) supplementation on resistance to fatigue, and muscle and liver-glycogen degradation, in trained rats," Nutrition (2013) vol. 29, pp. 1388-1394.

Capel et al., "Combining citrulline with atorvastatin preserves glucose homeostasis in a murine model of diet-induced obesity," Br J Pharmacol (2015) vol. 172, pp. 4996-5008.

Capel et al., "Lysosomal and proteasome-dependent proteolysis are differentially regulated by insulin and/or amino acids following feeding in young, mature and old rats," J Nutr Biochem (2009) vol. 20, pp. 570-576.

Carraro et al., "Whole body and plasma protein synthesis in exercise and recovery in human subjects," Am J Physiol Endocinol Metab (1990) vol. 258, pp. E821-E831.

Chang et al., "Leucine inhibits oxidation of glucose and pyruvate in skeletal muscles during fasting," J Biol Chem (1978) vol. 253, pp. 3696-3701.

Charlton, M., "Branched-Chain Amino Acid Enriched Supplements as Therapy for Liver Disease," 2006 J. Nutrition, 136: 295S-298S.

Chartrand et al., "Influence of Amino Acids in Dairy Products on Glucose Homeostasis: The Clinical Evidence," Can J Diabetes (2017), 9 pp.

Chen et al., "Therapeutic effect of L-ornithine-L-aspartate on liver cirrhosis complicated by hepatic encephalopathy," J First Mil Med Univ (2005) vol. 25, No. 6, pp. 718-722. Abstract Only.

Cheng et al., "Adipose Tissue Dysfunction and Altered Systemic Amino Acid Metabolism Are Associated with Non-Alcoholic Fatty Liver Disease," PLOS One (2015) doi:10.1371/journal.pone. 0138889, 17 pp.

Cholewa et al., "Dietary preoteins and amino acids in the control of the muscle mass during immobilization and aging: role of the MPS response," Amino Acids (2017) vol. 49, No. 5, pp. 811-820.

Churchward-Venne et al., "Leucine supplementation of a low-protein mixed macronutrient beverage enhances myofibrillar protein synthesis in young men: a double-blind, randomized trial," Am J Clin Nutr (2014) vol. 99, pp. 276-286.

(56) References Cited

OTHER PUBLICATIONS

Churchward-Venne et al., "Supplementation of a suboptimal protein dose with leucine or essential amino acids: effects on myofibrillar protein syntheses at rest and following resistance exercise in men," J Physiol (2012) vol. 590, No. 11, pp. 2751-2765.
Clemmensen et al., "Oral L-Arginine Stimulates GLP-1 Secretion to Improve Glucose Tolerance in Male Mice," Endocrinology (2013) vol. 154, No. 11, pp. 3978-3983.
ClincalTrials.gov Identifier NCT01434108 "Effects of the Administration of Ornithine Phenylacetate in Patients with Cirrhosis and Upper Gastrointestinal Bleeding," Clinicaltrials gov, last updated Mar. 24, 2015, 7 pages.
ClincalTrials.gov Identifier NCT01548690 "Safety Study of Ornithine Phenylacetate to Treat Patients With Acute Liver Failure (STOP-ALF)," Clinicaltrials.gov, last updated Jan. 12, 2018, 13 pages.
ClincalTrials.gov Identifier NCT01634230 "Emergency Use of OCR-002 in Acute Liver Failure," Clinicaltrials.gov, last updated Jun. 18, 2014, 4 pages.
ClincalTrials.gov Identifier NCT01966419 "Phase 2B Efficacy/Safety of Ornithine Phenylacetate in Hospitalized Cirrhotic Patients With Hepatc Encephalopathy (STOP-HE) (STOP-HE)," Clinicaltrials.gov, last updated Aug. 21, 2018, 6 pages.
ClincalTrials.gov Identifier NCT03159390 "Metabolism of Ornithine Phenylacetate (OCERA OP)," Clinicaltrials.gov, last updated May 23, 2017, 6 pages.
Cuthbertson et al., "Anabolic signaling deficits underlie amino acid resistance of wasting, aging muscle," The FASEB Journal (2005) vol. 19, pp. 422-424.
D'Antona et al., "A Peculiar Formula of Essential Amino Acids Prevents Rosuvastatin Myopathy in Mice," Antioxidents & Redox Signaling (2016) vol. 25, No. 11, pp. 595-608.
D'Antona et al., "Branched-Chain Amino Acid Supplementation Promotes Survival and Supports Cardiac and Skeletal Muscle Mitochondrial Biogenesis in Middle-Aged Mice," Cell Metabolism (2010) vol. 12, pp. 362-372.
Dam et al., "Branched-chain amino acids and muscle ammonia detoxification in cirrhosis," Metab Brain Dis (2013) vol. 28, pp. 217-220.
Dam et al., "Branched-chain amino acids increase arterial blood ammonia in spite of enhanced intrinsic muscle ammonia metabolism in patients with cirrhosis and healthy subjects," Am J Physiol Gastrointest Liver Physiol (2011) vol. 301, pp. G269-G277.
Dangin et al., "The digestion rate of protein is an independent regulating factor of postprandial protein retention," Am J Physiol Endocrinol Metab (2001) vol. 280, pp. E340-E348.
Dardevet et al., "Muscle Wasting and Resistance of Muscle Anabolism: The 'Anabolic Threshold Concept' for Adapted Nutritional Strategies during Sarcopenia" The Scientific World Journal (2012) vol. 93, article 269531.
Dashtabi, A. et al., "Oral L-Arginine Administration Improves Anthropometric and Biochemical Indices Associated With Cardiovascular Diseases in Obese Patients: A Randomized, Single Blind Placebo Controlled Clinical Trial," (2016) Res Cardiovasc Med, February; 5(1): e29419.
Davuluri et al., "Metabolic adaptation of skeletal muscle to hyperammonemia drives the beneficial effects of L-leucine in cirrhosis," J Hepatology (2016) vol. 65, pp. 929-937.
De Bandt et al., "A Randomized Controlled Trial of the Influence of the Mode of Enteral Onithine μ-Ketoglutarate Administration in Burn Patients," J Nutr (1998) vol. 128, pp. 563-569.
Deglaire et al., Hydrolyzed dietary casein as compared with the intact protein reduces postprandial peripheral, but not whole-body, uptake of nitrogen in humans, Am J Clin Nutr (2009) vol. 90, pp. 1011-1022.
Deldicque et al., "Antagonistic effects of leucine and glutamine on the mTOR pathway in myogenic C2C12 cells," Amino Acids (2008) vol. 35, No. 1, pp. 147-155, first published online Nov. 2007.
Deminice et al., "Creatine Supplementation Prevents the Accumulation of Fat in the Livers of Rats Fed a High-Fat Diet," J Nutr (2011) vol. 141, pp. 1799-1804.

Deutz et al., "Protein intake and exercise for optimal muscle function with again: Recoomndations from the ESPEN Expert Group," Clinical Nutrition (2014) vol. 33, pp. 929-936.
Diaz-Rua, E. et al., "Long-Term Intake of a High-Protein Diet Increases Liver Triacylglycerol Deposition Pathways and Hepatic Signs of Injury in Rats," Journal of Nutritional Biochemistry, 46 (2017) 39-48.
Diaz-Rua, E. et al., "Sustained Exposure to Diets with an Unbalanced Macronutrient Proportion Alters Key Genes Involved in Energy Homeostasis and Obesity-Related Metabolic Parameters in Rats," 2014 Food & Function, pp. 1-15.
Dickinson et al., "Aging differentially affects human skeletal muscle amino acid transporter expression when essential amino acids are ingested after exercise," Clin Nutr (2013) vol. 32, pp. 273-280.
Dickinson et al., "Mammalian Target of Rapamycin Complex 1 Activation Is Required for the Stimulation of Human Skeletal Muscle Protein Synthesis by Essential Amino Acids," J Nutr (2011) vol. 141, pp. 856-862.
Dilger et al., "Oral N-acetyl-L-cysteine is a safe and effective precursor of cysteine," J Anim Sci (2007) vol. 85, pp. 1712-1718.
Dillon, "Nutritionally essential amino acids and metabolic signaling in aging," Amino Acids (2012). doi:10.1007/s00726-012-1438-0, 11 pp.
Dirks et al., "Skeletal Muscle Disuse Atrophy Is Not Attenuated by Dietary Protein Supplementation in Healthy Older Men," J Nutr (2014) vol. 144, pp. 1196-1203.
Dohil, R., et al., "Enteric-Coated Cysteamine for the Treatment of Paediatric Non-Alcoholic Fatty Liver Disease," Alimentary Pharmacology & Therapeutics, 33.9 (2011): 1036 1044.
Doi et al., "Isoleucine, a Blood Glucose-Lowering Amino Acid, Increases Glucose Uptake in Rat Skeletal Muscle in the Absence of Increases in AMP-Activated Protein Kinase Activity," J Nutr (2005) vol. 135, pp. 2103-2108.
Doi, M. et al., "Hypoglycemic Effect of Isoleucine Involves Increased Muscle Glucose Uptake and Whole Body Glucose Oxidation and Decreased Hepatic Gluconeogenesis," Am. J. Physiol. Endocrinal Metab., 2007, pp. E1683-E1693, vol. 292.
Dou et al., "Ameliorative effects of glycine in an experimental nonalcoholic steatohepatitis and its correlation between TREM-1 and TREM-2," Am J Transl Res (2016) vol. 8, No. 2, pp. 284-297.
Dreyer et al., "Essential amino acid supplementation in patients following total knee arthroplasty," J Clin Invest (2013) vol. 123, No. 11, pp. 4654-4666.
Dreyer et al., "Leucine-enriched essential amino acid and carbohydrate ingestion following resistance exercise enhances mTOR signaling and protein synthesis in human muscle," Am J Physiol Endocrinol Metab (2008) vol. 294, E392-400.
Khoshbaten, M. et al., "N-Acetylcysteine Improves Liver Function in Patients with Non-Alcoholic Fatty Liver Disease," Hepat Mon, 2010 Winter; 10(1):12-16. Epub Mar. 1, 2010.
Kim et al., "Acetyl CoA Carboxylase Inhibition Reduces Hepatic Steatosis but Elevates Plasma Triglycerides in Mice and Humas: A Bedside to Bench Investigation," Cell Metabolism (2017) vol. 26, pp. 394-406.
Kim et al., "Quantity of dietary protein intake, but not pattern of intake, affects net protein balance primarily through differences in protein synthesis in older adults," Am J Physiol Endocrinol Metab (2015) vol. 308, No. 1, pp. E21-E28.
Kinny-Köster et al., "Plasma Amino Acid Concentrations Predct Mortality in Patients with End-Stage Liver Disease," PLOS One (2016) vol. 11, No. 7, Article e0159205, 13 pages.
Kircheis et al., "Assessment of low-grade hepatic encephalopathy: a critical analysis," Journal of Hepatology (2007) vol. 47, pp. 642-650.
Kircheis et al.,"Therapeutic Efficacy of L-Ornithine-L-Aspartate Infusions in Patients With Cirrhosis and Hepatic Encephalopathy: Results of a Placebo-Controlled, Double-Blind Study," Hepatology (1997) vol. 25, pp. 1351-1360.
Kitajima et al., "Supplementation with branched-chain amino acids ameliorates hypoalbuminemia, prevents sarcopenia, and reduces fat accumulation in the skeletal muscles of patients with liver cirrhosis," J Gastroenterol (2017) doi 10.1007/s00535-017-1370-x, 11 pages.

(56) References Cited

OTHER PUBLICATIONS

Knudsen et al., "L-leucine methyl ester stimulates insulin secretion and islet glutamate dehydrogenase," Am J Physiol (1983) vol. 245, pp. E338-46.

Krenitsky, "Nutrition Update in Hepatic Failure," Practical Gastroenterology (2014) pp. 47-55.

Kumar et al., "Ammonia lowering reverses sarcopenia or cirrhosis by restoring skeletal muscle proteostasis," Hepatol (2017) vol. 65, No. 6, pp. 2045-2058.

Kuwahata et al., "Supplementation with branched-chain amino acids attenuates hepatic apoptosis in rats with chronic liver disease," Nutrition Research (2012) vol. 32, pp. 522-529.

Kwanten et al., "Role of autophagy in the pathophysiology of nonalcoholic fatty liver disease: A controversial issue," World J Gastroenterol (2014) vol. 20, Issue 23, pp. 7325-7338.

Le Plénier et al., "Citrulline directly modulates muscle protein syntheses via the PI3K/MAPK/4E-BP1 pathway in a malnourished state: evidence from in vivo, ex vivo, and in vitro studies," Am J Physiol Endocrinol Metab (2017) vol. 312, pp. E27-E36.

Lee et al., "AXA1125, a novel defined amino acid composition (DAAC), improves NAFLD activity score (NAS) and reduces fibrosis in two rodent models of nonalcoholic steatohepatitis (NASH)," Easl Abstracts from the First NAFLD Summit (2017) Abstract P02-05, pp. 64-65.

Les et al., "Effects of Branched-Chain Amino Acids Supplementation in Patients with Cirrhosis and a Previous Episode of Hepatic Encephalopathy: A Randomized Study," Am J Gastroenterol (2011)vol. 106, pp. 1081-1088.

Li et al., "A Novel Dual Eigen-Analysis of Mouse Multi-Tissues' Expression Profiles Unveils New Perspectives into Type 2 Diabetes," Sci Rep (2017) vol. 7, Article 5044, 12 pp.

Li et al., "Leucine supplementation increases SIRT1 expression and prevents mitochondrial dysfunction and metabolic disorders in high-fat diet-induced obese mice," Am J Endocrinol Metab (2012) vol. 303, pp. E1234-E1244.

Li, T. et al., "Branched-Chain Amino Acids Alleviate Nonalcoholic Steatohepatitis in Rats," Appl Physiol Nutr Metab., Aug. 2013; 38(8):836-43. doi: 10 1139/apnm-2012-0496. Epub Mar. 8, 2013.

Liu et al., "Gene-metabolite network analysis in different nonalcoholic fatty liver disease phernotypes," Experimental & Molecular Medicine (2017) vol. 49, e283, 9 pp.

Liu et al., "Leucine Supplementation Differently Modulates Branched-Chain Amino Acid Catabolism, Mitochondrial Function and Metabolic Profiles at the Different Stages of Insulin Resistance in Rats on High-Fat Diet," Nutrients (2017) vol. 9, Article 565, 20 pp.

Liu, B. et al., "Glutamine Attenuates Obstructive Cholestasis in Rats Via famesoid X Receptor-Mediated Regulation of Bsep and Mrp2," Can J Physiol Pharmacol, Feb. 2017; 95(2):215-223. doi: 10 1139/cjpp-2016-0389. Epub Oct. 5, 2016.

Lomivorotov et al., "Does Glutamine Promote Benefits for Patients with Diabetes Mellitus Scheduled for Cardiac Surgery?" Heart Lung Circ (2013) vol. 22, No. 5, pp. 360-365.

Lucotti, P. et al., "Beneficial Effects of a Long-Term Oral L-Arginine Treatment Added to a Hypocaloric Diet and Exercise Training Program in Obese, Insulin-Resistant Type 2 Diabetic Patients," (2006) Am J Physiol Endocrinol Metab, 291: E906-E912.

Luiking et al., "Arginine de novo and nitric oxide production in disease states," Am J Physiol Endocrinol Metab (2012) vol. 303, pp. E1177-E1189.

Lynch et al., "Branched-chain amino acids in metabolic signalling and insulin resistance," Nat Rev Endocrinol (2014) vol. 10, No. 12, pp. 723-736.

Lynch et al.,"Tissue-specific effects of chronic dietary leucine and norleucine supplementation on protein synthesis in rats," Am J Physiol Endocrinol Metab (2002) vol. 283, pp. E824-E835.

Macotela et al., "Dietary Leucine—An Environmental Modifier of Insulin Resistance Acting on Multiple Levels of Metabolism," PLoS ONE (2011) vol. 6, e21187, 13 pp.

Madden et al., "Ten Amino Acids Essential for Plasma Protein Production Effective Orally or Intravenously," J Exper Med (1943) vol. 77, No. 3, pp. 277-295.

Maddrey, W.C., "Branched Chain Amino Acid Therapy in Liver Disease (abstract only)," J Am Coll Nutr. 1985;4(6):639-50.

Mager, D.R. et al., "Branched-Chain Amino Acid Needs in Children with Mild-to-Moderate Chronic Cholestatic Liver Disease," J. Nutr, 136: 133-139, 2006.

Malaguarnera et al., "Branched chain amino acids supplemented with L-acetylcamitine versus BCAA treatmentin hepatic coma: a randomized and controlled double blind study," Eur J Gastroenterol Hepatol (2009) vol. 21, No. 7, pp. 762-770, Abstract Only.

Mansoor et al., "Effect of an enteral diet supplemented with a specific protein blend of amino acid on plasma and muscle protein synthesis in ICU patients," Clinical Nutrition (2007) vol. 26, pp. 30-40.

Mansour et al., "Effect of glutamine supplementation on cardiovascular risk factors in patients with type 2 diabetes," Nutrition (2015) vol. 31, pp. 119-126.

Marchesini et al., "Branched-Chain Amino Acid Supplementation in Patients with Liver Diseases," J Nutr (2005) vol. 135, pp. 1596S-1601S.

Marchesini et al., "Long-term oral branched-chain amino acid treatment in chronic hepatic encephalopathy," Journal of Hepatology (1990) vol. 11, pp. 92-101.

Marchesini et al., "Nutritional Supplementation With Branched-Chain Amino Acids in Advanced Cirrhosis: A Double-Blind, Randomized Tial," Gastroenterology (2003) vol. 124, No. 7, pp. 1792-1801.

Mardinoglu et al., "Personal model-assisted identification of NAD+ and glutathione metabolism as intervention target in NAFLD," Mol Sys Biol (2017) vol. 13, Article 916, 17 pages.

Marra et al., "Lipotoxicity and the gut-liver axis in NASH pathogenesis," Journal of Hepatology (2017), doi: 10.1016/j.ihep.2017.11.014, 44 pp.

Marra et al., "Roles for Chemokines in Liver Disease," Gastroenterology (2014) vol. 147, pp. 577-594.

Martin et al., "Leucine elicits myotube hypertrophy and enhances maximal contractile force in tissue engineered skeletal muscle in vitro," J Cell Physiol (2017) vol. 232, pp. 2788-2797.

Martin et al., "Whey Proteins Are More Efficient than casein in the Recovery of Muscle Functional Properties following a Casting Induced Muscle Atrophy," PLOS One (2013) vol. 8, No. 9, Article e75408, 8 pp.

Martina et al., "Long-Term N-Acetylcysteine and L-Arginine Administration Reduces Endothelial Activation and Systolic Blood Pressure in Hyptertensive Patients With Type 2 Diabetes," Diabetes Care (2008) vol. 31, No. 5, pp. 940-944.

Massafra et al., "Farnesoid X Receptor Activation Promotes Hepatic Amino Acid Catabolism and Ammonium Clearance in Mice," Gastroenterology (2017) doi: 10.1053/j.gastro.2017.01.014, 48 pp.

Matoori et al., "Recent advances in the treatment of hyperammonemia," Adv Drug Deliv Rev (2015) doi: 10.1016/j.addr.2015.04 009, 14 pages.

McCarty et al., "The cardiometabolic benefits of glycine: Is glycine an 'antidote' to dietary fructose," Open Heart (2014) vol. 1, Article e000103, 9 pp.

McCarty, "Supplementation with Phycocyanobilin, Citrulline, Taurine, and Supranutritional Doses of Folic Acid and Biotin-Potential for Preventing or Slowing the Progression of Diabetic Complications," Healthcare (2017) vol. 5, Article 15, 28 pp.

McCormack et al., "Circulating Branched-chain Amino Acid Concentrations Are Associated with Obesity and Future Insulin Resistance in Children and Adolescents," Pediatr Obes (2013) vol. 8, No. 1, pp. 52-61.

McCullough et al., "Stable isotope-based flux studies in nonalcoholic fatty liver disease," Pharmacology & Therapeutics (2017) doi: 10.1016/j.pharmthera.2017.07.008, 12 pp.

McKnight et al., "Beneficial effects of L-arginine on reducing obesity: potential mechanisms and important implications for human health," Amino Acids (2010) vol. 39, pp. 349-357.

(56) References Cited

OTHER PUBLICATIONS

Meex et al., "Hepatokines: linking nonalcoholic fatty liver disease and insulin resistance," Nat Rev Endocrinol (2017) doi: 10.1038/nrendo.2017.56, 12 pp.
Drummond et al. "Bed rest impairs skeletal muscle amino acid transporter expression, mTORC1 signaling, and protein synthesis in response to essential amino acids in older adults," Am J Physiol Endocrinol Metab (2012) vol. 302, pp. E1113-E1122.
Drummond et al., "Skeletal muscle protein anabolic response to resistance exercise and essential amino acids is delayed with aging," J Appl Physiol (2008) vol. 104, pp. 1452-1461.
Dröge et al., "Role of Cysteine and Glutathione in HIV infection and cancer cachexia: Therapeutic intervention with N-acetylcysteine," Advances in Phamacology (1997) vol. 38, pp. 581-600.
Du et al., "Effects of Histidine Supplementation on Global Serum and Urine 1H NMR-based Metabolomics and Serum Amino Acid Profiles in Obese Women from a Randomized Controlled Study," J Proteome Res (2017) vol. 16, pp. 2221-2230.
Egberts et al., "Branched Chain Amino Acids in the Treatment of Latent Portosystemic Encephalopathy," Gastroenterology (1985) vol. 88, pp. 887-895.
Ejima et al., "A novel diet-induced murine model of steatohepatitis with fibrosis for screening and evaluation of drug candidates for nonalcoholic steatohepatitis," Physiol Rep (2016) vol. 4, No. 21, Article e13016, 13 pp.
Eley et al., "Effect of branched-chain amino acids on muscle atrophy in cancer cachexia," Biochem J (2007) vol. 407, pp. 113-120.
English et al., "Leucine partially protects muscle mass and function during bed rest in middle-aged adults," Am J Clin Nutr (2016) vol. 103, pp. 465-473.
Escobar et al., "Regulation of cardiac and skeletal muscle protein synthesis by individual branched-chain amino acids in neonatal pigs," Am J Physiol Endocrinol Metab (2006) vol. 290, pp. E612-E621.
Estes et al., "Modeling the Epidemic of Nonalcoholic Fatty Liver Disease Demonstrates an Exponential Increase in Burden of Disease," Presented at the American Association for Study of Liver Disease in Boston (2016), doi: 10.1002/hep.29466, 26 pp.
Evans et al., "Efficacy of a novel formulation of L-Carnitine, creatine, and leucine on lean body mass and functional muscle strength in healthy older adults: a randomized, double-blind placebo-controlled study," Nutrition & Metabolism (2017) vol. 14, No. 7, 15 pp.
Falach-Malik et al., "N-Acetyl-L-Cysteine inhibits the development of glucose intolerance and hepatic steatosis in diabetes-prone mice," Am J Transl Res (2016) vol. 8, No. 9, pp. 3744-3756.
Farghaly et al., "L-arginine and aminoguanidine reduce colonic damage of acetic acid-induced colitis in rats: potential modulation of nuclear factor-KB/p65," Clin Exp Pharmacol Physiol (2014) vol. 41, No. 10, pp. 769-779, Abstract Only.
Farid et al., "Effects of dietary curcumin or N-acetylcysteine on NF-KB activity and contractile performane in ambulatory and unloaded murine soleus," Nutrition & Metabolism (2005) vol. 2, No. 20, 8 pages.
Fazelian, S et al., "Effects of L-Arginine Supplementation on Antioxidant Status and Body Composition in Obese Patients with Pre-diabetes: A Randomized Controlled Clinical Trial," (2014) Adv Pharm Bull, 4(Suppl 1), 449-454.
Feher et al., "Effect of ornithine-aspartate infusion on elevated serum ammonia concentration in cirrhotic patients -results of a randomized, placebo-controlled double-blind multicentre trial," Med Sci Monit (1997) vol. 3, No. 5, pp. 669-673.
Ferrando et al., "EAA supplementation to increase nitrogen intake improves muscle function during bed rest in the elderly," Clinical Nutrition (2010) vol. 29, pp. 18-23.
Francaux et al., "Aging Reduces the Activation of the mTORCl Pathway after Resistance Exercise and Protein Intake in Human Skeletal Muscle: Potential Role of REDD1 and Impaired Anabolic Sensitivity," Nutrients (2016) vol. 8, Article 47, 16 pp.

Frank et al., "Dietary protein and lactose increase translation initiation factor activation and tissue protein synthesis in neonatal pigs," Am J Physiol Endocrinol Metab (2006) vol. 290, pp. E225-E233.
Fresenius Kabi New Zealand Limited, Data Sheet for Dipeptiven®, dated Mar. 19, 2012, 5 pages.
Fresenius Kabi, Kabiven® Product Information revised 2016, 24 pages.
Fresenius Kabi, Perikabiven® Product Information revised 2016, 24 pages.
Freudenberg, A et al., "Comparison of High-Protein Diets and Leucine Supplementation in the Prevention of Metabolic Syndrome and Related Disorders in Mice," J Nutr Biochem, Nov. 2012; 23(11):1524-30.
Freudenberg, A. et al., "Dietary L-Leucine and L-Alanine Supplementation Have Similar Acute Effects in the Prevention of High-Fat Diet-Induced Obesity," (2012) Amino Acids, 44:519-528.
Frontiers in Hepatology: NASH and Nutritional Therapy pp. 92-114 (Kiwamu Okita, Ed., 2005) Springer-Verlag, Toyko, Japan.
Fu et al., "Leucine amplifies the effects of metformin on insulin sensitivity and glycemic control in diet-induced obese mice," Metabolism Clinical and Experimental (2015), dx.doi.org/10.1016/j.metabol.2015.03.007, 12 pp.
Fujita et al., "Essential amino acid and carbohydrate ingestion before resistance exercise does not enhance postexercise muscle protein synthesis," J Appl Physiol (2009) vol. 106, pp. 1730-1739.
Fujita et al., "Nutrient signalling in the regulation of human muscle protein synthesis," The Journal of Physiology (2007) vol. 582, pp. 813-823.
Fujita, S. et al., "Amino Acids and Muscle Loss with Aging," J Nutr, Jan. 2006; 136(1 Suppl): 277S-280S.
Fukuda et al., "L-Ornithine affects peripheral clock gene expression in mice," Sci Rep (2016) vol. 6, Article 34665, 11 pp.
Gaggini et al., "Altered amino acid concentrations in NAFLD: impact of obesity and insulin resistance," Hepatology, doi: 10.1002/hep.29465, published online Nov. 2017.
Garcia Caraballo et al., "A high-protein diet is anti-steatotic and has no pro-inflammatory side effects in dyslipidaemic APOE2 knock-in mice," Br J Nutr (2014) vol. 112, pp. 1251-1265.
Garcia-Caraballo, S. et al., "Prevention and Reversal of Hepatic Steatosis with a High-Protein Diet in Mice," Biochim Biophys Acta, May 2013; 1832(5):685-95. doi: 10.1016/j.bbadis.2013.02.003. Epub Feb. 11, 2013.
Garg et al., "Therapeutic strategies for preventing skeletal muscle fibrosis after injury," Frontiers in Pharmacology (2015) vol. 6, Article 87, 9 pages.
Gebhardt et al., "Treatment of Cirrhotic Rats with L-Ornithine-L-Aspartate Enhances Urea Synthesis and Lowers Serum Ammonia Levels," J Pharmacol Exp Therapeutics (1997) vol. 283, No. 1, pp. 1-6.
Giam et al., "Effects of Dietary L-Arginine on Nitric Oxide Bioavailability in Obese Normotensive and Obese Hypertensive Subjects," Nutrients (2016) vol. 8, Article 364, 3 pp.
Glover et al., "Immobilization induces anabolic resistance in human myofibrillar protein synthesis with low and high dose amino acid infusion," J Physiol (2008) vol. 586, No. 24, pp. 6049-6061.
Gluchowski et al., "Lipid droplets and liver disease: from basic biology to clinical implications," Nat Rev Gastroenterol Hepatol (2017) doi:10.1038/nrgastro.2017.32, 13 pp.
Gluud et al., "Branched-chain amino acids for people with hepatic encephalopathy," The Cochrane Review (2015) Issue 9, 89 pages.
Gluud et al., "Oral Branched-chain Amino Acids Have a Beneficial Effect on Manifestations of Hepatic Encephaolpathy in a Systematic Review with Meta-Analyses of Randomized Controlled Trials," J Nutr (2013) doi: 10.3945/jn.113.174375, 6 pages.
Goh et al., "L-ornithine L-aspartate for prevention and treatment of hepatic encephalopathy in people with cirrhosis," Cochrane Database of Systematic Reviews (2018) Issue 5, Art No. CD012410, 4 pages.
Goldberg et al., "Oxidation of amino acids by diaphragms from fed and fasted rats," Am J Physiol (1972) vol. 223, pp. 1384-1391.
Goldberg, "Protein synthesis during work-induced growth of skeletal muscle," J Cell Biol (1968) vol. 36, pp. 653-658.

(56) References Cited

OTHER PUBLICATIONS

Goldberg, "Protein turnover in skeletal muscle. I. Protein catabolism during work-induced hypertrophy and growth induced with growth hormone," J Biol Chem (1969) vol. 244, No. 12, pp. 3217-3222.
Gomes et al., "Hepatic injury and disturbed amino acid metabolism in mice following prolonged exposure to organophosphorus pesticides," Human and Experimental Toxicology (1999) vol. 18, No. 1, pp. 33-37.
Gomes-Marcondes et al., "A leucine-supplemented diet improved protein content of skeletal muscle in young tumor-bearing rats," Braz J Med Biol Res (2003) vol. 36, pp. 1589-1594.
Gornik et al., "Arginine and Endothelial and Vascular Health," J Nutr (2004) vol. 134, pp. 2880S-2887S.
Graf et al., "Effects of whey protein supplements on metabolism: evidence from human intervention studies," Curr Opin Clin Nutr Metab Care (2011) vol. 14, pp. 569-580.
Greenfield et al., "Oral glutamine increases circulating glucagon-like peptide 1, glucagon, and insulin concentrations in lean, obese, and type 2 diabetic subjects," Am J Clin Nutr (2009) vol. 89, pp. 106-113.
Guillet et al., "Mitochondrial and sarcoplasmic proteins, but not myosin heavy chain, are sensitive to leucine supplementation in old rat skeletal muscle," Exp Gerontol (2004) vol. 39, pp. 745-751.
Sim et al., "L-Serine Supplementation Attenuates Alcoholic Fatty Liver by Enhancing Homocysteine Metabolism in Mice and Rats," J Nutr (2014) vol. 145, pp. 260-267.
Simpson et al., "The nutritional geometry of liver disease including non-alcoholic fatty liver disease (NAFLD)," J Hepatol (2017), doi: 10.1016/; j.jhep.2017.10.005, 10 pp.
Siniscalchi et al., "Effect of Different Intravenous Nutrients on Metabolic Changes in Short-Term Fasted Men," Drugs Exp Clin Res (1987) vol. 13, No. 7, pp. 451-456.
Smith et al., "Dietary omega-3 fatty acid supplementation increases the rate of muscle protein synthesis in older adults: a randomized controlled trial," American Journal of Clinical Nutrition (2011) vol. 93, pp. 402-412.
Smith et al., "Treatment of Non-Alcoholic Fatty Liver Disease (NAFLD): Role of AMPK," Am J Physiol Endocrinol Metab (2016) doi:10.1152/ajpendo.00225.2016, 25 pp.
Soomro et al., "Role of Branched Chain Amino Acids in the Management of Hepatic Encephalopathy," World J Med Sci (2008) vol. 3, No. 2, pp. 60-64.
Squires et al., "A Prospective Clinical Trial Shows That Intravenous N-Aceytlcysteine (NAC) Does Not Improve Survival in Pediatric Patients With Non-Acetaminophen Acute Liver Failure," Gastroenterology (2011) vol. 140, Issue 5, Supplement 1, p. S-897.
Staedt et al., "Effects of ornithine aspartate on plasma ammonia and plasma amino acids in patients with cirrhosis. A Touble-blind, randomized study using a four-fold crossover design," Journal of Hepatology (1993) vol. 19, pp. 424-430.
Stauch et al., "Oral L-ornithine-L-aspartate therapy of chronic heaptic encephalopathy: results of a placebo-controlled double-blind study," Journal of Hepatology (1998) vol. 28, pp. 856-864.
Stokes et al., "L-ornithine L-aspartate for people with cirrhosis and hepatic encephalopathy," Cochrane Database of Systematic Reviews (2016) Issue 10, Art No. CD012410, 14 pages.
Sun et al., "Melatonin improves non-alcoholic fatty liver disease via MAPK-JNK/P38 signaling in high-fat-diet-induced obese mice," Lipids in Health and Disease (2016) vol. 15, Article 202, 8 pp.
Sunny et al., "Cross-talk between branched-chain amino acids and hepatic mitochondria is compromised in nonalcoholic fatty liver disease," Am J Physiol Endocrinol Metab (2015) vol. 309, pp. E311-E319.
Suryawan et al., "Leucine stimulates protein synthesis in skeletal muscle of neonatal pigs by enhancing mTORC1 activation," Am J Physiol Endocrinol Metab (2008) vol. 295, pp. E868-E875.
Tachibana et al., "Intake of Mung Bean Protein Isolate Reduces Plasma Triglyceride Level in Rats," Functional Foods in Health and Disease (2013) vol. 3, No. 9, pp. 365-376.

Tajiri et al., "Branched-chain amino acids in liver diseases," World J Gastroenterol (2013) vol. 19, Issue 43, pp. 7620-7629.
Takaguchi et al., "Effects of branched-chain amino acid granules on serum albumin level and prognosis are dependent on treatment adherence in patients with liver cirrhosis," Hepatology Research (2013) vol. 43, pp. 459-466.
Takashi et al., "Branched-chain amino acids alleviate hepatic steatosis and liver injury in choline-deficient high-fat diet induced NASH mice," Metabolism (2017) doi: 10.1016/j.metabol.2016.12.013, 45 pp.
Takegoshi, K. et al., "Branched-Chain Amino Acids Prevent Hepatic Fibrosis and Development of Hepatocellular Carcinoma in a Non-Alcoholic Steatohepatitis Mouse Model," Oncotarget, Mar. 14, 2017; 8(11):18191-18205. doi:10.18632/oncotarget.15304.
Talvas et al., "Regulation of protein synthesis by leucine starvation involves distinct mechanisms in mouse C2C12 myoblasts and myotubes," J Nutr (2006) vol. 136, pp. 1466-1471.
Tan, B et al., "Regulatory Roles for L-Arginine in Reducing White Adipose Tissue," (2012) Frontiers in Bioscience, 17, 2237-2246, Jun. 1.
Tanaka et al., "Branched-chain Amino Acid-Rich Supplements Containing Microelements Have Antioxidant Effects on Nonalcoholic Steatohepatitis in Mice," J Parenteral and Enteral Nutrition (2016) vol. 40, No. 4, pp. 519-528.
Theytaz et al., "Effects of supplementation with essential amino acids on intrahepatic lipid concentrations during fructose overfeeding in mice," Am J Clin Nutr (2012) vol. 96, pp. 1008-1016.
Thomsen et al., "Experimental nonalcoholic steatohepatitis compromises ureagenesis, an essential hepatic metabolic function," Am J Physiol Gastrointest Liver Physiol (2014) vol. 307, pp. G295-G301.
Thong-Ngam et al., "N-acetylcysteine attenuates oxidative stress and liver pathoogy in rats with non-alcoholic steatohepatitis," World J Gastroenterol (2007) vol. 13, No. 38, pp. 5127-5132.
Tsien et al., "Metabolic and Molecular Responses to Leucine-Enriched Branched Chain Amino Acid Supplementation in the Skeletal Muscle of Alcoholic Cirrhosis," Hepatology (2015) vol. 61, No. 6, pp. 2018-2029.
Ullrich et al., "Intragastric administration of leucine or isoleucine lowers the blood glucose response to a mixed-nutrient drink by different mechanisms in healthy, lean volunteers," Am J Clin Nutr (2016) vol. 104, pp. 1274-1284.
U.S. Appl. No. 15/847,343, filed Dec. 19, 2017.
U.S. Appl. No. 15/858,387, filed Dec. 29, 2017.
U.S. Appl. No. 15/858,444, filed Dec. 29, 2017.
U.S. Appl. No. 15/858,475, filed Dec. 29, 2017.
U.S. Appl. No. 15/858,605, filed Dec. 29, 2017.
U.S. Appl. No. 16/674,317, filed Nov. 5, 2019.
Van De Poll et al., "Intestinal and hepatic metabolism of glutamine and citrulline in humans," J Physiol (2007) vol. 581, No. 2, pp. 819-827.
Van Loon et al., "Amino Acid Ingestion Strongly Enhances Insulin Secretion in Patients With Long-Term Type 2 Diabetes," Diabetes Care (2003) vol. 26, No. 3, pp. 625-630.
Van Vliet et al., "The Skeletal Muscle Anabolic Response to Plant—versus Animal-Based Protein Consumption," J Nut (2015) vol. 14, No. 5, pp. 1981-1991.
Varakanahalli et al., "Secondary prophylaxis of hepatic encephalopathy in cirrhosis of liver: a double-blind randomized controlled trial of L-ornithine L-aspartate versus placebo," Eur J Gastroenterol Hepatol (2018) vol. 30, pp. 951-958.
Vela et al., "Efficacy of oral L-orinthine L-aspartate in cirrhotic patients with hyperammonemic hepatic encephalopathy," Annals of Hepatology (2011) vol. 10, Supp. 2, pp. S55-S59.
Ventura et al., "Evidence for a role of the ileum in the control of nitrogen homeostasis via the regulation of arginine metabolism," Br J Nutr (2011) vol. 106, pp. 227-236.
Ventura-Cots et al., "Impact of ornithine phenylacetate (OCR-002) in lowering plasma ammonia after upper gastrointestinal bleeding in cirrhotic patients," Ther Adv Gastroenterol (2016) vol. 9, No. 6, pp. 823-836.

(56) References Cited

OTHER PUBLICATIONS

Wahren, J. et al., "Is Intravenous Administration of Branched Chain Amino Acids Effective in the Treatment of Hepatic Encephalopathy? A Multicenter Study (abstract only)," Hepatology, Jul.-Aug. 1983; 3(4):475-80.
Watanabe et al., Beneficial Effect of Food Substitute Containing L-Arginine, w-3 Poly Unsaturated Fatty Acid, and Ribonucleic Acid in Preventing or Improving Metabolic Syndrome: A Study in 15 Overweight Patients and a Study of Fatty Acid Metabolism in Animals, J Clin Biochem Nutr (2009) vol. 44, pp. 266-274.
Waugh et al., "Evidence that L-Arginine is a Key Amino Acid in Sickle Cell Anemia—A Preliminary Report," Nutrition Research (1999) vol. 19, No. 4, pp. 501-518.
Wilkinson et al., "Effects of leucine and its metabolite b-hydroxy-b-methylbutyrate on human skeletal muscle protein metabolism," J Physiol (2013) vol. 591, No. 11, pp. 2911-2923.
Wilson et al., "Differential effects of long-term leucine infusion on tissue protein synthesis in neonatal pigs," Amino Acids (2011) vol. 40, pp. 157-165.
Xu et al., "Ketogenic essential amino acids replacement diet ameliorated hepatosteatosis with altering autophagy-associated molecules," Biochimica et Biophysica Acta (2013) vol. 1832, pp. 1605-1612.
Yamada et al., Association between insulin resistance and plasma amino acid profile in non-diabetic Japanese subjects, J Diabetes Invest (2015) vol. 6, pp. 408-415.
Yamamoto et al., "Branched-chain amino acids protect against dexamethasone-induced soleus muscle atrophy in rats," Muscle Nerve (2010) vol. 41, pp. 819-827.
Yang et al., "Resistance exercise enhances myofibrillar protein synthesis with graded intakes of whey protein in older men," Br J Nutr (2012) vol. 108, pp. 1780-1788.
Yao et al., "Dietary Arginine Supplementation Increases mTOR Signaling Activity in Skeletal Muscle of Neonatal Pigs," J Nutr (2008) vol. 138, pp. 867-872.
Yatzidis, "Oral supplement of six selective amino acids arrest progression renal failure in uremic patients," International Urology and Nephrology (2004) vol. 36, pp. 591-598.
Piatti, P.M. et al., "Long-Term Oral L-Arginine Administration Improves Peripheral and Hepatic Insulin Sensitivity in Type 2 Diabetic Patients," (2001) Diabetes Care, vol. 24, No. 5, May 2001; 24(5):875-80.
Piccolo, B.D. et al., "Plasma Amino Acid and Metabolite Signatures Tracking Diabetes Progression in the UCD-T2DM Rat Model," Am J Physiol Endocrinol Metab, Jun. 1, 2016; 310(11):E958-69. doi: 10.1152/ajpendo.00052.2016. Epub Apr. 19, 2016.
Pilar et al., "L-Omithine Aspartate Among Cirrhotic Patients with Hepatic Encephalopathy: Does it make a difference?" Phil J of Gastroenterology (2006) vol. 2, pp. 87-94.
Pinheiro et al., "Metabolic and functional effects of beta-hydroxy-beta-methylbutyrate (HMB) supplementation in skeletal muscle," Eur J Appl Physiol (2012) vol. 112, pp. 2531-2537, first published online Nov. 2011, doi: 10.1007/s00421-011-2224-5.
Pintilie, D.G. et al., "Hepatic Stellate Cells' Involvement in Progenitor Mediated Liver Regeneration," Lab Invest, Aug. 2010; 90(8):1199-208. doi: 10.1038/labinvest.2010.88. Epub May 3, 2010.
Plauth et al., "Long-term treatment of latent portosystemic encephalopathy with branched-chain amino acids," Journal of Heaptology (1993) vol. 73, pp. 308-314.
Poo et al., "Efficacy of oral L-ornithine-L-aspartate in cirrhotic patients with hyperammonemic hepatic encephalopathy Results of a randomized, lactulose-controlled study," Annals of Hepatology (2006) vol. 5, No. 4, pp. 281-288.
Prod'Homme et al., "Insulin and amino acids both strongly participate to the regulation of protein metabolism," Curr Opin Clin Nutr Metab Care (2004) vol. 7, pp. 71-77.
Qiu et al., "Hyperammonemia-mediated autophagy in skeletal muscle contributes to sarcopenia of cirrhosis," Am J Physiol Endocrinol Metab (2012) vol. 303, pp. E983-E993.

Rathmacher et al., "Supplementation with a combination of beta-hydroxy-beta-methylbutyrate (HMB), arginine, and glutamine is safe and could improve hematological parameters," J Parenter Enteral Nutr (2004) vol. 28, No. 2, pp. 65-75.
Reccia et al., "Non-alcoholic fatty liver disease: A sign of systemic disease," Metabolism Clinical and Experimental (2017) vol. 72, pp. 94-108.
Rees et al., "Effect of L-omithine-L-aspartate on patients with and without TIPS undergoing glutamine challenge: a double-blind, placebo controlled trial," Gut (2000) vol. 47, pp. 571-574.
Ren et al., "Serum Amino Acids Profile and the Beneficial Effects of L-Arginine or L-Glutamine Supplementation in Dextran Sulfate Sodium Colitis," PLOS One (2014) vol. 9, Issue 2, Article e88335, 13 pages.
Ritze et al., "Effect of tryptophan supplementation on diet-induced non-alcoholic fatty liver disease in mice," Br J Nutr (2014) vol. 112, pp. 1-7.
Roederer et al., "N-Acetylcysteine: A New Approach to Anti-HIV Therapy," AIDS Research and Human Retroviruses (1992) vol. 8, No. 2, pp. 209-217.
Rombouts et al., "Targeting the muscle for the treatment and prevention of hepatic encephalopathy," Journal of Hepatology (2016) vol. 65, pp. 876-878.
Romero-Gómez et al., "Altered resonse to oral glutamine challenge as prognostic factor for overt episodes in patientswith minimal hepatic encephalopathy," Journal of Heaptology (2002) vol. 37, pp. 781-787.
Romero-Gómez et al., "Prognostic Value of Altered Oral Glutamine Challenge in PatientsWith Minimal Hepatic Encephalopathy," Hepatology (2004) vol. 39, No. 4, pp. 939-943.
Rose et al., "L-Ornithine-L-Aspartate in Experimental Portal-Systemic Encephalopathy: Therapeutic Efficacy and Mechanism of Action," Metab Brain Dis (1998) vol. 13, No. 2, pp. 147-157.
Rose et al., "L-Ornithine-L-Aspartate Lowers Plasma and Cerebrospinal Fluid Ammonia and Prevents Brain Edema in Rats with Acute Liver Failure," Hepatology (1999) vol. 30, No. 3, pp. 636-640.
Roseguini et al., "Effects of N-Acetylcysteine on skeletal muscle structure and function in a mouse model of peripheral arterial insufficiency," J Vasc Surg (2015) vol. 61, pp. 777-786.
Roth, "Nonnutritive Effects of Glutamine," J Nutr (2008) vol. 138, pp. 2025S to 2031S.
Rui, "Energy Metabolism in the Liver," Compr Physiol (2014) vol. 4, No. 1, pp. 177-197.
Saad et al., "Attenuation of carbon tetrachloride induced hepatic fibrosis by glycine, vitamin E, and vitamin C," J Exp Integr Med (2014) vol. 4, Issue 3, pp. 180-186.
Sabater et al., "Altered Nitrogen Balance and Decreased Urea Excretion in Male Rats Fed Cafeteria Diet Are Related to Arginine Availability," BioMed Research International (2014) vol. 2014, Article 959420, 9 pp.
Sahin et al., "Effects of glutamine-enriched total parenteral nutrition on acute pancreatitis," European Journal of Clinical Nutrition (2007) vol. 61, pp. 1429-1434.
Sakai, H. et al., "Chemoprevention of Obesity-Related Liver Carcinogenesis by Using Pharmaceutical and Nutraceutical Agents," World J Gastroenterol,Jan. 7, 2016; 22(1): 394-406.
Salvatore et al., "Prevention of Ammonia Toxicity by Amino-acids concerned in the Biosynthesis of Urea," Nature (1961) vol. 191, No. 4789, pp. 705-706.
Samocha-Bonet et al., "Glutamine reduces postprandial glycemia and augments the glucagon-like peptide-1 response in type 2 diabetes patients," J Nutr (2011) vol. 141, No. 7, pp. 1233-1238.
Samocha-Bonet et al., "Glycemic Effects and Safety of L-Glutamine Supplementation with or without Sitagliptin in Type 2 Diabetes Patients—A Randomized Study," PLOS One (2014) vol. 9, Issue 11, Article e113366, 7 pages.
Samuel et al., "Nonalcoholic Fatty Liver Disease as a Nexus of Metabolic and Hepatic Diseases," Cell Metabolism (2017) vol. 27, doi: 10.1016/j.cmet.2017.08.002, 20 pp.
Sansbury, B.E et al., "Regulation of Obesity and Insulin Resistance by Nitric Oxide," (2014)—Free Radical Biology and Medicine, 73: 383-399.

(56) References Cited

OTHER PUBLICATIONS

Schiffrin, "Enteral nutrition in the ICU. The Nestle Modulis innovation. Physiopathology of the traumatized patient in the ICU," Nutrition Clinique et metabolisme (2007) vol. 21, p. S6-S10. Abstract Only.

Schmid et al., "A double-blind, randomized, placebo-controlled trial of intravenous L-ornithine-L-aspartate on postural control in patients with cirrhosis," Liver International (2010) doi: 10.1111/j.1478-3231. 2010.02213.x, pp. 574-582.

Schuppan et al., "Determinants of Fibrosis Progression and Regression in NASH," Journal of Hepatology (2017), doi: 10.1016/j.jhep. 2017.11.012, 39 pp.

Schwarz et al., "Dietary Protein Affects Gene Expression and Prevents Lipid Accumulation in the Liver in Mice," PLOS One (2012) vol. 7, Issue 10, Article e47303, 9 pp.

Schwimmer, J.B. et al., "In Children With Nonalcoholic Fatty Liver Disease, Cysteamine Bitartrate Delayed Release mproves Liver Enzymes but Does Not Reduce Disease Activity Scores," Gastroenterology, 2016; 151:1141-1154.

Sellmann et al., "Oral arginine supplementation protects female mice from the onset of non-alcoholic steatohepatitis," Amino Acids (2016) vol. 49, No. 7, pp. 1215-1225.

Sellmann et al., "Oral Supplementation of Glutamine Attenuates the Progression of Nonalcoholic Steatohepatitis in C57BL/6J Mice," J Nutr (2017) doi: 10.3945/jn.117.253815, 9 pp.

Sellmann, C. et al., "Oral Glutamine Supplementation Protects Female Mice from Nonalcoholic Steatohepatitis," J Nutr, Oct. 2015; 145(10):2280-6. doi: 10.3945/jn.115.215517. Epub Aug. 5, 2015

Sen et al., "Oxidative stress after human exercise: effect of N-acetylcysteine supplementation," J Appl Physiol (1994) vol. 76, No. 6, pp. 2570-2577.

Sen et al., "Thiol homeostasis and supplements in physical exercise,"Am J Clin Nutr (2000) vol. 72, Supp., pp. 653S-659S.

Setshedi et al., "N-Acetylcysteine Improves Hepatic Insulin Resistance Associated with High-Fat Diet and Alcohol-nduced Steatohepatitis," Gastroenterology (2010) vol. 138, No. 5, p. S801, Abstract S1846.

Sharawy et al., "Attentuation of insulin resistance in rats by agmatine: role of SREBP-1c, mTOR and GLUT-2," Naunyn-Schmiedeberg's Arch Pharmacol (2016) vol. 389, pp. 45-56.

Sharawy et al., "The ergogenic suplement B-hydroxy-B-methylbutyrate (HMB) attenuates insulin resistance through suppressinf GLUT-2 in rat liver," Can J Physiol Pharmacol (2016) vol. 94, pp. 488-497.

Sharma et al., "Effect of Rifazimin, Probiotics, and I-Omithine I-Aspartate on Minimal Hepatic Encephalopathy: A Randomized Controlled Trial," Saudi J Gastroenterol (2014) vol. 20, pp. 225-232.

Shimizu, M. et al., "Nutraceutical Approach for Preventing Obesity-Related Colorectal and Liver Carcinogenesis," Int. J. Mol. Sci., 2012, 13, 579-595.

Shrestha et al., "Glutamine inhibits CCl4 induced liver fibrosis in mice and TGF-β1 mediated epithelial-mesenchymal transition in mouse hepatocytes," Food and Chemical Toxicology (2016) vol. 93, pp. 129-137.

Sidhu et al., "L-Omithine L-Aspartate in Bouts of Overt Hepatic Encephalopathy," Hepatology (2018) vol. 67, No. 2, pp. 700-710.

Sidransky et al., "Skeletal muscle protein metabolism changes in rats force-fed a diet inducing an experimental Kwashiorkor-like model," Am J Clin Nutr (1970) vol. 23, pp. 1154-1159.

Gumucio et al., "Aging-associated exacerbation in fatty degeneration and infiltration after rotator cuff tear," J Shoulder Elbow Surg (2014) vol. 23, pp. 99-108.

Guo et al., "Chronic leucine supplementation improves glycemic control in etiologically distinct mouse models of obesity and diabetes mellitus," Nutrition & Metabolism (2010) vol. 7, Article 57, 10 pp.

Habu et al., "Effect of oral supplementation with branched-chain amino acid granules on serum albumin level in the early stage of cirrhosis: a randomized pilot trial," Hepatology Research (2003) vol. 25, Issue 3, pp. 312-318, Abstract Only.

Haegens et al., "Leucine induces myofibrillar protein accretion in cultured skeletal muscle through mTOR dependent and -independent control of myosin heavy chain mRNA levels," Mol Nutr Food Res (2012) vol. 56, pp. 741-752.

Hagström et al., "Fibrosis stage but not NASH predicts mortality and time to development of severe liver disease in biopsy-proven NAFLD," Journal of Hepatology (2017), doi: 10.1016/j.jhep.2017. 07.027, 37 pp.

Ham et al., "Arginine protects muscle cells from wasting in vitro in a an mTORCI-dependent and No. independent manner," Amino Acids (2014) vol. 46, Issue 12, pp. 2643-2652.

Harris, L-A. et al., "Alterations in 3-Hydroxyisobutyrate and FGF21 Metabolism are Associated with Protein ngestion-lnduced Insulin Resistance," Diabetes (Publish Ahead of Print), published online May 4, 2017, 34 pages.

Harrison et al., "Vitamin E and Vitamin C Treatment Improves Fibrosis in Patients With Nonalcoholic Steatohepatitis," Am J Gastroenterol (2003) vol. 98, pp. 2485-2490.

Hassan, A. et al., "Effects of Oral L-Carnitine on Liver Functions after Transarterial Chemoembolization in ntemnediate-Stage HCC Patients," Mediators Inflamm, 2015; 2015:608216. doi: 10.1155/ 2015/608216. Epub Nov. 19, 2015.

Hayashi et al., "A Randomized Controlled Trial of Branched-Chain Amino Acid (BCAA)-Enriched Elemental Diet (ED-H) For Hepatic Encephalopathy," J Gastroenterol Hepatol (1991) vol. 6, p. 191, Abstract Only.

Herlong et al., "The Use of Ornithine Salts of Branched-Chain Ketoacids in Portal-Systemic Encephalopathy," Annals of Internal Medicine (1980) vol. 93, pp. 545-550.

Hermier et al., "NO synthesis from arginine is favored by a-linolenic acid in mice fed a high-fat diet," Amino Acids (2016) vol. 48, pp. 2157-2168.

Higuera-De-La-Tijera et al., Primary Prophylaxis to Preventthe Development of Hepatic Enchephalopathy in Cirrhotic Patients with Acute Variceal Bleeding, Candian Journal of Gastroenterology and Hepatology (2018) Article 3015891, 10 pages.

Holdsworth et al., "Body protein metabolism and plasma amino acits in cirrhosis of the liver. The effect of varying the branched chain amino acid content of intravenous amino acid solutions," Clinical Nutrition (1984) vol. 3, ppp. 153-162.

Holecek, "Branched-chain amino acid supplementation in treatment of liver cirrhosis: Updated views on how to attenuate their harmful effects on cataplerosis and ammonia formation," Nutrition (2017) vol. 41, pp. 80-85.

Holecek, "Branched-chain amino acids and ammonia metabolism in liver disease," Nutrition (2013) vol. 29, pp. 1186-1191.

Holecek, "Evidence of a vicious cycle in glutamine synthesis and breakdown in pathogenesis of hepatic encephalopathy-therapeutic perspectives," Metab Brain Dis (2014) vol. 29, pp. 9-17.

Holecek, "Three targets of branched-chain amino acid supplementation in the treatment of liver disease," Nutrition (2010) vol. 2 6, pp. 482-490.

Holloway et al., "A Novel Amino Acid Composition Ameliorates Short-Term Muscle Disuse Atrophy in Healthy Young Men," Frontiers in Nutrition (2019) vol. 6, Article 105, 10 pages.

Horst et al., "Comparison of Dietary Protein with an Oral, Branched Chain-Enriched Amino Acid Supplement in Chronic Portal-Systemic Encephalopathy: A Randomized Controlled Trial," Hepatology (1984) vol. 4, No. 2, pp. 279-287.

Hurt et al., "L-Arginine for the Treatment of Centrally Obese Subjects: A Pilot Study," Journal of Dietary Supplements (2014) vol. 11, No. 1, pp. 40-52.

International Search Report and Written Opinion issued in PCT/US2017/067345, dated Mar. 9, 2018, 13 pages.

International Search Report and Written Opinion issued in PCT/US2017/067368, dated Apr. 18, 2018, 12 pages.

International Search Report and Written Opinion issued in PCT/US2018/046705, dated Nov. 23, 2018, 13 pages.

International Search Report and Written Opinion issued in PCT/US2019/037932, dated Oct. 7, 2019.

(56) References Cited

OTHER PUBLICATIONS

International Search Report and Written Opinion issued in PCT/US2019/037936, dated Oct. 2, 2019.
Ishikawa, "Early administration of branched-chain amino acid granules," World J Gastroenterol (2012) vol. 18, Issue 33, pp. 4486-4490.
Iwakiri et al., "Nitric oxide in liver diseases," Trends in Pharmacological Sciences (2015) vol. 36, No. 8, pp. 524-536.
Iwasa et al., "Branched-Chain Amino Acid Supplementation Reduces Oxidative Stress and Prolongs Survival in Rats with Advanced Liver Cirrhosis," PLOS One (2013) vol. 8, Issue 7, Article e70309, 11 pages.
Jackman et al., "Branched-Chain Amino Acid Ingestion Stimulates Muscle Myofibrillar Protein Synthesis following Resistance Exercise in Humans," Frontiers in Physiology (2017) vol. 8, Article 390, 12 pages.
Jalan et al., "L-Ornithine phenylacetate (OP): A novel treatment for hyperammonemia and hepatic encephalopathy," Medical Hypotheses (2007) vol. 69, pp. 1064-1069.
Jang, C. et al., "A Branched-Chain Amino Acid Metabolite Drives Vascular Fatty Acid Transport and Causes Insulin Resistance," Nat Med., Apr. 2016; 22(4):421-6. doi: 10.1038/nm 4057. Epub Mar. 7, 2016.
Jegatheesan et al., "Hepatic steatosis: a role for citrulline," Curr Opin Clin Nutr Metab Care (2016) vol. 19, No. 5, pp. 360-365.
Jegatheesan et al., "Preventive effects of citrulline on Western diet-induced non-alcoholic fatty liver disease in rats," Br J Nutr (2016) vol. 1161, pp. 191-203.
Jegatheesan, P. et al., "Citrulline and Nonessential Amino Acids Prevent Fructose-Induced Nonalcoholic Fatty Liver Disease in Rats," Nutr, Oct. 2015; 145(10):2273-9.
Jegatheesan, P. et al., "Effect of Specific Amino Acids on Hepatic Lipid Metabolism in Fructose-Induced Non-Alcoholic Fatty Liver Disease," (2016) Clinical Nutrition, 35:175-182.
Jennings et al., "Associations between branched chain amino acid intake and biomarkers of adiposity and mardiometabolic health independent of genetic factors: A twin study," Intl J Cardiology (2016) vol. 223, pp. 992-998.
Jha et al., "Network Integration of Parallel Metabolic and Transcriptional Data Reveals Metabolic Modules that Regulate Macrophage Polarization," Immunity (2015) vol. 42, pp. 419-430.
Jiang et al., "The Impact of Alanyl-Glutamine on Clinical Safety, Nitrogen Balance, Intestinal Permeability, and Clinical Outcome in Postoperative Patients: A Randomized, Double-Blind, Controlled Study of 120 Patients," Journal of Parenteral and Enteral Nutrition (1999) vol. 23, No. 5, pp. S62-S66.
Jiao, J. et al., "Chronic leucine Supplementation Improves Lipid Metabolism in C57BL/6J Mice Fed with a High-Fat/Cholesterol Diet," Food Nutr Res , Sep. 9, 2016; 60:31304 doi: 10.3402/fnr v60.31304. eCollection 2016.
Jobgen, W. et al., "Dietary L-Arginine Supplementation Reduces White Fat Gain and Enhances Skeletal Muscle and Brown Fat Masses in Diet-Induced Obese Rats," J Nutr, Feb. 2009; 139(2):230-7.
Kakazu et al., "Plasma amino acids imbalance in cirrhotic patients disturbs the tricarboxylic acid cycle of dendritic cell," Sci Rep (2013) vol. 3, Article 3459, 8 pages.
Kakumitsu, S. et al., "Effects of L-Arginine on the Systemic, Mesenteric, and Hepatic Circulation in Patients With Cirrhosis," Hepatology, Feb. 1998; 27(2):377-82.
Kanda et al., "Post-exercise whey protein hydrolysate supplementation induces a greater increase in muscle protein synthesis than its constituent amino acid content," Br J Nutr (2013) vol. 110, pp. 981-987.
Katsanos et al., "Whey protein ingestion in elderly results in greater muscle protein accrual than ingestion of its constituent essential amino acid content," Nutr Res (2008) vol. 28, No. 10, pp. 651-658.

Kawaguchi et al., "Branched-Chain Amino Acids Prevent Hepatocarcinogenesis and Prolong Survival of Patients With Cirrhosis," Clinical Gastroenterology and Hepatology (2014) vol. 12, pp. 1012-1018.e1.
Kawaguchi et al., "Effects of Oral Branched-Chain Amino Acids on Hepatic Encephalopathy and Outcome in Patients With Liver Cirrhosis," Nutr Clin Pract (2013) vol. 28, No. 5, pp. 580-588.
Kawaguchi et al., "Wheat-bran autolytic peptides containing a branched-chain amino acid attenuate non-alcoholic steatohepatitis via the suppression of oxidative stress and the upregulation of AMPJ/ACC in high-fat diet-fed mice," International J Molecular Medicine (2017) vol. 39, pp. 407-414.
Kelleher et al., "The mTORCI signaling repressors REDD1/2 are rapidly induced and activation of p70S6K1 by leucine is defective in skeletal muscle of an immobilized rat hindlimb," Am J Physiol Endocrinol Metab (2013) vol. 304, pp. E229-E236.
Kerksick et al., "The Antioxidant Role of Glutathione and N-Acetyl-Cysteine Supplements and Exercise-Induced Oxidative Stress," Journal of the International Society of Sports Nutrition (2005), vol. 2, No. 2, pp. 38-44.
Alexander et al., "The Influence of Immunomodulatory Diets on Transplant Success and Complications," Transplantation (2005) vol. 79, No. 4, pp. 460-465.
Anavi et al., "Non-alcoholic fatty liver disease, to struggle with the strangle: Oxygen availability in fatty livers," Redox Biology (2017) vol. 13, pp. 386-392.
Armstrong et al., "Effect of oral nutritional supplementation on wound healing in diabetic foot ulcers: a prospective randomized controlled trial." Diabet Med (2014) vol. 31, pp. 1069-1077.
Bertrand et al., "Glutamine Restores Tight Junction Protein Claudin-1 Expression in Colonic Mucosa of Patients with Diarrhea-Predominant Irritable Bowel Syndrome," Journal of Parenteral and Enteral Nutrition (2016) vol. 40, No. 8, pp. 1170-1176.
Chin et al., "Nutritional support in children with end-stage liver disease: a randomized crossover trial of a branched-chain amino acid supplement," Am J Clin Nutr (1992) vol. 56, pp. 158-163.
Chin-Dusting et al., "Effects of In Vivo and In Vitro L-Arginine Supplementation on Healthy Human Vessels," Journal of Cardiovascular Pharmacology (1996) vol. 28, No. 1, pp. 158-166.
Coman et al., "New indications and controversies in arginine therapy," Clinical Nutrition (2008) vol. 27, pp. 489-496.
Dai et al., "Role of Gut Barrier Function in the Pathogenesis of Nonalcoholic Fatty Liver Disease," Gastroenterology Research and Practice (2015) vol. 2015, Article ID 287348, 6 pages.
De Nicola et al., "Randomized, double-blind, placebo-controlled study of arginine supplementation in chronic renal failure," Kidney International (1999) vol. 56, pp. 674-684.
Dean et al., "N-Acetylcysteine in psychiatry: current therapeutic evidence and potential mechanisms of action," J Psychiatry Neurosci (2011) vol. 36, No. 2, pp. 78-86.
De Andrade et al., "Oxidative Stress and Inflammation in Hepatic Diseases: Therapeutic Possibilities of N-Acetylcysteine," Int J Mol Sci (2015) vol. 16, pp. 30269-30308.
Dong et al., "Effect of oral L-arginine supplementation on blood pressure: A meta-analysis of randomized, double-blind, placebo-controlled trials," Am Heart J (2011) vol. 162, pp. 959-965.
European Review for Medical and Pharmacological Sciences (2012) vol. 16, pp. 1665-1674.
Eriksson et al., "Branched-chain amino acids in the treatment of chronic hepatic encephalopathy," Gut (1982) vol. 23, pp. 801-806.
Ezerina et al., "N-Acetyl Cysteine Functions as a Fast-Action Antioxidant by Triggering Intracellular H2S and Sulfane Sulfur Production," Cell Chemical Biology (2018) vol. 25, pp. 447-459.
Gluud et al., "Branched-chain amino acids for people with hepatic encephalopathy (Review)," Cochrane Database of Systemic Reviews (2017) Issue 5, Article No. CD001939, 70 pages.
Goh et al., "L-ornithine L-aspartate for prevention and treatment of hepatic encephalopathy in people with cirrhosis (Review)," Cochrane Database of Systematic Reviews (2018) Issue 5, Art No. CD012410, 125 pages.

(56) References Cited

OTHER PUBLICATIONS

Honda et al., "Branched-chain amino acids alleviate hepatic steatosis and liver injury in choline-deficient high-fat diet induced in NASH mice," Metabolism Clinical and Experimental (2017) vol. 69, pp. 177-187.

Hu et al., "Safety of long-term dietary supplementation with L-arginine in pigs," Amino Acids (2015) vol. 47, pp. 925-936.

Ijaz et al., "The effect of consecutively larger doses of L-arginine on hepatic microcirculation and tissue oxygenation in hepatic steatosis," Microvascular Research (2009) vol. 78, pp. 206-211.

Iwasa et al., "Elevation of branched-chain amino acid levels in diabetes and NAFL and changes with antidiabetic drug treatment," Obesity Research & Clinical Practice (2015) vol. 9, pp. 293-297.

Jablecka et al., "Oral L-arginine supplementation in patients with mild arterial hypertension and its effect on plasma level of asymmetric dimethylarginine, L-citrulline, L-arginine and antioxident status,".

Johnson et al., "Nutrition Assessment and Management in Advanced Liver Disease," Nutr Clin Pract (2013) vol. 28, pp. 15-29.

Kawaguchi et al., "Branched-chain amino acids improve insulin resistance in patients with hepatitis C virus-related liver disease: report of two cases," Liver International (2007) pp. 1287-1292.

Kleiner et al., Hepatology, (2005), vol. 41, No. 6, pp. 1313-1321.

Lake et al., "Branched chain amino acid metabolism profiles in progressive human nonalcoholic fatty liver disease," Amino Acids (2015) vol. 47, pp. 603-615.

Lin et al., "Effects of glutamine on oxidative stress and nuclear factor-KappaBeta expression in the livers of rats with nonalcoholic fatty liver diease," Experimental and Therapeutic Medicine (2014) vol. 7, pp. 366-370.

Madiraju et al., "Argininosuccinate synthetase regulates hepatic AMPK linking protein catabolism and ureagenesis to hepatic lipid metabolism," PNAS (2016) vol. 113, No. 24, pp. E3423-E3430.

Mardinoglu et al., "The Potential Use of Metabolic Cofactors in Treatment of NAFLD," Nutrients (2019) vol. 11, Article 1578, 17 pages.

McNeal et al., "Safety of dietary supplementation with arginine in adult humans," Amino Acids (2018) vol. 50, pp. 1215-1229.

Morris, "Arginine Metabolism Revisited," J Nutr (2016) vol. 146 (Suppl), pp. 2579S-2586S.

Neinast et al., "Quantitative Analysis of the Whole-Body Metabolic Fate of Branched-Chain Amino Acids," Cell Metabolism (2019) vol. 29, pp. 417-429.

Newgard, "Interplay between Lipids and Branched-Chain Amino Acids in Development of Insulin Resistance," Cell Metabolism (2012) vol. 15, pp. 606-614.

Nielsen et al., "Long-term oral refeeding of patients with cirrhosis of the liver," British Journal of Nutrition (1995) vol. 74, pp. 557-567.

Oliveira et al., "N-acetylcysteine and/or ursodeoxycholic acid associated with metformin in non-alcoholic steatohepatitis: an open-label multicenter randomized controlled trial," Arq Gastroenterol (2019) vol. 56, No. 2, pp. 184-190.

Ooi et al., "Effects of branched chain amino acid supplementation on patient care outcomes in adults and children with liver cirrhosis: A systematic review," Climical Nutrition ESPEN (2018) vol. 28, pp. 41-51.

Plauth et al., "ESPEN Guidelines on Enteral Nutrition: Liver disease," Clinical Nutrition (2006) vol. 25, pp. 285-294.

Rao et al., "Role of Glutamine in Protection of Intestinal Epithelial Tight Junctions," Journal of Epithelial Biology and Pharmacology (2012) vol. 5, Suppl 1-M7, pp. 47-54.

Shao et al., "Risk assessment for the amino acids taurine, L-glutamine and L-arginine," Regulatory Toxicology and Pharmacology (2008) vol. 50, pp. 376-399.

Smilkstein et al., "Efficacy of Oral N-Acetylcysteine in the Treatment of Acetaminophen Overdose," N Engl J Med (1988) vol. 319, pp. 1557-1562.

Sucher et al., "Comparison of the effects of diets high in anumal or plant protein on metabolic and cardiovascular markers in type 2 diabetes: A randomized clinical trial," Diabetes Obes Metab (2017) vol. 19, pp. 944-952.

Thomsen et al., "Ammonia: A novel target for the treatment of non-alcoholic steatohepatitis," Medical Hypotheses (2018) vol. 113, pp. 91-97.

Tsubuku et al., "Thirteen-Week Oral Toxicity Study of L-Arginine in Rats," International Journal of Toxicology (2004) vol. 23, pp. 101-105.

Wong et al., "Oral subchronic and genotoxicity studies conducted with the amino acid, L-glutamine," Food and Chemical Toxicology (2011) vol. 49, pp. 2096-2102.

Pinals et al., "Treatment of Rheumatoid Arthritis with L-Histidine: a Randomized, Placebo-Controlled, Double-Blind Trial," The Journal of Rheumatology (1977) vol. 4, No. 4, pp. 414-419.

Sellmann et al., "Oral citrulline supplementation protects female mice from the development of non-alcoholic fatty liver disease (NAFLD)," Eur J Nutr (2017) vol. 56, pp. 2519-2527.

Ishikawa et al., "L-Carnitine Prevents Progression of Non-Alcoholic Steatohepatitis in a Mouse Model with Upregulation of Mitochondrial Pathway," PLOS One (2014) vol. 9, No. 7, Article e100627, 12 pages.

Gu et al., Lingnan Journal of Emergency Medicine 2009, 14(6): 471-472.

Lambertucci AC, et al. ""Glutamine Supplementation Stimulates Protein-Synthetic and Inhibits Protein-Degradative Signaling Pathways in Skeletal Muscle of Diabetic Rats"" PLOS ONE 2012;7(12):e50390.

Medved I, et al. "N-acetylcysteine enhances muscle cysteine and glutathione availability and attersuates fatigue during prolonged exercise in endurance-trained individuals" J Appl Physiol 2004; 97: 1477-1485.

Moberg M, et al. "Activation of mTORC1 by leucine is potentiated by ranched-chain amino acids and even more so by essential amino acids following resistance exercise" Am J Physiol Ceil Physiol 2016;310: C874-C884. First published Apr. 6, 2016.

Xingang et al., "Observation on the Therapeutic effect of Fengnuoan on liver function damage in critically ill patients" Lingnan Journal of Emergency Medicine, Dec. 2009, vol. 14, No. 6.

Smith, "Animal Models of Cutaneous and Hepatic Fibrosis", Progress in Molecular Biology and Translational Science (2012) vol. 105, pp. 371-408.

U.S. Appl. No. 16/901,199, filed Jun. 15, 2020.

Miczke, A. et al., "Effect of L-Arginine Supplementation on Insulin Resistance and Serum Adiponectin Concentration in Rats with Fat Diet," (2015) Int J Clin Exp Med, 2015; 8(7); 10358-66.

Mikulski et al., "Effects of supplementation with branched chain amino acids and ornithine aspartate on plasma ammonia and central fatigue during exercise in healthy men," Folia Neuropathol (2015) vol. 53, No. 4, pp. 377-386.

Mirmiran, P. et al., "The Association of Dietary L-Arginine Intake and Serum Nitric Oxide Metabolites in Adults: A Population-Based Study," Nutrients, May 20, 2016; 8(5). pii: E311.

Mittal et al., "A randomized controlled trial comparing lactulose, probiotics, and L-ornithine L-aspartate in treatment of minimal hepatic encephalopathy," Eur J Gastroenterol Hepatol (2011) vol. 23, pp. 725-732.

Miyake et al., "Long-term Branched-chain Amino Acid Supplementation Improves Glucose Tolerance in Patients with Nonalcoholic Steatohepatitis-related Cirrhosis," Intern Med (2012) vol. 51, pp. 2151-2155.

Moinard et al., "Arginine behaviour after arginine or citrulline administration in older subjects," Br J Nutr (2016) vol. 115, pp. 399-404.

Moinard et al., "Dose-ranging effects of citrulline administration on plasma amino acids and hormonal patterns in healthy subjects: the Citrudose pharmacokinetic study," Br J Nutr (2007) vol. 99, pp. 855-862.

Monti, L.D. et al., "Beneficial Role of L-Arginine in Cardiac Matrix Remodelling in Insulin Resistant Rats," (2008)—European Journal of Clinical Investigation, vol. 38(11):849-56.

(56) References Cited

OTHER PUBLICATIONS

Monti, L.D. et al., "Effect of a Long-Term Oral L-Arginine Supplementation on Glucose Metabolism: a Randomized, Double-Blind, Placebo-Controlled Trial," (2012) Diabetes, Obesity and Metabolism 14: 893-900, 2012.
Mordier et al., "Leucine limitation induces autophagy and activation of lysosome-dependent proteolysis in C2C12 myotubes through a mammalian target of rapamycin-independent signaling pathway," J Biol Chem (2000) vol. 275, pp. 29900-29906.
Morgan et al., "Plasma amino-acid patterns in liver disease," Gut (1982) vol. 23, pp. 362-370.
Moriwaki et al., Branched-chain amino acids as a protein- and energy-source in liver cirrhosis, Biochemical and Biophysical Research Communications (2004) vol. 313, pp. 405-409.
Murgas Torrazza et al., "Leucine supplementation of a low-protein meal increases skeletal muscle and visceral tissue protein synthesis in neonatal pigs by stimulating mTOR-dependent translation initiation," J Nutr (2010) vol. 140, pp. 2145-2152.
Murphy et al., "Leucine supplemmentation enhances integrative myofibrillar protein syntesis in free-living older men consuming lower- and higher-protein diets: a parallel-group crossover study," Am J Clin Nutr (2016) vol. 104, pp. 1594-1606.
Musso et al., "Non-alcoholic steatohepatitis: emerging molecular targets and therapeutic strategies," Nat Rev Drug Discovery (2016) vol. 15, pp. 249-274.
Muto et al., "Overweight and obesity increase the risk for liver cancer in patients with liver cirrhosis and long-term oral supplementation with branched-chain amino acid granules inhibits liver carcinogenesis in heavier patients with liver cirrhosis," Hepatology Research (2006) vol. 35, pp. 204-214.
Muto, Y, et al., "Effect of Oral Branched-Chain Amino Acid Granules on Event-Free Survival in Patients with Liver Cirrhosis," Clin Gastroenterol Hepatol, Jul. 2005; 3(7):705-13.
Naganuma et al., "Effect of the Medical Walking and Leucine Enriced Amino acid Containing Food for Female Non-Alcoholic Fatty Liver Disease: Randomized Controlled Trial," Clinical Nutrition (2016) vol. 35, p. S62, Poster SUN-P050.
Najmi et al., "Effect of l-ornithine l-aspartate against thioacetamide-induced hepatic damage in rats," Indian J Pharmacol (2010) vol. 42, No. 6, pp. 384-387.
Nakanishi et al., "Treatment with L-Valine Ameliorates Liver Fibrosis and Restores Thrombopoiesis in Rats Exposed to Carbon Tetrachloride," Tohoku J Exp Med (2010) vol. 221, pp. 151-159.
Nakaya et al., "BCAA-enriched snack improves nutritional state of cirrhosis," Nutrition (2007) vol. 23, pp. 113-120.
Nakaya et al., "Severe catabolic state after prolonged fasting in cirrhotic patients: effect of oral branched-chain amino-acid-enriched nutrient mixture," J Gastroenterol (2002) vol. 37, pp. 531-536.
Nanji et al., "Arginine Reverses Ethanol-Induced Inflammatory and Fibrotic Changes in Liver Despite Continued Ethanol Administration," J Pharmacol Exp Ther (2010) vol. 299, No. 3, pp. 832-839.
Mdraha et al., "The Effect of L-ornithine L-aspartate and Branch Chain Amino Acids on Encephalopathy and Nutritional Status in Liver Cirrhosis with Malnutrition," Acta Med Indones-Indones J Intern Med (2011) vol. 43, No. 1, op. 18-22.
Mewgard, C.B et al., "A Branched-Chain Amino Acid-Related Metabolic Signature that Differentiates Obese and Lean Humans and Contributes to Insulin Resistance," Cell Metab., Apr. 2009; 9(4):311-26. doi: 10.1016/j.cmet.2009.02.002.
Nicastro et al., "An overview of the therapeutic effects of leucine supplementation on skeletal muscle under atrophic conditions," Amino Acids (2011) vol. 40, pp. 287-300.
Nielsen, "Systems Biology of Metabolism: A Driver for Developing Personalized and Precision Medicine," Cell Metabolism (2017) vol. 25, pp. 572-579.
Nilsson et al., "Metabolic effects of amino acid mixtures and whey protein in healthy subjects: studies using glucose-equivalent drinks," Am J Clin Nutr (2007) vol. 85, pp. 996-1004.
Nishiguchi et al., "Effect of oral supplementation with branched-chain amino acid granules in the early stage of cirrhosis," Hepatology Research (2004) vol. 30, Supplement, pp. 36-41, Abstract Only.
Nishikata et al., "Dietary lipid-dependent regulation of de novo lipogenesis and lipid partitioning by ketogenic essential amino acids in mice," Nutrition and Diabetes (2011) vol. 1, e5, 12 pp.
Nishitani et al., "Pharmacological activities of branched-chain amino acids: augmentation of albumin synthesis in liver and improvement of glucose metabolism in skeletal muscle," Hepatology Research (2004) vol. 30, Supplement, pp. 19-24, Abstract Only.
Nissen et al., "Effect of leucine metabolite b-hydroxy-b-methylbutyrate on muscle metabolism during resistance-exercise training," J Applied Physiology (1996) vol. 81, pp. 2095-2104.
Nissim et al., "Agmatine Stimulates Hepatic Fatty Acid Oxidation: A Possible Mechanism For Up-Regulation of Ureagenesis," J Biol Chem (2006) vol. 281, No. 13, pp. 8486-8496.
Nissim, I et al., "The Molecular and Metabolic Influence of Long Term Agmatine Consumption," (2014) - The Journal of Biological Chemistry, vol. 289, No. 14, pp. 9710-9729.
Noguchi et al., "Effect of Anaplerotic Fluxes and Amino Acid Availability on Hepatic Lipoapoptosis," J Biol Chem (2009) vol. 284, No. 48, pp. 33425-33436.
Noguchi et al., "Ketogenic Essential Amino Acids Modulate Lipid Synthetic Pathways and Prevent Hepatic Steatosis n Mice," PLOS One (2010) vol. 5, Issue 8, Article e12057, 14 pp.
Norton et al., "Leucine content of dietary proteins is a determinant of postprandial skeletal muscle protein synthesis in adult rats," Nutr Metab vol. 9, 67 (2012).
Norton et al., "The leucine content of a complete meal directs peak activation but not duration of skeletal muscle protein synthesis and mammalian target of rapamycin signaling in rats," J Nutr (2009) vol. 139, pp. 1103-1109.
Ohara et al., "L-Carnitine Suppresses Loss of Skeletal Muscle Mass in Patients With Liver Cirrhosis," Hepatology Communications (2018) vol. 2, No. 8, pp. 906-918.
Okita et al., "Nutritional Treatment of Liver Cirrhosis by Branched-Chain Amino Acid-Enriched Nutrient Mixture," J Nutr Sci Vitaminol (1985) vol. 31, No. 3, pp. 291-303.
Opara et al., "L-Glutamine Supplementation of a High Fat Diet Reduces Body Weight and Attenuates Hyperglycemia and Hyperinsulinemia in C57BL/6J Mice," J Nutr (1996) vol. 126, pp. 273-279.
Opposition Filed in Ecuadorean Application No. SENADI-2019-43710, dated Feb. 5, 2020, 9 pages.
Ortiz de Montellano et al., "A New Step in the Treatment of Sickle Cell Disease," Biochemistry (2018) vol. 57, No. 5, pp. 470-471, Abstract.
Pacana, T. et al., "Dysregulated Hepatic Methionine Metabolism Drives Homocysteine Elevation in Diet-Induced Nonalcoholic Fatty Liver Disease," PLoS One, Aug. 3, 20151; 10(8):e0136822. doi: 10.1371/journal.pone.0136822. eCollection 2015.
Pace et al., "Effect of N-acetylcysteine on Dense Cell Formation in Sickle Cell Disease," American Journal of Hematology (2003) vol. 73, No. 1, pp. 26-32.
Paddon-Jones et al., "Essential Amino Acid and Carbohydrate Supplementation Ameliorates Muscle Protein Loss in Humans during 28 Days Bedrest," J Clin Endocrinol Metab (2004) vol. 89, pp. 4351-4358.
Palacio et al., "Anti-inflammatory properties of N-acetylcysteine on lipopolysaccharide-activated macrophages," Inflamm Res (2011) vol. 60, pp. 695-704.
Pennings et al., "Whey protein stimulates postprandial muscle protein accretion more effectively than do casein hydrolysate in older men," Am J Clin Nutr (2011) vol. 93 pp. 997-1005.
Peters et al., "Dose-dependent effects of leucine supplementation on preservation of muscle mass in cancer cachectic mice," Oncol Rep (2011) vol. 26, pp. 247-254.
Petrat et al., "Glycine, a simple physiological compund protecting by yet puzzling mechanism(s) against ischaemia-reperfusion injury: current knowledge," Br J Pharmacol (2011) vol. 165, pp. 2059-2072.

(56) References Cited

OTHER PUBLICATIONS

Yi et al., N-Acetylcysteine improves intestinal function in lipopolysaccharides challenged piglets through multiple signaling pathways, Amino Acids (2017) doi: 10.1007/s00726-017-2389-2, 15 pp.
Yin et al., "Supplementing L-leucine to a low-protein diet increases tissue protein synthesis in weanling pigs," Amino Acids (2010) vol. 39, pp. 1477-1486.
Yokota et al., "Leucine restores murine hepatic triglyceride accumulation induced by a low-protein diet by suppressing autophagy and excessive endoplasmic reticulum stress," Amino Acids (2016) vol. 48, pp. 1013-1021.
Yoshiji et al., "Branched-chain amino acids suppress the cumulative recurrence of hepatocellular carcinoma under condititions of insulin-resistance," Oncology Reports (2013) vol. 30, pp. 545-552.
Younossi et al., "Global burden of NAFLD and NASH: trends, predictions, risk factors and prevention," Nat Rev (2017) doi:10 1038/nrgastro 2017.109, 10 pp.
Yuan et al., "Leucine supplementation improves leptin sensitivity in high-fat diet fed rats," Food & Nutrition Research (2015) vol. 59, Article 27373, 6 pp.
Zarfeshani et al., "Leucine alters hepatic glucose/lipid homeostasis via the myostatin-AMP-activated protein kinase pathway—potential implications for nonalcoholic fatty liver disease," Clinical Epigenetics (2014) vol. 6, Article 27, 12 pages.
Zeanandin et al., "Differential effect of long-term leucine supplementation on skeletal muscle and adipose tissue in old rats: an insulin signaling pathway approach," Age (2012) vol. 34, pp. 371-387.
Zhang et al., "Branched Chain Amino Acids Cause Liver Injury in Obese/Diabetic Mice by Promoting Adipocyte Lipolysis and Inhibiting Hepatic Autophagy," EBioMedicine (2016) vol. 13, pp. 157-167.
Zhang et al., Supporting Materials for "Branched Chain Amino Acids Cause Liver Injury in Diabetic Mice by Promoting Adipocyte Lipolysis and Inhibiting Hepatic Autophagy," EBioMedicine (2016) doi.org/10.1016/j.ebiom.2016.10.013, 15 pp.
Zhang, Y. et al., "Increasing Dietary Leucine Intake Reduces Diet-Induced Obesity and Improves Glucose and Cholesterol Metabolism in Mice via Multimechanisms," Diabetes. Jun. 2007; 56(6): 1647-54. Epub Mar. 14, 2007.
Zhou et al., "Glycine protects against high sucrose and high fat-induced non-alcoholic steatohepatitis in rats," Oncotarget (2016) vol. 7, No. 49, pp. 80223-8237.
Ziegler et al., "Safety and Metabolic Effects of L-Glutamine Administration in Humans," Journal of Parenteral and Enteral Nutrition (1990) vol. 14, No. 4, pp. 137S-146S.
[No Author Listed] 2016 Nutricia Product Reference Guide, downloaded from nutricia-na.com/pages/2016_Canada_PRG.pdf on Nov. 20, 2019.
[No Author Listed] MediKAL Nutrience Hepatosol-LOLA product information, retrieved from www medikalnutrience.com/EN/Product/By-Brand/Hepatosol-LOLA, last accessed Sep. 13, 2018, 9 pages.
[No Author Listed] National Guideline Centre, Royal College of Physicians, "Cirrhosis in over 16s, Assessment and Management," NICE guideline NG50, Appendices A-H, Jul. 2016, 351 pages.
[No Author Listed] New Drug Application 18-676 and Approval Letter for HepatAmine (1982), 73 pages.
[No Author Listed] Nutricia Metabolics, "Practical Guide for the Use of Nutricia's TYR Products," downloaded from www. nutricialearningcenter.com/globalassets/pdfs/metabolics/tyr_gudelines on Nov. 20, 2019. Publicly available on Jan. 11, 2013.
[No Author Listed] NUTRIHEP product information, retrieved from www.nestlehealthscience-me.com/en/brands/nutrihep/nutrihep, last accessed Sep. 12, 2013, 3 pages.
[No Author Listed] PubChem entry for L-Orinthine-L-aspartate, PubChem CID 10220941 (2019), 17 pages.
[No Author Listed] Twinlab "Anti-catabolic HMB Fuel Plus: HMB, NAC, Glutamine & Creatine," Product Label, 1996.

Abid et al., "Efficacy of L-omithine-L-aspartate as an Adjuvant Therapy in Cirrhotic Patients with Hepatic Encephalopathy," Journal of the College of Physicians and Surgeons Pakistan (2011) vol. 21, No. 11, pp. 666-671.
Abu-Serie, M.M. et al., "Investigation into the Antioxidant Role of Arginine in the Treatment and the Protection for Intralipid-Induced NASH," (2015), Lipids in Health and Disease, 14:128.
Achamrah et al., "Glutamine and the regulation of intestinal permeability: from bench to bedside," Curr Opin Clin Nutr Metab Care (2017) vol. 20, pp. 86-91.
Acharya et al., "Efficacy of L-Ornithine L-Aspartate in Acute Liver Failure: A Double-Blind, Randomized, Placebo-Controlled Study," Gastroenterology (2009) vol. 136, pp. 2159-2168.
Addison et al., "Intermuscular Fat: A Review of the Consequences and Causes," International Journal of Endrocrinology (2014)vol. 2014, Article 309570, 11 pages.
Adeva et al., "Insulin resistance and the metabolism of branched-chain amino acids in humans," Amino Acids (2012) vol. 43, pp. 171-181.
Adibi et al., "Metabolism of branched-chain amino acids in altered nutrition," Metab Clin Exp (1976) vol. 25, pp. 1287-1302.
Agarwal et al., "Supplemental Citrulline Is More Efficient than Arginine in Increasing Systemic Arginine Availability in Mice," J Nutr (2017) doi: 10.3945/jn.116.240382, 7 pp.
Agli et al., "Erythrocytes participate significantly in blood transport of amino acids during the post absorptive state in normal humans," Eur J Appl Physiol (1998) vol. 78, pp. 502-508.
Agtien et al., "N-Acetylcysteine protects the rat diaphragm from the decreased contractility associated with controlled mechanical ventilation," Crit Care Med (2011) vol. 39, No. 4, pp. 777-782.
Ahmad et al., "L-Ornithine-L-Aspartate Infusion Efficacy in Hepatic Encephalopathy," Journal of the College of Physicians and Surgeons Pakistan (2008) vol. 18, No. 11, pp. 684-687.
Alvares-da-Silva et al., "Oral I-ornithine-I-aspartate in minimal hepatic encephalopathy: A randomized, doubleblind, placebo-controlled trial," Hepatology Research (2014) vol. 44, pp. 956-963.
Amodio et al., "Nutritional Management of Hepatic Encephalopathy in Patients With Cirrhosis: International Society tor Hepatic Encephalopathy and Nitrogen Metabolism Consensus," Hepatology (2013) vol. 58, pp. 325-336.
Anthony et al., "Leucine stimulates translation initiation in skeletal muscle of postabsorptive rats via a rapamycin-sensitive pathway," J Nutr (2000) vol. 130, pp. 2413-2419.
Apostol et al., "A Decrease in Glucose Production is Associated With an Increase in Plasma Citrulline Response to Dral Arginine in Normal Volunteers," Metabolism (2003) vol. 52, No. 11, pp. 1512-1516.
Araujo et al., "Benefits of L-alanine or L-arginine supplementation against adiposity and glucose intolerance in monosodium glutamate-induced obesity," Eur J Nutr (2016) doi: 10.1007/s00394-016-1245-6, 12 pp.
Argilés et al., "Branched-chain amino acid catabolism and cancer cachexia (Review)," Oncol Rep (1996) vol. 3, No. 4, pp. 687-690.
Wersa et al., "β-hydroxy-β-methylbutyrate (HMB) attenuates muscle and body weight loss in experimental cancer cachexia," International J of Oncology (2011) vol. 38, pp. 713-720.
B. Braun Medical Inc., Package Insert for HepatAmine, NDA 18-676/S-022 pp. 5-15, Revised May 2003.
B. Braun Medical Inc., Product Catalog for HepatAmine (8% Amino Acid Injection), 2012, retrieved from www.bbraunusa.com/content/dam/catalog/bbraun/bbraunProductCatalog/CW_US/en-us/b0/hepatamine-8-aminoacidinjectionbrochure.pdf.bb-.38324315/hepatamine-8-aminoacidinjectionbrochure.pdf.
B. Braun Medical Inc., Product Catalog, retrieved from www. bbraunusa.com/en/products-and-therapies/product-catalog.html, last accessed Sep. 13, 2018.
Backx et al., "Leucine Supplementation Does Not Attenuate Skeletal Muscle Loss during Leg Immobilization in Healthy, Young Men," Nutrients (2018) vol. 10, Article 635, 12 pages.
Bahadoran et al., "Dietary L-arginine intake and the incidence of coronary heart disease: Tehran lipid and glucose study," Nutrition & Metabolism (2016) vol. 13, No. 23, 9 pp.

(56) References Cited

OTHER PUBLICATIONS

Bai et al., "Randomised clinical trial: L-ornithine-L-aspartate reduces significantly the increase of venous ammonia concentralion after TIPSS," Ailment Pharmacol Ther (2014) vol. 40, pp. 63-71.

Balage et al., "Leucine supplementation in rats induced a delay in muscle IR/PI3K signaling pathway associated with overall impaired glucose tolerance," The Journal of Nutritional Biochemistry (2011) vol. 22, pp. 219-226 (Abstract Only).

Balage et al., "Long-term effects of leucine supplementation on body composition," Curr Opin Clin Nutr Metab Care (2010) vol. 13, pp. 265-270.

Ballard et al., "Effect of L-Glutamine Supplementation on Impaired Glucose Regulation During Intravenous Lipid Administration," Nutrition (1996) vol. 12, No. 5, pp. 349-354.

Baptista et al., "Leucine attenuates skeletal muscle wasting via inhibition of ubiquitin ligases," Muscle Nerve (2010) vol. 41, pp. 800-808.

Bauchart-Thevrei et al., "Arginine-induced stimulation of protein synthesis and survival in IPEC-J2 cells is mediated by mTOR but not nitric oxide," Am J Physiol Endocrinol Metab (2010) vol. 299, pp. E899-E909.

Baum et al., "Docosahexaenoic Acid (DHA), not Leucine, May Protect HepG2 Cells from Palmitate-Induced Non-Alcoholic Fatty Liver Disease," FASEB J (2017) Abstract No. 1036.7.

Baum et al., "Leucine reduces the duration of insulin-induced PI 3-kinase activity in rat skeletal muscle," Am J Physiol Endocrinol Metab (2005) vol. 288, pp. E86-E91.

Baumgardner, J.N. et al., "N-Acetylcysteine Attenuates Progression of Liver Pathology in a Rat Model of Nonalcoholic Steatohepatitis," J Nutr, Oct. 2008; 138(10):1872-9.

Bernard et al., "An amino acid mixture is essential to optimize insulin-stimulated glucose uptake and GLUT4 translocation in perfused rodent hindlimb muscle," J Appl Physiol (2012) vol. 113, pp. 97-104.

Binder et al., "Leucine Supplementation Protects from Insulin Resistance by Regulating Adiposity Levels," PLOS One (2013) vol. 8, No. 9, Article e74705, 12 pp.

Bos et al., "Postprandial Kinetics of Dietary Amino Acids Are the Main Determinant of Their Metabolism after Soy or Milk Protein Ingestion in Humans," J Nutr (2003) vol. 133, pp. 1308-1315.

Bostock et al., "Effects of Essential Amino Acid Supplementation on Muscular Adaptations to 3 Weeks of Combined Unilateral Glenohumeral & Radiohumeral Joints Immobilisation," J Athl Enhancemnet (2013) vol. 2, No. 3, Article 1000116, 9 pp.

Breen et al., "Skeletal muscle protein metabolism in the elderly: Interventions to counteract the 'anabolic resistance' of ageing," Nutr Metab (2011) vol. 8: 68, 11 pp.

Breuillard et al., "Citrulline and nitrogen homeostasis: an overview," Amino Acids (2015) vol. 47, pp. 685-691.

Breuille et al., "Beneficial effect of amino acid supplementation especially cysteine, on body nitrogen economy in septic rats," Clinical Nutrition (2006) vol. 25, pp. 634-642.

Brioche et al., "Muscle wasting and aging: Experimental models, fatty infiltrations, and prevention," Molecular Aspects of Medicine (2016) VI. 50, pp. 56-87.

Butterworth et al., "Hepatoprotection by L-Omithine L-Aspartate in Non-Alcoholic Fatty Liver Disease," Dig Dis (2018) DOI: 10.1159/000491429, 6 pages.

Bémeur et al., "Nutrition in the Management of Cirrhosis and its Neurological Complications," J Clin Exp Hepatol (2014) vol. 4, No. 2, pp. 141-150.

\* cited by examiner

AMINO ACID COMPOSITIONS AND METHODS FOR THE TREATMENT OF LIVER DISEASES

RELATED APPLICATIONS

This application is a continuation application of U.S. application Ser. No. 15/847,289 filed Dec. 19, 2017, which claims priority to U.S. Ser. No. 62/436,073 filed Dec. 19, 2016, U.S. Ser. No. 62/443,205 filed Jan. 6, 2017, U.S. Ser. No. 62/491,773 filed Apr. 28, 2017, U.S. Ser. No. 62/545,322 filed Aug. 14, 2017, and U.S. Ser. No. 62/576,267 filed Oct. 24, 2017, the contents of which are each incorporated herein by reference in their entireties.

BACKGROUND

Non-alcoholic fatty liver disease (NAFLD) is a disease characterized by fatty deposits in the liver due to causes other than alcohol. NAFLD is the most prevalent liver disease in developed countries and affects close to 25% of the people in the United States. Non-alcoholic steatohepatitis (NASH) is the most severe form of NAFLD, which can lead to inflammation of the liver, fibrosis, cirrhosis, chronic liver failure, and hepatocellular carcinoma (HCC).

Currently, there are no approved therapies for treating NASH or NAFLD. Accordingly, there is an unmet need for new treatments in NAFLD and NASH.

SUMMARY

Disclosed herein, at least in part, is a composition including at least four different amino acid entities.

In some embodiments, the composition is capable of one, two, three, four, five, or six or all of:
  a) decreasing or preventing liver fibrosis;
  b) decreasing or preventing liver injury;
  c) decreasing or preventing hepatocyte inflammation;
  d) improving, e.g., increasing, glucose tolerance;
  e) decreasing or preventing steatosis;
  f) decreasing or preventing hepatocyte ballooning; or
  g) improving gut function.

In some embodiments, the composition comprises a leucine (L)-amino acid entity, an arginine (R)-amino acid entity, a glutamine (Q)-amino acid entity; and an antioxidant or reactive oxygen species (ROS) scavenger (e.g., a N-acetylcysteine (NAC) entity, e.g., NAC). In some embodiments, at least one amino acid entity is not provided as a peptide of more than 20 amino acid residues in length.

In some embodiments:
  (i) an amino acid entity (e.g., at least one, two, or three of the amino acid entities) of (a) is selected from Table 2; and/or
  (ii) (A) one or both of the R-amino acid entity and the Q-amino acid entity are present at a higher amount (wt. %) than the L-amino acid entity, or (B) the composition further comprises a serine (S)-amino acid entity.

In any of the aspects and embodiments disclosed herein, the wt. ratio of the L-amino acid entity, the R-amino acid entity, the L-glutamine or a salt thereof, and the NAC or salt thereof is about 0.5 to 3:0.5 to 4:1 to 4:0.1 to 2.5, e.g., the wt. ratio of the L-amino acid entity, the R-amino acid entity, the L-glutamine or a salt thereof, and the NAC or salt thereof is about 1:1.5:2:0.15 or about 1:1.5:2:0.3. In certain embodiments, the wt. ratio of the L-amino acid entity, the R-amino acid entity, the L-glutamine or a salt thereof, and the NAC or salt thereof is about 1+/−15%:1.5+/−15%:2+/−15%: 0.15+/−15% or about 1+/−15%:1.5+/−15%:2+/−15%:0.3+/−15%. In any of the aforesaid embodiments in this paragraph, the wt. ratio of the L-amino acid entity, the R-amino acid entity, the L-glutamine or a salt thereof, and the NAC or salt thereof is about 1:0.75:2:0.15 or about 1:0.75:2:0.3. In any of the aforesaid embodiments in this paragraph, the wt. ratio of the L-amino acid entity, the R-amino acid entity, the L-glutamine or a salt thereof, and the NAC or salt thereof is about 1+/−15%:0.75+/−15%:2+/−15%:0.15+/−15% or about 1+/−15%:0.75+/−15%:2+/−15%:0.3+/−15%.

In any of the aspects and embodiments disclosed herein, the wt. ratio of the L-amino acid entity, the I-amino acid entity, the V-amino acid entity, the R-amino acid entity, the L-glutamine or salt thereof, and the NAC or salt thereof is about 1:0.5:0.5:1.5:2:0.15 or about 1:0.5:0.5:1.5:2:0.3.

In any of the aspects and embodiments disclosed herein, the composition further comprises one or both of L-glycine and L-serine. In some embodiments, the composition comprises an L-amino acid entity, an I-amino acid entity, an V-amino acid entity, an R-amino acid entity, an L-glutamine or a salt thereof, an NAC or a salt thereof, and an L-glycine. In certain embodiments, the composition comprises an L-amino acid entity, an I-amino acid entity, a V-amino acid entity, an R-amino acid entity, an L-glutamine or a salt thereof, an NAC or a salt thereof, and an L-serine. In certain embodiments, the composition comprises an L-amino acid entity, an I-amino acid entity, an V-amino acid entity, an R-amino acid entity, an L-glutamine or a salt thereof, an NAC or a salt thereof, an L-glycine, and an L-serine. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1:0.5:0.5:1.5:2:0.15 or about 1:0.5:0.5:1.5:2:0.3. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1+/−15%: 0.5+/−15%:0.5+/−15%:1.5+/−15%:2+/−15%:0.15+/−15% or about 1+/−15%:0.5+/−15%:0.5+/−15%:1.5+/−15%:2+/−15%:0.3+/−15%.

In any of the aspects and embodiments disclosed herein, the composition comprises about 0.5 g to about 10 g of the L-amino acid entity, about 0.25 g to about 5 g of the I-amino acid entity, about 0.25 g to about 5 g of the V-amino acid entity, about 0.5 g to about 20 g of the R-amino acid entity, about 1 g to about 20 g of the L-glutamine or a salt thereof, and about 0.1 g to about 5 g of the NAC or a salt thereof, e.g., the composition comprises about 1 g of the L-amino acid entity, about 0.5 g of the I-amino acid entity, about 0.5 g of V-amino acid entity, about 1.5 g of R-amino acid entity, about 2 g of L-glutamine or a salt thereof, and about 0.15 g or about 0.3 g of NAC or a salt thereof. In certain embodiments, the composition comprises about 0.15 g of NAC. In certain embodiments, the composition comprises about 0.3 g of NAC. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, and about 0.9 g of NAC or a salt thereof.

In any of the aspects and embodiments disclosed herein, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, and about 6 g of L-serine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, and about 6.67 g of L-serine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, about 9 g of L-serine or a salt thereof, and about 9 g of L-glycine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, about 3.33 g of L-serine or a salt thereof, and about 3.33 g of L-glycine or a salt thereof.

In one aspect, the invention features a composition including free amino acids, wherein the amino acids include arginine, glutamine, N-acetylcysteine, and a branched-chain amino acid chosen from one, two, or all of leucine, isoleucine, and valine.

In any of the aspects and embodiments disclosed herein, the branched-chain amino acid is leucine, isoleucine, and valine.

In any of the aspects and embodiments disclosed herein, the wt ratio of leucine, isoleucine, valine, arginine, glutamine, N-acetylcysteine is 1:0.5:0.5:1.5:2:0.15. In certain embodiments, the wt ratio of leucine, isoleucine, valine, arginine, glutamine, N-acetylcysteine is 1+/−15%:0.5+/−15%:0.5+/−15%:1.5+/−15%:2+/−15%:0.15+/−15%.

In any of the aspects and embodiments disclosed herein, a total weight (wt) of the amino acids is about 2 g to about 60 g. In some embodiments, the total wt of the amino acids is about 6 g, about 12 g, about 18 g, about 24 g, or about 48 g.

In any of the aspects and embodiments disclosed herein, the composition includes about 0.5 g to about 10 g of leucine, about 0.25 g to about 5 g of isoleucine, about 0.25 g to about 5 g of valine, about 1 g to about 20 g of arginine, about 1 g to about 20 g of glutamine, and about 0.1 g to about 5 g of N-acetylcysteine.

In any of the aspects and embodiments disclosed herein, the composition includes about 1 g of leucine, about 0.5 g of isoleucine, about 0.5 g of valine, about 1.5 g of arginine, about 2 g of glutamine, and about 0.15 g of N-acetylcysteine.

In any of the aspects and embodiments disclosed herein, the composition includes about 2 g of leucine, about 1 g of isoleucine, about 1 g of valine, about 3.0 g of arginine, about 4 g of glutamine, and about 0.3 g of N-acetylcysteine.

In any of the aspects and embodiments disclosed herein, the composition includes about 4 g of leucine, about 2 g of isoleucine, about 2 g of valine, about 6.0 g of arginine, about 8 g of glutamine, and about 0.6 g of N-acetylcysteine.

In any of the aspects and embodiments disclosed herein, the amino acids include about 10 wt % to about 30 wt % leucine, about 5 wt % to about 15 wt % isoleucine, about 5 wt % to about 15 wt % valine, about 15 wt % to about 40 wt % arginine, about 20 wt % to about 50 wt % glutamine, and about 1 wt % to about 8 wt % n-acetylcysteine.

In any of the aspects and embodiments disclosed herein, the amino acids include about 16 wt % to about 18 wt % leucine, about 7 wt % to about 9 wt % isoleucine, about 7 wt % to about 9 wt % valine, about 28 wt % to about 32 wt % arginine, about 31 wt % to about 34 wt % glutamine, and about 1 wt % to about 5 wt % n-acetylcysteine.

In any of the aspects and embodiments disclosed herein, the amino acids include about 16.8 wt % leucine, about 8.4 wt % isoleucine, about 8.4 wt % valine, about 30.4 wt % arginine, about 33.6 wt % glutamine, and about 2.5 wt % n-acetylcysteine.

In some embodiments of any of the compositions or methods disclosed herein (wherein the ratios discussed in (1)-(26) below are weight ratios):

1) the ratio of the L-amino acid entity to the I-amino acid entity is at least 1.5:1, or at least 1.75:1, and not more than 2.5:1 or not more than 3:1, e.g., the ratio of the L-amino acid entity to the I-amino acid entity is about 2:1;

2) the ratio of L-amino acid entity to V-amino acid entity is at least 2:1, at least 3:1, at least 3.5:1, at least 4:1, or at least 5:1, and not more than 6:1, e.g., the ratio of L-amino acid entity to V-amino acid entity is about 4:1;

3) the ratio of the L-amino acid entity to the R-amino acid entity is at least 1:1, at least 3.5:3, at least 4:3, or at least 2:1, and not more than 5:2, e.g., the ratio of the L-amino acid entity to the R-amino acid entity is about 4:3;

4) the ratio of the L-amino acid entity to the L-glutamine or a salt thereof is at least 0.5:1, or at least 0.75:1, and not more than 1.5 to 1 or not more than 2:1, e.g., the ratio of the L-amino acid entity to the L-glutamine or salt thereof is about 1:1;

5) the ratio of the L-amino acid entity to the NAC entity or a salt thereof is at least 2:1, at least 3:1, at least 3.5:1, or at least 4:1, and not more than 5 to 1 or not more than 6:1, e.g., the ratio of the L-amino acid entity to the NAC entity or salt thereof is about 4:1 (e.g., 4:0.9);

6) optionally wherein the ratio of the L-amino acid entity to the S-amino acid entity or a salt thereof is greater than 1:3, greater than 1.5:3, about 2:3, or about 3:5, and not more than 2.5:3 or 1:1, e.g., the ratio of the L-amino acid entity to the S-amino acid entity is about 2:3, or the ratio of the L-amino acid entity to the S-amino acid entity is about 3:5; or 7) a combination of two, three, four, five, or six of (1)-(6).

In some embodiments of any of the compositions or methods disclosed herein:

8) the ratio of I-amino acid entity to V-amino acid entity is at least 1:1, at least 1.5:1, or about 2:1, and not more than 2.5:1 or not more than 3:1, e.g., the ratio of I-amino acid entity to V-amino acid entity is about 2:1;

9) the ratio of the I-amino acid entity to the R-amino acid entity is greater than 1:3, greater than 1.5:3, or about 2:3, and not more than 2.5:3 or not more than 1:1, e.g., the ratio of the I-amino acid entity to the R-amino acid entity is about 2:3;

10) the ratio of the I-amino acid entity to the L-glutamine or a salt thereof is at least 1:4, at least 1:3, or about 1:2, and not more than 1:1 or not more than 2:1, e.g., the ratio of the I-amino acid entity to the L-glutamine or salt thereof is about 1:2;

11) the ratio of the I-amino acid entity to the NAC entity or a salt thereof is at least 1:1, at least 1.5:1, or about 2:1, and not more than 2.5:1 or not more than 3:1, e.g., the ratio of the I-amino acid entity to the NAC entity or salt thereof is about 2:1 (e.g., 2:0.9);

12) optionally wherein the ratio of the I-amino acid entity to the S-amino acid entity or a salt thereof is greater than 1:4, greater than 1.5:4, about 1:3, or about 3:10, and not more than 1.5:3 or 2:3, e.g., the ratio of the I-amino acid entity to the S-amino acid entity is about 1:3, or the ratio of the I-amino acid entity to the S-amino acid entity is about 3:10; or 13) a combination of two, three, four, or five of (8)-(12).

In some embodiments of any of the compositions or methods disclosed herein:

14) the ratio of the V-amino acid entity to the R-amino acid entity is greater than 1:4, greater than 1.5:4, or about 1:3, and not more than 1:2 or not more than 1:1, e.g., the ratio of the V-amino acid entity to the R-amino acid entity is about 1:3;

15) the ratio of the V-amino acid entity to the L-glutamine or a salt thereof is greater than 1:5, or greater than 1.5:5, about 1:4, and not more than 1.5:4 or not more than 1:3, e.g., the ratio of the V-amino acid entity to the L-glutamine or salt thereof is about 1:4;

16) the ratio of the V-amino acid entity to the NAC entity or a salt thereof is at least 1:2, at least 1.5:2, or about 1:1, and not more than 1.5:1 or not more than 2:1, e.g., the ratio of the V-amino acid entity to the NAC entity or salt thereof is about 1:1 (e.g., 1:0.9);

17) optionally wherein the ratio of the V-amino acid entity to the S-amino acid entity or a salt thereof is greater than 1:8, greater than 1:7, about 1:6, or about 3:20, and not more than 1.5:6 or 1:3, e.g., the ratio of the V-amino acid entity to the S-amino acid entity is about 1:6, or the ratio of the V-amino acid entity to the S-amino acid entity is about 3:20; or 18) a combination of two, three, or four of (14)-(17).

In some embodiments of any of the compositions or methods disclosed herein:

19) the ratio of the R-amino acid entity to the L-glutamine or a salt thereof is greater than 1:2, greater than 1.25:2, or about 3:4, and not more than 3.5:4 or not more than 1:1, e.g., the ratio of the R-amino acid entity to the L-glutamine or salt thereof is about 3:4;

20) the ratio of the R-amino acid entity to the NAC entity or a salt thereof is at least 4:1, at least 4:1.5, or about 3:1, and not more than 3:1.5 or not more than 3:2, e.g., the ratio of the R-amino acid entity to the NAC entity or salt thereof is about 3:1 (e.g., 3:0.9);

21) optionally wherein the ratio of the R-amino acid entity to the S-amino acid entity or a salt thereof is greater than 1:4, greater than 1:3, about 1:2, or about 9:20, and not more than 1.5:2 or 1:1, e.g., the ratio of the R-amino acid entity to the S-amino acid entity is about 1:2, or the ratio of the R-amino acid entity to the S-amino acid entity is about 9:20; or 22) a combination of two or three of (19)-(21).

In some embodiments of any of the compositions or methods disclosed herein:

23) the ratio of the L-glutamine to the NAC entity or a salt thereof is at least 5:1, at least 5:1.5, or about 4:1, and not more than 4:1.5 or not more than 3:1, e.g., the ratio of the L-glutamine to the NAC entity or salt thereof is about 4:1 (e.g., 4:0.9);

24) optionally wherein the ratio of the L-glutamine to the S-amino acid entity or a salt thereof is greater than 1:3, greater than 1.25:3, about 2:3, or about 3:5, and not more than 2.5:3 or 1:1, e.g., the ratio of the L-glutamine to the S-amino acid entity is about 2:3, or the ratio of the L-glutamine to the S-amino acid entity is about 3:5; or 25) a combination of (23) and (24).

In some embodiments of any of the compositions or methods disclosed herein:

26) the ratio of the NAC entity to the S-amino acid entity or a salt thereof is greater than 1:8, greater than 1:7, or about 1:6, and not more than 1:5 or not more than 1.5:5, e.g., the ratio of the NAC entity to the S-amino acid entity is about 1:6 (e.g., 0.9:6 or 2.7:20).

In an embodiment, the composition satisfies the properties of (1)-(7) defined above.

In certain embodiments, the composition satisfies the properties of at least 2, 3, 4, 5, 6, or 7 of any of properties (1)-(26) defined above.

In an embodiment, the ratio of the L-amino acid-entity, the I-amino acid-entity, and the V-amino acid-entity in combination to the R-amino acid entity, L-glutamine or a salt thereof, and NAC or a salt thereof is 12:6:3:9:12:2.7.

In an embodiment, the ratio of the L-amino acid-entity, the I-amino acid-entity, and the V-amino acid-entity in combination to the R-amino acid entity, L-glutamine or a salt thereof, NAC or a salt thereof, and the S-amino acid entity is 12:6:3:9:12:2.7:18.

In an embodiment, the ratio of the L-amino acid-entity, the I-amino acid-entity, and the V-amino acid-entity in combination to the R-amino acid entity, L-glutamine or a salt thereof, NAC or a salt thereof, and the S-amino acid entity is 12:6:3:9:12:2.7:20.

In an embodiment, the ratio of the L-amino acid-entity, the I-amino acid-entity, and the V-amino acid-entity in combination to the R-amino acid entity, L-glutamine or a salt thereof, and NAC or a salt thereof is $12+/-15\%$:$6+/-15\%$:$3+/-15\%$:$9+/-15\%$:$12+/-15\%$:$2.7+/-15\%$.

In an embodiment, the ratio of the L-amino acid-entity, the I-amino acid-entity, and the V-amino acid-entity in combination to the R-amino acid entity, L-glutamine or a salt thereof, NAC or a salt thereof, and the S-amino acid entity is $12+/-15\%$:$6+/-15\%$:$3+/-15\%$:$9+/-15\%$:$12+/-15\%$:$2.7+/-15\%$:$18+/-15\%$.

In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12:6:3:9:12:2.7:9:9.

In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12:6:3:9:12:2.7:10:10.

In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is $12+/-15\%$:$6+/-15\%$:$3+/-15\%$:$9+/-15\%$:$12+/-15\%$:$2.7+/-15\%$:$9+/-15\%$:$9+/-15\%$. In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is $12+/-15\%$:$6+/-15\%$:$3+/-15\%$:$9+/-15\%$:$12+/-15\%$:$2.7+/-15\%$:$10+/-15\%$:$10+/-15\%$.

In any of the aspects and embodiments disclosed herein, the composition further includes one or more pharmaceutically acceptable excipients.

In some embodiments, the excipients are selected from the group consisting of citric acid, lecithin, a sweetener, a dispersion enhancer, a flavoring, a bitterness masking agent, and a natural or artificial coloring.

In some embodiments, the composition is in the form of a solid, powder, solution, or gel.

In some embodiments, the amino acids consist of leucine, isoleucine, valine, arginine, glutamine and N-acetylcysteine.

Another aspect of the invention features a dietary composition including the composition of any one of the foregoing aspects or embodiments, e.g., wherein the dietary composition is chosen from a medical food, a functional food, or a supplement.

In some embodiments, the dietary composition is chosen from a medical food, a functional food, or a supplement.

In some embodiments, the subject has type 2 diabetes and/or a relatively high BMI.

In some embodiments, the subject has non-alcoholic fatty liver disease (NAFLD).

In some embodiments, the subject has non-alcoholic fatty liver (NAFL).

In some embodiments, the subject has pediatric NAFLD.

In some embodiments, the patient has steatosis.

In some embodiments, the subject has non-alcoholic steatohepatitis (NASH).

In some embodiments, the subject has fibrosis.

In some embodiments, the subject has cirrhosis.

In some embodiments, the subject has AFLD.

In some embodiments, the subject has ASH.

In some embodiments, the subject has hepatocarcinoma, an increased risk of liver failure, or an increased risk of death.

In some embodiments, the subject has type 2 diabetes.

In some embodiments, the composition promotes weight loss in the subject.

In some embodiments of the method or the dietary composition for use, the composition is administered at a dose of about 15 g/d to about 90 g/d.

In some embodiments of the method or the dietary composition for use, the composition is administered at a dose of about 18 g/d, about 24 g/d, about 36/d, about 54 g/d, or about 72 g/d.

In some embodiments of the method or the dietary composition for use, the composition is administered one, two, to three times per day.

In some embodiments of the method or the dietary composition for use, the composition is administered at a dose of about 6 g, about 8 g, about 12 g, about 16 g, about 18 g, or about 24 g three times per day.

One embodiment provides a nutritional supplement, dietary formulation, functional food, medical food, food, or beverage comprising a composition described herein. Another embodiment provides a nutritional supplement, dietary formulation, functional food, medical food, food, or beverage comprising a composition described herein for use in the management of any of the diseases or disorders described herein. The composition disclosed herein can be used to improve liver function in a subject with fatty liver disease, such as non-alcoholic fatty liver disease (NAFLD; e.g. NAFL or non-alcoholic steatohepatitis (NASH)) or alcoholic fatty liver disease (AFLD; e.g., alcoholic steatohepatitis (ASH)). Thus, a method, including a dosage regimen, for treating (e.g., inhibiting, reducing, ameliorating, or preventing) various liver disorders, diseases, or symptoms thereof using the amino acid entity compositions is disclosed herein. The composition can also be used as a dietary composition, e.g., a medical food, a functional food, or a supplement.

Another aspect of the invention features a method for treating one or more symptoms selected from the group consisting of decreased fat metabolism, hepatocyte apoptosis, hepatocyte ballooning, inflammation of adipose tissue, inflammation of hepatic tissue, fibrosis, and oxidative stress, wherein the method includes administering to a subject in need thereof an effective amount of the composition of any one of aspects or embodiments disclosed herein.

In some embodiments, the subject has non-alcoholic fatty liver disease (NAFLD).

In some embodiments, the subject has non-alcoholic fatty liver (NAFL).

In some embodiments, the subject has pediatric NAFLD.

In some embodiments, the patient has steatosis.

In some embodiments, the subject has non-alcoholic steatohepatitis (NASH).

In some embodiments, the subject has alcoholic fatty liver disease (AFLD).

In some embodiments, the subject has alcoholic steatohepatitis (ASH)).

In some embodiments, the subject has fibrosis.

In some embodiments, the subject has cirrhosis.

In some embodiments, the subject has one, two, or more (e.g., all) of hepatocarcinoma, an increased risk of liver failure, or an increased risk of death.

In some embodiments, the subject has type 2 diabetes.

Another aspect of the invention features a method for treating non-alcoholic fatty liver disease (NAFLD) including administering to a subject in need thereof an effective amount of the composition of any one of the aspects or embodiments disclosed herein.

In some embodiments, the subject has NAFL.

In some embodiments, the subject has pediatric NAFLD.

In some embodiments, the patient has steatosis.

Another aspect of the invention features a method for treating non-alcoholic steatohepatitis (NASH) including administering to a subject in need thereof an effective amount of the composition of any one of the aspects or embodiments disclosed herein.

In some embodiments, the subject has fibrosis.

Another aspect of the invention features a method for treating AFLD including administering to a subject in need thereof an effective amount of the composition of any one of the aspects or embodiments disclosed herein.

In some embodiments, the subject has ASH.

Another aspect of the invention features a method for treating cirrhosis including administering to a subject in need thereof an effective amount of the composition of any one of the aspects or embodiments disclosed herein.

In some embodiments, the subject has hepatocarcinoma, an increased risk of liver failure, or an increased risk of death.

In some embodiments, administering the composition results in an improvement in one or more metabolic symptoms in the subject. In some embodiments, the improvement in one or more metabolic symptoms is selected from the following: increased free fatty acid and lipid metabolism, improved mitochondrial function, white adipose tissue (WAT) browning, decreased reactive oxygen species (ROS), increased levels of glutathione (GSH), decreased hepatic inflammation, decreased hepatocyte ballooning, improved gut barrier function, increased insulin secretion, or improved glucose tolerance.

In some embodiments, the increased free fatty acid and lipid metabolism occurs in the liver.

In some embodiments, administration of the composition results in an improvement in one or more metabolic symptoms after a treatment period of 24 hours.

In some embodiments, the method further includes determining the level of one, two, three, four, five, six, seven, eight, nine, ten, or more (e.g., all) of the following:

a) alanine aminotransferase (ALT);
b) aspartate aminotransferase (AST);
c) adiponectin;
d) N-terminal fragment of type III collagen (proC3);
e) caspase-cleaved keratin 18 fragments (M30 and M65);
f) IL-1 beta;
g) C-reactive protein;
h) PIIINP;

i) a tissue inhibitor of metalloproteinase (TIMP); e.g., TIMP1 or TIMP2;
j) MCP-1;
k) FGF-21;
l) Col1a1;
m) Acta2;
n) a matrix metalloproteinase (MMP), e.g., MMP-13, MMP-2, MMP-9, MT1-MMP, MMP-3, or MMP-10;
o) ACOX1;
p) IL-10; or
q) NF-kB.

In some embodiments, administration of the composition results in an improvement in one or more of a)-q) after a treatment period of 24 hours.

In some embodiments, the composition is administered prior to a meal.

In some embodiments, the composition is administered concurrent with a meal.

In some embodiments, the composition is administered following a meal.

In some embodiments, the composition is administered with a second agent.

In some embodiments, the second agent is selected from the group consisting of a farnesoid X receptor (FXR) agonist, a stearoyl CoA desaturase inhibitor, a CCR2 and CCR5 chemokine antagonist, a PPAR alpha and delta agonist, a caspase inhibitor, a galectin-3 inhibitor, an acetyl CoA carboxylase inhibitor, or an ileal sodium bile acid co-transporter inhibitor. Another aspect of the invention provides a method of maintaining or improving liver health comprising administering to a subject an effective amount of any of the compositions described herein. Another embodiment provides a method of providing nutritional support or supplementation to a subject suffering from NAFLD (e.g., NASH or NAFL) or AFLD (e.g., ASH) comprising administering to the subject an effective amount of a composition described herein. Yet another embodiment provides a method of providing nutritional supplementation that aids in the management of NAFLD (e.g., NASH or NAFL) or AFLD (e.g., ASH) to a subject comprising administering to the subject in need thereof an effective amount of a composition described herein.

Additional features and embodiments of the present invention include one or more of the following.

Another aspect of the invention features a composition comprising:

a) a L-amino acid entity chosen from L-leucine or a salt thereof, or β-hydroxy-β-methylbutyrate (HMB) or a salt thereof, or a combination of L-leucine or a salt thereof and HMB or a salt thereof;

b) an R-amino acid entity chosen from: L-arginine or a salt thereof, ornithine or a salt thereof, or creatine or a salt thereof, or a combination of two or three of L-arginine or a salt thereof, ornithine or a salt thereof, or creatine or a salt thereof;

c) L-glutamine or a salt thereof; and d) N-acetylcysteine (NAC) or a salt thereof.

In an embodiment, L-leucine is provided as part of a dipeptide comprising L-leucine, or a salt thereof, or a tripeptide comprising L-leucine, or a salt thereof.

In an embodiment, L-arginine is provided as part of a dipeptide comprising L-arginine, or a salt thereof, or a tripeptide comprising L-arginine, or a salt thereof.

In an embodiment L-glutamine is provided as part of a dipeptide comprising L-glutamine, or a salt thereof, or a tripeptide comprising L-glutamine, or a salt thereof.

In an embodiment NAC is provided as a part of a dipeptide comprising NAC, or a salt thereof, or a tripeptide comprising NAC, or a salt thereof.

In some embodiments of any of the compositions or methods disclosed herein, one, two, three, or four of methionine (M), tryptophan (W), valine (V), or cysteine (C) is absent, or if present, is present at a percentage of the composition by weight (wt. %) of less than 10%. In some embodiments, the total wt. % of (a)-(d) is greater than the total wt. % of any other amino acid entity in the composition.

In some embodiments of any of the compositions or methods disclosed herein, one, two, three, or four of the amino acids in (a)-(d) is provided as part of a dipeptide or tripeptide, e.g., in an amount of at least 10 wt. % of the composition. In certain embodiments, the dipeptide is a homodipeptide or heterodipeptide of any of the amino acids in (a)-(d), e.g., one, two, three, or four of the amino acids in (a)-(d) is a homodipeptide or heterodipeptide. In certain embodiments, the tripeptide is a homotripeptide or heterotripeptide of any of (a)-(d), e.g., one, two, three, or four of (a)-(d) is a homotripeptide or heterotripeptide.

In some embodiments of any of the compositions or methods disclosed herein, (a) is a L-amino acid entity dipeptide or a salt thereof (e.g., a L-leucine dipeptide or a salt thereof). In some embodiments, (a) is a homodipeptide. In some embodiments, (a) is a heterodipeptide, e.g., Ala-Leu.

In some embodiments of any of the compositions or methods disclosed herein, (b) is a L-arginine dipeptide or a salt thereof. In some embodiments, (b) is a homodipeptide. In some embodiments, (b) is a heterodipeptide, e.g., Ala-Arg.

In some embodiments of any of the compositions or methods disclosed herein, (c) is a L-glutamine dipeptide or a salt thereof. In some embodiments, (c) is a homodipeptide, e.g., Gln-Gln. In some embodiments, (c) is a heterodipeptide, e.g., Ala-Gln.

In some embodiments of any of the compositions or methods disclosed herein:

f) a wt. % of the L-glutamine or a salt thereof in the composition is greater than the wt. % of the R-amino acid entity;

g) the wt. % of the L-glutamine or a salt thereof in the composition is greater than the wt. % of the L-amino acid entity;

h) the wt. % of the R-amino acid entity in the composition is greater than the wt. % of the L-amino acid entity; or i) a combination of two or three of (f)-(h).

In some embodiments of any of the compositions or methods disclosed herein, the wt. % of the L-glutamine or a salt thereof in the composition is at least 5% greater than the wt. % of the R-amino acid entity, e.g., the wt. % of the L-glutamine or a salt thereof is at least 10%, 15%, 20%, or 25% greater than the wt. % of the R-amino acid entity.

In some embodiments of any of the compositions or methods disclosed herein, the wt. % of the L-glutamine or a salt thereof in the composition is at least 20% greater than the wt. % of the L-amino acid entity, e.g., the wt. % of the L-glutamine or a salt thereof in the composition is at least 25%, 30%, 35%, 40%, 45%, or 50% greater than the wt. % of the L-amino acid entity.

In some embodiments of any of the compositions or methods disclosed herein, the wt. % of the R-amino acid entity in the composition is at least 10% greater than the wt. % of the L-amino acid entity, e.g., the wt. % of the R-amino acid entity in the composition is at least 15%, 20%, 25%, or 30% greater than the wt. % of the L-amino acid entity.

In some embodiments of any of the compositions or methods disclosed herein:

j) the ratio of the L-amino acid entity to the R-amino acid entity is at least 1:4, or at least 2:5, and not more than 3:4, e.g., the ratio of L-amino acid entity to R-amino acid entity is about 2:3;

k) the ratio of the L-amino acid entity to the L-glutamine or a salt thereof is at least 1:4, or at least 1:3, and not more than 3:4, e.g., the ratio of the L-amino acid entity to the L-glutamine or a salt thereof is about 1:2;

l) the ratio of the R-amino acid entity to the L-glutamine or a salt thereof is at least 1:4, or at least 1:2, and not more than 6:7, e.g., the ratio of the R-amino acid entity to the L-glutamine or a salt thereof is about 3:4; or m) a combination of two or three of (j)-(l).

In an embodiment, the composition satisfies the properties of (j)-(l) defined above.

In certain embodiments, the composition satisfies the properties of at least 2, 3, or 4 of any of properties (j)-(m) defined above.

In some embodiments of any of the compositions or methods disclosed herein, the composition further comprises one or both of an isoleucine (I)-amino acid-entity and a valine (V)-amino acid-entity, e.g., both the I-amino acid-entity and the V-amino acid-entity are present.

In some embodiments of any of the compositions or methods disclosed herein:

n) the wt. % of the L-amino acid-entity in the composition is greater than or equal to the wt. % of the I-amino acid-entity and the V-amino acid-entity in combination;

o) the wt. % of the L-amino acid-entity, the I-amino acid-entity, and the V-amino acid-entity in combination in the composition is greater than or equal to the wt. % of the L-glutamine or a salt thereof;

p) the wt. % of the L-amino acid-entity, the I-amino acid-entity, and the V-amino acid-entity in combination in the composition is less than the wt. % of the R-amino acid entity;

q) the wt. % of the R-amino acid entity and the L-glutamine or a salt thereof in the composition is greater than the wt. % of the L-amino acid-entity, the I-amino acid-entity, and the V-amino acid-entity in combination; or r) a combination of two, three, or four of (n)-(q).

In some embodiments of any of the compositions or methods disclosed herein:

s) the wt. % of the R-amino acid entity, the L-glutamine or a salt thereof, and the NAC or a salt thereof is at least 50% of the composition, or at least 70% of the composition, but not more than 90% of the composition;

t) the wt. % of the NAC or a salt thereof is at least 1%, or at least 2%, but not more than 10% of the composition;

u) the wt. % of the L-amino acid-entity, the I-amino acid-entity, and the V-amino acid-entity in combination is at least 15%, or at least 20%, but not more than 50% of the composition;

v) the wt. % of the R-amino acid entity, the L-glutamine or a salt thereof, and the NAC or a salt thereof is at least 40%, or at least 50%, but not more than 80% of the composition; or w) a combination of two, three, or four of (s)-(v).

In some embodiments of any of the compositions or methods disclosed herein:

x) the ratio of the L-amino acid entity to the I-amino acid entity is at least 1.5:1, or at least 1.75:1, and not more than 2.5 to 1 or not more than 3:1, e.g., the ratio of the L-amino acid entity to the I-amino acid entity is about 2:1;

y) the ratio of L-amino acid entity to V-amino acid entity is at least 1.5:1, or at least 1.75:1, and not more than 2.5 to 1 or not more than 3:1, e.g., the ratio of L to V is about 2:1;

z) the ratio of the L-amino acid entity to the R-amino acid entity is greater than 1:3, greater than 1.5 to 3, and less than 3:3, e.g., the ratio of the L-amino acid entity to the R-amino acid entity is about 2:3;

aa) the ratio of the L-amino acid entity to the L-glutamine or a salt thereof is greater than 1:4, greater than 1.5 to 4 and less than 4:4, or less than 3:4, e.g., the ratio of the L-amino acid entity to the L-glutamine or a salt thereof is about 1:2; or bb) a combination of two, three, or four of (x)-(aa).

In an embodiment, the composition satisfies the properties of (x)-(aa) defined above.

In certain embodiments, the composition satisfies the properties of at least 2, 3, 4, or 5 of any of properties (x)-(bb) defined above.

In some embodiments of any of the compositions or methods disclosed herein:

cc) the ratio of the I-amino acid entity to the V-amino acid entity is at least 0.5:1, or at least 0.75:1, and not more than 1.5 to 1 or not more than 2:1, e.g., the ratio of the L-amino acid entity to the I-amino acid entity is about 1:1;

dd) the ratio of the I-amino acid entity to the R-amino acid entity is at least 0.5:3, or at least 0.75:3, and not more than 2:3, or not more than 1.5:3, e.g., the ratio of the L-amino acid entity to the I-amino acid entity is about 1:3;

ee) the ratio of the I-amino acid entity to the L-glutamine or a salt thereof is at least 0.5:4, or at least 0.75:4, and not more than 3:4, or not more than 2:4, e.g., the ratio of the L-amino acid entity to the L-glutamine or a salt thereof is about 1:4; or ff) or a combination of two or three of (cc)-(ee).

In an embodiment, the composition satisfies the properties of (cc)-(ee) defined above.

In certain embodiments, the composition satisfies the properties of at least 2, 3, or 4 of any of properties (cc)-(ff) defined above.

In some embodiments of any of the compositions or methods disclosed herein:

gg) the ratio of the L-amino acid entity to the V-amino acid entity is at least 1.5:1, or at least 1.75:1, and not more than 2.5 to 1 or not more than 3:1, e.g., the ratio of the L-amino acid entity to the V-amino acid entity is about 2:1;

hh) the ratio of the L-amino acid entity to the R-amino acid entity is greater than 1:3 or greater than 1.5 to 3, and less than 3:3, e.g., the ratio of the L-amino acid entity to the R-amino acid entity is about 2:3;

ii) the ratio of the L-amino acid entity to the L-glutamine or a salt thereof is greater than 1:4 or greater than 1.5 to 4, and less than 4:4 or less than 3:4, e.g., the ratio of the L-amino acid entity to the L-glutamine or a salt thereof is about 1:2; or jj) a combination of two or three of (gg)-(ii).

In an embodiment, the composition satisfies the properties of (gg)-(ii) defined above.

In certain embodiments, the composition satisfies the properties of at least 2, 3, or 4 of any of properties (gg)-(jj) defined above.

In some embodiments of any of the compositions or methods disclosed herein:

kk) the ratio of the V-amino acid entity to the L-glutamine or a salt thereof is at least 0.5:4, or at least 0.75:4, and not more than 3:4, or not more than 2:4, e.g., the ratio of the L-amino acid entity to the L-glutamine or a salt thereof is about 1:4;

ll) the ratio of the V-amino acid entity to the R-amino acid entity is at least 0.5:3, or at least 0.75:3, and not more than 2:3, or not more than 1.5:3, e.g., the ratio of the V-amino acid entity to the R-amino acid entity is about 1:3;

mm) the ratio of the L-amino acid-entity, the I-amino acid-entity, and the V-amino acid-entity in combination to the R-amino acid entity, L-glutamine or a salt thereof, and NAC or a salt thereof is at least 1:4, or at least 2:3, or not more than 5:7, or not more than 6:7, e.g., the ratio is about 6:11; or nn) a combination of two or three of (kk)-(mm).

In an embodiment, the composition satisfies the properties of (kk)-(mm) defined above.

In certain embodiments, the composition satisfies the properties of at least 2, 3, or 4 of any of properties (kk)-(nn) defined above.

In some embodiments of any of the compositions or methods disclosed herein, the composition further comprises an S-amino acid entity.

In some embodiments of any of the compositions or methods disclosed herein:

1) the ratio of the L-amino acid entity to the I-amino acid entity is at least 1.5:1, or at least 1.75:1, and not more than 2.5:1 or not more than 3:1, e.g., the ratio of the L-amino acid entity to the I-amino acid entity is about 2:1;

2) the ratio of L-amino acid entity to V-amino acid entity is at least 2:1, at least 3:1, at least 3.5:1, at least 4:1, or at least 5:1, and not more than 6:1, e.g., the ratio of L-amino acid entity to V-amino acid entity is about 4:1;

3) the ratio of the L-amino acid entity to the R-amino acid entity is at least 1:1, at least 3.5:3, at least 4:3, or at least 2:1, and not more than 5:2, e.g., the ratio of the L-amino acid entity to the R-amino acid entity is about 4:3;

4) the ratio of the L-amino acid entity to the L-glutamine or a salt thereof is at least 0.5:1, or at least 0.75:1, and not more than 1.5 to 1 or not more than 2:1, e.g., the ratio of the L-amino acid entity to the L-glutamine or salt thereof is about 1:1;

5) the ratio of the L-amino acid entity to the NAC entity or a salt thereof is at least 2:1, at least 3:1, at least 3.5:1, or at least 4:1, and not more than 5 to 1 or not more than 6:1, e.g., the ratio of the L-amino acid entity to the NAC entity or salt thereof is about 4:1 (e.g., 4:0.9);

6) optionally wherein the ratio of the L-amino acid entity to the S-amino acid entity or a salt thereof is greater than 1:3, greater than 1.5:3, about 2:3, or about 3:5, and not more than 2.5:3 or 1:1, e.g., the ratio of the L-amino acid entity to the S-amino acid entity is about 2:3, or the ratio of the L-amino acid entity to the S-amino acid entity is about 3:5; or 7) a combination of two, three, four, five, or six of (1)-(6).

In some embodiments of any of the compositions or methods disclosed herein:

8) the ratio of I-amino acid entity to V-amino acid entity is at least 1:1, at least 1.5:1, or about 2:1, and not more than 2.5:1 or not more than 3:1, e.g., the ratio of I-amino acid entity to V-amino acid entity is about 2:1;

9) the ratio of the I-amino acid entity to the R-amino acid entity is greater than 1:3, greater than 1.5:3, or about 2:3, and not more than 2.5:3 or not more than 1:1, e.g., the ratio of the I-amino acid entity to the R-amino acid entity is about 2:3;

10) the ratio of the I-amino acid entity to the L-glutamine or a salt thereof is at least 1:4, at least 1:3, or about 1:2, and not more than 1:1 or not more than 2:1, e.g., the ratio of the I-amino acid entity to the L-glutamine or salt thereof is about 1:2;

11) the ratio of the I-amino acid entity to the NAC entity or a salt thereof is at least 1:1, at least 1.5:1, or about 2:1, and not more than 2.5:1 or not more than 3:1, e.g., the ratio of the I-amino acid entity to the NAC entity or salt thereof is about 2:1 (e.g., 2:0.9);

12) optionally wherein the ratio of the I-amino acid entity to the S-amino acid entity or a salt thereof is greater than 1:4, greater than 1.5:4, about 1:3, or about 3:10, and not more than 1.5:3 or 2:3, e.g., the ratio of the I-amino acid entity to the S-amino acid entity is about 1:3, or the ratio of the I-amino acid entity to the S-amino acid entity is about 3:10; or 13) a combination of two, three, four, or five of (8)-(12).

In some embodiments of any of the compositions or methods disclosed herein:

14) the ratio of the V-amino acid entity to the R-amino acid entity is greater than 1:4, greater than 1.5:4, or about 1:3, and not more than 1:2 or not more than 1:1, e.g., the ratio of the V-amino acid entity to the R-amino acid entity is about 1:3;

15) the ratio of the V-amino acid entity to the L-glutamine or a salt thereof is greater than 1:5, or greater than 1.5:5, about 1:4, and not more than 1.5:4 or not more than 1:3, e.g., the ratio of the V-amino acid entity to the L-glutamine or salt thereof is about 1:4;

16) the ratio of the V-amino acid entity to the NAC entity or a salt thereof is at least 1:2, at least 1.5:2, or about 1:1, and not more than 1.5:1 or not more than 2:1, e.g., the ratio of the V-amino acid entity to the NAC entity or salt thereof is about 1:1 (e.g., 1:0.9);

17) optionally wherein the ratio of the V-amino acid entity to the S-amino acid entity or a salt thereof is greater than 1:8, greater than 1:7, about 1:6, or about 3:20, and not more than 1.5:6 or 1:3, e.g., the ratio of the V-amino acid entity to the S-amino acid entity is about 1:6, or the ratio of the V-amino acid entity to the S-amino acid entity is about 3:20; or 18) a combination of two, three, or four of (14)-(17).

In some embodiments of any of the compositions or methods disclosed herein:

19) the ratio of the R-amino acid entity to the L-glutamine or a salt thereof is greater than 1:2, greater than 1.25:2, or about 3:4, and not more than 3.5:4 or not more than 1:1, e.g., the ratio of the R-amino acid entity to the L-glutamine or salt thereof is about 3:4;

20) the ratio of the R-amino acid entity to the NAC entity or a salt thereof is at least 4:1, at least 4:1.5, or about 3:1, and not more than 3:1.5 or not more than 3:2, e.g., the ratio of the R-amino acid entity to the NAC entity or salt thereof is about 3:1 (e.g., 3:0.9);

21) optionally wherein the ratio of the R-amino acid entity to the S-amino acid entity or a salt thereof is greater than 1:4, greater than 1:3, about 1:2, or about 9:20, and not more than 1.5:2 or 1:1, e.g., the ratio of the R-amino acid entity to the S-amino acid entity is about 1:2, or the ratio of the R-amino acid entity to the S-amino acid entity is about 9:20; or 22) a combination of two or three of (19)-(21).

In some embodiments of any of the compositions or methods disclosed herein:

23) the ratio of the L-glutamine to the NAC entity or a salt thereof is at least 5:1, at least 5:1.5, or about 4:1, and not more than 4:1.5 or not more than 3:1, e.g., the ratio of the L-glutamine to the NAC entity or salt thereof is about 4:1 (e.g., 4:0.9);

24) optionally wherein the ratio of the L-glutamine to the S-amino acid entity or a salt thereof is greater than 1:3, greater than 1.25:3, about 2:3, or about 3:5, and not more than 2.5:3 or 1:1, e.g., the ratio of the L-glutamine to the S-amino acid entity is about 2:3, or the ratio of the L-glutamine to the S-amino acid entity is about 3:5; or 25) a combination of (23) and (24).

In some embodiments of any of the compositions or methods disclosed herein:

26) the ratio of the NAC entity to the S-amino acid entity or a salt thereof is greater than 1:8, greater than 1:7, or about 1:6, and not more than 1:5 or not more than 1.5:5, e.g., the ratio of the NAC entity to the S-amino acid entity is about 1:6 (e.g., 0.9:6 or 2.7:20).

In an embodiment, the composition satisfies the properties of (1)-(7) defined above.

In certain embodiments, the composition satisfies the properties of at least 2, 3, 4, 5, 6, or 7 of any of properties (1)-(26) defined above.

In an embodiment, the ratio of the L-amino acid-entity, the I-amino acid-entity, and the V-amino acid-entity in combination to the R-amino acid entity, L-glutamine or a salt thereof, and NAC or a salt thereof is 12:6:3:9:12:2.7.

In an embodiment, the ratio of the L-amino acid-entity, the I-amino acid-entity, and the V-amino acid-entity in combination to the R-amino acid entity, L-glutamine or a salt thereof, NAC or a salt thereof, and the S-amino acid entity is 12:6:3:9:12:2.7:18.

In an embodiment, the ratio of the L-amino acid-entity, the I-amino acid-entity, and the V-amino acid-entity in combination to the R-amino acid entity, L-glutamine or a salt thereof, NAC or a salt thereof, and the S-amino acid entity is 12:6:3:9:12:2.7:20.

In an embodiment, the ratio of the L-amino acid-entity, the I-amino acid-entity, and the V-amino acid-entity in combination to the R-amino acid entity, L-glutamine or a salt thereof, and NAC or a salt thereof is 12+/−15%:6+/−15%:3+/−15%:9+/−15%:12+/−15%:2.7+/−15%.

In an embodiment, the ratio of the L-amino acid-entity, the I-amino acid-entity, and the V-amino acid-entity in combination to the R-amino acid entity, L-glutamine or a salt thereof, NAC or a salt thereof, and the S-amino acid entity is 12+/−15%:6+/−15%:3+/−15%:9+/−15%:12+/−15%:2.7+/−15%:18+/−15%.

In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12:6:3:9:12:2.7:9:9. In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12:6:3:9:12:2.7:10:10.

In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12+/−15%:6+/−15%:3+/−15%:9+/−15%:12+/−15%:2.7+/−15%:9+/−15%:9+/−15%. In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12+/−15%:6+/−15%:3+/−15%:9+/−15%:12+/−15%:2.7+/−15%:10+/−15%:10+/−15%.

In some embodiments of any of the compositions or methods disclosed herein:

oo) a wt. % of the L-amino acid entity in the composition is greater than the wt. % of the NAC or a salt thereof;

pp) a wt. % of the R-amino acid entity in the composition is greater than the wt. % of the NAC or a salt thereof;

qq) a wt. % of the L-glutamine or a salt thereof in the composition is greater than the wt. % of the NAC or a salt thereof; or rr) a combination of two or three of (oo)-(qq).

In some embodiments of any of the compositions or methods disclosed herein, at least one of (a)-(d) is a free amino acid, e.g., two, three, or four of (a)-(d) are a free amino acid, e.g., at least 50 wt. % of the total wt. of the composition is one or more amino acid entities in free form.

In some embodiments of any of the compositions or methods disclosed herein, at least one of (a)-(d) is in a salt form, e.g., one, two, three, or four of (a)-(d) is in a salt form, e.g., at least 10 wt. % of the total wt. of the composition is one or more amino acid entities in salt form.

In some embodiments of any of the compositions or methods disclosed herein, the composition is capable of one, two, three, four, five, or all of:

a) decreasing or preventing liver fibrosis;
b) decreasing or preventing liver injury;
c) decreasing or preventing hepatocyte inflammation;
d) improving, e.g., increasing, glucose tolerance;
e) decreasing or preventing steatosis;
f) decreasing or preventing hepatocyte ballooning; or
g) improving gut function.

In some embodiments of any of the compositions or methods disclosed herein, the composition further comprises one or both of L-glycine and L-serine. In certain embodiments, the composition comprises an L-amino acid entity, an I-amino acid entity, an V-amino acid entity, an R-amino acid entity, an L-glutamine or a salt thereof, an NAC or a salt thereof, and an L-glycine. In certain embodiments, the composition comprises an L-amino acid entity, an I-amino acid entity, an V-amino acid entity, an R-amino acid entity, an L-glutamine or a salt thereof, an NAC or a salt thereof, and an L-serine. In certain embodiments, the composition comprises an L-amino acid entity, an I-amino acid entity, an V-amino acid entity, an R-amino acid entity, an L-glutamine or a salt thereof, an NAC or a salt thereof, an L-glycine, and an L-serine. In any of the aforesaid embodiments in this paragraph, the wt. ratio of the L-amino acid entity, the I-amino acid entity, the V-amino acid entity, the R-amino acid entity, the L-glutamine or salt thereof, and the NAC or salt thereof is about 1:0.5:0.5:1.5:2:0.15 or about 1:0.5:0.5:1.5:2:0.3.

In some embodiments of any of the compositions or methods disclosed herein, the wt. ratio of the L-amino acid entity, the R-amino acid entity, the L-glutamine or a salt thereof, and the NAC or salt thereof is about 0.5 to 3:0.5 to 4:1 to 4:0.1 to 2.5, e.g., the wt. ratio of the L-amino acid entity, the R-amino acid entity, the L-glutamine or a salt thereof, and the NAC or salt thereof is about 1:1.5:2:0.15, about 1:1.5:2:0.225, about 1:1.5:2:0.3, or about 1:1.5:2:0.5. In any of the aforesaid embodiments in this paragraph, the wt. ratio of the L-amino acid entity, the R-amino acid entity, the L-glutamine or a salt thereof, and the NAC or salt thereof is about 1:0.75:2:0.15, about 1:0.75:2:0.225, about 1:0.75:2:0.3, or about 1:0.75:2:0.5.

In some embodiments, the wt. ratio of the L-amino acid entity, the I-amino acid entity, the V-amino acid entity, the R-amino acid entity, the L-glutamine or salt thereof, and the NAC or salt thereof is about 1:0.5:0.5:1.5:2:0.15, about 1:0.5:0.5:1.5:2:0.225, about 1:0.5:0.5:1.5:2:0.3, or about 1:0.5:0.5:1.5:2:0.5.

In some embodiments of any of the compositions or methods disclosed herein, the composition comprises about 0.5 g to about 10 g of the L-amino acid entity, about 0.25 g to about 5 g of the I-amino acid entity, about 0.25 g to about 5 g of the V-amino acid entity, about 0.5 g to about 20 g of the R-amino acid entity, about 1 g to about 20 g of the L-glutamine or a salt thereof, and about 0.1 g to about 5 g of the NAC or a salt thereof, e.g., the composition comprises about 1 g of the L-amino acid entity, about 0.5 g of the I-amino acid entity, about 0.5 g of V-amino acid entity, about 1.5 g of R-amino acid entity, about 2 g of L-glutamine or a salt thereof, and about 0.15 g, about 0.225 g, about 0.3 g, or about 0.5 g of NAC or a salt thereof. In certain embodiments, the composition comprises about 0.15 g of NAC. In certain embodiments, the composition comprises about 0.3 g of NAC. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, and about 0.9 g of NAC or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, and about 6 g of L-serine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, and about 6.67 g of L-serine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, about 3 g of L-serine or a salt thereof, and about 3 g of L-glycine or a salt thereof. In embodiments, the composition comprises about 4 g of the L-amino acid entity, about 2 g of the I-amino acid entity, about 1 g of V-amino acid entity, about 3 g of R-amino acid entity, about 4 g of L-glutamine or a salt thereof, about 0.9 g of NAC or a salt thereof, about 3.33 g of L-serine or a salt thereof, and about 3.33 g of L-glycine or a salt thereof.

In some embodiments of any of the compositions or methods disclosed herein, the composition comprises:
 a) L-Leucine or a salt thereof;
 b) L-Isoleucine or a salt thereof;
 c) L-Valine or a salt thereof;
 d) L-Arginine or a salt thereof;
 e) L-Glutamine or a salt thereof; and
 f) NAC or a salt thereof.

In an embodiment, L-Leucine is provided as part of a dipeptide comprising L-Leucine, or a salt thereof, or a tripeptide comprising L-Leucine, or a salt thereof.

In an embodiment, L-Isoleucine is provided as part of a dipeptide comprising L-Isoleucine, or a salt thereof, or a tripeptide comprising L-Isoleucine, or a salt thereof.

In an embodiment, L-Valine is provided as part of a dipeptide comprising L-Valine, or a salt thereof, or a tripeptide comprising L-Valine, or a salt thereof.

In an embodiment, L-Arginine is provided as part of a dipeptide comprising L-Arginine, or a salt thereof, or a tripeptide comprising L-Arginine, or a salt thereof.

In an embodiment L-Glutamine is provided as part of a dipeptide comprising L-Glutamine, or a salt thereof, or a tripeptide comprising L-Glutamine, or a salt thereof.

In an embodiment NAC is provided as a part of a dipeptide comprising NAC, or a salt thereof, or a tripeptide comprising NAC, or a salt thereof.

In some embodiments of any of the compositions or methods disclosed herein, the composition comprises a combination of 4 to 20 different amino acid entities, e.g., a combination of 5 to 15 different amino acid entities.

In some embodiments of any of the compositions or methods disclosed herein, at least two, three, four, or more amino acid entities are not comprised in a peptide of more than 4, 5, 6, 7, 8, 9, 10, 11, 12, 13, 14, 15, 16, 17, 18, 19, or 20 amino acid residues in length.

Another aspect of the invention features a method for improving liver function, wherein the method comprises administering to a subject in need thereof an effective amount of a composition comprising:
 a) a L-amino acid entity chosen from L-leucine or a salt thereof, or β-hydroxy-β-methybutyrate (HMB) or a salt thereof, or a combination of L-leucine or a salt thereof and HMB or a salt thereof;
 b) an R-amino acid entity chosen from: L-arginine or a salt thereof, ornithine or a salt thereof, or creatine or a salt thereof, or a combination of two or three of L-arginine or a salt thereof, ornithine or a salt thereof, or creatine or a salt thereof;
 c) L-glutamine or a salt thereof; and
 d) N-acetylcysteine (NAC) or a salt thereof.

In an embodiment, L-Leucine is provided as part of a dipeptide comprising L-Leucine, or a salt thereof, or a tripeptide comprising L-Leucine, or a salt thereof.

In an embodiment, L-Arginine is provided as part of a dipeptide comprising L-Arginine, or a salt thereof, or a tripeptide comprising L-Arginine, or a salt thereof.

In an embodiment L-Glutamine is provided as part of a dipeptide comprising L-Glutamine, or a salt thereof, or a tripeptide comprising L-Glutamine, or a salt thereof.

In an embodiment NAC is provided as a part of a dipeptide comprising NAC, or a salt thereof, or a tripeptide comprising NAC, or a salt thereof.

Another aspect of the invention features a method for treating one or more symptoms selected from the group consisting of decreased fat metabolism, hepatocyte apoptosis, hepatocyte ballooning, inflammation of adipose tissue, inflammation of hepatic tissue, fibrosis, liver injury, steatosis, glucose tolerance, and oxidative stress, wherein the method comprises administering to a subject in need thereof an effective amount of a composition comprising:
 a) a L-amino acid entity chosen from L-leucine or a salt thereof, or β-hydroxy-β-methybutyrate (HMB) or a salt thereof, or a combination of L-leucine or a salt thereof and HMB or a salt thereof;
 b) an R-amino acid entity chosen from: L-arginine or a salt thereof, ornithine or a salt thereof, or creatine or a salt thereof, or a combination of two or three of L-arginine or a salt thereof, ornithine or a salt thereof, or creatine or a salt thereof;
 c) L-glutamine or a salt thereof; and
 d) N-acetylcysteine (NAC) or a salt thereof.

In an embodiment, L-Leucine is provided as part of a dipeptide comprising L-Leucine, or a salt thereof, or a tripeptide comprising L-Leucine, or a salt thereof.

In an embodiment, L-Arginine is provided as part of a dipeptide comprising L-Arginine, or a salt thereof, or a tripeptide comprising L-Arginine, or a salt thereof.

In an embodiment L-Glutamine is provided as part of a dipeptide comprising L-Glutamine, or a salt thereof, or a tripeptide comprising L-Glutamine, or a salt thereof.

In an embodiment NAC is provided as a part of a dipeptide comprising NAC, or a salt thereof, or a tripeptide comprising NAC, or a salt thereof.

Another aspect of the invention features a method for treating fatty liver disease, wherein the method comprises administering to a subject in need thereof an effective amount of a composition comprising:

a) a L-amino acid entity chosen from L-leucine or a salt thereof, or β-hydroxy-β-methybutyrate (HMB) or a salt thereof, or a combination of L-leucine or a salt thereof and HMB or a salt thereof;

b) an R-amino acid entity chosen from: L-arginine or a salt thereof, ornithine or a salt thereof, or creatine or a salt thereof, or a combination of two or three of L-arginine or a salt thereof, ornithine or a salt thereof, or creatine or a salt thereof;

c) L-glutamine or a salt thereof; and d) N-acetylcysteine (NAC) or a salt thereof.

In an embodiment, L-Leucine is provided as part of a dipeptide comprising L-Leucine, or a salt thereof, or a tripeptide comprising L-Leucine, or a salt thereof.

In an embodiment, L-Arginine is provided as part of a dipeptide comprising L-Arginine, or a salt thereof, or a tripeptide comprising L-Arginine, or a salt thereof.

In an embodiment L-Glutamine is provided as part of a dipeptide comprising L-Glutamine, or a salt thereof, or a tripeptide comprising L-Glutamine, or a salt thereof.

In an embodiment NAC is provided as a part of a dipeptide comprising NAC, or a salt thereof, or a tripeptide comprising NAC, or a salt thereof.

In some embodiments of any of the compositions or methods disclosed herein, e.g., of any of the methods described herein, the subject has a disease or disorder selected from the group consisting of non-alcoholic fatty liver (NAFL), non-alcoholic fatty liver disease (NAFLD), non-alcoholic steatohepatitis (NASH), alcoholic fatty liver disease (AFLD), and alcoholic steatohepatitis (ASH). In certain embodiments, the subject has pediatric NAFLD.

In some embodiments of any of the compositions or methods disclosed herein, e.g., of any of the methods described herein, the subject has a high BMI, obesity, gut leakiness, gut dysbiosis, or gut microbiome disturbance.

In some embodiments of any of the compositions or methods disclosed herein, e.g., of any of the methods described herein, the subject has cirrhosis, hepatocarcinoma, an increased risk of liver failure, an increased risk of death, metabolic syndrome, or type 2 diabetes.

In some embodiments of any of the compositions or methods disclosed herein, e.g., of any of the methods described herein, the subject has increased levels of inflammatory cytokines relative to a normal subject, e.g., the subject has increased levels of TNFα relative to a normal subject e.g., without the one or more symptoms or without the fatty liver disease.

In some embodiments, e.g., of any of the methods described herein, the subject exhibits muscle atrophy or has a decreased ratio of muscle tissue to adipose tissue relative to a normal subject, e.g., without the one or more symptoms or without a fatty liver disease, e.g., the subject exhibits muscle atrophy without one or both of fibrosis or cirrhosis.

In some embodiments, e.g., of any of the methods described herein, the subject exhibits reverse lipid transport from adipose tissue to liver tissue.

In some embodiments, e.g., of any of the methods described herein, the subject is treated with a composition, e.g., any composition as described herein. In some embodiments of any of the aspects described herein:

(i) an amino acid entity (e.g., at least one, two, or three of the amino acid entities) of (a) is selected from Table 2; and/or (ii) one or both of the R-amino acid entity and the Q-amino acid entity are present at a higher amount (wt. %) than the L-amino acid entity.

BRIEF DESCRIPTION OF THE DRAWINGS

FIGS. 9I-9L).

Figure 1A:
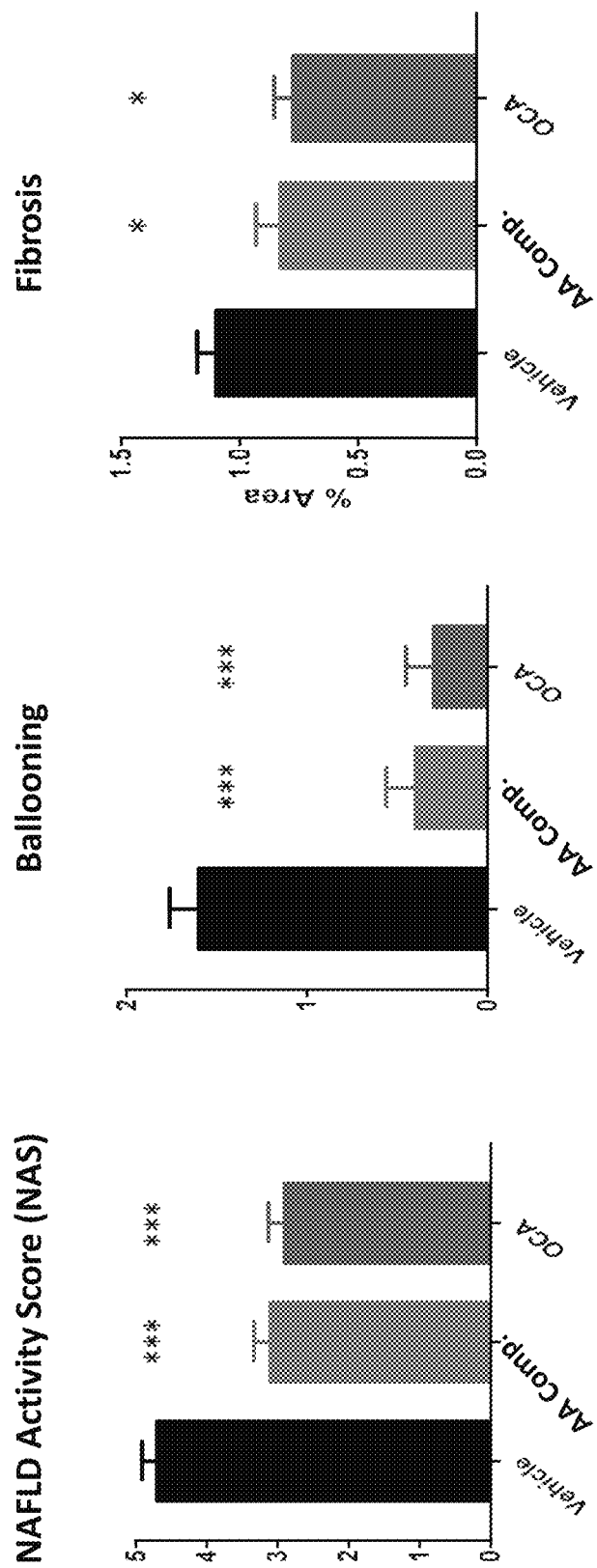
FIGS. 1A-1B are graphs showing the effect of treatment with an amino acid composition (Amino Acid Composition A-1) on the NAFLD activity score, ballooning, and fibrosis in the STAM mouse model (FIG. 1A) and in the FATZO mouse model (FIG. 1B).

observed in fixed liver tissues from FATZO mice after administration of the indicated amino acid compositions.

DETAILED DESCRIPTION

The present invention provides, at least in part, methods and compositions comprising at least four different amino acid entities. In some embodiments, the composition is capable of one, two, three, four, five, or six or all of:
  a) decreasing or preventing liver fibrosis;
  b) decreasing or preventing liver injury;
  c) decreasing or preventing hepatocyte inflammation;
  d) improving, e.g., increasing, glucose tolerance;
  e) decreasing or preventing steatosis;
  f) decreasing or preventing hepatocyte ballooning; or
  g) improving gut function.

In some embodiments, at least one amino acid entity in the compositions is not a peptide of more than 20 amino acid residues in length.

In some embodiments, the composition comprises a leucine (L)-amino acid entity, an arginine (R)-amino acid entity, a glutamine (Q)-amino acid entity; and an antioxidant or reactive oxygen species (ROS) scavenger (e.g., a N-acetylcysteine (NAC) entity, e.g., NAC). In some embodiments, at least one amino acid entity is not a peptide of more than 20 amino acid residues in length. In some embodiments, the composition is capable of improving gut barrier function.

The composition described herein can be administered to a subject to provide a beneficial effect in one or both of improving liver function or treating (e.g., revering, reducing, ameliorating, or preventing) a liver disease (e.g., a fatty liver disease). A subject that may be treated with the composition include a subject having non-alcoholic fatty liver disease (NAFLD; e.g., pediatric NAFLD), such as a subject with non-alcoholic steatohepatitis (NASH) or NAFL, or subjects with alcoholic fatty liver disease (AFLD), such as alcoholic steatohepatitis (ASH). In particular, the subject may have one, two, or more (e.g., all) of a high BMI, obesity, fibrosis, or cirrhosis. The subject may also have one, two, or more (e.g., all) of gut leakiness, gut dysbiosis, or gut microbiome disturbance.

The subject may exhibit an improvement in liver function or liver disease (e.g., NAFLD (e.g., NASH or NAFL) or AFLD (e.g., ASH)) after administration of a composition comprising a L-amino acid entity, a R-amino acid entity, a Q-amino acid entity; and an antioxidant or ROS scavenger, e.g., a NAC entity, e.g., NAC. For example, the amino acid entity composition may be administered to the subject for a treatment period of, e.g., two weeks, three weeks, four weeks, five weeks, six weeks, seven weeks, eight weeks, nine weeks, 10 weeks, 11 weeks, 12 weeks, 13 weeks, 14 weeks, 15 weeks, 16 weeks, or longer at a dose of about 15 total grams per day to about 90 total grams per day (e.g., a total of about 48 g or a total of about 72 g per day).

Treatment with the amino acid entity composition can result in improved liver function in a subject, e.g., by one, two, three, four, five or more (e.g., all) of increasing free fatty acid and lipid metabolism, improving mitochondrial function, browning of white adipose tissue (WAT), decreasing reactive oxygen species (ROS), increasing levels of glutathione (GSH), decreasing hepatic inflammation, improving gut barrier function, increasing insulin secretion, or improving glucose tolerance.

In some embodiments, the composition is for use as a medicament in improving liver function in a subject (e.g., a subject with a liver disease (e.g., NAFLD (e.g., NASH or NAFL) or AFLD (e.g., ASH)). In some embodiments, the composition including amino acid entities is for use as a medicament in treating (e.g., reversing, reducing, ameliorating, or preventing) a liver disease (e.g., NAFLD (e.g., NASH or NAFL) or AFLD (e.g., ASH)) in a subject.

In some embodiments, the composition is for use in the manufacture of a medicament for improving liver function in a subject (e.g., a subject with a liver disease (e.g., NAFLD (e.g., NASH or NAFL) or AFLD (e.g., ASH)). In some embodiments, the composition including amino acid entities is for use in the manufacture of a medicament for treating (e.g., reversing, reducing, ameliorating, or preventing) a liver disease (e.g., NAFLD (e.g., NASH or NAFL) or AFLD (e.g., ASH)) in a subject.

Additionally, the compositions can be used in methods of dietary management of a subject (e.g., a subject without a liver disease or with a liver disease (e.g., NAFLD (e.g., NASH or NAFL) or AFLD (e.g., ASH)).

One embodiment provides a nutritional supplement, dietary formulation, functional food, medical food, food, or beverage comprising a composition described herein. Another embodiment provides a nutritional supplement, dietary formulation, functional food, medical food, food, or beverage comprising a composition described herein for use in the management of any of the diseases or disorders described herein.

One embodiment provides a method of maintaining or improving liver health comprising administering to a subject an effective amount of a composition described herein. Another embodiment provides a method of providing nutritional support or supplementation to a subject with a liver disease (e.g., NAFLD (e.g., NASH or NAFL) or AFLD (e.g., ASH)) comprising administering to the subject an effective amount of a composition described herein. Yet another embodiment provides a method of providing nutritional supplementation that aids in the management of liver disease (e.g., NAFLD (e.g., NASH or NAFL) or AFLD (e.g., ASH)) comprising administering to the subject in need thereof an effective amount of a composition described herein.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise.

As used herein, the term "amino acid entity" refers to an amino acid in one or both of free form or salt form, an amino acid residue of a peptide (e.g., of a dipeptide, oligopeptide, or polypeptide), a derivative of an amino acid, a precursor of an amino acid, or a metabolite of an amino acid.

As used herein the term "XXX amino acid entity" refers to an amino acid entity that if a free amino acid, comprises free XXX or XXX in salt form; if a peptide, refers to a peptide comprising an XXX residue; if a derivative, refers to a derivative of XXX; if a precursor, refers to a precursor of XXX; and if a metabolite, refers to a XXX metabolite. For example, where XXX is leucine (L), then L-amino acid entity refers to free L or L in salt form, a peptide comprising a L residue, a L derivative, a L precursor, or a metabolite of L; where XXX is arginine (R), then R-amino acid entity refers to free R or R in salt form, a peptide comprising a R residue, a R derivative, a R precursor, or a metabolite of R; where XXX is glutamine (Q), then Q-amino acid entity refers to free Q or Q in salt form, a peptide comprising a Q residue, a Q derivative, a Q precursor, or a metabolite of Q;

and where XXX is N-acetylcysteine (NAC), then NAC-amino acid entity refers to free NAC or NAC in salt form, a peptide comprising a NAC residue, a NAC derivative, a NAC precursor, or a metabolite of NAC.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

An "amino acid" refers to an organic compound having an amino group (—NH$_2$), a carboxylic acid group (—C(=O) OH), and a side chain bonded through a central carbon atom, and includes essential and non-essential amino acids, as well as natural and unnatural amino acids.

The proteogenic amino acids, shown below, are known by three- and one-letter abbreviations in addition to their full names. For a given amino acid, these abbreviations are used interchangeably herein. For example, Leu, L or leucine all refer to the amino acid leucine; Ile, I or isoleucine all refer to the amino acid isoleucine; Val, V or valine all refer to the amino acid valine; Arg, R or arginine all refer to the amino acid arginine; and Gln, Q or glutamine all refer to the amino acid glutamine.

Likewise, the non-natural amino acid derivative N-acetylcysteine may be referred to interchangeably by "NAC" or "N-acetylcysteine."

Amino acids may be present as D- or L-isomers. Unless otherwise indicated, amino acids referred to herein are L-isomers of amino acids.

TABLE 1

Amino acid names and abbreviations.

| Amino acid | Three-letter | One-letter |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "effective amount" as used herein means an amount of an amino acid, or pharmaceutical composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of treatment, the nature of concurrent therapy, the particular active ingredient(s) being employed, the particular pharmaceutically-acceptable excipient(s) and/or carrier(s) utilized, and like factors with the knowledge and expertise of the attending physician.

A "pharmaceutical composition" described herein comprises at least one amino acid and a pharmaceutically acceptable carrier or excipient. In some embodiments, the pharmaceutical composition is used as a therapeutic, a nutraceutical, a medical food, or as a supplement.

The term "pharmaceutically acceptable" as used herein, refers to amino acids, materials, excipients, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A composition, formulation or product is "therapeutic" if it provides a beneficial clinical effect. A beneficial clinical effect can be shown by lessening the progression of a disease and/or alleviating one or more symptoms of the disease.

A "unit dose" or "unit dosage" as used herein means an amount or dose of medicine prepared in an individual packet or container for convenience, safety, or monitoring. A "unit dose" or "unit dosage" comprises the drug product or drug products in the form in which they are marketed for use, with a specific mixture of active ingredients and inactive components (excipients), in a particular configuration (such as a capsule shell, for example), and apportioned into a particular dose.

As used herein, the terms "treat," "treating," or "treatment" of a liver disease refer in one embodiment, to ameliorating, e.g., NAFLD (e.g., NASH or NAFL) or AFLD (e.g., ASH), (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating a symptom of a liver disease (e.g., NAFLD (e.g., NASH or NAFL) or AFLD (e.g., ASH)), either physically, (e.g., stabilization of a discernible symptom), physiologically, (e.g., stabilization of a physical parameter), or both. In yet another embodiment, "treat," "treating," or "treatment" refers to preventing or delaying the onset or development or progression of a liver disease (e.g., NAFLD (e.g., NASH or NAFL) or AFLD (e.g., ASH)).

Determination of Amino Acid Weight Percent and Amino Acid Ratios in a Composition The weight ratio of a particular amino acid or particular amino acids in a composition or mixture of amino acids is the ratio of the weight of the particular amino acid or amino acids in the composition or mixture compared to the total weight of amino acids present in the composition or mixture. This value is calculated by dividing the weight of the particular amino acid or of the particular amino acids in the composition or mixture by the weight of all amino acids present in the composition or mixture.

Compositions Comprising Amino Acid Entities

The present disclosure provides compositions, e.g., pharmaceutical compositions, comprising amino acid entities. These pharmaceutical compositions are made up of amino acid entities including amino acids in one or both of free form or salt form, amino acid residues of a peptide (e.g., of a dipeptide, oligopeptide, or polypeptide), derivatives of an amino acid, precursors of an amino acid, or metabolites of an amino acid. For example, the compositions can include a leucine (L)-amino acid entity, a arginine (R)-amino acid entity, a glutamine (Q)-amino acid entity; and an antioxidant or reactive oxygen species (ROS) scavenger, e.g., a N-acetylcysteine (NAC) entity, e.g., NAC (Table 2). In particular, at least one amino acid entity is not a peptide of more than 20 amino acid residues in length.

TABLE 2

Amino acid entities include amino acids, precursors, metabolites, and derivatives of the compositions described herein.

| | Exemplary Amino Acid | Precursors | Metabolites | Derivatives |
|---|---|---|---|---|
| L | L-Leucine | Oxo-leucine | HMB (beta-hydroxy-beta-methybutyrate); Oxo-leucine; Isovaleryl-CoA | D-Leucine; N-Acetyl-Leucine |
| I | L-Isoleucine | 2-Oxo-3-methyl-valerate; Threonine | 2-Oxo-3-methyl-valerate; Methylbutyrl-CoA | D-Isoleucine; N-Acetyl-Isoleucine |
| V | L-Valine | 2-Oxo-valerate | Isobutryl-CoA; 3-HIB-CoA; 3-HIB | D-Valine; N-Acetyl-Valine |
| R | L-Arginine | Argininosuccinate; Citrulline; Aspartate; Glutamate | Ornithine; Citrulline; Agmatine; Creatine | D-Arginine; N-Acetyl-Arginine; |
| Q | L-Glutamine | Glutamate | Carbamoyl-P; Glutamate | D-Glutamine; N-Acetyl-Glutamine; |
| NAC | N-Acetyl-cysteine | Serine; Acetylserine; Cystathionine; | Glutathione; Cystathionine; Homocysteine; Methionine | D-Cysteine; L-Cysteine; Cystine; Cysteamine |
| S | L-Serine | Phosphoserine, P-hydroxypyruvate, L-Glycine | Glycine, Tryptophan, Acetylserine, Cystathionine, Phosphatidylserine | |

It is contemplated that alternatives to serine that can be an S-amino acid entity include, for example, glycine, threonine, or a combination of serine and glycine (e.g., a 1:1 ratio of serine and glycine).

In some embodiments, the total weight of the L-amino acid entity, R-amino acid entity, Q-amino acid entity; and ROS scavenger, e.g., a NAC entity, e.g., NAC, is greater than the total wt. of other amino acid entities in the composition. In certain embodiments, two, three, or more (e.g., all) of methionine (M), trytophan (W), or valine (V) may be absent from the amino acid entity composition, or if present, are present at less than 2 weight (wt.) %.

In some embodiments, one or both of the R-amino acid entity and the Q-amino acid entity are present at a higher amount (wt. %) than the L-amino acid entity. The R-amino acid entity can be present, e.g., at an amount of at least 2 wt. %, at least 3 wt. %, at least 4 wt. %, at least 5 wt. %, at least 6 wt. %, at least 7 wt. %, or at least 8 wt. % greater than the L-amino acid entity. The Q-amino acid entity can be present, e.g., at an amount of at least 2 wt. %, at least 3 wt. %, at least 4 wt. %, or at least 5 wt. % greater than the L-amino acid entity.

In some embodiments, the L-amino acid entity is selected from the group consisting of a precursor, a metabolite, and a derivative. In certain embodiments, the L-amino acid entity is selected from the group consisting of L-leucine, β-hydroxy-β-methybutyrate (HMB), oxo-leucine, isovaleryl-CoA, D-leucine, and n-acetylleucine. In one embodiment, the L-amino acid entity is L-leucine. In another embodiment, the L-amino acid entity is HMB.

In some embodiments, the R-amino acid entity is selected from the group consisting of a precursor, a metabolite, and a derivative. In certain embodiments, the R-amino acid entity is selected from the group consisting of L-arginine, D-arginine, ornithine, argininosuccinate, citrulline, aspartate, glutamate, agmatine, and N-acetyl-arginine. In one embodiment, the R-amino acid entity is L-arginine. In one embodiment, the R-amino acid entity is creatine. In another embodiment, the R-amino acid entity is ornithine.

In some embodiments, the Q-amino acid entity is selected from the group consisting of a precursor, a metabolite, and a derivative. In certain embodiments, the Q-amino acid entity is selected from the group consisting of L-glutamine, glutamate, carbamoyl-P, glutamate, D-glutamine, and n-acetylglutamine. In one embodiment, the Q-amino acid entity is L-glutamine.

In some embodiments, the NAC-amino acid entity is selected from the group consisting of a precursor, a metabolite, and a derivative. In certain embodiments, the NAC-amino acid entity is selected from the group consisting NAC, serine, acetylserine, cystathionine, cystathionine, homocysteine, methionine, glutathione, D-cysteine, and L-cysteine. In one embodiment, the NAC entity is NAC. In one embodiment, the NAC entity is glutathione.

In various embodiments, the composition further comprises one or two additional branched-chain amino acid (BCAA)-entities, e.g., one or both of an isoleucine (I)-amino acid-entity and a valine (V)-amino acid-entity. In some embodiments, both the I-amino acid-entity and the V-amino acid-entity are present. In certain embodiments, the L-entity is present at a higher amount (% by weight) than one or both of the I-amino acid-entity and the V-amino acid-entity (e.g., the L-entity is present at an amount of at least 10 wt. %, at least 15 wt. %, at least 20 wt. %, at least 25 wt. %, at least 30 wt. %, at least 35 wt. %, at least 40 wt. %, at least 45 wt. %, or at least 50 wt. % greater than one or both of the I-amino acid-entity and the V-amino acid-entity).

In some embodiments, the I-amino acid entity is selected from the group consisting of a salt, a precursor, a metabolite, and a derivative. In certain embodiments, the I-amino acid entity is selected from the group consisting of L-isoleucine, 2-oxo-3-methyl-valerate, threonine, 2-oxo-3-methyl-valerate, methylbutyrl-CoA, D-isoleucine, and N-acetyl-isoleucine. In one embodiment, the I-amino acid entity is L-isoleucine.

In some embodiments, the V-amino acid entity is selected from the group consisting of a precursor, a metabolite, and a derivative. In certain embodiments, the V-amino acid entity is selected from the group consisting of L-valine, 2-oxo-valerate, isobutryl-CoA, 3-HIB-CoA, 3-HIB, D-valine, and N-acetyl-valine. In one embodiment, the I-amino acid entity is L-valine.

In some embodiments, the composition comprises L-leucine or a leucine metabolite (e.g., HMB), L-arginine or an L-arginine metabolite (e.g., creatine or ornithine), L-glutamine, and NAC or a NAC metabolite, e.g., glutathione. In one embodiment, the composition comprises L-leucine, L-arginine, L-glutamine, and NAC. In one embodiment, the composition comprises HMB, creatine, L-glutamine, and glutathione. In one embodiment, the composition comprises HMB, ornithine, L-glutamine, and glutathione. In one embodiment, the composition comprises HMB, L-arginine, L-glutamine, and NAC. In one embodiment, the composition comprises L-leucine, creatine, L-glutamine, and NAC. In one embodiment, the composition comprises L-leucine, ornithine, L-glutamine, and NAC. In one embodiment, the composition comprises L-leucine, L-arginine, L-glutamine, and glutathione.

In some embodiments, the weight (wt.) ratio of the L-amino acid entity, the R-amino acid entity, the Q-amino acid entity, and the NAC-amino acid entity is about 0.5 to 3:0.5 to 4:1 to 4:0.1 to 2.5. In one embodiment, the wt. ratio of the L-amino acid entity, the R-amino acid entity, the Q-amino acid entity, and the NAC-amino acid entity is about 1:1.5:2:0.15.

In some embodiments, the wt. ratio of the L-amino acid entity, the I-amino acid entity, the V-amino acid entity, the R-amino acid entity, the Q-amino acid entity, and the NAC-amino acid entity is about 0.5 to 2:0.1 to 1:0.1 to 1:0.5 to 3:0.5 to 4:0.1 to 0.5. In an embodiment, the wt. ratio of the L-amino acid entity, the I-amino acid entity, the V-amino acid entity, the R-amino acid entity, the Q-amino acid entity, and the NAC-amino acid entity is about 1:0.5:0.5:1.5:2:0.15.

In various embodiments, the total wt. of amino acids present is about 2 g to about 60 g. In certain embodiments, the total wt. of amino acids present is about 6 g, about 12 g, about 18 g, about 24 g, or about 48 g. In one embodiment, the total wt. of amino acids present is about 6 g. In one embodiment, the total wt. of amino acids present is about 12 g. In one embodiment, the total wt. of amino acids present is about 18 g. In an embodiment, the total wt. of amino acids present is about 24 g. In one embodiment, the total wt. of amino acids present is about 48 g.

In some embodiments, the composition comprises about 0.5 g to about 10 g of the L-amino acid entity, about 0.25 g to about 5 g of the I-amino acid entity, about 0.25 g to about 5 g of the V-amino acid entity, about 1 g to about 20 g of the R-amino acid entity, about 1 g to about 20 g of the Q-amino acid entity, and about 0.1 g to about 5 g of the NAC-amino acid entity. In an embodiment, the composition comprises about 1 g of the L-amino acid entity, about 0.5 g of the I-amino acid entity, about 0.5 g of V-amino acid entity, about 1.5 g of R-amino acid entity, about 2 g of Q-amino acid entity, and about 0.15 g of NAC-amino acid entity. In an embodiment, the composition comprises about 2 g of the L-amino acid entity, about 1 g of the I-amino acid entity, about 1 g of the V-amino acid entity, about 3 g of the R-amino acid entity, about 4 g of the Q-amino acid entity, and about 0.3 g of the NAC-amino acid entity. In an embodiment, the composition comprises about 4 g of the L-amino acid entity, about 2 g of the I-amino acid entity, about 2 g of the V-amino acid entity, about 6 g of the R-amino acid entity, about 8 g of the Q-amino acid entity, and about 0.6 g of the NAC-amino acid entity.

In some embodiments, the amino acids comprise about 10 wt % to about 30 wt % leucine, about 5 wt % to about 15 wt % isoleucine, about 5 wt % to about 15 wt % valine, about 15 wt % to about 40 wt % arginine, about 20 wt % to about 50 wt % glutamine, and about 1 wt % to about 8 wt % n-acetylcysteine. In certain embodiments, the amino acids comprise about 16 wt % to about 18 wt % leucine, about 7 wt % to about 9 wt % isoleucine, about 7 wt % to about 9 wt % valine, about 28 wt % to about 32 wt % arginine, about 31 wt % to about 34 wt % glutamine, and about 1 wt % to about 5 wt % n-acetylcysteine. In an embodiment, the amino acids comprise about 16.8 wt % leucine, about 8.4 wt % isoleucine, about 8.4 wt % valine, about 30.4 wt % arginine, about 33.6 wt % glutamine, and about 2.5 wt % n-acetylcysteine.

In any of the foregoing embodiments, at least one amino acid entity is a free amino acid, e.g., one, two, three, or more (e.g., all) amino acid entities are a free amino acid. In some embodiments, the L-amino acid entity, the R-amino acid entity, the Q-amino acid entity, and the NAC-amino acid entity is a free amino acid. In certain embodiment, the L-amino acid entity, the I-amino acid entity, the V-amino acid entity, the R-amino acid entity, the Q-amino acid entity, and the NAC-amino acid entity a free amino acid.

In any of the foregoing embodiments, at least one amino acid entity is in a salt form, e.g., one, two, three, or more (e.g., all) of the amino acid entities is in a salt form. In some embodiments, wherein the L-amino acid entity, the R-amino acid entity, the Q-amino acid entity, and the NAC-amino acid entity is in a salt form. In certain embodiments, the L-amino acid entity, the I-amino acid entity, the V-amino acid entity, the R-amino acid entity, the Q-amino acid entity, and the NAC-amino acid entity is in a salt form.

In any of the foregoing embodiments, the composition comprises a combination of 2 to 20 different amino acid entities, e.g., 5 to 15 different amino acid entities.

In some embodiments, the NAC entity is more stable than cysteine. In certain embodiments, the NAC entity does not comprise cysteine.

In some embodiments, the composition further comprises one, two, three, four, five, six, seven, eight, nine, ten, or more (e.g., all) or more of serine, glycine, glutamine, HMB, arginine, L-leucine, citrulline, glutamine, ornithine, L-cysteine, cystine, or glutathione.

In some embodiments, the composition further comprises serine.

In some embodiments, the composition further comprises glycine.

In some embodiments, the composition further comprises carnitine.

In some embodiments, the composition includes arginine, glutamine, N-acetylcysteine, and a branched-chain amino acid (BCAA) chosen from one, two, or all of leucine, isoleucine, and valine.

In some embodiments, the BCAA is leucine.
In some embodiments, the BCAA is isoleucine.
In some embodiments, the BCAA is valine.
In some embodiments, the BCAA is leucine and isoleucine.
In some embodiments, the BCAA is leucine and valine.
In some embodiments, the BCAA is isoleucine and valine.
In some embodiments, the BCAA is leucine, isoleucine, and valine.

In particular, the composition may consist of leucine, isoleucine, valine, arginine, glutamine, and N-acetylcysteine.

In some embodiments, the amino acids leucine, isoleucine, valine, arginine, glutamine and N-acetylcysteine are present in a weight ratio of about 1:0.5:0.5:1.5:2:0.1-0.3. In some embodiments, the amino acids leucine, isoleucine, valine, arginine, glutamine and N-acetylcysteine are present in a weight ratio of about 1:0.5:0.5:1.5:2:0.15. In some embodiments, the amino acids leucine, isoleucine, valine, arginine, glutamine and N-acetylcysteine are present in a weight ratio of about 1:0.5:0.5:1.5:2:0.25.

In some embodiments, the amino acids leucine, isoleucine, valine, arginine (e.g., arginine HCl), glutamine and N-acetylcysteine are present in a weight ratio of about 1:0.5:0.5:1.5-1.81:2:0.1-0.3. In some embodiments, the amino acids leucine, isoleucine, valine, arginine (e.g., arginine HCl), glutamine and N-acetylcysteine are present in a weight ratio of about 1:0.5:0.5:1.5-1.81:2:0.15. In some embodiments, the amino acids leucine, isoleucine, valine, arginine (e.g., arginine HCl), glutamine, and N-acetylcysteine are present in a weight ratio of about 1:0.5:0.5:1.5-1.81:2:0.25.

In some embodiments, the amino acids leucine, isoleucine, valine, arginine (e.g., arginine HCl), glutamine and N-acetylcysteine are present in a weight ratio of about 1:0.5:0.5:1.81:2:0.1-0.3. In some embodiments, the amino acids leucine, isoleucine, valine, arginine (e.g., arginine HCl), glutamine and N-acetylcysteine are present in a weight ratio of about 1:0.5:0.5:1.81:2:0.15. In some embodiments, the amino acids leucine, isoleucine, valine, arginine (e.g., arginine HCl), glutamine, and N-acetylcysteine are present in a weight ratio of about 1:0.5:0.5:1.81:2:0.25.

In some embodiments, the amino acids leucine, isoleucine, valine, arginine HCl, glutamine and N-acetylcysteine are present in a weight ratio of about 1:0.5:0.5:1.5:2:0.1 to 0.3. In some embodiments, the amino acids leucine, isoleucine, valine, arginine HCl, glutamine and N-acetylcysteine are present in a weight ratio of about 1:0.5:0.5:1.5:2:0.25. In some embodiments, the amino acids leucine, isoleucine, valine, arginine HCl, glutamine and N-acetylcysteine are present in a weight ratio of 1:0.5:0.5:1.5:2:0.15.

In some embodiments, the amino acids leucine, isoleucine, valine, arginine HCl, glutamine and N-acetylcysteine are present in a weight ratio of about 1:0.5:0.5:1.81:2:0.1 to 0.3. In some embodiments, the amino acids leucine, isoleucine, valine, arginine HCl, glutamine and N-acetylcysteine are present in a weight ratio of about 1:0.5:0.5:1.81:2:0.25. In some embodiments, the amino acids leucine, isoleucine, valine, arginine HCl, glutamine and N-acetylcysteine are present in a weight ratio of 1:0.5:0.5:1.81:2:0.15.

In some embodiments, the amino acids leucine, isoleucine, valine, arginine, glutamine and N-acetylcysteine are present in a weight ratio of about 1:0.5:0.5:1.81:2:0.1-0.3. In some embodiments, the amino acids leucine, isoleucine, valine, arginine, glutamine and N-acetylcysteine are present in a weight ratio of about 1:0.5:0.5:1.81:2:0.15. In some embodiments, the amino acids leucine, isoleucine, valine, arginine, glutamine, and N-acetylcysteine are present in a weight ratio of about 1:0.5:0.5:1.81:2:0.25.

In some embodiments, the amino acids leucine, isoleucine, valine, arginine, glutamine and N-acetylcysteine are present in a weight ratio of about 1:0.5:0.5:1.5:2:0.1 to 0.3. In some embodiments, the amino acids leucine, isoleucine, valine, arginine, glutamine and N-acetylcysteine are present in a weight ratio of about 1:0.5:0.5:1.5:2:0.25. In some embodiments, the amino acids leucine, isoleucine, valine, arginine, glutamine and N-acetylcysteine are present in a weight ratio of 1:0.5:0.5:1.5:2:0.15.

In some embodiments, a total weight (wt) of the amino acids is about 2 g to about 60 g. In some embodiments, the total weight of amino acids present is about 5 g, about 6 g, about 7 g, about 11 g, about 12 g, about 13 g, about 14 g, about 15 g, about 16 g, about 17 g, about 18 g, about 19 g, about 20 g, about 21 g, about 22 g, about 23 g, about 24 g, about 25 g, about 26 g, about 27 g, about 28 g, about 29 g, about 30 g, about 31 g, about 32 g, about 33 g, about 34 g, about 35 g, about 36 g, about 37 g, about 38 g, about 39 g, about 40 g, about 41 g, about 42 g, about 43 g, about 44 g, about 45 g, about 46 g, about 47 g, about 48 g, about 49 g, or about 50 g.

In certain embodiments, the total wt of the amino acids is about 6 g.

In certain embodiments, the total wt of the amino acids is about 12 g.

In certain embodiments, the total wt of the amino acids is about 18 g.

In certain embodiments, the total wt of the amino acids is about 24 g.

In certain embodiments, the total wt of the amino acids is about 48 g.

In some embodiments, the composition includes about 0.5 g to about 10 g of leucine, about 0.25 g to about 5 g of isoleucine, about 0.25 g to about 5 g of valine, about 1 g to about 20 g of arginine, about 1 g to about 20 g of glutamine, and about 0.1 g to about 5 g of N-acetylcysteine.

In some embodiments, the composition includes at least 1 g of leucine, at least 0.5 g of isoleucine, at least 0.5 g of valine, at least 1.5 g of arginine (or 1.81 g of arginine HCl), at least 2 g of glutamine, and at least 0.15 g of N-acetylcysteine.

In some embodiments, the composition includes about 1 g of leucine, about 0.5 g of isoleucine, about 0.5 g of valine, about 1.5 g of arginine (or 1.81 g of arginine HCl), about 2 g of glutamine, and about 0.15 g of N-acetylcysteine.

In some embodiments, the composition includes at least 2 g of leucine, at least 1 g of isoleucine, at least 1 g of valine, at least 3.0 g of arginine (or 3.62 g of arginine HCl), at least 4 g of glutamine, and at least 0.3 g of N-acetylcysteine.

In some embodiments, the composition includes about 2 g of leucine, about 1 g of isoleucine, about 1 g of valine, about 3.0 g of arginine (or 3.62 g of arginine HCl), about 4 g of glutamine, and about 0.3 g of N-acetylcysteine.

In some embodiments, the composition includes at least 4 g of leucine, at least 2 g of isoleucine, at least 2 g of valine, at least 6.0 g or arginine (or 7.24 g of arginine HCl), at least 8 g of glutamine, and at least 0.6 g of N-acetylcysteine.

In some embodiments, the composition includes about 4 g of leucine, about 2 g of isoleucine, about 2 g of valine, about 6.0 g or arginine (or 7.24 g of arginine HCl), about 8 g of glutamine, and about 0.6 g of N-acetylcysteine.

In some embodiments, the composition includes at least 1.0 g of leucine, at least 0.5 g of isoleucine, at least 0.5 g of valine, at least 1.5 g of arginine, at least 2.0 g of glutamine, or at least 0.15 g of N-acetylcysteine. In some embodiments, the composition includes about 1.0 g of leucine, about 0.5 g of isoleucine, about 0.5 g of valine, about 1.5 g of arginine, about 2.0 g of glutamine, or about 0.15 g of N-acetylcysteine.

In some embodiments, the composition includes at least 1.0 g of leucine, at least 0.5 g of isoleucine, at least 0.5 g of valine, at least 1.5 g of arginine, at least 2.0 g of glutamine, and at least 0.25 g of N-acetylcysteine. In some embodiments, the composition includes about 1.0 g of leucine, about 0.5 g of isoleucine, about 0.5 g of valine, about 1.5 g of arginine, about 2.0 g of glutamine, and about 0.25 g of N-acetylcysteine.

In some embodiments, the amino acids of the composition include about 10 wt % to about 30 wt % leucine, about 5 wt % to about 15 wt % isoleucine, about 5 wt % to about 15 wt % valine, about 15 wt % to about 40 wt % arginine, about 20 wt % to about 50 wt % glutamine, and about 1 wt % to about 8 wt % n-acetylcysteine.

In some embodiments, the amino acids of the composition include about 16 wt % to about 18 wt % leucine, about 7 wt % to about 9 wt % isoleucine, about 7 wt % to about 9 wt % valine, about 28 wt % to about 32 wt % arginine, about 31 wt % to about 34 wt % glutamine, and about 1 wt % to about 5 wt % n-acetylcysteine.

In some embodiments, the amino acids of the composition include about 16.8 wt % leucine, about 8.4 wt % isoleucine, about 8.4 wt % valine, about 30.4 wt % arginine, about 33.6 wt % glutamine, and about 2.5 wt % n-acetylcysteine.

In some embodiments, the composition comprises one or more excipients selected from the group consisting of: citric acid, lecithin, a sweetener, a dispersion enhancer, a flavoring, a bitterness masking agent, and a natural or artificial coloring.

In some embodiments, the composition comprises citric acid.

In some embodiments, the composition is in the form of a solid, powder, solution, or gel. In certain embodiments, the composition is in the form of a powder (e.g. in a packet)

In some embodiments, the composition includes one or more pharmaceutically acceptable excipients, wherein the amino acids comprise leucine, arginine, glutamine, and N-acetylcysteine. An aspect of the present disclosure provides a composition comprising free amino acids and one or more pharmaceutically acceptable excipients, wherein the amino acids consist of leucine, arginine, glutamine, and N-acetylcysteine. In some embodiments, the amino acids leucine, arginine, glutamine, N-acetylcysteine and glycine are present in a weight ratio of 1:1.5:2:0.15. In some embodiments, the composition comprises at least 1.0 g of leucine, at least 1.5 g of arginine, at least 2.0 g of glutamine, or at least 0.15 g of N-acetylcysteine. In some embodiments, the composition comprises at least 1.5 g of arginine and at least 2.0 g of glutamine. In some embodiments, the amino acids leucine, arginine, glutamine, and N-acetylcysteine are present in weight % of each compared to total amino acid weight of 20.4 to 22.6%, 30.6 to 33.9%, 40.9 to 45.2%, and 3.1 to 3.4%, respectively. In some embodiments, the amino acids leucine, arginine, glutamine, and N-acetylcysteine, are present in weight % of each compared to total amino acid weight of 21.5%, 32.3%, 43.0%, and 3.2%, respectively.

In some embodiments, the composition further includes a farnesoid X receptor (FXR) agonist, a stearoyl CoA desaturase inhibitor, a CCR2 and CCR5 chemokine antagonist, a PPAR alpha and delta agonist, a caspase inhibitor, a galectin-3 inhibitor, an acetyl CoA carboxylase inhibitor, or an ileal sodium bile acid co-transporter inhibitor. In some embodiments, the composition further comprises an FXR agonist. In certain embodiments, the FXR agonist is obeticholic acid. In some embodiments, the composition further includes one or more of: LMB-763, LJN-452, emricasan, and cenicriviroc.

An exemplary Amino Acid Composition includes leucine, isoleucine, valine, arginine HCl, glutamine, and N-acetylcysteine as its amino acid entities in a wt. ratio of 1:0.5:0.5:1.81:2:0.15 (Table 3). An exemplary Amino Acid Composition includes leucine, isoleucine, valine, arginine, glutamine, and N-acetylcysteine as its amino acid entities in a wt. ratio of 1:0.5:0.5:1.5:2:0.15 (Table 4).

TABLE 3

Exemplary amino acid components of the composition including Arginine HCl.

| Amino acid | wt. ratio | wt. % | g/packet | g dose #1 | g dose #2 |
|---|---|---|---|---|---|
| Leucine | 1 | 16.78 | 1.00 g | 2 g | 4 g |
| Isoleucine | 0.5 | 8.39 | 0.50 g | 1 g | 2 g |
| Valine | 0.5 | 8.39 | 0.50 g | 1 g | 2 g |
| Arginine HCl | 1.81 | 30.37 | 1.81 g | 3.62 g | 7.24 g |
| Glutamine | 2 | 33.56 | 2.00 g | 4 g | 8 g |
| N-acetylcysteine | 0.15 | 2.52 | 0.15 g | 0.3 g | 0.6 g |
| Total amino acids | | | 5.96 g | ~12 g | ~24 g |

TABLE 4

Exemplary amino acid components of the composition including Arginine.

| Amino acid | wt. ratio | wt. % | g/packet | g dose #1 | g dose #2 |
|---|---|---|---|---|---|
| Leucine | 1 | 17.70 | 1.00 g | 2 | 4 |
| Isoleucine | 0.5 | 8.85 | 0.50 g | 1 | 2 |

TABLE 4-continued

Exemplary amino acid components of the composition including Arginine.

| Amino acid | wt. ratio | wt. % | g/packet | g dose #1 | g dose #2 |
|---|---|---|---|---|---|
| Valine | 0.5 | 8.85 | 0.50 g | 1 | 2 |
| Arginine | 1.5 | 26.55 | 1.5 g | 3 | 6 |
| Glutamine | 2 | 35.4 | 2.00 g | 4 | 8 |
| N-acetylcysteine | 0.15 | 2.65 | 0.15 g | 0.3 | 0.6 |
| Total amino acids | | | 5.65 g | 11.3 g | 22.6 g |

An exemplary Amino Acid Composition includes leucine, isoleucine, valine, arginine HCl, glutamine, and N-acetylcysteine as its amino acid entities in a wt. ratio of 1:0.5:0.5:0.905:2:0.15 (Table 5). An exemplary Amino Acid Composition includes leucine, isoleucine, valine, arginine, glutamine, and N-acetylcysteine as its amino acid entities in a wt. ratio of 1:0.5:0.5:0.75:2:0.15 (Table 6).

TABLE 5

Exemplary amino acid components of the composition including Arginine HCl.

| Amino acid | wt. ratio | wt. % | g/packet | g dose #1 | g dose #2 |
|---|---|---|---|---|---|
| Leucine | 1 | 19.78 | 1.00 g | 2 g | 4 g |
| Isoleucine | 0.5 | 9.89 | 0.50 g | 1 g | 2 g |
| Valine | 0.5 | 9.89 | 0.50 g | 1 g | 2 g |
| Arginine HCl | 0.905 | 17.90 | 0.905 g | 1.81 g | 3.62 g |
| Glutamine | 2 | 39.56 | 2.00 g | 4 g | 8 g |
| N-acetylcysteine | 0.15 | 2.97 | 0.15 g | 0.3 g | 0.6 g |
| Total amino acids | | | 5.06 g | ~10 g | ~20 g |

TABLE 6

Exemplary amino acid components of the composition including Arginine.

| Amino acid | wt. ratio | wt. % | g/packet | g dose #1 | g dose #2 |
|---|---|---|---|---|---|
| Leucine | 1 | 20.41 | 1.00 g | 2 | 4 |
| Isoleucine | 0.5 | 10.20 | 0.50 g | 1 | 2 |
| Valine | 0.5 | 10.20 | 0.50 g | 1 | 2 |
| Arginine | 0.75 | 15.31 | 0.75 g | 1.5 | 3 |
| Glutamine | 2 | 40.82 | 2.00 g | 4 | 8 |
| N-acetylcysteine | 0.15 | 3.06 | 0.15 g | 0.3 | 0.6 |
| Total amino acids | | | 4.9 g | 9.8 g | 19.6 g |

An exemplary Amino Acid Composition includes leucine, isoleucine, valine, arginine HCl, glutamine, and N-acetylcysteine as its amino acid entities in a wt. ratio of 1:0.5:0.25:0.905:1:0.225 (Table 7). An exemplary Amino Acid Composition includes leucine, isoleucine, valine, arginine, glutamine, and N-acetylcysteine as its amino acid entities in a wt. ratio of 1:0.5:0.25:0.75:1:0.225 (Table 8).

TABLE 7

Exemplary amino acid components of the composition including Arginine HCl.

| Amino acid | wt. ratio | wt. % | g/packet | g dose #1 | g dose #2 |
|---|---|---|---|---|---|
| Leucine | 1 | 25.77 | 1.00 g | 2 g | 4 g |
| Isoleucine | 0.5 | 12.89 | 0.50 g | 1 g | 2 g |

TABLE 7-continued

Exemplary amino acid components of the composition including Arginine HCl.

| Amino acid | wt. ratio | wt. % | g/packet | g dose #1 | g dose #2 |
|---|---|---|---|---|---|
| Valine | 0.25 | 6.44 | 0.25 g | 0.50 g | 1 g |
| Arginine HCl | 0.905 | 23.32 | 0.905 g | 1.81 g | 3.62 g |
| Glutamine | 1 | 25.77 | 1.00 g | 2 g | 4 g |
| N-acetylcysteine | 0.225 | 5.80 | 0.225 g | 0.45 g | 0.9 g |
| Total amino acids | | | 3.88 g | 7.76 g | 15.52 g |

TABLE 8

Exemplary amino acid components of the composition including Arginine.

| Amino acid | wt. ratio | wt. % | g/packet | g dose #1 | g dose #2 |
|---|---|---|---|---|---|
| Leucine | 1 | 26.85 | 1.00 g | 2 | 4 |
| Isoleucine | 0.5 | 13.42 | 0.50 g | 1 | 2 |
| Valine | 0.25 | 6.71 | 0.25 g | 0.5 | 1 |
| Arginine | 0.75 | 20.13 | 0.75 g | 1.5 | 3 |
| Glutamine | 1 | 26.85 | 1.00 g | 2 | 4 |
| N-acetylcysteine | 0.225 | 6.04 | 0.225 g | 0.45 | 0.9 |
| Total amino acids | | | 3.725 g | 7.45 g | 14.9 g |

An exemplary Amino Acid Composition includes leucine, isoleucine, valine, arginine HCl, glutamine, N-acetylcysteine, and serine as its amino acid entities in a wt. ratio of 1:0.5:0.25:0.905:1:0.225:0.667 (Table 9). An exemplary Amino Acid Composition includes leucine, isoleucine, valine, arginine, glutamine, N-acetylcysteine, and serine as its amino acid entities in a wt. ratio of 1:0.5:0.25:0.75:1:0.225:1.5 (Table 10).

TABLE 9

Exemplary amino acid components of the composition including Arginine HCl.

| Amino acid | wt. ratio | wt. % | g/packet | g dose #1 | g dose #2 |
|---|---|---|---|---|---|
| Leucine | 1 | 18.59 | 1.00 g | 2 g | 4 g |
| Isoleucine | 0.5 | 9.29 | 0.50 g | 1 g | 2 g |
| Valine | 0.25 | 4.65 | 0.25 g | 0.50 g | 1 g |
| Arginine HCl | 0.905 | 16.82 | 0.905 g | 1.81 g | 3.62 g |
| Glutamine | 1 | 18.59 | 1.00 g | 2 g | 4 g |
| N-acetylcysteine | 0.225 | 4.18 | 0.225 g | 0.45 g | 0.9 g |
| Serine | 1.5 | 27.88 | 1.5 | 3 | 6 |
| Total amino acids | | | 5.38 g | 10.76 g | 21.52 g |

TABLE 10

Exemplary amino acid components of the composition including Arginine.

| Amino acid | wt. ratio | wt. % | g/packet | g dose #1 | g dose #2 |
|---|---|---|---|---|---|
| Leucine | 1 | 19.14 | 1.00 g | 2 | 4 |
| Isoleucine | 0.5 | 9.57 | 0.50 g | 1 | 2 |
| Valine | 0.25 | 4.78 | 0.25 g | 0.5 | 1 |
| Arginine | 0.75 | 14.35 | 0.75 g | 1.5 | 3 |
| Glutamine | 1 | 19.14 | 1.00 g | 2 | 4 |
| N-acetylcysteine | 0.225 | 4.31 | 0.225 g | 0.45 | 0.9 |
| Serine | 1.5 | 28.71 | 1.5 | 3 | 6 |
| Total amino acids | | | 5.225 | 10.45 | 20.9 |

An exemplary Amino Acid Composition includes leucine, isoleucine, valine, arginine HCl, glutamine, N-acetylcysteine, and serine as its amino acid entities in a wt. ratio of 1:0.5:0.25:0.905:1:0.225:0.667 (Table 11). An exemplary Amino Acid Composition includes leucine, isoleucine, valine, arginine, glutamine, N-acetylcysteine, and serine as its amino acid entities in a wt. ratio of 1:0.5:0.25:0.75:1:0.225:1.667 (Table 12).

TABLE 11

Exemplary amino acid components of the composition including Arginine HCl.

| Amino acid | wt. ratio | wt. % | g/packet | g dose #1 | g dose #2 |
|---|---|---|---|---|---|
| Leucine | 1 | 18.02 | 1.00 g | 2 g | 4 g |
| Isoleucine | 0.5 | 9.01 | 0.50 g | 1 g | 2 g |
| Valine | 0.25 | 4.50 | 0.25 g | 0.50 g | 1 g |
| Arginine HCl | 0.905 | 16.31 | 0.905 g | 1.81 g | 3.62 g |
| Glutamine | 1 | 18.02 | 1.00 g | 2 g | 4 g |
| N-acetylcysteine | 0.225 | 4.05 | 0.225 g | 0.45 g | 0.9 g |
| Serine | 1.667 | 30.09 | 1.67 g | 3.33 g | 6.67 g |
| Total amino acids | | | 5.55 g | 11.09 g | 22.19 g |

TABLE 12

Exemplary amino acid components of the composition including Arginine.

| Amino acid | wt. ratio | wt. % | g/packet | g dose #1 | g dose #2 |
|---|---|---|---|---|---|
| Leucine | 1 | 18.54 | 1.00 g | 2 | 4 |
| Isoleucine | 0.5 | 9.27 | 0.50 g | 1 | 2 |
| Valine | 0.25 | 4.64 | 0.25 g | 0.5 | 1 |
| Arginine | 0.75 | 13.91 | 0.75 g | 1.5 | 3 |
| Glutamine | 1 | 18.54 | 1.00 g | 2 | 4 |
| N-acetylcysteine | 0.225 | 4.17 | 0.225 g | 0.45 | 0.9 |
| Serine | 1.667 | 30.92 | 1.67 g | 3.33 g | 6.67 g |
| Total amino acids | | | 5.395 g | 10.78 g | 21.57 g |

The disclosure also provides a composition including at least four different amino acid entities (e.g., four, five, six, or more different amino acid entities), in which the composition is capable of one, two, three, four, five, or all of:

a) one or both of decreasing or preventing one or both of liver fibrosis or liver injury;

b) one or both of decreasing or preventing hepatocyte inflammation;

c) improving, e.g., increasing, glucose tolerance;

d) one or both of decreasing or preventing steatosis; or e) one or both of decreasing or preventing hepatocyte ballooning, provided that at least one amino acid entity is not a peptide of more than 20 amino acid residues in length.

In some embodiments, the composition includes at least four different amino acid entities (e.g., four, five, six, or more different amino acid entities) that decreases or prevents one or both of liver fibrosis or liver injury. For instance, the reducing and/or inhibiting liver fibrosis and/or liver injury comprises can include reducing a level of one or both of collagen, e.g., type I and III collagen or α-smooth muscle actin (αSMA).

In some embodiments, the composition includes at least four different amino acid entities (e.g., four, five, six, or more different amino acid entities) that decreases or prevents hepatocyte inflammation. In some embodiments, the reducing and/or inhibiting liver fibrosis and/or liver injury includes reducing a level or activity of one, two, three, four, or more (e.g., all) of a matrix metalloproteinase (MMP) (e.g., MMP-13, MMP-2, MMP-9, MT1-MMP, MMP-3, or MMP-10), a tissue inhibitor of metalloproteinase (TIMP) (e.g., TIMP1), aspartate transaminase (AST), alanine transaminase (ALT), or N-terminal fragment of type III collagen (proC3).

In some embodiments, the decreasing or preventing hepatocyte inflammation comprises reducing a level or activity of one, two, three, four, five, six, seven or more (e.g., all) of NF-kB, interferons, IL-1b, IL-2, MCP-1, MIP-1, a caspase-cleaved keratin 18 fragments (e.g., one or both of M30 or M65), or C-reactive protein. In an embodiment, the decreasing or preventing hepatocyte inflammation comprises increasing a level or activity of IL-10.

In an embodiment, the improving, e.g., increasing, glucose tolerance, comprises increasing a level or activity of adiponectin. In an embodiment, the improving, e.g., increasing, glucose tolerance, comprises decreasing a level or activity of FGF-21.

In certain embodiments, the hepatocyte inflammation comprises LPS induced hepatocyte inflammation.

In some embodiments, the composition is capable of enhancing fatty acid oxidation, e.g., one or both of reducing levels of unsaturated fatty acids or increasing levels of acylcarnitine (e.g., in a STAM mouse model or a FATZO mouse model). In certain embodiments, the reduction in levels of unsaturated fatty acids is at least 25%, 30%, 35%, 40%, 45%, 50%, 55%, 60%, 65%, 70%, 75%, 80%, 85%, 90%, 95%, or 99% of the level of change shown in Table 53, e.g., measured as described in Example 9. In certain embodiments, the increase in levels of acylcarnitine is at least 25%, 30%, 35%, 40%, 45%, 50%, 55%, 60%, 65%, 70%, 75%, 80%, 85%, 90%, 95%, or 99% of the level of change shown in Table 53, e.g., measured as described in Example 9.

In certain embodiments, the composition is capable of reducing, or reduces, liver fibrosis or liver injury by at least 5%, 10%, 15%, 20%, 21%, 22%, 23%, 24%, 25%, 26%, 27%, 28%, 29%, or 30%, as detected using an assay of alanine transaminase (ALT), e.g., an antibody-based detection assay, e.g., an ELISA, e.g., as described in Example 4, e.g., relative to a reference composition (e.g., a vehicle control).

In certain embodiments, the composition is capable of reducing, or reduces, liver fibrosis or liver injury by at least 5%, 10%, 15%, 20%, 21%, 22%, 23%, 24%, 25%, 26%, 27%, 28%, 29%, or 30%, as detected using an assay of aspartate transaminase (AST), e.g., an antibody-based detection assay, e.g., an ELISA, e.g., as described in Example 4, e.g., relative to a reference composition (e.g., a vehicle control).

In certain embodiments, the composition is capable of reducing, or reduces, alanine transaminase (ALT) by at least 5%, 10%, 15%, 20%, 21%, 22%, 23%, 24%, 25%, 26%, 27%, 28%, 29%, or 30%, as detected using an assay of ALT, e.g., an antibody-based detection assay, e.g., an ELISA, e.g., as described in Example 4, e.g., relative to a reference composition (e.g., a vehicle control).

In certain embodiments, the composition is capable of reducing, or reduces, aspartate transaminase (AST) by at least 5%, 10%, 15%, 20%, 21%, 22%, 23%, 24%, 25%, 26%, 27%, 28%, 29%, or 30%, as detected using an assay of AST, e.g., an antibody-based detection assay, e.g., an ELISA, e.g., as described in Example 4, e.g., relative to a reference composition (e.g., a vehicle control).

In certain embodiments, the composition is capable of reducing, or reduces, liver fibrosis or liver injury by at least 5%, 10%, 15%, 20%, 21%, 22%, 23%, 24%, 25%, 26%, 27%, 28%, 29%, or 30%, as detected using an assay of hydroxyproline, e.g., an antibody-based detection assay, e.g., an ELISA, e.g., as described in Example 4, e.g., relative to a reference composition (e.g., a vehicle control).

In certain embodiments, the composition is capable of reducing, or reduces, hydroxyproline levels by at least 5%, 10%, 15%, 20%, 21%, 22%, 23%, 24%, 25%, 26%, 27%, 28%, 29%, or 30%, as detected using an assay of hydroxyproline, e.g., an antibody-based detection assay, e.g., an ELISA, e.g., as described in Example 4, e.g., relative to a reference composition (e.g., a vehicle control).

In certain embodiments, the composition is capable of reducing, or reduces, liver fibrosis or liver injury by at least 5%, 10%, 15%, 20%, 20%, 30%, 40%, 45%, 50%, 55%, 60%, 65%, 70%, 75%, 80%, 85%, or 90% as detected using LX-2 cells, e.g., levels of Col1a1, Acta2, and/or TIMP2 in LX-2 cells, e.g., as assessed using a nucleic acid amplification method, e.g., PCR or qRT-PCR, e.g., as described in Example 7, e.g., relative to a reference composition (e.g., a vehicle control; an amino acid composition comprising L-leucine, L-isoleucine, L-valine; NAC; or an amino acid composition comprising L-arginine, L-glutamine, and NAC).

In certain embodiments, the composition is capable of reducing, or reduces, expression of one or more collagen biomarkers (e.g., Col1a1, Acta2, and/or TIMP2) by at least 5%, 10%, 15%, 20%, 20%, 30%, 40%, 45%, 50%, 55%, 60%, 65%, 70%, 75%, 80%, 85%, or 90% as detected using LX-2 cells, e.g., levels of Col1a1, Acta2, and/or TIMP2 in LX-2 cells, e.g., as assessed using a nucleic acid amplification method, e.g., PCR or qRT-PCR, e.g., as described in Example 7, e.g., relative to a reference composition (e.g., a vehicle control; an amino acid composition comprising L-leucine, L-isoleucine, L-valine; an amino acid composition comprising L-arginine, L-glutamine, and NAC; or NAC).

In certain embodiments, the composition is capable of reducing, or reduces, expression of one or more collagen biomarkers (e.g., Col1a1) by at least 5%, 10%, 15%, 20%, 20%, 30%, 40%, 45%, 50%, 55%, 60%, 65%, 70%, 75%, 80%, 85%, or 90% as detected using primary hepatic stellate cells, e.g., levels of Col1a1 in primary hepatic stellate cells, e.g., as assessed using an antibody-based detection assay, e.g., an ELISA, e.g., as described in Example 12, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC).

In certain embodiments, the composition is capable of increasing, or increases, expression of one or more collagen biomarkers (e.g., procollagen 1α1) by at least 5%, 10%, 15%, 20%, 20%, 30%, 40%, 45%, 50%, 55%, 60%, 65%, 70%, 75%, 80%, 85%, or 90% as detected using primary hepatic stellate cells, e.g., levels of procollagen 1α1 in primary hepatic stellate cells, e.g., as assessed using an antibody-based detection assay, e.g., an ELISA, e.g., as described in Example 12, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC).

In certain embodiments, the composition is capable of reducing, or reduces, hepatocyte inflammation by at least 5%, 10%, 15%, 20%, 20%, 30%, 40%, 45%, 50%, 55%, 60%, 65%, 70%, 75%, 80%, 85%, or 90% as detected using HepG2 cells, e.g., decreased activity, e.g., decreased TNFα-induced activity of NF-kB in a reporter assay in HepG2 cells, as described in Example 8, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of reducing, or reduces, TNFα-induced activity of NF-kB in HepG2 cells by at least 5%, 10%, 15%, 20%, 20%, 30%, 40%, 45%, 50%, 55%, 60%, 65%, 70%, 75%, 80%, 85%, or 90% as detected using HepG2 cells, e.g., decreased activity, e.g., decreased TNFα-induced activity of NF-kB in a reporter assay in HepG2 cells, as described in Example 8, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

In certain embodiments, the composition is capable of increasing, or increases, glucose tolerance, e.g., in a STAM mouse model or in a FATZO mouse model, by at least 1%, 2%, 3%, 4%, 5%, 6%, 7%, 8%, 9%, or 10%, as detected using an assay of glucose levels, e.g., using glucose oxidase, e.g., using a glucometer, e.g., as described in Example 5, e.g., relative to a reference composition (e.g., a vehicle control or a positive control, e.g., metformin).

In certain embodiments, the composition is capable of increasing, or increases, blood glucose metabolism, e.g., in a STAM mouse model or in a FATZO mouse model, by at least 1%, 2%, 3%, 4%, 5%, 6%, 7%, 8%, 9%, or 10%, as detected using an assay of glucose levels, e.g., using glucose oxidase, e.g., using a glucometer, e.g., as described in Example 5, e.g., relative to a reference composition (e.g., a vehicle control or a positive control, e.g., metformin).

In certain embodiments, the composition is capable of decreasing, or decreases, steatosis and/or inflammation by at least 1%, 2%, 3%, 4%, 5%, 6%, 7%, 8%, 9%, or 10%, as detected using an assay of MCP1/CCL2, e.g., in primary hepatocytes, e.g., using an antibody-based detection assay, e.g., an ELISA, e.g., as described in Example 10, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC).

In certain embodiments, the composition is capable of decreasing, or decreases, MCP1/CCL2 levels by at least 1%, 2%, 3%, 4%, 5%, 6%, 7%, 8%, 9%, or 10%, as detected using an assay of MCP1/CCL2, e.g., in primary hepatocytes, e.g., using an antibody-based detection assay, e.g., an ELISA, e.g., as described in Example 10, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC). In certain embodiments, the composition is capable of decreasing, or decreases, TNFα inflammatory response by at least 1%, 2%, 3%, 4%, 5%, 6%, 7%, 8%, 9%, or 10%, as detected using an assay of MCP1/CCL2 or an assay of IL-6, e.g., in primary hepatic stellate cells, e.g., using an antibody-based detection assay, e.g., an ELISA, e.g., as described in Example 11, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC).

In certain embodiments, the composition is capable of decreasing, or decreases, MCP1/CCL2 levels and/or IL-6 levels by at least 1%, 2%, 3%, 4%, 5%, 6%, 7%, 8%, 9%, or 10%, as detected using an assay of MCP1/CCL2 or an assay of IL-6, e.g., in primary hepatic stellate cells, e.g., using an antibody-based detection assay, e.g., an ELISA, e.g., as described in Example 11, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC).

In any of the foregoing embodiments, the reference composition comprises a single amino acid entity, e.g., a L-amino acid entity, an I-amino acid entity, a V-amino acid entity, a R-amino acid entity, a Q-amino acid entity, or a NAC-amino acid entity, each assayed separately as a free amino acid, or a combination of amino acid entities (e.g., a L-amino acid entity, an I-amino acid entity, and a V-amino acid entity; a R-amino acid entity, a Q-amino acid entity, and a NAC-amino acid entity; a L-amino acid entity, an I-amino acid entity, V-amino acid entity, a R-amino acid entity, and a Q-amino acid entity). In certain embodiments, the reference composition comprises vehicle (e.g., PBS or saline).

In some embodiments, the composition that decreases and/or prevents liver fibrosis and/or liver injury comprises one or more branched-chain amino acid (BCAAs), one or more conditionally essential amino acid (CEAAs), and an antioxidant or reactive oxygen species (ROS) scavenger.

In some embodiments, the composition that decreases and/or prevents hepatocyte inflammation comprises one or more BCAAs, one or more CEAAs, and an antioxidant or ROS scavenger.

In some embodiments, the composition that increases glucose tolerance comprises one or more BCAAs, one or more CEAAs, and an antioxidant or ROS scavenger.

In some embodiments, the composition that decreases and/or prevents steatosis comprises one or more BCAAs, one or more CEAAs, and an antioxidant or ROS scavenger.

In some embodiments, the composition that decreases and/or prevents hepatocyte ballooning comprises one or more BCAAs, one or more CEAAs, and an antioxidant or ROS scavenger.

In an embodiment, the BCAA comprises a L-amino acid entity. In an embodiment, the BCAAs comprise a L-amino acid entity and an I-amino acid entity. In an embodiment, the BCAAs comprise a L-amino acid entity and a V-amino acid entity. In an embodiment, the BCAAs comprise a L-amino acid entity, a V-amino acid entity, and an I-amino acid entity. In an embodiment, the CEAA comprises a R-amino acid entity. In an embodiment, the CEAA comprises a Q-amino acid entity. In an embodiment, the CEAA comprises a R-amino acid entity and a Q-amino acid entity. In an embodiment, the antioxidant or ROS scavenger comprises a NAC entity, e.g., NAC.

In some embodiments, the composition comprises a) a L-amino acid entity, an R-amino acid entity, and a Q-amino acid entity; and b) an antioxidant or ROS scavenger, e.g., a NAC entity, e.g., NAC.

In some embodiments, the composition further comprises an I-amino acid-entity or a V-amino acid-entity. In other embodiments, the composition further comprises an I-amino acid-entity and a V-amino acid-entity.

Production of the Amino Acid Compositions

Amino acids used to make the compositions may be agglomerated, and/or instantized to aid in dispersal and/or solubilization.

The amino acid compositions of the present disclosure may be made using amino acids and amino acid derivatives from the following sources, or other sources may used: FUSI-BCAA™ Instantized Blend (L-Leucine, L-Isoleucine and L-Valine in 2:1:1 weight ratio), FUSIL™ Instantized L-Leucine, L-Arginine HCl, and L-Glutamine may be obtained from Ajinomoto Co., Inc; N-acetyl-cysteine may be obtained from Spectrum Chemical.

To produce the amino acid compositions of the instant disclosure, the following general steps may be used: the starting materials (individual amino acids and excipients) may be blended in a blending unit, followed by verification of blend uniformity and amino acid content, and filling of the blended powder into stick packs or other unit dosage form. The content of stick packs or other unit dosage forms may be dispersed in water at time of use for oral administration.

Formulations

The pharmaceutical compositions of the present disclosure may be in a form suitable for oral use (for example as tablets, lozenges, hard or soft capsules, aqueous or oily suspensions, emulsions, dispersible powders or granules, syrups or elixirs, medical food products, nutraceuticals), for topical use (for example as creams, ointments, gels, or aqueous or oily solutions or suspensions), for administration by inhalation (for example as finely divided powder) or for parental administration (for example as a sterile aqueous or oily solution for intravenous, subcutaneous, intramuscular dosing or as a suppository for rectal dosing).

Excipients

The amino acid compositions of the present disclosure may be compounded or formulated with one or more excipients. Non-limiting examples of suitable excipients include a tastant, a flavorant, a buffering agent, a preservative, a stabilizer, a binder, a compaction agent, a lubricant, a dispersion enhancer, a disintegration agent, a flavoring agent, a sweetener, and a coloring agent.

In some embodiments, the excipient comprises a buffering agent. Non-limiting examples of suitable buffering agents include citric acid, sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, xanthan gum, bentonite, purified wood cellulose, sodium starch glycolate, isoamorphous silicate, and microcrystalline cellulose as high HLB emulsifier surfactants.

In some embodiments, the composition comprises a disintegrant as an excipient. In some embodiments, the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In some embodiments, the disintegrant is an effervescent disintegrant. Non-limiting examples of suitable effervescent disintegrants include sodium bicarbonate in combination with citric acid, and sodium bicarbonate in combination with tartaric acid.

In some embodiments, the excipient comprises a flavoring agent. Flavoring agents can be chosen from synthetic flavor oils and flavoring aromatics; natural oils; extracts from plants, leaves, flowers, and fruits; and combinations thereof. In some embodiments, the flavoring agent is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments, the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In some embodiments, the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

Particular excipients may include one or more of: citric acid, lecithin, (e.g. Alcolec F100), sweeteners (e.g. sucralose, sucralose micronized NF, acesulfame potassium (e.g. Ace-K)), a dispersion enhancer (e.g. xanthan gum (e.g. Ticaxan Rapid-3)), flavorings (e.g. vanilla custard #4306, Nat Orange WONF #1326, lime 865.0032U, and lemon 862.2169U), a bitterness masking agent (e.g. 936.2160U), and natural or artificial colorings (e.g. FD&C Yellow 6).

Methods of Treatment

The composition as described herein can be administered to improve liver function, e.g., in a patient with a liver disease. The composition as described herein can also be administered to treat (e.g., reverse, reduce, ameliorate, or prevent) a disorder, e.g., a liver disease in a subject. The present disclosure provides methods of treating a liver disease selected from fatty liver disease (steatohepatitis), alcoholic steatohepatitis (ASH), non-alcoholic fatty liver disease (NAFLD), non-alcoholic fatty liver (NAFL), non-alcoholic steatohepatitis (NASH), liver fibrosis, and cirrhosis. In particular, an effective amount of the composition can be administered (e.g., according to a dosage regimen described herein) to treat a subject with non-alcoholic fatty liver disease (NAFLD), non-alcoholic fatty liver (NAFL), non-alcoholic steatohepatitis (NASH), or cirrhosis.

Patients with Liver Disease

In some embodiments, a subject has fatty liver disease selected from NAFLD and AFLD. In some embodiments, the subject has pediatric NAFLD. In some embodiments, the subject with NAFLD has NASH or NAFL. In some embodiments, the subject with AFLD has ASH.

In certain embodiments, the subject exhibits symptoms of gut leakiness. In certain embodiments, the subject has gut dysbiosis. In certain embodiments, the subject has gut microbiome disturbance. The subject may have increased levels of inflammatory cytokines, e.g., increased TNFα, relative to a normal subject without a fatty liver disease.

In certain embodiments, the subject exhibits muscle atrophy, e.g., has a decreased ratio of muscle tissue to adipose tissue, e.g., relative to a normal subject without a fatty liver disease. For example, the subject exhibits muscle atrophy without fibrosis and/or cirrhosis.

In certain embodiments, the subject exhibits reverse lipid transport from adipose tissue to liver tissue.

In some embodiments, the subject has fibrosis. The subject may have cirrhosis. The subject may also have a metabolic syndrome.

In certain embodiments, the subject has one, two, or more (e.g., all) of hepatocarcinoma, an increased risk of liver failure, or an increased risk of death.

In some embodiments, the subject has type 2 diabetes.

In some embodiments, the subject with a liver disease (e.g., NAFLD (e.g., NASH or NAFL) or AFLD (e.g., ASH)) is a mammal (e.g., a human). In some embodiments, the subject has been diagnosed with NAFLD, NASH or cirrhosis. In some embodiments, the subject has not received prior treatment with a composition as described herein (e.g., the subject is a naïve subject). In some embodiments, the subject with NAFLD, NASH or cirrhosis has diabetes (e.g., type 2 diabetes).

In some embodiments, the subject has NAFLD. In some embodiments, the subject has NAFL. In certain embodiments, the subject (e.g., a child or an adolescent) has pediatric NAFLD. In some embodiments, the subject has hepatic steatosis. In some embodiments, a subject with pediatric NAFLD has steatosis.

In some embodiments, the subject has non-alcoholic steatohepatitis (NASH). In some embodiments, the subject with NASH has fibrosis.

In some embodiments, the subject has cirrhosis. In some embodiments, the subject with cirrhosis has fibrosis. In some embodiments, the subject with cirrhosis has hepatocarcinoma. In some embodiments, the subject with cirrhosis has an increased risk of liver failure. In some embodiments, the subject with cirrhosis has hepatocarcinoma, an increased risk of liver failure, and an increased risk of death.

In some embodiments, a subject exhibits a symptom of liver disease (e.g. NAFLD, NASH, or cirrhosis), e.g., a metabolic symptom, prior to administration of the composition. In some embodiments, a subject exhibits a metabolic symptom of liver disease (e.g. NAFLD, NASH, or cirrhosis) selected from one, two, three, four, five, six, or more (e.g., all) of decreased fat metabolism, hepatocyte apoptosis, hepatocyte ballooning, inflammation of adipose tissue, inflammation of hepatic tissue, hepatocyte ballooning, oxidative stress (e.g., reactive oxygen species (ROS), decreased gut barrier function, decreased insulin secretion, or decreased glucose tolerance (e.g., relative to a healthy subject without a liver disease).

In some embodiments, a subject exhibits modulated (e.g., increased) levels of a biomarker prior to administration of the composition. In some embodiments, a subject exhibits modulated levels of a biomarker selected from one, two, three, four, five, six, seven, eight, nine, or more (e.g., all) of ACOX1; IL-10; NF-kB, an interferon, IL-2; glutathione (GSH); alanine aminotransferase (ALT); aspartate aminotransferase (AST); adiponectin; N-terminal fragment of type III collagen (proC3); caspase-cleaved keratin 18 fragments (M30 and M65); IL-1β; C-reactive protein; PIIINP; TIMP1; MCP-1; or FGF-21 (e.g., relative to a healthy subject without a liver disease).

In some embodiments, the subject exhibits increased levels of ALT, e.g., relative to a healthy subject without a liver disease.

In some embodiments, the subject exhibits increased levels of AST, e.g., relative to a healthy subject without a liver disease.

Improvement in Symptoms of Liver Disease

The composition as described herein can be administered to treat (e.g., reverse, reduce, ameliorate, or prevent) a subject (e.g., a human) with a liver disease, thereby improving a symptom of a liver disease in the patient. In some embodiments, the composition is administered to a subject with NAFLD. In some embodiments, the composition is administered to a subject with NAFL. In some embodiments, the composition is administered to a subject with NASH. In some embodiments, the composition is administered to a subject with cirrhosis of the liver.

In some embodiments, administration of a composition (e.g., at a dosage regimen described herein) results in an improvement in one or more symptoms of NAFLD, e.g., a metabolic symptom of NAFLD, in a subject.

In some embodiments, administration of the composition results in increased free fatty acid and lipid metabolism in a subject with NAFLD (e.g., a subject with pediatric NAFLD). In some embodiments, administration of the composition results in improved mitochondrial function in a subject with NAFLD (e.g., a subject with pediatric NAFLD). In some embodiments, administration of the composition results in white adipose tissue (WAT) browning in a subject with NAFLD (e.g., a subject with pediatric NAFLD).

In some embodiments, administration of the composition results in decreased reactive oxygen species (ROS) in a subject with NAFLD (e.g., a subject with pediatric NAFLD). In some embodiments, administration of the composition results in increased levels of glutathione (GSH) in a subject with NAFLD (e.g., a subject with pediatric NAFLD).

In some embodiments, administration of the composition results in decreased hepatic inflammation in a subject with NAFLD (e.g., a subject with pediatric NAFLD). In some embodiments, administration of the composition results in decreased hepatocyte ballooning in a subject with NAFLD (e.g., a subject with pediatric NAFLD).

In some embodiments, administration of the composition results in improved gut barrier function in a subject with NAFLD (e.g., a subject with pediatric NAFLD).

In some embodiments, administration of the composition results in increased insulin secretion in a subject with NAFLD (e.g., a subject with pediatric NAFLD). In some embodiments, administration of the composition results in improved glucose tolerance in a subject with NAFLD (e.g., a subject with pediatric NAFLD).

In some embodiments, the composition reduces or inhibits liver fibrosis in a subject with NAFLD (e.g., a subject with pediatric NAFLD). In some embodiments, the composition reduces or inhibits liver fibrosis in a subject with NAFLD (e.g., a subject with pediatric NAFLD).

In some embodiments, the composition reduces liver fat in a subject with NAFLD (e.g., a subject with pediatric NAFLD). In some embodiments, the composition reduces liver enzyme levels (e.g., ALT or AST) in blood or plasma from a subject with NAFLD (e.g., a subject with pediatric NAFLD).

In some embodiments, administration of a composition (e.g., at a dosage regimen described herein) including amino acid entities results in an improvement in one or more symptoms of NASH, e.g., a metabolic symptom of NASH, in a subject.

In some embodiments, administration of the composition results in increased free fatty acid and lipid metabolism in a subject with NASH (e.g., a subject with NAFLD, fibrosis, and type 2 diabetes). In some embodiments, administration of the composition results in improved mitochondrial function in a subject with NASH. In some embodiments, administration of the composition results in white adipose tissue (WAT) browning in a subject with NASH (e.g., a subject with NAFLD, fibrosis, and type 2 diabetes).

In some embodiments, administration of the composition results in decreased reactive oxygen species (ROS) in a subject with NASH (e.g., a subject with NAFLD, fibrosis, and type 2 diabetes). In some embodiments, administration of the composition results in increased levels of glutathione (GSH) in a subject with NASH (e.g., a subject with NAFLD, fibrosis, and type 2 diabetes).

In some embodiments, administration of the composition results in decreased hepatic inflammation in a subject with NASH (e.g., a subject with NAFLD, fibrosis, and type 2 diabetes). In some embodiments, administration of the composition results in decreased hepatocyte ballooning in a subject with NASH (e.g., a subject with NAFLD, fibrosis, and type 2 diabetes).

In some embodiments, administration of the composition results in improved gut barrier function in a subject with NASH (e.g., a subject with NAFLD, fibrosis, and type 2 diabetes).

In some embodiments, administration of the composition results in increased insulin secretion in a subject with NASH (e.g., a subject with NAFLD, fibrosis, and type 2 diabetes). In some embodiments, administration of the composition results in improved glucose tolerance in a subject with NASH (e.g., a subject with NAFLD, fibrosis, and type 2 diabetes).

In some embodiments, the composition reduces or inhibits liver fibrosis in a subject with NASH (e.g., a subject with NAFLD, fibrosis, and type 2 diabetes). In some embodiments, the composition reduces or inhibits liver fibrosis in a subject with NASH (e.g., a subject with NAFLD, fibrosis, and type 2 diabetes).

In some embodiments, the composition reduces liver fat in a subject with NASH (e.g., a subject with NAFLD, fibrosis, and type 2 diabetes). In some embodiments, the composition reduces liver enzyme levels (e.g., ALT or AST) in blood or plasma from a subject with NASH (e.g., a subject with NAFLD, fibrosis, and type 2 diabetes).

In some embodiments, administration of a composition (e.g., at a dosage regimen described herein) including amino acid entities results in an improvement in one or more symptoms of cirrhosis, e.g., a metabolic symptom of cirrhosis, in a subject.

In some embodiments, administration of the composition results in decreased reactive oxygen species (ROS) in a subject with cirrhosis (e.g., a subject with hepatocarcinoma, increased risk of liver failure, and increased risk of death). In some embodiments, administration of the composition results in increased levels of glutathione (GSH) in a subject with cirrhosis (e.g., a subject with hepatocarcinoma, increased risk of liver failure, and increased risk of death).

In some embodiments, administration of the composition results in decreased hepatic inflammation in a subject with cirrhosis (e.g., a subject with hepatocarcinoma, increased risk of liver failure, and increased risk of death). In some embodiments, administration of the composition results in decreased hepatocyte ballooning in a subject with cirrhosis (e.g., a subject with hepatocarcinoma, increased risk of liver failure, and increased risk of death).

In some embodiments, administration of the composition results in improved gut barrier function in a subject with cirrhosis (e.g., a subject with hepatocarcinoma, increased risk of liver failure, and increased risk of death).

In some embodiments, administration of the composition results in increased insulin secretion in a subject with cirrhosis (e.g., a subject with hepatocarcinoma, increased risk of liver failure, and increased risk of death). In some embodiments, administration of the composition results in improved glucose tolerance in a subject with cirrhosis (e.g., a subject with hepatocarcinoma, increased risk of liver failure, and increased risk of death).

In some embodiments, the composition reduces or inhibits liver fibrosis in a subject with cirrhosis (e.g., a subject with hepatocarcinoma, increased risk of liver failure, and increased risk of death). In some embodiments, the composition reduces or inhibits liver fibrosis in a subject with cirrhosis (e.g., a subject with hepatocarcinoma, increased risk of liver failure, and increased risk of death).

In some embodiments, the composition reduces liver fat in a subject with cirrhosis (e.g., a subject with hepatocarcinoma, increased risk of liver failure, and increased risk of death). In some embodiments, the composition reduces liver enzyme levels (e.g., ALT or AST) in blood or plasma from a subject with cirrhosis (e.g., a subject with hepatocarcinoma, increased risk of liver failure, and increased risk of death).

Dosage Regimens

The composition can be administered according to a dosage regimen described herein to treat (e.g., inhibit, reduce, ameliorate, or prevent) a disorder, e.g., a liver disease in a subject (e.g., a human). In some embodiments, the subject has NAFLD. In some embodiments, the subject has NAFL. In some embodiments, the subject has NASH. In some embodiments, the subject has cirrhosis.

The composition can be provided to a patient with a liver disease (e.g., NAFL, NASH, or cirrhosis) in either a single or multiple dosage regimens. In some embodiments, doses are administered, e.g., twice daily, three times daily, four times daily, five times daily, six times daily, seven times daily, or more. In some embodiments, the composition is administered for at least 2 days, 3 days, 4 days, 5 days, 6 days, 7 days, or 2 weeks. In some embodiments, the composition is administered for at least 10 weeks, 11 weeks, 12 weeks, 13 weeks, 14 weeks, 15 weeks, 16 weeks, 17 weeks, 18 weeks, 19 weeks, 20 weeks, or longer. In some embodiments, the composition is administered chronically, e.g., more than 30 days, e.g., 31 days, 40 days, 50 days, 60 days, 3 months, 6 months, 9 months, one year, two years, or three years).

In some embodiments, the composition is administered at a dose of about 2 g to about 60 g total amino acids, e.g., once per day, twice per day, three times per day, four times per day, five times per day, or six times per day (e.g., three times per day). In some embodiments, the composition is administered at a dose of about 5 g to about 15 g, about 10 g to about 20 g, about 20 g to about 40 g, or about 30 g to about 50 g total amino acids, e.g., once per day, twice per day, three times per day, four times per day, five times per day, or six times per day (e.g., three times per day).

In some embodiments, the composition is administered at a dose of about 5 g to about 10 g total amino acids, e.g., once per day, twice per day, three times per day, four times per day, five times per day, or six times per day (e.g., three times per day). In some embodiments, the composition is administered at a dose of about 6 g total amino acids, e.g., once per day, twice per day, three times per day, four times per day, five times per day, or six times per day (e.g., three times per day). In an embodiment, the composition is administered at a dose of about 6 g total amino acids three times per day.

In some embodiments, the composition is administered at a dose of about 10 g to about 20 g total amino acids, e.g., once per day, twice per day, three times per day, four times per day, five times per day, or six times per day (e.g., three times per day). In some embodiments, the composition is administered at a dose of about 12 g total amino acids, e.g., once per day, twice per day, three times per day, four times per day, five times per day, or six times per day (e.g., three times per day). In an embodiment, the composition is administered at a dose of about 12 g total amino acids three times per day.

In some embodiments, the composition is administered at a dose of about 20 g to about 40 g total amino acids, e.g., once per day, twice per day, three times per day, four times per day, five times per day, or six times per day (e.g., three times per day). In some embodiments, the composition is administered at a dose of about 18 g total amino acids, e.g., once per day, twice per day, three times per day, four times per day, five times per day, or six times per day (e.g., three times per day). In an embodiment, the composition is administered at a dose of about 18 g total amino acids three times per day.

In some embodiments, the composition is administered at a dose of about 20 g to about 40 g total amino acids, e.g., once per day, twice per day, three times per day, four times per day, five times per day, or six times per day (e.g., three times per day). In some embodiments, the composition is administered at a dose of about 24 g total amino acids, e.g., once per day, twice per day, three times per day, four times per day, five times per day, or six times per day (e.g., three times per day). In an embodiment, the composition is administered at a dose of about 24 g total amino acids three times per day.

In some embodiments, the composition is administered at a dose of about 30 g to about 50 g total amino acids, e.g., once per day, twice per day, three times per day, four times per day, five times per day, or six times per day (e.g., three times per day). In some embodiments, the composition is administered at a dose of about 48 g total amino acids, e.g., once per day, twice per day, three times per day, four times per day, five times per day, or six times per day (e.g., three times per day). In an embodiment, the composition is administered at a dose of about 48 g total amino acids three times per day.

In some embodiments, the composition is administered at a dose of about 5 grams, about 8 grams, about 9 grams, about 10 grams, about 11 grams, about 12 grams, about 13 grams, about 14 grams, about 15 grams, about 16 grams, about 17 grams, about 18 grams, about 19 about grams, about 20 grams, about 21 grams, about 22 grams, about 24 grams, about 25 grams, about 26 grams, about 27 grams, about 28 grams, about 29 grams, or about 30 grams total amino acids (e.g., about 12 g or about 24 g), e.g., once per day, twice per day, three times per day, four times per day, five times per day, or six times per day (e.g., three times per day).

In some embodiments, the composition is administered every 2 hours, every 3 hours, every 4 hours, every 5 hours, every 6 hours, every 7 hours, every 8 hours, every 9 hours, or every 10 hours to a subject with a liver disease (e.g., NAFLD (e.g., NASH or NAFL) or AFLD (e.g., ASH)).

In an embodiment, the composition is administered to a subject with NAFLD prior to a meal. In an embodiment, the composition is administered to a subject with NAFLD concurrent with a meal. In an embodiment, the composition is administered to a subject with NAFLD following a meal.

In an embodiment, the composition is administered to a subject with NAFL prior to a meal. In an embodiment, the composition is administered to a subject with NAFL concurrent with a meal. In an embodiment, the composition is administered to a subject with NAFL following a meal.

In an embodiment, the composition is administered to a subject with NASH prior to a meal. In an embodiment, the composition is administered to a subject with NASH concurrent with a meal. In an embodiment, the composition is administered to a subject with NASH following a meal.

In an embodiment, the composition is administered to the subject with cirrhosis prior to a meal. In an embodiment, the composition is administered to a subject with cirrhosis concurrent with a meal. In an embodiment, the composition is administered to a subject with cirrhosis following a meal.

In an embodiment, the composition includes at least 1 g of leucine, at least 0.5 g of isoleucine, at least 0.5 g of valine, at least 1.5 g of arginine (or 1.81 g of arginine HCl), at least 2 g of glutamine, and at least 0.15 g of N-acetylcysteine for administration three times per day (e.g., for a total of at least 18 g per day).

In an embodiment, the composition includes about 1 g of leucine, about 0.5 g of isoleucine, about 0.5 g of valine, about 1.5 g of arginine (or 1.81 g of arginine HCl), about 2 g of glutamine, and about 0.15 g of N-acetylcysteine for administration three times per day (e.g., for a total of about 18 g per day).

In an embodiment, the composition includes at least 2 g of leucine, at least 1 g of isoleucine, at least 1 g of valine, at least 3.0 g of arginine (or 3.62 g of arginine HCl), at least 4 g of glutamine, and at least 0.3 g of N-acetylcysteine for administration three times per day (e.g., a total of at least 36 g per day).

In an embodiment, the composition includes about 2 g of leucine, about 1 g of isoleucine, about 1 g of valine, about 3.0 g or arginine (or 3.62 g of arginine HCl), about 4 g of glutamine, and about 0.3 g of N-acetylcysteine for administration three times per day (e.g., a total of about 36 g per day).

In an embodiment, the composition includes at least 4 g of leucine, at least 2 g of isoleucine, at least 2 g of valine, at least 6.0 g of arginine (or 7.24 g of arginine HCl), at least 8 g of glutamine, and at least 0.6 g of N-acetylcysteine for administration three times per day (e.g., a total of at least 72 g per day).

In an embodiment, the composition includes about 4 g of leucine, about 2 g of isoleucine, about 2 g of valine, about 6.0 g of arginine (or 7.24 g of arginine HCl), about 8 g of glutamine, and about 0.6 g of N-acetylcysteine for administration three times per day (e.g., a total of about 72 g per day).

In an embodiment, the composition includes at least 1 g of leucine, at least 0.5 g of isoleucine, at least 0.5 g of valine, at least 0.75 g of arginine (or 0.905 g of arginine HCl), at least 2 g of glutamine, and at least 0.15 g of N-acetylcysteine for administration three times per day (e.g., for a total of at least 18 g per day).

In an embodiment, the composition includes about 1 g of leucine, about 0.5 g of isoleucine, about 0.5 g of valine, about 0.75 g of arginine (or 0.905 g of arginine HCl), about 2 g of glutamine, and about 0.15 g of N-acetylcysteine for administration three times per day (e.g., for a total of about 18 g per day).

In an embodiment, the composition includes at least 2 g of leucine, at least 1 g of isoleucine, at least 1 g of valine, at least 1.5 g of arginine (or 1.81 g of arginine HCl), at least 4 g of glutamine, and at least 0.3 g of N-acetylcysteine for administration three times per day (e.g., a total of at least 36 g per day).

In an embodiment, the composition includes about 2 g of leucine, about 1 g of isoleucine, about 1 g of valine, about 1.5 g or arginine (or 1.81 g of arginine HCl), about 4 g of glutamine, and about 0.3 g of N-acetylcysteine for administration three times per day (e.g., a total of about 36 g per day).

In an embodiment, the composition includes at least 4 g of leucine, at least 2 g of isoleucine, at least 2 g of valine, at least 3.0 g of arginine (or 3.62 g of arginine HCl), at least 8 g of glutamine, and at least 0.6 g of N-acetylcysteine for administration three times per day (e.g., a total of at least 72 g per day).

In an embodiment, the composition includes about 4 g of leucine, about 2 g of isoleucine, about 2 g of valine, about 3.0 g of arginine (or 3.62 g of arginine HCl), about 8 g of glutamine, and about 0.6 g of N-acetylcysteine for administration three times per day (e.g., a total of about 72 g per day).

In an embodiment, the composition includes at least 1 g of leucine, at least 0.5 g of isoleucine, at least 0.25 g of valine, at least 0.75 g of arginine (or 0.905 g of arginine HCl), at least 1 g of glutamine, and at least 0.225 g of N-acetylcysteine for administration three times per day (e.g., for a total of at least 18 g per day).

In an embodiment, the composition includes about 1 g of leucine, about 0.5 g of isoleucine, about 0.25 g of valine, about 0.75 g of arginine (or 0.905 g of arginine HCl), about 1 g of glutamine, and about 0.225 g of N-acetylcysteine for administration three times per day (e.g., for a total of about 18 g per day).

In an embodiment, the composition includes at least 2 g of leucine, at least 1 g of isoleucine, at least 0.5 g of valine, at least 1.5 g of arginine (or 1.81 g of arginine HCl), at least 2 g of glutamine, and at least 0.45 g of N-acetylcysteine for administration three times per day (e.g., a total of at least 36 g per day).

In an embodiment, the composition includes about 2 g of leucine, about 1 g of isoleucine, about 0.5 g of valine, about 1.5 g or arginine (or 1.81 g of arginine HCl), about 2 g of glutamine, and about 0.45 g of N-acetylcysteine for administration three times per day (e.g., a total of about 36 g per day).

In an embodiment, the composition includes at least 4 g of leucine, at least 2 g of isoleucine, at least 1 g of valine, at least 3 g of arginine (or 3.62 g of arginine HCl), at least 4 g of glutamine, and at least 0.9 g of N-acetylcysteine for administration three times per day (e.g., a total of at least 72 g per day).

In an embodiment, the composition includes about 4 g of leucine, about 2 g of isoleucine, about 1 g of valine, about 3 g of arginine (or 3.62 g of arginine HCl), about 4 g of glutamine, and about 0.9 g of N-acetylcysteine for administration three times per day (e.g., a total of about 72 g per day).

In an embodiment, the composition includes at least 1 g of leucine, at least 0.5 g of isoleucine, at least 0.25 g of valine, at least 0.75 g of arginine (or 0.905 g of arginine HCl), at least 1 g of glutamine, at least 0.225 g of N-acetylcysteine, and at least 1.5 g or about 1.67 g of serine for administration three times per day (e.g., for a total of at least 18 g per day or for a total of at least 20 g per day).

In an embodiment, the composition includes about 1 g of leucine, about 0.5 g of isoleucine, about 0.25 g of valine, about 0.75 g of arginine (or 0.905 g of arginine HCl), about 1 g of glutamine, about 0.225 g of N-acetylcysteine, and about 1.5 g or about 1.67 g of serine for administration three times per day (e.g., for a total of about 18 g per day or for a total of at least 20 g per day).

In an embodiment, the composition includes at least 2 g of leucine, at least 1 g of isoleucine, at least 0.5 g of valine, at least 1.5 g of arginine (or 1.81 g of arginine HCl), at least 2 g of glutamine, at least 0.45 g of N-acetylcysteine, and at least 3 g or about 3.33 g of serine for administration three times per day (e.g., a total of at least 36 g per day or for a total of at least 40 g per day).

In an embodiment, the composition includes about 2 g of leucine, about 1 g of isoleucine, about 0.5 g of valine, about 1.5 g or arginine (or 1.81 g of arginine HCl), about 2 g of glutamine, about 0.45 g of N-acetylcysteine, and about 3 g or about 3.33 g of serine for administration three times per day (e.g., a total of about 36 g per day or for a total of at least 40 g per day).

In an embodiment, the composition includes at least 4 g of leucine, at least 2 g of isoleucine, at least 1 g of valine, at least 3 g of arginine (or 3.62 g of arginine HCl), at least 4 g of glutamine, at least 0.9 g of N-acetylcysteine, and at least 6 g or about 6.67 g of serine for administration three times per day (e.g., a total of at least 90 g per day).

In an embodiment, the composition includes about 4 g of leucine, about 2 g of isoleucine, about 1 g of valine, about 3 g of arginine (or 3.62 g of arginine HCl), about 4 g of glutamine, about 0.9 g of N-acetylcysteine, and about 6 g or about 6.67 g of serine for administration three times per day (e.g., a total of about 90 g per day). In some embodiments, the composition comprises four stick packs, each stick pack comprising 25% of the quantity of each amino acid included in the composition (e.g., as described herein).

Secondary Agents

In some embodiments, the method further comprises administering a farnesoid X receptor (FXR) agonist, a stearoyl CoA desaturase inhibitor, a CCR2 and CCR5 chemokine antagonist, a PPAR alpha and delta agonist, a caspase inhibitor, a galectin-3 inhibitor, an acetyl CoA carboxylase inhibitor, or an ileal sodium bile acid co-transporter inhibitor prior to, concurrently with, or after administration of the amino acid composition.

In some embodiments, the method further includes administering an FXR agonist. In some embodiments, the FXR agonist is obeticholic acid. In some embodiments, the method further includes administering one or more of: LMB-763, LJN-452, emricasan, and cenicriviroc.

Dietary Compositions

The composition including amino acid entities can be dietary compositions, e.g., chosen from a medical food, a functional food, or a supplement.

The composition including amino acid entities can be for use as a dietary composition, e.g., chosen from a medical food, a functional food, or a supplement. In some embodiments, the dietary composition is for use in a method comprising administering the composition to a subject.

In some embodiments, the subject has one or both of type 2 diabetes or a relatively high BMI.

In some embodiments, the subject has fatty liver disease.

In some embodiments, the subject has NAFLD (e.g., pediatric NAFLD). In an embodiment, the subject has NASH. In an embodiment, the subject has NAFL.

In some embodiments, the subject has AFLD. In an embodiment, the subject has ASH.

In some embodiments, the subject has one, two, three, four, or more (e.g., all) of fibrosis, cirrhosis, hepatocarcinoma, an increased risk of liver failure, or an increased risk of death.

In some embodiments, the composition promotes weight loss in the subject.

In some embodiments, administration of the dietary composition results in an improvement in one or more metabolic symptoms in the subject, e.g., one or more metabolic symptoms is selected from the following: increased free fatty acid and lipid metabolism (e.g., in the liver), improved mitochondrial function, white adipose tissue (WAT) browning, decreased reactive oxygen species (ROS), increased levels of glutathione (GSH), decreased hepatic inflammation, decreased hepatocyte ballooning, improved gut barrier function, increased insulin secretion, or glucose tolerance. In certain embodiments, administration of the composition results in an improvement in one or more metabolic symptoms after a treatment period of 24 hours.

The method can further include determining the level of one, two, three, four, five, six, seven, eight, nine, ten, eleven, twelve, thirteen, fourteen, or more (e.g., all) of the following:

a) alanine aminotransferase (ALT);
b) aspartate aminotransferase (AST);
c) adiponectin;
d) N-terminal fragment of type III collagen (proC3);
e) caspase-cleaved keratin 18 fragments (M30 and M65);
f) IL-1 beta;
g) C-reactive protein;
h) PIIINP;
i) a tissue inhibitor of metalloproteinase (TIMP); e.g., TIMP1 or TIMP2;
j) MCP-1;
k) FGF-21;
l) Col1a1;
m) Acta2;
n) a matrix metalloproteinase (MMP), e.g., MMP-13, MMP-2, MMP-9, MT1-MMP, MMP-3, or MMP-10;
o) ACOX1;
p) IL-10; or
q) NF-kB.

In certain embodiments, administration of the composition results in an improvement in one or more of a)-q) after a treatment period of 24 hours.

In some embodiments, the subject exhibits increased levels of one or both of ALT or AST prior to administration of the composition, e.g., relative to a healthy subject without a liver disease. In some embodiments, administration of the composition results in a decrease in levels of one or both of ALT or AST.

Methods of Providing an Amino Acid to a Subject

The present disclosure features a method of providing amino acid entities to a subject comprising administering to the subject an effective amount of a composition described herein, e.g., a composition comprising a leucine (L)-amino acid entity, a arginine (R)-amino acid entity, a glutamine (Q)-amino acid entity; and an antioxidant or reactive oxygen species (ROS) scavenger, e.g., a N-acetylcysteine (NAC) entity, e.g., NAC. In some embodiments, at least one amino acid entity is not a peptide of more than 20 amino acid residues in length.

The present disclosure also features a method of increasing one, two, three, or more (e.g., all) amino acid entities in a subject comprising administering to the subject an effective amount of the composition described herein. In some embodiments, administration of the composition results in an increase in the amino acid entities in one, two, or more (e.g., all) of blood, plasma, or serum of the subject, e.g., in a blood, plasma, or serum sample from the subject.

Biomarkers

Any of the methods disclosed herein can include evaluating or monitoring the effectiveness of administering a composition including amino acid entities to a subject with a liver disease (e.g., NAFLD (e.g., NASH or NAFL) or AFLD (e.g., ASH)).

In embodiments, the value of effectiveness to the composition in treating a subject with a liver disease (e.g., NAFLD (e.g., NASH or NAFL) or AFLD (e.g., ASH)) comprises a measure of one, two, three, four, five, six, seven, eight, nine, ten, eleven, twelve, thirteen, fourteen, fifteen, sixteen, or more (e.g., all) of the following:

a) alanine aminotransferase (ALT);
b) aspartate aminotransferase (AST);
c) adiponectin;
d) N-terminal fragment of type III collagen (proC3);
e) caspase-cleaved keratin 18 fragments (M30 and M65);
f) IL-1 beta;
g) C-reactive protein;
h) PIIINP;
i) a tissue inhibitor of metalloproteinase (TIMP); e.g., TIMP1 or TIMP2;
j) MCP-1;
k) FGF-21;
l) Col1a1;
m) Acta2;
n) a matrix metalloproteinase (MMP), e.g., MMP-13, MMP-2, MMP-9, MT1-MMP, MMP-3, or MMP-10;
o) ACOX1;
p) IL-10; or
q) NF-kB.

In some embodiments of any of the methods disclosed herein, the measure of one or more of a)-q) is obtained from a sample acquired from the subject with a liver disease (e.g., NAFLD (e.g., NASH or NAFL) or AFLD (e.g., ASH)). In some embodiments, the sample is chosen from a blood sample (e.g., a plasma sample) or a liver sample.

In some embodiments, the subject is evaluated prior to receiving, during, or after receiving, a composition including amino acid entities.

In some embodiments, administration of the composition including amino acid entities (e.g., at a dose of about 2 g to about 60 g total amino acids, e.g., about 6 g, about 12 g, about 18 g, about 24 g, or about 48 g), results in an improvement in one, two, three, four, five, six, seven, eight, nine, ten, eleven, twelve, thirteen, fourteen, fifteen, sixteen, or more (e.g., all) of the following:
a) alanine aminotransferase (ALT);
b) aspartate aminotransferase (AST);
c) adiponectin;
d) N-terminal fragment of type III collagen (proC3);
e) caspase-cleaved keratin 18 fragments (M30 and M65);
f) IL-1 beta;
g) C-reactive protein;
h) PIIINP;
i) a tissue inhibitor of metalloproteinase (TIMP); e.g., TIMP1 or TIMP2;
j) MCP-1;
k) FGF-21;
l) Col1a1;
m) Acta2;
n) a matrix metalloproteinase (MMP), e.g., MMP-13, MMP-2, MMP-9, MT1-MMP, MMP-3, or MMP-10;
o) ACOX1;
p) IL-10; or
q) NF-kB.

In some embodiments, administration of the composition including amino acid entities (e.g., at a dose of about 2 g to about 60 g total amino acids, e.g., about 6 g, about 12 g, about 18 g, about 24 g, or about 48 g three times daily), results in an improvement in one, two, three, four, five, six, seven, eight, nine, ten, or more (e.g., all) of a)-k) after a treatment period of, about 24 hours, about 72 hours, about 1 week, about 2 weeks, about 3 weeks, about 4 weeks, about 5 weeks, about 6 weeks, about 7 weeks, about 8 weeks, about 9 weeks, about 10 weeks, about 11 weeks, or 12 weeks. In certain embodiments, administration of the composition results in an improvement in one, two, three, four, five, or more (e.g., all) of a)-k) after a treatment period of about 2 weeks.

Numbered Embodiments

The invention is further described with reference to the following numbered embodiments.

1. A composition comprising:
a) a leucine (L)-amino acid entity, an arginine (R)-amino acid entity, and a glutamine (Q)-amino acid entity; and
b) an antioxidant or reactive oxygen species (ROS) scavenger, e.g., a N-acetylcysteine (NAC) entity, e.g., NAC;
provided that:
c) at least one amino acid entity is not provided as a peptide of more than 20 amino acid residues in length, and optionally wherein:
(i) an amino acid entity (e.g., at least one, two, or three of the amino acid entities) of (a) is selected from Table 2; or
(ii) (A) one or both of the R-amino acid entity and the Q-amino acid entity are present at a higher amount (wt. %) than the L-amino acid entity, or (B) the composition further comprises a serine (S)-amino acid entity.

1A. The composition of embodiment 1, wherein the composition satisfies the property of 1B. The composition of any of the preceding embodiments, wherein the composition satisfies the property of (ii)(A).

1C. The composition of any of the preceding embodiments, wherein the composition satisfies the property of (ii)(B).

1D. The composition of any of the preceding embodiments, wherein the composition further comprises an S-amino acid entity, and wherein the S-amino acid entity is present at a higher amount than any other amino acid entity.

2. The composition of any of embodiments 1-1D, wherein the composition comprises an amino acid and three amino acid entities.

3. The composition of any of embodiments 1-1D, wherein the composition comprises an amino acid precursor and three amino acid entities.

4. The composition of any of embodiments 1-1D, wherein the composition comprises an amino acid metabolite and three amino acid entities.

5. The composition of any of embodiments 1-1D, wherein the composition comprises an amino acid derivative and three amino acid entities.

6. The composition of any of embodiments 1-1D, wherein the composition comprises two amino acids and two amino acid entities.

7. The composition of any of embodiments 1-1D, wherein the composition comprises two amino acid precursors and two amino acid entities.

8. The composition of any of embodiments 1-1D, wherein the composition comprises two amino acid metabolites and two amino acid entities.

9. The composition of any of embodiments 1-1D, wherein the composition comprises two amino acid derivatives and two amino acid entities.

10. The composition of any of embodiments 1-1D, wherein the composition comprises three amino acids and one amino acid entity.

11. The composition of any of embodiments 1-1D, wherein the composition comprises three amino acid precursors and one amino acid entity.

12. The composition of any of embodiments 1-1D, wherein the composition comprises three amino acid metabolites and one amino acid entity.

13. The composition of any of embodiments 1-1D, wherein the composition comprises three amino acid derivatives and one amino acid entity.

14. The composition of any of embodiments 1-2, wherein the composition comprises L-leucine, a R-amino acid entity, and a Q-amino acid entity, and an antioxidant or ROS scavenger, e.g., a NAC entity.

15. The composition of any of embodiments 1-2, 2, 14, or 380, wherein the composition comprises L-leucine, R-arginine, a Q-amino acid entity, and an antioxidant or ROS scavenger, e.g., a NAC entity.

16. The composition of any of embodiments 1-2, 14, or 381, wherein the composition comprises L-leucine, argininosuccinate, a Q-amino acid entity, and an antioxidant or ROS scavenger, e.g., a NAC entity.

17. The composition of any of embodiments 1-2, 14, or 382, wherein the composition comprises L-leucine, citrulline, a Q-amino acid entity, and an antioxidant or ROS scavenger, e.g., a NAC entity.

18. The composition of any of embodiments 1-2, 14, or 383, wherein the composition comprises L-leucine, aspartate, a Q-amino acid entity, and an antioxidant or ROS scavenger, e.g., a NAC entity.

19. The composition of any of embodiments 1-2, 14, or 384, wherein the composition comprises L-leucine, L-glutamate, a Q-amino acid entity, and an antioxidant or ROS scavenger, e.g., a NAC entity.

20. The composition of any of embodiments 1-2, 14, or 385, wherein the composition comprises L-leucine, ornithine, a Q-amino acid entity, and an antioxidant or ROS scavenger, e.g., a NAC entity.

21. The composition of any of embodiments 1-2, 14, or 386, wherein the composition comprises a L-leucine, agmatine, a Q-amino acid entity, and an antioxidant or ROS scavenger, e.g., a NAC entity.

22. The composition of any of embodiments 1-2, 14, or 387, wherein the composition comprises a L-leucine, creatine, a Q-amino acid entity, and an antioxidant or ROS scavenger, e.g., a NAC entity.

23. The composition of any of embodiments 1-2, 14, or 388, wherein the composition comprises L-leucine, D-arginine, a Q-amino acid entity, and an antioxidant or ROS scavenger, e.g., a NAC entity.

24. The composition of any of embodiments 1-2, 14, or 389, wherein the composition comprises L-leucine, N-acetyl-arginine, a Q-amino acid entity, and an antioxidant or ROS scavenger, e.g., a NAC entity.

25. The composition of any of embodiments 1-2, 14, or 428, wherein the composition comprises L-leucine, a R-amino acid entity, L-glutamine, and an antioxidant or ROS scavenger, e.g., a NAC entity.

26. The composition of any of embodiments 1-2, 14, or 429, wherein the composition comprises L-leucine, a R-amino acid entity, glutamate, and an antioxidant or ROS scavenger, e.g., a NAC entity.

27. The composition of any of embodiments 1-2, 14, or 430, wherein the composition comprises L-leucine, a R-amino acid entity, carbamoyl-P, and an antioxidant or ROS scavenger, e.g., a NAC entity.

28. The composition of any of embodiments 1-2, 14, or 431, wherein the composition comprises L-leucine, a R-amino acid entity, D-glutamine, and an antioxidant or ROS scavenger, e.g., a NAC entity.

29. The composition of any of embodiments 1-2, 14, or 432, wherein the composition comprises L-leucine, a R-amino acid entity, N-acetyl-glutamine, and an antioxidant or ROS scavenger, e.g., a NAC entity.

30. The composition of any of embodiments 1-2, 14, or 445, wherein the composition comprises L-leucine, a R-amino acid entity, a Q-amino acid entity, and NAC.

31. The composition of any of embodiments 1-2, 14, or 446, wherein the composition comprises L-leucine, a R-amino acid entity, a Q-amino acid entity, and serine.

32. The composition of any of embodiments 1-2, 14, or 447, wherein the composition comprises L-leucine, a R-amino acid entity, a Q-amino acid entity, and acetylserine.

33. The composition of any of embodiments 1-2, 14, or 448, wherein the composition comprises L-leucine, a R-amino acid entity, a Q-amino acid entity, and cystathionine.

34. The composition of any of embodiments 1-2, 14, or 449, wherein the composition comprises L-leucine, a R-amino acid entity, a Q-amino acid entity, and glutathione.

35. The composition of any of embodiments 1-2, 14, or 450, wherein the composition comprises L-leucine, a R-amino acid entity, a Q-amino acid entity, and homocysteine.

36. The composition of any of embodiments 1-2, 14, or 451, wherein the composition comprises L-leucine, a R-amino acid entity, a Q-amino acid entity, and methionine.

37. The composition of any of embodiments 1-2, 14, or 452, wherein the composition comprises L-leucine, a R-amino acid entity, a Q-amino acid entity, and D-cysteine.

38. The composition of any of embodiments 1-2, 14, or 453, wherein the composition comprises L-leucine, a R-amino acid entity, a Q-amino acid entity, and L-cysteine.

39. The composition of any of embodiments 1-2, 14, or 454, wherein the composition comprises L-leucine, a R-amino acid entity, a Q-amino acid entity, and cystine.

40. The composition of any of embodiments 1-2, 14, 380, or 428, wherein the composition comprises L-leucine, L-arginine, L-glutamine, and an antioxidant or ROS scavenger, e.g., a NAC entity.

41. The composition of any of embodiments 1-2, 14, 381, or 429, wherein the composition comprises L-leucine, argininosuccinate, glutamate, and an antioxidant or ROS scavenger, e.g., a NAC entity.

42. The composition of any of embodiments 1-2, 14, 382, or 431, wherein the composition comprises L-leucine, citrulline, D-glutamine, and an antioxidant or ROS scavenger, e.g., a NAC entity.

43. The composition of any of embodiments 1-2, 14, or 383, wherein the composition comprises L-leucine, aspartate, N-acetyl-glutamine, and an antioxidant or ROS scavenger, e.g., a NAC entity.

44. The composition of any of embodiments 1-2, 14, 380, or 445, wherein the composition comprises L-leucine, L-arginine, a Q-amino acid entity, and NAC.

45. The composition of any of embodiments 1-2, 14, 381, or 446, wherein the composition comprises L-leucine, argininosuccinate, a Q-amino acid entity, and serine.

46. The composition of any of embodiments 1-2, 14, 382, or 447, wherein the composition comprises L-leucine, citrulline, a Q-amino acid entity, and acetylserine.

47. The composition of any of embodiments 1-2, 14, 383, or 448, wherein the composition comprises L-leucine, aspartate, a Q-amino acid entity, and cystathionine.

48. The composition of any of embodiments 1-2, 14, 384, or 449, wherein the composition comprises L-leucine, glutamate, a Q-amino acid entity, and glutathione.

49. The composition of any of embodiments 1-2, 14, 385, or 450, wherein the composition comprises L-leucine, ornithine, a Q-amino acid entity, and homocysteine.

50. The composition of any of embodiments 1-2, 14, 386, or 451, wherein the composition comprises L-leucine, agmatine, a Q-amino acid entity, and methionine.

51. The composition of any of embodiments 1-2, 14, 387, or 452, wherein the composition comprises L-leucine, creatine, a Q-amino acid entity, and D-cysteine.

52. The composition of any of embodiments 1-2, 14, 388, or 453, wherein the composition comprises L-leucine, D-arginine, a Q-amino acid entity, and L-cysteine.

53. The composition of any of embodiments 1-2, 14, 389, or 454, wherein the composition comprises L-leucine, N-acetyl-arginine, a Q-amino acid entity, and cystine.

54. The composition of any of embodiments 1-2, 14, 428, or 445, wherein the composition comprises L-leucine, a R-amino acid entity, L-glutamine, and NAC.

55. The composition of any of embodiments 1-2, 14, 429, or 446, wherein the composition comprises L-leucine, a R-amino acid entity, glutamate, and serine.

56. The composition of any of embodiments 1-2, 14, 430, or 447, wherein the composition comprises L-leucine, a R-amino acid entity, carbamoyl-P, and acetylserine.

57. The composition of any of embodiments 1-2, 14, 432, or 448, wherein the composition comprises L-leucine, a R-amino acid entity, N-acetyl-glutamine, and cystathionine.

58. The composition of any of embodiments 1-2, 14, 433, or 449, wherein the composition comprises L-leucine, a R-amino acid entity, L-glutamine, and glutathione.

59. The composition of any of embodiments 1-2, 14, or 450, wherein the composition comprises L-leucine, a R-amino acid entity, glutamate, and homocysteine.

60. The composition of any of embodiments 1-2, 14, or 451, wherein the composition comprises L-leucine, a R-amino acid entity, carbamoyl-P, and methionine.

61. The composition of any of embodiments 1-2, 14, or 452, wherein the composition comprises L-leucine, a R-amino acid entity, N-acetyl-glutamine, and D-cysteine.

62. The composition of any of embodiments 1-2, 14, or 453, wherein the composition comprises L-leucine, a R-amino acid entity, L-glutamine, and L-cysteine.

63. The composition of any of embodiments 1-2, 14, or 454, wherein the composition comprises L-leucine, a R-amino acid entity, a glutamate, and cystine.

64. The composition of any of embodiments 1-2, 14, 380, or 445, wherein the composition comprises L-leucine, L-arginine, L-glutamine, and NAC.

65. The composition of any of embodiments 1-2, 14, 381, or 446, wherein the composition comprises L-leucine, argininosuccinate, glutamate, and serine.

66. The composition of any of embodiments 1-2, 14, 382, or 447, wherein the composition comprises L-leucine, citrulline, carbamoyl-P, and acetylserine.

67. The composition of any of embodiments 1-2, 14, 383, or 448, wherein the composition comprises L-leucine, aspartate, D-glutamine, and cystathionine.

68. The composition of any of embodiments 1-2, 14, 384, or 449, wherein the composition comprises L-leucine, glutamate, L-glutamine, and glutathione.

69. The composition of any of embodiments 1-2, 14, 385, or 450, wherein the composition comprises L-leucine, ornithine, glutamate, and homocysteine.

70. The composition of any of embodiments 1-2, 14, 386, or 451, wherein the composition comprises L-leucine, agmatine, carbamoyl-P, and methionine.

71. The composition of any of embodiments 1-2, 14, 387, or 452, wherein the composition comprises L-leucine, creatine, D-glutamine and D-cysteine.

72. The composition of any of embodiments 1-2, 14, 388, or 453, wherein the composition comprises L-leucine, D-arginine, a Q-amino acid entity, and L-cysteine.

73. The composition of any of embodiments 1-2, 14, 389, or 454, wherein the composition comprises L-leucine, N-acetyl-arginine, argininosuccinate, and cystine.

74. The composition of embodiment 1 or 3, wherein the composition comprises oxo-leucine, a R-amino acid entity, a Q-amino acid entity, and an antioxidant or ROS scavenger, e.g., a NAC entity.

75. The composition of embodiment 1-D, 3, or 74, wherein the composition comprises oxo-leucine, a R-amino acid entity, and a Q-amino acid entity, and an antioxidant or ROS scavenger, e.g., a NAC entity.

76. The composition of embodiment 1-1D, 3, or 74, wherein the composition comprises oxo-leucine, L-arginine, a Q-amino acid entity, and an antioxidant or ROS scavenger, e.g., a NAC entity.

77. The composition of embodiment 1-1D, 3, or 74, wherein the composition comprises oxo-leucine, argininosuccinate, a Q-amino acid entity, and an antioxidant or ROS scavenger, e.g., a NAC entity.

78. The composition of embodiment 1-1D, 3, or 74, wherein the composition comprises oxo-leucine, citrulline, a Q-amino acid entity, and an antioxidant or ROS scavenger, e.g., a NAC entity.

79. The composition of embodiment 1-1D, 3, or 74, wherein the composition comprises oxo-leucine, aspartate, a Q-amino acid entity, and an antioxidant or ROS scavenger, e.g., a NAC entity.

80. The composition of embodiment 1-1D, 3, or 74, wherein the composition comprises oxo-leucine, glutamate, a Q-amino acid entity, and an antioxidant or ROS scavenger, e.g., a NAC entity.

81. The composition of embodiment 1-1D, 3, or 74, wherein the composition comprises oxo-leucine, ornithine, a Q-amino acid entity, and an antioxidant or ROS scavenger, e.g., a NAC entity.

82. The composition of embodiment 1-1D, 3, or 74, wherein the composition comprises oxo-leucine, agmatine, a Q-amino acid entity, and an antioxidant or ROS scavenger, e.g., a NAC entity.

83. The composition of embodiment 1-1D, 3, or 74, wherein the composition comprises oxo-leucine, creatine, a Q-amino acid entity, and an antioxidant or ROS scavenger, e.g., a NAC entity.

84. The composition of embodiment 1-1D, 3, or 74, wherein the composition comprises oxo-leucine, D-arginine, a Q-amino acid entity, and an antioxidant or ROS scavenge, e.g., a NAC entity.

85. The composition of embodiment 1-1D, 3, or 74, wherein the composition comprises oxo-leucine, N-acetyl-arginine, a Q-amino acid entity, and an antioxidant or ROS scavenger, e.g., a NAC entity.

86. The composition of embodiment 1-1D, 3, or 74, wherein the composition comprises oxo-leucine, a R-amino acid entity, L-glutamine, and an antioxidant or ROS scavenger, e.g., a NAC entity.

87. The composition of embodiment 1-1D, 3, or 74, wherein the composition comprises oxo-leucine, a R-amino acid entity, glutamate, and an antioxidant or ROS scavenger, e.g., a NAC entity.

88. The composition of embodiment 1-1D, 3, or 74, wherein the composition comprises oxo-leucine, a R-amino acid entity, carbamoyl-P, and an antioxidant or ROS scavenger, e.g., a NAC entity.

89. The composition of embodiment 1-1D, 3, or 74, wherein the composition comprises oxo-leucine, a R-amino acid entity, D-glutamine, and an antioxidant or ROS scavenger, e.g., a NAC entity.

90. The composition of embodiment 1-1D, 3, or 74, wherein the composition comprises oxo-leucine, a R-amino acid entity, N-acetyl-glutamine, and an antioxidant or ROS scavenger, e.g., a NAC entity.

91. The composition of embodiment 1-1D, 3, or 74, wherein the composition comprises oxo-leucine, a R-amino acid entity, a Q-amino acid entity, and NAC.

92. The composition of embodiment 1-1D, 3, or 74, wherein the composition comprises oxo-leucine, a R-amino acid entity, a Q-amino acid entity, and serine.

93. The composition of embodiment 1-1D, 3, or 74, wherein the composition comprises oxo-leucine, a R-amino acid entity, a Q-amino acid entity, and acetylserine.

94. The composition of embodiment 1-1D, 3, or 74, wherein the composition comprises oxo-leucine, a R-amino acid entity, a Q-amino acid entity, and cystathionine.

95. The composition of embodiment 1-1D, 3, or 74, wherein the composition comprises oxo-leucine, a R-amino acid entity, a Q-amino acid entity, and glutathione.

96. The composition of embodiment 1-1D, 3, or 74, wherein the composition comprises oxo-leucine, a R-amino acid entity, a Q-amino acid entity, and homocysteine.

97. The composition of embodiment 1-1D, 3, or 74, wherein the composition comprises oxo-leucine, a R-amino acid entity, a Q-amino acid entity, and methionine.

98. The composition of embodiment 1-1D, 3, or 74, wherein the composition comprises oxo-leucine, a R-amino acid entity, a Q-amino acid entity, and D-cysteine.

99. The composition of embodiment 1-1D, 3, or 74, wherein the composition comprises oxo-leucine, a R-amino acid entity, a Q-amino acid entity, and L-cysteine.

100. The composition of embodiment 1-1D, 3, or 74, wherein the composition comprises oxo-leucine, a R-amino acid entity, a Q-amino acid entity, and a NAC entity.

101. The composition of embodiment 1-1D, 3, or 74, wherein the composition comprises oxo-leucine, a R-amino acid entity, a Q-amino acid entity, and cystine.

102. The composition of embodiment 1-1D, 3, or 74, wherein the composition comprises oxo-leucine, L-arginine, L-glutamine, and an antioxidant or ROS scavenger, e.g., a NAC entity.

103. The composition of embodiment 1-1D, 3, or 74, wherein the composition comprises oxo-leucine, arginino-succinate, glutamate, and an antioxidant or ROS scavenger, e.g., a NAC entity.

104. The composition of embodiment 1-1D, 3, or 74, wherein the composition comprises oxo-leucine, citrulline, D-glutamine, and an antioxidant or ROS scavenger, e.g., a NAC entity.

105. The composition of embodiment 1-1D, 3, or 74, wherein the composition comprises oxo-leucine, aspartate, N-acetyl-glutamine, and an antioxidant or ROS scavenger, e.g., a NAC entity.

106. The composition of embodiment 1-1D, 3, or 74, wherein the composition comprises oxo-leucine, L-arginine, a Q-amino acid entity, and NAC.

107. The composition of embodiment 1-1D, 3, or 74, wherein the composition comprises oxo-leucine, arginino-succinate, a Q-amino acid entity, and serine.

108. The composition of embodiment 1-1D, 3, or 74, wherein the composition comprises oxo-leucine, citrulline, a Q-amino acid entity, and acetylserine.

109. The composition of embodiment 1-1D, 3, or 74, wherein the composition comprises oxo-leucine, aspartate, a Q-amino acid entity, and cystathionine.

110. The composition of embodiment 1-1D, 3, or 74, wherein the composition comprises oxo-leucine, glutamate, a Q-amino acid entity, and glutathione.

111. The composition of embodiment 1-1D, 3, or 74, wherein the composition comprises oxo-leucine, ornithine, a Q-amino acid entity, and homocysteine.

112. The composition of embodiment 1-1D, 3, or 74, wherein the composition comprises oxo-leucine, agmatine, a Q-amino acid entity, and methionine.

113. The composition of embodiment 1-1D, 3, or 74, wherein the composition comprises oxo-leucine, creatine, a Q-amino acid entity, and D-cysteine.

114. The composition of embodiment 1-1D, 3, or 74, wherein the composition comprises oxo-leucine, D-arginine, a Q-amino acid entity, and L-cysteine.

115. The composition of embodiment 1-1D, 3, or 74, wherein the composition comprises oxo-leucine, N-acetyl-arginine, a Q-amino acid entity, and cystine.

116. The composition of embodiment 1-1D, 3, or 74, wherein the composition comprises oxo-leucine, a R-amino acid entity, L-glutamine, and NAC.

117. The composition of embodiment 1-1D, 3, or 74, wherein the composition comprises oxo-leucine, a R-amino acid entity, glutamate, and serine.

118. The composition of embodiment 1-1D, 3, or 74, wherein the composition comprises oxo-leucine, a R-amino acid entity, carbamoyl-P, and acetylserine.

119. The composition of embodiment 1-1D, 3, or 74, wherein the composition comprises oxo-leucine, a R-amino acid entity, N-acetyl-glutamine, and cystathionine.

120. The composition of embodiment 1-1D, 3, or 74, wherein the composition comprises oxo-leucine, a R-amino acid entity, L-glutamine, and glutathione.

121. The composition of embodiment 1-1D, 3, or 74, wherein the composition comprises oxo-leucine, a R-amino acid entity, glutamate, and homocysteine.

122. The composition of embodiment 1-1D, 3, or 74, wherein the composition comprises oxo-leucine, a R-amino acid entity, carbamoyl-P, and methionine.

123. The composition of embodiment 1-1D, 3, or 74, wherein the composition comprises oxo-leucine, a R-amino acid entity, N-acetyl-glutamine, and D-cysteine.

124. The composition of embodiment 1-1D, 3, or 74, wherein the composition comprises oxo-leucine, a R-amino acid entity, L-glutamine, and L-cysteine.

125. The composition of embodiment 1-1D, 3, or 74, wherein the composition comprises oxo-leucine, a R-amino acid entity, a glutamate, and cystine.

126. The composition of embodiment 1-1D, 3, or 74, wherein the composition comprises oxo-leucine, L-arginine, L-glutamine, and NAC.

127. The composition of embodiment 1-1D, 3, or 74, wherein the composition comprises oxo-leucine, arginino-succinate, glutamate, and serine.

128. The composition of embodiment 1-1D, 3, or 74, wherein the composition comprises oxo-leucine, citrulline, carbamoyl-P, and acetylserine.

129. The composition of embodiment 1-1D, 3, or 74, wherein the composition comprises oxo-leucine, aspartate, D-glutamine, and cystathionine.

130. The composition of embodiment 1-1D, 3, or 74, wherein the composition comprises oxo-leucine, N-acetyl-glutamine, L-glutamine, and glutathione.

131. The composition of embodiment 1-1D, 3, or 74, wherein the composition comprises oxo-leucine, ornithine, glutamate, and homocysteine.

132. The composition of embodiment 1-1D, 3, or 74, wherein the composition comprises oxo-leucine, agmatine, carbamoyl-P, and methionine.

133. The composition of embodiment 1-1D, 3, or 74, wherein the composition comprises oxo-leucine, creatine, D-glutamine and D-cysteine.

134. The composition of embodiment 1-1D, 3, or 74, wherein the composition comprises oxo-leucine, D-arginine, a Q-amino acid entity, and L-cysteine.

135. The composition of embodiment 1-1D, 3, or 74, wherein the composition comprises oxo-leucine, N-acetyl-arginine, argininosuccinate, and cystine.

136. The composition of embodiment 1-1D or 4, wherein the composition comprises HMB, a R-amino acid entity, a Q-amino acid entity, and an antioxidant or ROS scavenger, e.g., a NAC entity.

137. The composition of embodiment 1-1D, 4, or 136, wherein the composition comprises HMB, L-arginine, a Q-amino acid entity, and an antioxidant or ROS scavenger, e.g., a NAC entity.

138. The composition of embodiment 1-1D, 4, or 136, wherein the composition comprises HMB, argininosucci-nate, a Q-amino acid entity, and an antioxidant or ROS scavenger, e.g., a NAC entity.

139. The composition of embodiment 1-1D, 4, or 136, wherein the composition comprises HMB, citrulline, a Q-amino acid entity, and an antioxidant or ROS scavenger, e.g., a NAC entity.

140. The composition of embodiment 1-1D, 4, or 136, wherein the composition comprises HMB, aspartate, a Q-amino acid entity, and an antioxidant or ROS scavenger, e.g., a NAC entity.

141. The composition of embodiment 1-1D, 4, or 136, wherein the composition comprises HMB, glutamate, a Q-amino acid entity, and an antioxidant or ROS scavenger, e.g., a NAC entity.

142. The composition of embodiment 1-1D, 4, or 136, wherein the composition comprises HMB, ornithine, a Q-amino acid entity, and an antioxidant or ROS scavenger, e.g., a NAC entity.

143. The composition of embodiment 1-1D, 4, or 136, wherein the composition comprises HMB, agmatine, a Q-amino acid entity, and an antioxidant or ROS scavenger e.g., a NAC entity.

144. The composition of embodiment 1-1D, 4, or 136, wherein the composition comprises HMB, creatine, a Q-amino acid entity, and an antioxidant or ROS scavenger, e.g., a NAC entity.

145. The composition of embodiment 1-1D, 4, or 136, wherein the composition comprises HMB, D-arginine, a Q-amino acid entity, and an antioxidant or ROS scavenge e.g., a NAC entity.

146. The composition of embodiment 1-1D, 4, or 136, wherein the composition comprises HMB, N-acetyl-arginine, a Q-amino acid entity, and an antioxidant or ROS scavenger, e.g., a NAC entity.

147. The composition of embodiment 1-1D, 4, or 136, wherein the composition comprises HMB, a R-amino acid entity, L-glutamine, and an antioxidant or ROS scavenger, e.g., an antioxidant, e.g., a NAC entity.

148. The composition of embodiment 1-1D, 4, or 136, wherein the composition comprises HMB, a R-amino acid entity, glutamate, and an antioxidant or ROS scavenger, e.g., an antioxidant, e.g., a NAC entity.

149. The composition of embodiment 1-1D, 4, or 136, wherein the composition comprises HMB, a R-amino acid entity, carbamoyl-P, and an antioxidant or ROS scavenger, e.g., an antioxidant, e.g., a NAC entity.

150. The composition of embodiment 1-1D, 4, or 136, wherein the composition comprises HMB, a R-amino acid entity, D-glutamine, and an antioxidant or ROS scavenger, e.g., an antioxidant, e.g., a NAC entity.

151. The composition of embodiment 1-1D, 4, or 136, wherein the composition comprises HMB, a R-amino acid entity, N-acetyl-glutamine, and an antioxidant or ROS scavenger, e.g., an antioxidant, e.g., a NAC entity.

152. The composition of embodiment 1-1D, 4, or 136, wherein the composition comprises HMB, a R-amino acid entity, a Q-amino acid entity, and NAC.

153. The composition of embodiment 1-1D, 4, or 136, wherein the composition comprises HMB, a R-amino acid entity, a Q-amino acid entity, and serine.

154. The composition of embodiment 1-1D, 4, or 136, wherein the composition comprises HMB, a R-amino acid entity, a Q-amino acid entity, and acetylserine.

155. The composition of embodiment 1-1D, 4, or 136, wherein the composition comprises HMB, a R-amino acid entity, a Q-amino acid entity, and cystathionine.

156. The composition of embodiment 1-1D, 4, or 136, wherein the composition comprises HMB, a R-amino acid entity, a Q-amino acid entity, and glutathione.

157. The composition of embodiment 1-1D, 4, or 136, wherein the composition comprises HMB, a R-amino acid entity, a Q-amino acid entity, and homocysteine.

158. The composition of embodiment 1-1D, 4, or 136, wherein the composition comprises HMB, a R-amino acid entity, a Q-amino acid entity, and methionine.

159. The composition of embodiment 1-1D, 4, or 136, wherein the composition comprises HMB, a R-amino acid entity, a Q-amino acid entity, and D-cysteine.

160. The composition of embodiment 1-1D, 4, or 136, wherein the composition comprises HMB, a R-amino acid entity, a Q-amino acid entity, and L-cysteine.

161. The composition of embodiment 1-1D, 4, or 136, wherein the composition comprises HMB, a R-amino acid entity, a Q-amino acid entity, and cysteine.

162. The composition of embodiment 1-1D, 4, or 136, wherein the composition comprises HMB, a R-amino acid entity, a Q-amino acid entity, and cystine.

163. The composition of embodiment 1-1D, 4, or 136, wherein the composition comprises HMB, L-arginine, L-glutamine, and an antioxidant or ROS scavenger, e.g., a NAC entity.

164. The composition of embodiment 1-1D, 4, or 136, wherein the composition comprises HMB, argininosuccinate, glutamate, and an antioxidant or ROS scavenger, e.g., a NAC entity.

165. The composition of embodiment 1-1D, 4, or 136, wherein the composition comprises HMB, citrulline, D-glutamine, and an antioxidant or ROS scavenger, e.g., a NAC entity.

166. The composition of embodiment 1-1D, 4, or 136, wherein the composition comprises HMB, aspartate, N-acetyl-glutamine, and an antioxidant or ROS scavenger, e.g., a NAC entity.

167. The composition of embodiment 1-1D, 4, or 136, wherein the composition comprises HMB, L-arginine, a Q-amino acid entity, and NAC.

168. The composition of embodiment 1-1D, 4, or 136, wherein the composition comprises HMB, argininosuccinate, a Q-amino acid entity, and serine.

169. The composition of embodiment 1-1D, 4, or 136, wherein the composition comprises HMB, citrulline, a Q-amino acid entity, and acetylserine.

170. The composition of embodiment 1-1D, 4, or 136, wherein the composition comprises HMB, aspartate, a Q-amino acid entity, and cystathionine.

171. The composition of embodiment 1-1D, 4, or 136, wherein the composition comprises HMB, glutamate, a Q-amino acid entity, and glutathione.

172. The composition of embodiment 1-1D, 4, or 136, wherein the composition comprises HMB, ornithine, a Q-amino acid entity, and homocysteine.

173. The composition of embodiment 1-1D, 4, or 136, wherein the composition comprises HMB, agmatine, a Q-amino acid entity, and methionine.

174. The composition of embodiment 1-1D, 4, or 136, wherein the composition comprises HMB, creatine, a Q-amino acid entity, and D-cysteine.

175. The composition of embodiment 1-1D, 4, or 136, wherein the composition comprises HMB, D-arginine, a Q-amino acid entity, and L-cysteine.

176. The composition of embodiment 1-1D, 4, or 136, wherein the composition comprises HMB, N-acetyl-arginine, a Q-amino acid entity, and cystine.

177. The composition of embodiment 1-1D, 4, or 136, wherein the composition comprises HMB, a R-amino acid entity, L-glutamine, and NAC.

178. The composition of embodiment 1-1D, 4, or 136, wherein the composition comprises HMB, a R-amino acid entity, glutamate, and serine.

179. The composition of embodiment 1-1D, 4, or 136, wherein the composition comprises HMB, a R-amino acid entity, carbamoyl-P, and acetylserine.

180. The composition of embodiment 1-1D, 4, or 136, wherein the composition comprises HMB, a R-amino acid entity, N-acetyl-glutamine, and cystathionine.

181. The composition of embodiment 1-1D, 4, or 136, wherein the composition comprises HMB, a R-amino acid entity, L-glutamine, and glutathione.

182. The composition of embodiment 1-1D, 4, or 136, wherein the composition comprises HMB, a R-amino acid entity, glutamate, and homocysteine.

183. The composition of embodiment 1-1D, 4, or 136, wherein the composition comprises HMB, a R-amino acid entity, carbamoyl-P, and methionine.

184. The composition of embodiment 1-1D, 4, or 136, wherein the composition comprises HMB, a R-amino acid entity, N-acetyl-glutamine, and D-cysteine.

185. The composition of embodiment 1-1D, 4, or 136, wherein the composition comprises HMB, a R-amino acid entity, L-glutamine, and L-cysteine.

186. The composition of embodiment 1-1D, 4, or 136, wherein the composition comprises HMB, a R-amino acid entity, a glutamate, and cystine.

187. The composition of embodiment 1-1D, 4, or 136, wherein the composition comprises HMB, L-arginine, L-glutamine, and NAC.

188. The composition of embodiment 1-1D, 4, or 136, wherein the composition comprises HMB, argininosuccinate, glutamate, and serine.

189. The composition of embodiment 1-1D, 4, or 136, wherein the composition comprises HMB, citrulline, carbamoyl-P, and acetylserine.

190. The composition of embodiment 1-1D, 4, or 136, wherein the composition comprises HMB, aspartate, D-glutamine, and cystathionine.

191. The composition of embodiment 1-1D, 4, or 136, wherein the composition comprises HMB, N-acetyl-glutamine, L-glutamine, and glutathione.

192. The composition of embodiment 1-1D, 4, or 136, wherein the composition comprises HMB, ornithine, glutamate, and homocysteine.

193. The composition of embodiment 1-1D, 4, or 136, wherein the composition comprises HMB, agmatine, carbamoyl-P, and methionine.

194. The composition of embodiment 1-1D, 4, or 136, wherein the composition comprises HMB, creatine, D-glutamine and D-cysteine.

195. The composition of embodiment 1-1D, 4, or 136, wherein the composition comprises HMB, D-arginine, a Q-amino acid entity, and L-cysteine.

196. The composition of embodiment 1-1D, 4, or 136, wherein the composition comprises HMB, N-acetyl-arginine, argininosuccinate, and cystine.

197. The composition of embodiment 1-1D, or 4, wherein the composition comprises isovaleryl-CoA, a R-amino acid entity, a Q-amino acid entity, and an antioxidant or ROS scavenger, e.g., a NAC entity.

198. The composition of embodiment 1-1D, 4, or 197, wherein the composition comprises isovaleryl-CoA, L-arginine, a Q-amino acid entity, and an antioxidant or ROS scavenger, e.g., a NAC entity.

199. The composition of embodiment 1-1D, 4, or 197, wherein the composition comprises isovaleryl-CoA, argininosuccinate, a Q-amino acid entity, and an antioxidant or ROS scavenger, e.g., a NAC entity.

200. The composition of embodiment 1-1D, 4, or 197, wherein the composition comprises isovaleryl-CoA, citrulline, a Q-amino acid entity, and an antioxidant or ROS scavenger, e.g., a NAC entity.

201. The composition of embodiment 1-1D, 4, or 197, wherein the composition comprises isovaleryl-CoA, aspartate, a Q-amino acid entity, and an antioxidant or ROS scavenger, e.g., a NAC entity.

202. The composition of embodiment 1-1D, 4, or 197, wherein the composition comprises isovaleryl-CoA, glutamate, a Q-amino acid entity, and an antioxidant or ROS scavenger, e.g., a NAC entity.

203. The composition of embodiment 1-1D, 4, or 197, wherein the composition comprises isovaleryl-CoA, ornithine, a Q-amino acid entity, and an antioxidant or ROS scavenger, e.g., a NAC entity.

204. The composition of embodiment 1-1D, 4, or 197, wherein the composition comprises isovaleryl-CoA, agmatine, a Q-amino acid entity, and an antioxidant or ROS scavenger, e.g., a NAC entity.

205. The composition of embodiment 1-1D, 4, or 197, wherein the composition comprises isovaleryl-CoA, creatine, a Q-amino acid entity, and an antioxidant or ROS scavenger, e.g., a NAC entity.

206. The composition of embodiment 1-1D, 4, or 197, wherein the composition comprises isovaleryl-CoA, D-arginine, a Q-amino acid entity, and an antioxidant or ROS scavenger, e.g., a NAC entity.

207. The composition of embodiment 1-1D, 4, or 197, wherein the composition comprises isovaleryl-CoA, N-acetyl-arginine, a Q-amino acid entity, and an antioxidant or ROS scavenger, e.g., a NAC entity.

208. The composition of embodiment 1-1D, 4, or 197, wherein the composition comprises isovaleryl-CoA, a R-amino acid entity, L-glutamine, and an antioxidant or ROS scavenger, e.g., a NAC entity.

209. The composition of embodiment 1-1D, 4, or 197, wherein the composition comprises isovaleryl-CoA, a R-amino acid entity, glutamate, and an antioxidant or ROS scavenger, e.g., a NAC entity.

210. The composition of embodiment 1-1D, 4, or 197, wherein the composition comprises isovaleryl-CoA, a R-amino acid entity, carbamoyl-P, and an antioxidant or ROS scavenger, e.g., a NAC entity.

211. The composition of embodiment 1-1D, 4, or 197, wherein the composition comprises isovaleryl-CoA, a R-amino acid entity, D-glutamine, and an antioxidant or ROS scavenger, e.g., a NAC entity.

212. The composition of embodiment 1-1D, 4, or 197, wherein the composition comprises isovaleryl-CoA, a R-amino acid entity, N-acetyl-glutamine, and an antioxidant or ROS scavenger, e.g., a NAC entity.

213. The composition of embodiment 1-1D, 4, or 197, wherein the composition comprises isovaleryl-CoA, a R-amino acid entity, a Q-amino acid entity, and NAC.

214. The composition of embodiment 1-1D, 4, or 197, wherein the composition comprises isovaleryl-CoA, a R-amino acid entity, a Q-amino acid entity, and serine.

215. The composition of embodiment 1-1D, 4, or 197, wherein the composition comprises isovaleryl-CoA, a R-amino acid entity, a Q-amino acid entity, and acetylserine.

216. The composition of embodiment 1-1D, 4, or 197, wherein the composition comprises isovaleryl-CoA, a R-amino acid entity, a Q-amino acid entity, and cystathionine.

217. The composition of embodiment 1-1D, 4, or 197, wherein the composition comprises isovaleryl-CoA, a R-amino acid entity, a Q-amino acid entity, and glutathione.

218. The composition of embodiment 1-1D, 4, or 197, wherein the composition comprises isovaleryl-CoA, a R-amino acid entity, a Q-amino acid entity, and homocysteine.

219. The composition of embodiment 1-1D, 4, or 197, wherein the composition comprises isovaleryl-CoA, a R-amino acid entity, a Q-amino acid entity, and methionine.

220. The composition of embodiment 1-1D, 4, or 197, wherein the composition comprises isovaleryl-CoA, a R-amino acid entity, a Q-amino acid entity, and D-cysteine.

221. The composition of embodiment 1-1D, 4, or 197, wherein the composition comprises isovaleryl-CoA, a R-amino acid entity, a Q-amino acid entity, and L-cysteine.

222. The composition of embodiment 1-1D, 4, or 197, wherein the composition comprises isovaleryl-CoA, a R-amino acid entity, a Q-amino acid entity, and cysteine.

223. The composition of embodiment 1-1D, 4, or 197, wherein the composition comprises isovaleryl-CoA, a R-amino acid entity, a Q-amino acid entity, and cystine.

224. The composition of embodiment 1-1D, 4, or 197, wherein the composition comprises isovaleryl-CoA, L-arginine, L-glutamine, and an antioxidant or ROS scavenger, e.g., a NAC entity.

225. The composition of embodiment 1-1D, 4, or 197, wherein the composition comprises isovaleryl-CoA, argininosuccinate, glutamate, and an antioxidant or ROS scavenger, e.g., a NAC entity.

226. The composition of embodiment 1-1D, 4, or 197, wherein the composition comprises isovaleryl-CoA, citrulline, D-glutamine, and an antioxidant or ROS scavenger, e.g., a NAC entity.

227. The composition of embodiment 1-1D, 4, or 197, wherein the composition comprises isovaleryl-CoA, aspartate, N-acetyl-glutamine, and an antioxidant or ROS scavenger, e.g., a NAC entity.

228. The composition of embodiment 1-1D, 4, or 197, wherein the composition comprises isovaleryl-CoA, L-arginine, a Q-amino acid entity, and NAC.

229. The composition of embodiment 1-1D, 4, or 197, wherein the composition comprises isovaleryl-CoA, argininosuccinate, a Q-amino acid entity, and serine.

230. The composition of embodiment 1-1D, 4, or 197, wherein the composition comprises isovaleryl-CoA, citrulline, a Q-amino acid entity, and acetylserine.

231. The composition of embodiment 1-1D, 4, or 197, wherein the composition comprises isovaleryl-CoA, aspartate, a Q-amino acid entity, and cystathionine.

232. The composition of embodiment 1-1D, 4, or 197, wherein the composition comprises isovaleryl-CoA, glutamate, a Q-amino acid entity, and glutathione.

233. The composition of embodiment 1-1D, 4, or 197, wherein the composition comprises isovaleryl-CoA, ornithine, a Q-amino acid entity, and homocysteine.

234. The composition of embodiment 1-1D, 4, or 197, wherein the composition comprises isovaleryl-CoA, agmatine, a Q-amino acid entity, and methionine.

235. The composition of embodiment 1-1D, 4, or 197, wherein the composition comprises isovaleryl-CoA, creatine, a Q-amino acid entity, and D-cysteine.

236. The composition of embodiment 1-1D, 4, or 197, wherein the composition comprises isovaleryl-CoA, D-arginine, a Q-amino acid entity, and L-cysteine.

237. The composition of embodiment 1-1D, 4, or 197, wherein the composition comprises isovaleryl-CoA, N-acetyl-arginine, a Q-amino acid entity, and cystine.

238. The composition of embodiment 1-1D, 4, or 197, wherein the composition comprises isovaleryl-CoA, a R-amino acid entity, L-glutamine, and NAC.

239. The composition of embodiment 1-1D, 4, or 197, wherein the composition comprises isovaleryl-CoA, a R-amino acid entity, glutamate, and serine.

240. The composition of embodiment 1-1D, 4, or 197, wherein the composition comprises isovaleryl-CoA, a R-amino acid entity, carbamoyl-P, and acetylserine.

241. The composition of embodiment 1-1D, 4, or 197, wherein the composition comprises isovaleryl-CoA, a R-amino acid entity, N-acetyl-glutamine, and cystathionine.

242. The composition of embodiment 1-1D, 4, or 197, wherein the composition comprises isovaleryl-CoA, a R-amino acid entity, L-glutamine, and glutathione.

243. The composition of embodiment 1-1D, 4, or 197, wherein the composition comprises isovaleryl-CoA, a R-amino acid entity, glutamate, and homocysteine.

244. The composition of embodiment 1-1D, 4, or 197, wherein the composition comprises isovaleryl-CoA, a R-amino acid entity, carbamoyl-P, and methionine.

245. The composition of embodiment 1-1D, 4, or 197, wherein the composition comprises isovaleryl-CoA, a R-amino acid entity, N-acetyl-glutamine, and D-cysteine.

246. The composition of embodiment 1-1D, 4, or 197, wherein the composition comprises isovaleryl-CoA, a R-amino acid entity, L-glutamine, and L-cysteine.

247. The composition of embodiment 1-1D, 4, or 197, wherein the composition comprises isovaleryl-CoA, a R-amino acid entity, a glutamate, and cystine.

248. The composition of embodiment 1-1D, 4, or 197, wherein the composition comprises isovaleryl-CoA, L-arginine, L-glutamine, and NAC.

249. The composition of embodiment 1-1D, 4, or 197, wherein the composition comprises isovaleryl-CoA, argininosuccinate, glutamate, and serine.

250. The composition of embodiment 1-1D, 4, or 197, wherein the composition comprises isovaleryl-CoA, citrulline, carbamoyl-P, and acetylserine.

251. The composition of embodiment 1-1D, 4, or 197, wherein the composition comprises isovaleryl-CoA, aspartate, D-glutamine, and cystathionine.

252. The composition of embodiment 1-1D, 4, or 197, wherein the composition comprises isovaleryl-CoA, N-acetyl-glutamine, L-glutamine, and glutathione.

253. The composition of embodiment 1-1D, 4, or 197, wherein the composition comprises isovaleryl-CoA, ornithine, glutamate, and homocysteine.

254. The composition of embodiment 1-1D, 4, or 197, wherein the composition comprises isovaleryl-CoA, agmatine, carbamoyl-P, and methionine.

255. The composition of embodiment 1-1D, 4, or 197, wherein the composition comprises isovaleryl-CoA, creatine, D-glutamine and D-cysteine.

256. The composition of embodiment 1-1D, 4, or 197, wherein the composition comprises isovaleryl-CoA, D-arginine, a Q-amino acid entity, and L-cysteine.

257. The composition of embodiment 1-1D, 4, or 197, wherein the composition comprises isovaleryl-CoA, N-acetyl-arginine, argininosuccinate, and cystine.

258. The composition of embodiment 1-1D or 5, wherein the composition comprises D-leucine, a R-amino acid entity, a Q-amino acid entity, and an antioxidant or ROS scavenger, e.g., a NAC entity.

259. The composition of embodiment 1-1D, 5, or 258, wherein the composition comprises D-leucine, L-arginine, a Q-amino acid entity, and an antioxidant or ROS scavenger, e.g., a NAC entity.

260. The composition of embodiment 1-1D, 5, or 258, wherein the composition comprises D-leucine, argininosuccinate, a Q-amino acid entity, and an antioxidant or ROS scavenger, e.g., a NAC entity.

261. The composition of embodiment 1-1D, 5, or 258, wherein the composition comprises D-leucine, citrulline, a Q-amino acid entity, and an antioxidant or ROS scavenger, e.g., a NAC entity.

262. The composition of embodiment 1-1D, 5, or 258, wherein the composition comprises D-leucine, aspartate, a Q-amino acid entity, and an antioxidant or ROS scavenger, e.g., a NAC entity.

263. The composition of embodiment 1-1D, 5, or 258, wherein the composition comprises D-leucine, glutamate, a Q-amino acid entity, and an antioxidant or ROS scavenger, e.g., a NAC entity.

264. The composition of embodiment 1-1D, 5, or 258, wherein composition comprises D-leucine, ornithine, a Q-amino acid entity, and an antioxidant or ROS scavenger, e.g., a NAC entity.

265. The composition of embodiment 1-1D, 5, or 258, wherein the composition comprises D-leucine, agmatine, a Q-amino acid entity, and an antioxidant or ROS scavenger, e.g., a NAC entity.

266. The composition of embodiment 1-1D, 5, or 258, wherein the composition comprises D-leucine, creatine, a Q-amino acid entity, and an antioxidant or ROS scavenger, e.g., a NAC entity.

267. The composition of embodiment 1-1D, 5, or 258, wherein the composition comprises D-leucine, D-arginine, a Q-amino acid entity, and an antioxidant or ROS scavenger, e.g., a NAC entity.

268. The composition of embodiment 1-1D, 5, or 258, wherein the composition comprises D-leucine, N-acetyl-arginine, a Q-amino acid entity, and an antioxidant or ROS scavenger, e.g., a NAC entity.

269. The composition of embodiment 1-1D, 5, or 258, wherein the composition comprises D-leucine, a R-amino acid entity, L-glutamine, and an antioxidant or ROS scavenger, e.g., a NAC entity.

270. The composition of embodiment 1-1D, 5, or 258, wherein the composition comprises D-leucine, a R-amino acid entity, glutamate, and an antioxidant or ROS scavenger, e.g., a NAC entity.

271. The composition of embodiment 1-1D, 5, or 258, wherein the composition comprises D-leucine, a R-amino acid entity, carbamoyl-P, and an antioxidant or ROS scavenger, e.g., a NAC entity.

272. The composition of embodiment 1-1D, 5, or 258, wherein the composition comprises D-leucine, a R-amino acid entity, D-glutamine, and an antioxidant or ROS scavenger, e.g., a NAC entity.

273. The composition of embodiment 1-1D, 5, or 258, wherein the composition comprises D-leucine, a R-amino acid entity, N-acetyl-glutamine, and an antioxidant or ROS scavenger, e.g., a NAC entity.

274. The composition of embodiment 1-1D, 5, or 258, wherein the composition comprises D-leucine, a R-amino acid entity, a Q-amino acid entity, and NAC.

275. The composition of embodiment 1-1D, 5, or 258, wherein the composition comprises D-leucine, a R-amino acid entity, a Q-amino acid entity, and serine.

276. The composition of embodiment 1-1D, 5, or 258, wherein the composition comprises D-leucine, a R-amino acid entity, a Q-amino acid entity, and acetylserine.

277. The composition of embodiment 1-1D, 5, or 258, wherein the composition comprises D-leucine, a R-amino acid entity, a Q-amino acid entity, and cystathionine.

278. The composition of embodiment 1-1D, 5, or 258, wherein the composition comprises D-leucine, a R-amino acid entity, a Q-amino acid entity, and glutathione.

279. The composition of embodiment 1-1D, 5, or 258, wherein the composition comprises D-leucine, a R-amino acid entity, a Q-amino acid entity, and homocysteine.

280. The composition of embodiment 1-1D, 5, or 258, wherein the composition comprises D-leucine, a R-amino acid entity, a Q-amino acid entity, and methionine.

281. The composition of embodiment 1-1D, 5, or 258, wherein the composition comprises D-leucine, a R-amino acid entity, a Q-amino acid entity, and D-cysteine.

282. The composition of embodiment 1-1D, 5, or 258, wherein the composition comprises D-leucine, a R-amino acid entity, a Q-amino acid entity, and L-cysteine.

283. The composition of embodiment 1-1D, 5, or 258, wherein the composition comprises D-leucine, a R-amino acid entity, a Q-amino acid entity, and cysteine.

284. The composition of embodiment 1-1D, 5, or 258, wherein the composition comprises D-leucine, a R-amino acid entity, a Q-amino acid entity, and cystine.

285. The composition of embodiment 1-1D, 5, or 258, wherein the composition comprises D-leucine, L-arginine, L-glutamine, and an antioxidant or ROS scavenger, e.g., a NAC entity.

286. The composition of embodiment 1-1D, 5, or 258, wherein the composition comprises D-leucine, argininosuccinate, glutamate, and an antioxidant or ROS scavenger e.g., a NAC entity.

287. The composition of embodiment 1-1D, 5, or 258, wherein the composition comprises D-leucine, citrulline, D-glutamine, and an antioxidant or ROS scavenger e.g., a NAC entity.

288. The composition of embodiment 1-1D, 5, or 258, wherein the composition comprises D-leucine, aspartate, N-acetyl-glutamine, and an antioxidant or ROS scavenger, e.g., a NAC entity.

289. The composition of embodiment 1-1D, 5, or 258, wherein the composition comprises D-leucine, L-arginine, a Q-amino acid entity, and NAC.

290. The composition of embodiment 1-1D, 5, or 258, wherein the composition comprises D-leucine, argininosuccinate, a Q-amino acid entity, and serine.

291. The composition of embodiment 1-1D, 5, or 258, wherein the composition comprises D-leucine, citrulline, a Q-amino acid entity, and acetylserine.

292. The composition of embodiment 1-1D, 5, or 258, wherein the composition comprises D-leucine, aspartate, a Q-amino acid entity, and cystathionine.

293. The composition of embodiment 1-1D, 5, or 258, wherein the composition comprises D-leucine, glutamate, a Q-amino acid entity, and glutathione.

294. The composition of embodiment 1-1D, 5, or 258, wherein the composition comprises D-leucine, ornithine, a Q-amino acid entity, and homocysteine.

295. The composition of embodiment 1-1D, 5, or 258, wherein the composition comprises D-leucine, agmatine, a Q-amino acid entity, and methionine.

296. The composition of embodiment 1-1D, 5, or 258, wherein the composition comprises D-leucine, creatine, a Q-amino acid entity, and D-cysteine.

297. The composition of embodiment 1-1D, 5, or 258, wherein the composition comprises D-leucine, D-arginine, a Q-amino acid entity, and L-cysteine.

298. The composition of embodiment 1-1D, 5, or 258, wherein the composition comprises D-leucine, N-acetyl-arginine, a Q-amino acid entity, and cystine.

299. The composition of embodiment 1-1D, 5, or 258, wherein the composition comprises D-leucine, a R-amino acid entity, L-glutamine, and NAC.

300. The composition of embodiment 1-1D, 5, or 258, wherein the composition comprises D-leucine, a R-amino acid entity, glutamate, and serine.

301. The composition of embodiment 1-1D, 5, or 258, wherein the composition comprises D-leucine, a R-amino acid entity, carbamoyl-P, and acetylserine.

302. The composition of embodiment 1-1D, 5, or 258, wherein the composition comprises D-leucine, a R-amino acid entity, N-acetyl-glutamine, and cystathionine.

303. The composition of embodiment 1-1D, 5, or 258, wherein the composition comprises D-leucine, a R-amino acid entity, L-glutamine, and glutathione.

304. The composition of embodiment 1-1D, 5, or 258, wherein the composition comprises D-leucine, a R-amino acid entity, glutamate, and homocysteine.

305. The composition of embodiment 1-1D, 5, or 258, wherein the composition comprises D-leucine, a R-amino acid entity, carbamoyl-P, and methionine.

306. The composition of embodiment 1-1D, 5, or 258, wherein the composition comprises D-leucine, a R-amino acid entity, N-acetyl-glutamine, and D-cysteine.

307. The composition of embodiment 1-1D, 5, or 258, wherein the composition comprises D-leucine, a R-amino acid entity, L-glutamine, and L-cysteine.

308. The composition of embodiment 1-1D, 5, or 258, wherein the composition comprises D-leucine, a R-amino acid entity, a glutamate, and cystine.

309. The composition of embodiment 1-1D, 5, or 258, wherein the composition comprises D-leucine, L-arginine, L-glutamine, and NAC.

310. The composition of embodiment 1-1D, 5, or 258, wherein the composition comprises D-leucine, argininosuccinate, glutamate, and serine.

311. The composition of embodiment 1-1D, 5, or 258, wherein the composition comprises D-leucine, citrulline, carbamoyl-P, and acetylserine.

312. The composition of embodiment 1-1D, 5, or 258, wherein the composition comprises D-leucine, aspartate, D-glutamine, and cystathionine.

313. The composition of embodiment 1-1D, 5, or 258, wherein the composition comprises D-leucine, N-acetyl-glutamine, L-glutamine, and glutathione.

314. The composition of embodiment 1-1D, 5, or 258, wherein the composition comprises D-leucine, ornithine, glutamate, and homocysteine.

315. The composition of embodiment 1-1D, 5, or 258, wherein the composition comprises D-leucine, agmatine, carbamoyl-P, and methionine.

316. The composition of embodiment 1-1D, 5, or 258, wherein the composition comprises D-leucine, creatine, D-glutamine and D-cysteine.

317. The composition of embodiment 1-1D, 5, or 258, wherein the composition comprises D-leucine, D-arginine, a Q-amino acid entity, and L-cysteine.

318. The composition of embodiment 1-1D, 5, or 258, wherein the composition comprises D-leucine, N-acetyl-arginine, argininosuccinate, and cystine.

319. The composition of embodiment 1-1D or 5, wherein the composition comprises N-acetyl-leucine, a R-amino acid entity, a Q-amino acid entity, and an antioxidant or ROS scavenger, e.g., a NAC entity.

320. The composition of embodiment 1-1D, 5, or 319, wherein the composition comprises N-acetyl-leucine, L-arginine, a Q-amino acid entity, and an antioxidant or ROS scavenger, e.g., a NAC entity.

321. The composition of embodiment 1-1D, 5, or 319, wherein the composition comprises N-acetyl-leucine, argininosuccinate, a Q-amino acid entity, and an antioxidant or ROS scavenger, e.g., a NAC entity.

322. The composition of embodiment 1-1D, 5, or 319, wherein the composition comprises N-acetyl-leucine, citrulline, a Q-amino acid entity, and an antioxidant or ROS scavenger, e.g., a NAC entity.

323. The composition of embodiment 1-1D, 5, or 319, wherein the composition comprises N-acetyl-leucine, aspartate, a Q-amino acid entity, and an antioxidant or ROS scavenger, e.g., a NAC entity.

324. The composition of embodiment 1-1D, 5, or 319, wherein the composition comprises N-acetyl-leucine, glutamate, a Q-amino acid entity, and an antioxidant or ROS scavenger, e.g., a NAC entity.

325. The composition of embodiment 1-1D, 5, or 319, wherein the composition comprises N-acetyl-leucine, ornithine, a Q-amino acid entity, and an antioxidant or ROS scavenger, e.g., a NAC entity.

326. The composition of embodiment 1-1D, 5, or 319, wherein the composition comprises N-acetyl-leucine, agmatine, a Q-amino acid entity, and an antioxidant or ROS scavenger, e.g., a NAC entity.

327. The composition of embodiment 1-1D, 5, or 319, wherein the composition comprises N-acetyl-leucine, creatine, a Q-amino acid entity, and an antioxidant or ROS scavenger, e.g., a NAC entity.

328. The composition of embodiment 1-1D, 5, or 319, wherein the composition comprises N-acetyl-leucine, D-arginine, a Q-amino acid entity, and an antioxidant or ROS scavenger, e.g., a NAC entity.

329. The composition of embodiment 1-1D, 5, or 319, wherein the composition comprises N-acetyl-leucine, N-acetyl-arginine, a Q-amino acid entity, and an antioxidant or ROS scavenger, e.g., a NAC entity.

330. The composition of embodiment 1-1D, 5, or 319, wherein the composition comprises N-acetyl-leucine, a R-amino acid entity, L-glutamine, and an antioxidant or ROS scavenger, e.g., a NAC entity.

331. The composition of embodiment 1-1D, 5, or 319, wherein the composition comprises N-acetyl-leucine, a R-amino acid entity, glutamate, and an antioxidant or ROS scavenger, e.g., a NAC entity.

332. The composition of embodiment 1-1D, 5, or 319, wherein the composition comprises N-acetyl-leucine, a R-amino acid entity, carbamoyl-P, and an antioxidant or ROS scavenger, e.g., a NAC entity.

333. The composition of embodiment 1-1D, 5, or 319, wherein the composition comprises N-acetyl-leucine, a R-amino acid entity, D-glutamine, and an antioxidant or ROS scavenger, e.g., a NAC entity.

334. The composition of embodiment 1-1D, 5, or 319, wherein the composition comprises N-acetyl-leucine, a R-amino acid entity, N-acetyl-glutamine, and an antioxidant or ROS scavenger, e.g., a NAC entity.

335. The composition of embodiment 1-1D, 5, or 319, wherein the composition comprises N-acetyl-leucine, a R-amino acid entity, a Q-amino acid entity, and NAC.

336. The composition of embodiment 1-1D, 5, or 319, wherein the composition comprises N-acetyl-leucine, a R-amino acid entity, a Q-amino acid entity, and serine.

337. The composition of embodiment 1-1D, 5, or 319, wherein the composition comprises N-acetyl-leucine, a R-amino acid entity, a Q-amino acid entity, and acetylserine.

338. The composition of embodiment 1-1D, 5, or 319, wherein the composition comprises N-acetyl-leucine, a R-amino acid entity, a Q-amino acid entity, and cystathionine.

339. The composition of embodiment 1-1D, 5, or 319, wherein the composition comprises N-acetyl-leucine, a R-amino acid entity, a Q-amino acid entity, and glutathione.

340. The composition of embodiment 1-1D, 5, or 319, wherein the composition comprises N-acetyl-leucine, a R-amino acid entity, a Q-amino acid entity, and homocysteine.

341. The composition of embodiment 1-1D, 5, or 319, wherein the composition comprises N-acetyl-leucine, a R-amino acid entity, a Q-amino acid entity, and methionine.

342. The composition of embodiment 1-1D, 5, or 319, wherein the composition comprises N-acetyl-leucine, a R-amino acid entity, a Q-amino acid entity, and D-cysteine.

343. The composition of embodiment 1-1D, 5, or 319, wherein the composition comprises N-acetyl-leucine, a R-amino acid entity, a Q-amino acid entity, and L-cysteine.

344. The composition of embodiment 1-1D, 5, or 319, wherein the composition comprises N-acetyl-leucine, a R-amino acid entity, a Q-amino acid entity, and cysteine.

345. The composition of embodiment 1-1D, 5, or 319, wherein the composition comprises N-acetyl-leucine, a R-amino acid entity, a Q-amino acid entity, and cystine.

346. The composition of embodiment 1-1D, 5, or 319, wherein the composition comprises N-acetyl-leucine, L-arginine, L-glutamine, and an antioxidant or ROS scavenger, e.g., a NAC entity.

347. The composition of embodiment 1-1D, 5, or 319, wherein the composition comprises N-acetyl-leucine, argininosuccinate, glutamate, and an antioxidant or ROS scavenger, e.g., a NAC entity.

348. The composition of embodiment 1-1D, 5, or 319, wherein the composition comprises N-acetyl-leucine, citrulline, D-glutamine, and an antioxidant or ROS scavenger, e.g., a NAC entity.

349. The composition of embodiment 1-1D, 5, or 319, wherein the composition comprises N-acetyl-leucine, aspartate, N-acetyl-glutamine, and an antioxidant or ROS scavenger, e.g., a NAC entity.

350. The composition of embodiment 1-1D, 5, or 319, wherein the composition comprises N-acetyl-leucine, L-arginine, a Q-amino acid entity, and NAC.

351. The composition of embodiment 1-1D, 5, or 319, wherein the composition comprises N-acetyl-leucine, argininosuccinate, a Q-amino acid entity, and serine.

352. The composition of embodiment 1-1D, 5, or 319, wherein the composition comprises N-acetyl-leucine, citrulline, a Q-amino acid entity, and acetylserine.

353. The composition of embodiment 1-1D, 5, or 319, wherein the composition comprises N-acetyl-leucine, aspartate, a Q-amino acid entity, and cystathionine.

354. The composition of embodiment 1-1D, 5, or 319, wherein the composition comprises N-acetyl-leucine, glutamate, a Q-amino acid entity, and glutathione.

355. The composition of embodiment 1-1D, 5, or 319, wherein the composition comprises N-acetyl-leucine, ornithine, a Q-amino acid entity, and homocysteine.

356. The composition of embodiment 1-1D, 5, or 319, wherein the composition comprises N-acetyl-leucine, agmatine, a Q-amino acid entity, and methionine.

357. The composition of embodiment 1-1D, 5, or 319, wherein the composition comprises N-acetyl-leucine, creatine, a Q-amino acid entity, and D-cysteine.

358. The composition of embodiment 1-1D, 5, or 319, wherein the composition comprises N-acetyl-leucine, D-arginine, a Q-amino acid entity, and L-cysteine.

359. The composition of embodiment 1-1D, 5, or 319, wherein the composition comprises N-acetyl-leucine, N-acetyl-arginine, a Q-amino acid entity, and cystine.

360. The composition of embodiment 1-1D, 5, or 319, wherein the composition comprises N-acetyl-leucine, a R-amino acid entity, L-glutamine, and NAC.

361. The composition of embodiment 1-1D, 5, or 319, wherein the composition comprises N-acetyl-leucine, a R-amino acid entity, glutamate, and serine.

362. The composition of embodiment 1-1D, 5, or 319, wherein the composition comprises N-acetyl-leucine, a R-amino acid entity, carbamoyl-P, and acetylserine.

363. The composition of embodiment 1-1D, 5, or 319, wherein the composition comprises N-acetyl-leucine, a R-amino acid entity, N-acetyl-glutamine, and cystathionine.

364. The composition of embodiment 1-1D, 5, or 319, wherein the composition comprises N-acetyl-leucine, a R-amino acid entity, L-glutamine, and glutathione.

365. The composition of embodiment 1-1D, 5, or 319, wherein the composition comprises N-acetyl-leucine, a R-amino acid entity, glutamate, and homocysteine.

366. The composition of embodiment 1-1D, 5, or 319, wherein the composition comprises N-acetyl-leucine, a R-amino acid entity, carbamoyl-P, and methionine.

367. The composition of embodiment 1-1D, 5, or 319, wherein the composition comprises N-acetyl-leucine, a R-amino acid entity, N-acetyl-glutamine, and D-cysteine.

368. The composition of embodiment 1-1D, 5, or 319, wherein the composition comprises N-acetyl-leucine, a R-amino acid entity, L-glutamine, and L-cysteine.

369. The composition of embodiment 1-1D, 5, or 319, wherein the composition comprises N-acetyl-leucine, a R-amino acid entity, a glutamate, and cystine.

370. The composition of embodiment 1-1D, 5, or 319, wherein the composition comprises N-acetyl-leucine, L-arginine, L-glutamine, and NAC.

371. The composition of embodiment 1-1D, 5, or 319, wherein the composition comprises N-acetyl-leucine, argininosuccinate, glutamate, and serine.

372. The composition of embodiment 1-1D, 5, or 319, wherein the composition comprises N-acetyl-leucine, citrulline, carbamoyl-P, and acetylserine.

373. The composition of embodiment 1-1D, 5, or 319, wherein the composition comprises N-acetyl-leucine, aspartate, D-glutamine, and cystathionine.

374. The composition of embodiment 1-1D, 5, or 319, wherein the composition comprises N-acetyl-leucine, N-acetyl-glutamine, L-glutamine, and glutathione.

375. The composition of embodiment 1-1D, 5, or 319, wherein the composition comprises N-acetyl-leucine, ornithine, glutamate, and homocysteine.

376. The composition of embodiment 1-1D, 5, or 319, wherein the composition comprises N-acetyl-leucine, agmatine, carbamoyl-P, and methionine.

377. The composition of embodiment 1-1D, 5, or 319, wherein the composition comprises N-acetyl-leucine, creatine, D-glutamine and D-cysteine.

378. The composition of embodiment 1-1D, 5, or 319, wherein the composition comprises N-acetyl-leucine, D-arginine, a Q-amino acid entity, and L-cysteine.

379. The composition of embodiment 1-1D, 5, or 319, wherein the composition comprises N-acetyl-leucine, N-acetyl-arginine, argininosuccinate, and cystine.

380. The composition of embodiment 1-1D or 2, wherein the composition comprises a L-amino acid entity, L-arginine, a Q-amino acid entity, and an antioxidant or ROS scavenger, e.g., a NAC entity.

381. The composition of embodiment 1-1D or 2, wherein the composition comprises a L-amino acid entity, argininosuccinate, a Q-amino acid entity, and an antioxidant or ROS scavenger, e.g., a NAC entity.

382. The composition of embodiment 1-1D, 3, or 4, wherein the composition comprises a L-amino acid entity, citrulline, a Q-amino acid entity, and an antioxidant or ROS scavenger, e.g., a NAC entity.

383. The composition of embodiment 1-1D or 3, wherein the composition comprises a L-amino acid entity, aspartate, a Q-amino acid entity, and an antioxidant or ROS scavenger, e.g., a NAC entity.

384. The composition of embodiment 1-1D or 3, wherein the composition comprises a L-amino acid entity, glutamate, a Q-amino acid entity, and an antioxidant or ROS scavenger, e.g., a NAC entity.

385. The composition of embodiment 1-1D or 4, wherein the composition comprises a L-amino acid entity, ornithine, a Q-amino acid entity, and an antioxidant or ROS scavenger, e.g., a NAC entity.

386. The composition of embodiment 1-1D or 4, wherein the composition comprises a L-amino acid entity, agmatine, a Q-amino acid entity, and an antioxidant or ROS scavenger, e.g., a NAC entity.

387. The composition of embodiment 1-1D or 4, wherein the composition comprises a L-amino acid entity, creatine, a Q-amino acid entity, and an antioxidant or ROS scavenger, e.g., a NAC entity.

388. The composition of embodiment 1-1D or 5, wherein the composition comprises a L-amino acid entity, D-arginine, a Q-amino acid entity, and an antioxidant or ROS scavenger, e.g., a NAC entity.

389. The composition of embodiment 1-1D or 5, wherein the composition comprises a L-amino acid entity, N-acetyl-arginine, a Q-amino acid entity, and an antioxidant or ROS scavenger, e.g., a NAC entity.

390. The composition of embodiment 1-1D, 3, or 384, wherein the composition comprises L-leucine, glutamate, L-glutamine, and an antioxidant or ROS scavenger, e.g., a NAC entity.

391. The composition of embodiment 1-1D, 4, or 385, wherein the composition comprises L-leucine, ornithine, L-glutamine, and an antioxidant or ROS scavenger, e.g., a NAC entity.

392. The composition of embodiment 1-1D, 4, or 386, wherein the composition comprises a L-amino acid entity, agmatine, L-glutamine, and an antioxidant or ROS scavenger, e.g., a NAC entity.

393. The composition of embodiment 1-1D, 4, or 387, wherein the composition comprises a L-amino acid entity, creatine, L-glutamine, and an antioxidant or ROS scavenger, e.g., a NAC entity.

394. The composition of embodiment 1-1D, 4, or 388, wherein the composition comprises a L-amino acid entity, D-arginine, L-glutamine, and an antioxidant or ROS scavenger, e.g., a NAC entity.

395. The composition of embodiment 1-1D, 4, or 389, wherein the composition comprises a L-amino acid entity, D-arginine, N-acetyl-arginine, and an antioxidant or ROS scavenger, e.g., a NAC entity.

396. The composition of embodiment 1-1D or 380, wherein the composition comprises a L-amino acid entity, L-arginine, L-glutamine, and an antioxidant or ROS scavenger, e.g., a NAC entity.

397. The composition of any of embodiments 1-2, or 381, wherein the composition comprises a L-amino acid entity, argininosuccinate, glutamate, and an antioxidant or ROS scavenger, e.g., a NAC entity.

398. The composition of embodiment 1-1D, 3, 4, or 382, wherein the composition comprises a L-amino acid entity, citrulline, carbamoyl-P, and an antioxidant or ROS scavenger, e.g., a NAC entity.

399. The composition of embodiment 1-1D, 3, or 383, wherein the composition comprises a L-amino acid entity, aspartate, glutamate, and an antioxidant or ROS scavenger, e.g., a NAC entity.

400. The composition of embodiment 1-1D, 3, or 384, wherein the composition comprises a L-amino acid entity, glutamate, D-glutamine, and an antioxidant or ROS scavenger, e.g., a NAC entity.

401. The composition of embodiment 1-1D, 4, or 385, wherein the composition comprises a L-amino acid entity, ornithine, N-acetyl-glutamine, and an antioxidant or ROS scavenger, e.g., a NAC entity.

402. The composition of embodiment 1-1D, 4, or 386, wherein the composition comprises a L-amino acid entity, agmatine, L-glutamine, and an antioxidant or ROS scavenger, e.g., a NAC entity.

403. The composition of embodiment 1-1D, 4, or 387, wherein the composition comprises a L-amino acid entity, creatine, glutamate, and an antioxidant or ROS scavenger, e.g., a NAC entity.

404. The composition of embodiment 1-1D, 5, or 388, wherein the composition comprises a L-amino acid entity, D-arginine, carbamoyl-P, and an antioxidant or ROS scavenger, e.g., a NAC entity.

405. The composition of embodiment 1-1D, 5, or 389, wherein the composition comprises a L-amino acid entity, N-acetyl-arginine, glutamate, and an antioxidant or ROS scavenger, e.g., a NAC entity.

406. The composition of embodiment 1-1D, 3, 80, or 445, wherein the composition comprises a L-amino acid entity, L-arginine, L-glutamine, and NAC.

407. The composition of any of embodiments 1-2, 381, or 446, wherein the composition comprises a L-amino acid entity, argininosuccinate, glutamate, and serine.

408. The composition of embodiment 1-1D, 3, 4, 382, or 447, wherein the composition comprises a L-amino acid entity, citrulline, carbamoyl-P, and acetylserine.

409. The composition of embodiment 1-1D, 3, 383, or 448, wherein the composition comprises a L-amino acid entity, aspartate, glutamate, and cystathionine.

410. The composition of embodiment 1-1D, 3, 384, or 449, wherein the composition comprises a L-amino acid entity, glutamate, D-glutamine, and glutathione.

411. The composition of embodiment 1-1D, 4, 385, or 448, wherein the composition comprises a L-amino acid entity, ornithine, N-acetyl-glutamine, and cystathionine.

412. The composition of embodiment 1-1D, 4, 386, or 450, wherein the composition comprises a L-amino acid entity, agmatine, L-glutamine, and homocysteine.

413. The composition of embodiment 1-1D, 4, 387, or 451, wherein the composition comprises a L-amino acid entity, creatine, glutamate, and methionine.

414. The composition of embodiment 1-1D, 5, 388, or 454, wherein the composition comprises a L-amino acid entity, D-arginine, carbamoyl-P, and D-cysteine.

415. The composition of embodiment 1-1D, 5, 389, or 453, wherein the composition comprises a L-amino acid entity, N-acetyl-arginine, glutamate, and L-cysteine.

416. The composition of embodiment 1-1D, 380, or 454, wherein the composition comprises a L-amino acid entity, L-arginine, L-glutamine, and cystine.

417. The composition of embodiment 1-1D, 6, or 445, wherein the composition comprises a L-amino acid entity, L-arginine, a Q-amino acid, and NAC.

418. The composition of any of embodiments 1-2, or 446, wherein the composition comprises a L-amino acid entity, argininosuccinate, a Q-amino acid, and serine.

419. The composition of embodiment 1-1D, 3, or 447, wherein the composition comprises a L-amino acid entity, citrulline, a Q-amino acid, and acetylserine.

420. The composition of embodiment 1-1D, 4, or 448, wherein the composition comprises a L-amino acid entity, aspartate, a Q-amino acid, and cystathionine.

421. The composition of embodiment 1-1D, 3, or 449, wherein the composition comprises a L-amino acid entity, glutamate, a Q-amino acid, and glutathione.

422. The composition of embodiment 1-1D, 4, or 448, wherein the composition comprises a L-amino acid entity, ornithine, a Q-amino acid, and cystathionine.

423. The composition of embodiment 1-1D, 4, or 450, wherein the composition comprises a L-amino acid entity, agmatine, a Q-amino acid, and homocysteine.

424. The composition of embodiment 1-1D, 4, or 451, wherein the composition comprises a L-amino acid entity, creatine, a Q-amino acid, and methionine.

425. The composition of embodiment 1-1D, 5, or 452, wherein the composition comprises a L-amino acid entity, D-arginine, a Q-amino acid, and D-cysteine.

426. The composition of embodiment 1-1D, 5, or 453, wherein the composition comprises a L-amino acid entity, N-acetyl-arginine, a Q-amino acid, and L-cysteine.

427. The composition of embodiment 1-1D, 5, or 454, wherein the composition comprises a L-amino acid entity, L-arginine, a Q-amino acid, and cystine.

428. The composition of embodiment 1-1D or 2, wherein the composition comprises a L-amino acid entity, a R-amino acid entity, L-glutamine, and an antioxidant or ROS scavenger, e.g., a NAC entity.

429. The composition of embodiment 1-1D, 3, or 4, wherein the composition comprises a L-amino acid entity, a R-amino acid entity, glutamate, and an antioxidant or ROS scavenger, e.g., a NAC entity.

430. The composition of embodiment 1-1D or 4, wherein the composition comprises a L-amino acid entity, a R-amino acid entity, carbamoyl-P, and an antioxidant or ROS scavenger, e.g., a NAC entity.

431. The composition of embodiment 1-1D or 5, wherein the composition comprises a L-amino acid entity, a R-amino acid entity, D-glutamine, and an antioxidant or ROS scavenger, e.g., a NAC entity.

432. The composition of embodiment 1-1D or 5, wherein the composition comprises a L-amino acid entity, a R-amino acid entity, N-acetyl-glutamine, and an antioxidant or ROS scavenger, e.g., a NAC entity.

433. The composition of embodiment 1-1D, 5, or 431, wherein the composition comprises a L-leucine, a R-amino acid entity, D-glutamine, and an antioxidant or ROS scavenger, e.g., a NAC entity.

434. The composition of embodiment 1-1D, 4 or 430, wherein the composition comprises a L-leucine, L-arginine, carbamoyl-P, and an antioxidant or ROS scavenger, e.g., a NAC entity.

435. The composition of any of embodiments 1-2, 428, or 445, wherein the composition comprises a L-amino acid entity, a R-amino acid entity, L-glutamine, and NAC.

436. The composition of embodiment 1-1D, 4, 429, or 446, wherein the composition comprises a L-amino acid entity, a R-amino acid entity, glutamate, and serine.

437. The composition of embodiment 1-1D, 4, 430, or 447, wherein the composition comprises a L-amino acid entity, a R-amino acid entity, carbamoyl-P, and acetylserine.

438. The composition of embodiment 1-1D, 5, 431, or 448, wherein the composition comprises a L-amino acid entity, a R-amino acid entity, D-glutamine, and cystathionine.

439. The composition of embodiment 1-1D, 5, 432, or 449, wherein the composition comprises a L-amino acid entity, a R-amino acid entity, N-acetyl-glutamine, and glutathione.

440. The composition of any of embodiments 1-2, 428, or 450, wherein the composition comprises a L-amino acid entity, a R-amino acid entity, L-glutamine, and homocysteine.

441. The composition of embodiment 1-1D, 3, 4, 429, or 451, wherein the composition comprises a L-amino acid entity, a R-amino acid entity, glutamate, and methionine.

442. The composition of embodiment 1-1D, 4, 430, or 452, wherein the composition comprises a L-amino acid entity, a R-amino acid entity, carbamoyl-P, and D-cysteine 443. The composition of embodiment 1-1D, 5, 431, or 453, wherein the composition comprises a L-amino acid entity, a R-amino acid entity, D-glutamine, and L-cysteine.

444. The composition of embodiment 1-1D, 5, 432, or 454, wherein the composition comprises a L-amino acid entity, a R-amino acid entity, N-acetyl-glutamine, and cystine.

445. The composition of embodiment 1-1D or 5, wherein the composition comprises a L-amino acid entity, a R-amino acid entity, a Q-amino acid entity, and NAC.

446. The composition of embodiment 1-1D or 3, wherein the composition comprises a L-amino acid entity, a R-amino acid entity, a Q-amino acid entity, and serine.

447. The composition of embodiment 1-1D or 3, wherein the composition comprises a L-amino acid entity, a R-amino acid entity, a Q-amino acid entity, and acetylserine.

448. The composition of embodiment 1-1D or 3, wherein the composition comprises a L-amino acid entity, a R-amino acid entity, a Q-amino acid entity, and cystathionine.

449. The composition of embodiment 1-1D or 4, wherein the composition comprises a L-amino acid entity, a R-amino acid entity, a Q-amino acid entity, and glutathione.

450. The composition of embodiment 1-1D or 4, wherein the composition comprises a L-amino acid entity, a R-amino acid entity, a Q-amino acid entity, and homocysteine.

451. The composition of embodiment 1-1D or 4, wherein the composition comprises a L-amino acid entity, a R-amino acid entity, a Q-amino acid entity, and methionine.

452. The composition of embodiment 1-1D or 5, wherein the composition comprises a L-amino acid entity, a R-amino acid entity, a Q-amino acid entity, and D-cysteine.

453. The composition of embodiment 1-1D or 5, wherein the composition comprises a L-amino acid entity, a R-amino acid entity, a Q-amino acid entity, and L-cysteine.

454. The composition of embodiment 1-1D or 5, wherein the composition comprises a L-amino acid entity, a R-amino acid entity, a Q-amino acid entity, and cystine.

455. The composition of embodiment 1-1D or 2, wherein the composition comprises a L-amino acid, ornithine, a Q-amino acid entity, and an antioxidant or ROS scavenger, e.g., a NAC entity.

456. The composition of embodiment 1-1D or 455, wherein the composition comprises L-leucine, ornithine, 1-glutamine, and NAC.

457. The composition of embodiment 1-1D or 455, wherein the composition comprises HMB, ornithine, 1-glutamine, and NAC.

458. The composition of any of the foregoing embodiments, wherein the composition comprises L-leucine or a leucine metabolite (e.g., HMB), L-arginine or an L-arginine metabolite (e.g., creatine), 1-glutamine, and NAC or a NAC metabolite, e.g., glutathione.

459. The composition of any of the foregoing embodiments, wherein the composition comprises L-leucine or a leucine metabolite (e.g., HMB), L-arginine or an L-arginine metabolite (e.g., creatine), L-glutamine, and NAC or a NAC metabolite, e.g., glutathione.

460. The composition of any of the previous embodiments, further comprising an isoleucine (I)-amino acid entity.

461. The composition of embodiment 460, wherein the I-amino acid entity is an amino acid.

462. The composition of embodiment 460 or 461, wherein the amino acid entity is L-isoleucine.

463. The composition of embodiment 460, wherein the I-amino acid entity is an amino acid precursor.

464. The composition of embodiment 460 or 463, wherein the I-amino acid entity is 2-oxo-3-methyl-valerate.

465. The composition of embodiment 460 or 463, wherein the I-amino acid entity is threonine.

466. The composition of embodiment 460, wherein the I-amino acid entity is an amino acid metabolite.

467. The composition of embodiment 460 or 466, wherein the I-amino acid entity is 2-oxo-3-methyl-valerate 468. The composition of embodiment 460 or 466, wherein the I-amino acid entity is methylbutyrl-CoA.

469. The composition of embodiment 460, wherein the I-amino acid entity is an amino acid derivative.

470. The composition of embodiment 460 or 469, wherein the I-amino acid entity is D-isoleucine.

471. The composition of embodiment 460 or 469, wherein the I-amino acid entity is N-acetyl-isoleucine.

472. The composition of any of the previous embodiments, further comprising a valine (V)-amino acid entity.

473. The composition of embodiment 472, wherein the V-amino acid entity is an amino acid.

474. The composition of embodiment 472 or 473, wherein the V-amino acid entity is L-valine.

475. The composition of embodiment 472, wherein the V-amino acid entity is an amino acid precursor.

476. The composition of embodiment 472 or 475, wherein the V-amino acid entity is 2-oxo-valerate.

477. The composition of embodiment 472, wherein the V-amino acid entity is an amino acid metabolite.

478. The composition of embodiment 472 or 477, wherein the V-amino acid entity is isobutryl-CoA.

479. The composition of embodiment 472 or 477, wherein the V-amino acid entity is 3-HIB-CoA.

480. The composition of embodiment 472 or 477, wherein the V-amino acid entity is 3-HIB.

481. The composition of embodiment 472, wherein the V-amino acid entity is an amino acid derivative.

482. The composition of embodiment 472 or 481, wherein the V-amino acid entity is D-valine.

483. The composition of embodiment 472 or 481, wherein the V-amino acid entity is N-acetyl-valine.

484. The composition of any of the preceding embodiments, further comprising L-glycine.

485. The composition of any of the preceding embodiments, further comprising an S-amino acid entity (e.g., L-serine, phosphoserine, β-hydroxypyruvate, L-glycine, tryptophan, acetylserine, cystathionine, phosphatidylserine, or any combination thereof, e.g., L-serine and L-glycine).

486. The composition of any of the preceding embodiments, further comprising carnitine.

487. The composition of any of the preceding embodiments, comprising:

a) a L-amino acid entity chosen from L-leucine or a salt thereof, or β-hydroxy-β-methylbutyrate (HMB) or a salt thereof or a combination of L-leucine or a salt thereof and HMB or a salt thereof;

b) an R-amino acid entity chosen from L-arginine or a salt thereof, ornithine or a salt thereof, or creatine or a salt thereof or a combination of two or three of L-arginine or a salt thereof, ornithine or a salt thereof, or creatine or a salt thereof;

c) L-glutamine or a salt thereof; and d) N-acetylcysteine (NAC) or a salt thereof.

488. The composition of any of the preceding embodiments, wherein the L-Leucine is provided as part of a dipeptide comprising L-Leucine, or a salt thereof, or a tripeptide comprising L-Leucine, or a salt thereof.

489. The composition of any of the preceding embodiments, wherein the L-Arginine is provided as part of a dipeptide comprising L-Arginine, or a salt thereof, or a tripeptide comprising L-Arginine, or a salt thereof.

490. The composition of any of the preceding embodiments, wherein the L-Glutamine is provided as part of a dipeptide comprising L-Glutamine, or a salt thereof, or a tripeptide comprising L-Glutamine, or a salt thereof 491. The composition of any of the preceding embodiments, wherein the NAC is provided as a part of a dipeptide comprising NAC, or a salt thereof, or a tripeptide comprising NAC, or a salt thereof.

492. The composition of any of the preceding embodiments, wherein one, two, three, or four of methionine (M), tryptophan (W), valine (V), or cysteine (C) is absent, or if present, is present at less than 10 weight (wt.) % of the composition.

493. The composition of any of the preceding embodiments, wherein the total wt. % of (a)-(d) is greater than the total wt. % of any other amino acid entity in the composition.

494. The composition of any of the preceding embodiments, wherein one, two, three, or four of the amino acids in (a)-(d) is provided as part of a dipeptide or tripeptide, e.g., in an amount of at least 10 wt. % of the composition.

495. The composition of embodiment 494, wherein the dipeptide is a homodipeptide or heterodipeptide of any of the amino acids in (a)-(d), e.g., one, two, three, or four of the amino acids in (a)-(d) is a homodipeptide or heterodipeptide.

496. The composition of embodiment 494, wherein the tripeptide is a homotripeptide or heterotripeptide of any of the amino acids in (a)-(d), e.g., one, two, three, or four of the amino acids in (a)-(d) is a homotripeptide or heterotripeptide.

497. The composition of any of the preceding embodiments, wherein (a) is a L-amino acid entity dipeptide or a salt thereof (e.g., a L-leucine dipeptide or a salt thereof)

498. The composition of embodiment 497, wherein (a) is a homodipeptide or a heterodipeptide, e.g., Ala-Leu.

499. The composition of any of the preceding embodiments, wherein (b) is a L-arginine dipeptide or a salt thereof.

500. The composition of embodiment 499, wherein (b) is a homodipeptide or a heterodipeptide, e.g., Ala-Arg.

501. The composition of any of the preceding embodiments, wherein (c) is a L-glutamine dipeptide or a salt thereof.

502. The composition of embodiment 501, wherein (c) is a homodipeptide, e.g., Gln-Gln, or wherein (c) is a heterodipeptide, e.g., Ala-Gln.

503. The composition of any of the preceding embodiments, wherein:
f) a wt. % of the L-glutamine or a salt thereof in the composition is greater than the wt. % of the R-amino acid entity;
g) the wt. % of the L-glutamine or a salt thereof in the composition is greater than the wt. % of the L-amino acid entity;
h) the wt. % of the R-amino acid entity in the composition is greater than the wt. % of the L-amino acid entity; or
i) a combination of two or three of (f)-(h).

504. The composition of any of the preceding embodiments, wherein the wt. % of the L-glutamine or a salt thereof in the composition is at least 5% greater than the wt. % of the R-amino acid entity, e.g., the wt. % of the L-glutamine or a salt thereof is at least 10%, 15%, 20%, or 25% greater than the wt. % of the R-amino acid entity 505. The composition of any of the preceding embodiments, wherein the wt. % of the L-glutamine or a salt thereof in the composition is at least 20% greater than the wt. % of the L-amino acid entity, e.g., the wt. % of the L-glutamine or a salt thereof in the composition is at least 25%, 30%, 35%, 40%, 45%, or 50% greater than the wt. % of the L-amino acid entity.

506. The composition of any of the preceding embodiments, wherein the wt. % of the R-amino acid entity in the composition is at least 10% greater than the wt. % of the L-amino acid entity, e.g., the wt. % of the R-amino acid entity in the composition is at least 15%, 20%, 25%, or 30% greater than the wt. % of the L-amino acid entity.

507. The composition of any of the preceding embodiments, wherein:
j) the ratio of the L-amino acid entity to the R-amino acid entity is at least 1:4, or at least 2:5, and not more than 3:4, e.g., the ratio of L-amino acid entity to R-amino acid entity is about 2:3;
k) the ratio of the L-amino acid entity to the L-glutamine or a salt thereof is at least 1:4, or least 1:3, and not more than 3:4, e.g., the ratio of the L-amino acid entity to the L-glutamine or a salt thereof is about 1:2;
l) the ratio of the R-amino acid entity to the L-glutamine or a salt thereof is at least 1:4, or at least 1:2, and not more than 6:7, e.g., the ratio of the R-amino acid entity to the L-glutamine or a salt thereof is about 3:4; or
m) a combination of two or three of (j)-(l).

508. The composition of any of the preceding embodiments, further comprising one or both of an isoleucine (I)-amino acid-entity and a valine (V)-amino acid-entity, e.g., both the I-amino acid-entity and the V-amino acid-entity are present.

509. The composition of embodiment 508, wherein:
n) the wt. % of the L-amino acid-entity in the composition is greater than or equal to the wt. % of the I-amino acid-entity and the V-amino acid-entity in combination;
o) the wt. % of the L-amino acid-entity, the I-amino acid-entity, and the V-amino acid-entity in combination in the composition is greater than or equal to the wt. % of the L-glutamine or a salt thereof;
p) the wt. % of the L-amino acid-entity, the I-amino acid-entity, and the V-amino acid-entity in combination in the composition is less than the wt. % of the R-amino acid entity;
q) the wt. % of the R-amino acid entity and the L-glutamine or a salt thereof in the composition is greater than the wt. % of the L-amino acid-entity, the I-amino acid-entity, and the V-amino acid-entity in combination; or
r) a combination of two, three, or four of (n)-(q).

510. The composition of embodiment 508 or 509, wherein:
s) the wt. % of the R-amino acid entity, the L-glutamine or a salt thereof, and the NAC or a salt thereof is at least 50% of the composition, or at least 70% of the composition, but not more than 90% of the composition;
t) the wt. % of the NAC or a salt thereof is at least 1%, or at least 2%, but not more than 10% of the composition;
u) the wt. % of the L-amino acid-entity, the I-amino acid-entity, and the V-amino acid-entity in combination is at least 15%, or at least 20%, but not more than 50% of the composition;
v) the wt. % of the R-amino acid entity, the L-glutamine or a salt thereof, and the NAC or a salt thereof is at least 40%, or at least 50%, but not more than 80% of the composition; or
w) a combination of two, three, or four of (s)-(v).

511. The composition of any of embodiments 508-510, wherein:
x) the ratio of the L-amino acid entity to the I-amino acid entity is at least 1.5:1, or at least 1.75:1, and not more than 2.5 to 1 or not more than 3:1, e.g., the ratio of the L-amino acid entity to the I-amino acid entity is about 2:1;
y) the ratio of L-amino acid entity to V-amino acid entity is at least 1.5:1, or at least 1.75:1, and not more than 2.5 to 1 or not more than 3:1, e.g., the ratio of L to V is about 2:1;
z) the ratio of the L-amino acid entity to the R-amino acid entity is greater than 1:3, greater than 1.5 to 3, and less than 3:3, e.g., the ratio of the L-amino acid entity to the R-amino acid entity is about 2:3;
aa) the ratio of the L-amino acid entity to the L-glutamine or a salt thereof is greater than 1:4, greater than 1.5 to 4 and less than 4:4, or less than 3:4, e.g., the ratio of the L-amino acid entity to the L-glutamine or a salt thereof is about 1:2; or
bb) a combination of two, three, or four of (x)-(aa).

512. The composition of any of embodiments 508-511, wherein:
cc) the ratio of the I-amino acid entity to the V-amino acid entity is at least 0.5:1, or at least 0.75:1, and not more than 1.5 to 1 or not more than 2:1, e.g., the ratio of the L-amino acid entity to the I-amino acid entity is about 1:1;
dd) the ratio of the I-amino acid entity to the R-amino acid entity is at least 0.5:3, or at least 0.75:3, and not more than 2:3, or not more than 1.5:3, e.g., the ratio of the L-amino acid entity to the I-amino acid entity is about 1:3;

ee) the ratio of the I-amino acid entity to the L-glutamine or a salt thereof is at least 0.5:4, or at least 0.75:4, and not more than 3:4, or not more than 2:4, e.g., the ratio of the L-amino acid entity to the L-glutamine or a salt thereof is about 1:4; or ff) or a combination of two or three of (cc)-(ee).

513. The composition of any of embodiments 508-512, wherein:

gg) the ratio of the L-amino acid entity to the V-amino acid entity is at least 1.5:1, or at least 1.75:1, and not more than 2.5 to 1 or not more than 3:1, e.g., is the ratio of the L-amino acid entity to the V-amino acid entity is about 2:1;

hh) the ratio of the L-amino acid entity to the R-amino acid entity is greater than 1:3, greater than 1.5 to 3, and less than 3:3, e.g., the ratio of the L-amino acid entity to the R-amino acid entity is about 2:3;

ii) the ratio of the L-amino acid entity to the L-glutamine or a salt thereof is greater than 1:4, greater than 1.5 to 4 and less than 4:4, or less than 3:4, e.g., the ratio of the L-amino acid entity to the L-glutamine or a salt thereof is about 1:2; or jj) a combination of two or three of (gg)-(ii).

514. The composition of any of embodiments 508-513, wherein:

kk) the ratio of the V-amino acid entity to the L-glutamine or a salt thereof is at least 0.5:4, or at least 0.75:4, and not more than 3:4, or not more than 2:4, e.g., the ratio of the L-amino acid entity to the L-glutamine or a salt thereof is about 1:4;

ll) the ratio of the V-amino acid entity to the R-amino acid entity is at least 0.5:3, or at least 0.75:3, and not more than 2:3, or not more than 1.5:3, e.g., the ratio of the V-amino acid entity to the R-amino acid entity is about 1:3;

mm) the ratio of the L-amino acid-entity, the I-amino acid-entity, and the V-amino acid-entity in combination to the R-amino acid entity, L-glutamine or a salt thereof, and NAC or a salt thereof is at least 1:4, or at least 2:3, or not more than 5:7, or not more than 6:7, e.g., the ratio is about 6:11; or nn) a combination of two or three of (kk)-(mm).

515. The composition of any of the preceding embodiments, wherein:

oo) a wt. % of the L-amino acid entity in the composition is greater than the wt. % of the NAC or a salt thereof;

pp) a wt. % of the R-amino acid entity in the composition is greater than the wt. % of the NAC or a salt thereof;

qq) a wt. % of the L-glutamine or a salt thereof in the composition is greater than the wt. % of the NAC or a salt thereof; or rr) a combination of two or three of (oo)-(qq).

516. The composition of any of the preceding embodiments, wherein at least one of the amino acids of (a)-(d) is a free amino acid, e.g., two, three, or four of the amino acids of (a)-(d) are a free amino acid, e.g., at least 50 wt. % of the total wt. of the composition is one or more amino acid entities in free form.

517. The composition of any of the preceding embodiments, wherein at least one of the amino acids of (a)-(d) is in a salt form, e.g., one, two, three, or four of the amino acids of (a)-(d) is in a salt form, e.g., at least 10 wt. % of the total wt. of the composition is one or more amino acid entities in salt form.

518. The composition of embodiment 517, wherein at least 10 wt. % of the total wt. of the composition is one or more amino acid entities in salt form.

519. The composition of any of the preceding embodiments, wherein the composition is capable of one, two, three, four, five, or all of:

a) decreasing or preventing liver fibrosis;
b) decreasing or preventing liver injury;
c) decreasing or preventing hepatocyte inflammation;
d) improving, e.g., increasing, glucose tolerance;
e) decreasing or preventing steatosis;
f) decreasing or preventing hepatocyte ballooning; or
g) improving gut function.

520. The composition of any of the preceding embodiments, wherein the composition further comprises a serine (S)-amino acid entity, e.g., a S-amino acid entity chosen from L-serine, phosphoserine, β-hydroxypyruvate, L-glycine, tryptophan, acetylserine, cystathionine, cysteine, phosphatidylserine, and D-serine or a combination thereof, e.g., a combination of L-serine and L-glycine.

521. The composition of embodiment 520, wherein the composition comprises an L-amino acid entity, an I-amino acid entity, an V-amino acid entity, an R-amino acid entity, an L-glutamine or a salt thereof, an NAC or a salt thereof, and an L-glycine.

522. The composition of embodiment 520, wherein the composition comprises an L-amino acid entity, an I-amino acid entity, an V-amino acid entity, an R-amino acid entity, an L-glutamine or a salt thereof, an NAC or a salt thereof, and an L-serine.

523. The composition of embodiment 520, wherein the composition comprises an L-amino acid entity, an I-amino acid entity, an V-amino acid entity, an R-amino acid entity, an L-glutamine or a salt thereof, an NAC or a salt thereof, an L-glycine, and an L-serine.

524. The composition of any of embodiments 520-523, wherein the wt. ratio of the L-amino acid entity, the I-amino acid entity, the V-amino acid entity, the R-amino acid entity, the L-glutamine or salt thereof, and the NAC or salt thereof is about 1:0.5:0.5:1.5:2:0.15 or about 1:0.5:0.5:1.5:2:0.3.

525. The composition of any of the preceding embodiments, wherein the wt. ratio of the L-amino acid entity, the R-amino acid entity, the L-glutamine or a salt thereof, and the NAC or salt thereof is about 0.5 to 3:0.5 to 4:1 to 4:0.1 to 2.5, e.g., the wt. ratio of the L-amino acid entity, the R-amino acid entity, the L-glutamine or a salt thereof, and the NAC or salt thereof is about 1:1.5:2:0.15 or about 1:1.5:2:0.3.

526. The composition of embodiment 525, wherein the wt. ratio of the L-amino acid entity, the R-amino acid entity, the L-glutamine or a salt thereof, and the NAC or salt thereof is about 1:0.75:2:0.15 or about 1:0.75:2:0.3.

527. The composition of any of the preceding embodiments, wherein the wt. ratio of the L-amino acid entity, the I-amino acid entity, the V-amino acid entity, the R-amino acid entity, the L-glutamine or salt thereof, and the NAC or salt thereof is about 1:0.5:0.5:1.5:2:0.15 or about 1:0.5:0.5:1.5:2:0.3.

528. The composition of any of embodiments 13-33, wherein the composition comprises about 0.5 g to about 10 g of the L-amino acid entity, about 0.25 g to about 5 g of the I-amino acid entity, about 0.25 g to about 5 g of the V-amino acid entity, about 0.5 g to about 20 g of the R-amino acid entity, about 1 g to about 20 g of the L-glutamine or a salt thereof, and about 0.1 g to about 5 g of the NAC or salt thereof, e.g., the composition comprises about 1 g of the L-amino acid entity, about 0.5 g of the I-amino acid entity, about 0.5 g of V-amino acid entity, about 1.5 g of R-amino acid entity, about 2 g of L-glutamine or a salt thereof, and about 0.15 g or about 0.3 g of NAC or salt thereof.

529. The composition of embodiment 528, wherein the composition comprises about 4 g of the L-amino acid entity, about 2 g of the I-amino acid entity, about 1 g of V-amino acid entity, about 3 g of R-amino acid entity, about 4 g of L-glutamine or a salt thereof, and about 0.9 g of NAC or a salt thereof.

530. The composition of any of the preceding embodiments, wherein the composition comprises:
 a) L-leucine or a salt thereof;
 b) L-isoleucine or a salt thereof;
 c) L-valine or a salt thereof;
 b) L-arginine or a salt thereof;
 e) L-glutamine or a salt thereof; and
 f) NAC or a salt thereof.

531. The composition of embodiment 530, wherein the L-Leucine is provided as part of a dipeptide comprising L-Leucine, or a salt thereof, or a tripeptide comprising L-Leucine, or a salt thereof.

532. The composition of embodiment 530 or 531, wherein the L-Isoleucine is provided as part of a dipeptide comprising L-Isoleucine, or a salt thereof, or a tripeptide comprising L-Isoleucine, or a salt thereof.

533. The composition of any of embodiments 530-532, wherein the L-Valine is provided as part of a dipeptide comprising L-Valine, or a salt thereof, or a tripeptide comprising L-Valine, or a salt thereof.

534. The composition of any of embodiments 530-533, wherein the L-Arginine is provided as part of a dipeptide comprising L-Arginine, or a salt thereof, or a tripeptide comprising L-Arginine, or a salt thereof.

535. The composition of any of embodiments 530-534, wherein the L-Glutamine is provided as part of a dipeptide comprising L-Glutamine, or a salt thereof, or a tripeptide comprising L-Glutamine, or a salt thereof.

536. The composition of any of embodiments 530-535, wherein the NAC is provided as a part of a dipeptide comprising NAC, or a salt thereof, or a tripeptide comprising NAC, or a salt thereof.

537. The composition of any of the preceding embodiments, wherein the composition comprises a combination of 4 to 20 different amino acid entities, e.g., a combination of 5 to 15 different amino acid entities.

538. The composition of any of the preceding embodiments, wherein at least two, three, four, or more amino acid entities is not a peptide of more than 4, 5, 6, 7, 8, 9, 10, 11, 12, 13, 14, 15, 16, 17, 18, 19, or 20 amino acid residues in length.

539. A method for improving liver function, wherein the method comprises administering to a subject in need thereof an effective amount of a composition of any of the preceding embodiments.

540. The method of embodiment 539, wherein the L-Leucine is provided as part of a dipeptide comprising L-Leucine, or a salt thereof, or a tripeptide comprising L-Leucine, or a salt thereof.

541. The method of embodiment 539 or 540, wherein the L-Arginine is provided as part of a dipeptide comprising L-Arginine, or a salt thereof, or a tripeptide comprising L-Arginine, or a salt thereof.

542. The method of any of embodiments 539-541, wherein the L-Glutamine is provided as part of a dipeptide comprising L-Glutamine, or a salt thereof, or a tripeptide comprising L-Glutamine, or a salt thereof.

543. The method of any of embodiments 539-542, wherein the NAC is provided as a part of a dipeptide comprising NAC, or a salt thereof, or a tripeptide comprising NAC, or a salt thereof.

544. A method for treating one or more symptoms selected from the group consisting of decreased fat metabolism, hepatocyte apoptosis, hepatocyte ballooning, inflammation of adipose tissue, inflammation of hepatic tissue, fibrosis, liver injury, steatosis, glucose tolerance, and oxidative stress, wherein the method comprises administering to a subject in need thereof an effective amount of a composition of any of the preceding embodiments.

545. The method of embodiment 544, wherein the L-Leucine is provided as part of a dipeptide comprising L-Leucine, or a salt thereof, or a tripeptide comprising L-Leucine, or a salt thereof.

546. The method of embodiment 544 or 545, wherein the L-Arginine is provided as part of a dipeptide comprising L-Arginine, or a salt thereof, or a tripeptide comprising L-Arginine, or a salt thereof.

547. The method of any of embodiments 544-546, wherein the L-Glutamine is provided as part of a dipeptide comprising L-Glutamine, or a salt thereof, or a tripeptide comprising L-Glutamine, or a salt thereof.

548. The method of any of embodiments 544-547, wherein the NAC is provided as a part of a dipeptide comprising NAC, or a salt thereof, or a tripeptide comprising NAC, or a salt thereof.

549. A method for treating fatty liver disease, wherein the method comprises administering to a subject in need thereof an effective amount of a composition of any of the preceding embodiments.

550. The method of embodiment 549, wherein the L-Leucine is provided as part of a dipeptide comprising L-Leucine, or a salt thereof, or a tripeptide comprising L-Leucine, or a salt thereof.

551. The method of embodiment 549 or 550, wherein the L-Arginine is provided as part of a dipeptide comprising L-Arginine, or a salt thereof, or a tripeptide comprising L-Arginine, or a salt thereof.

552. The method of any of embodiments 549-551, wherein the L-Glutamine is provided as part of a dipeptide comprising L-Glutamine, or a salt thereof, or a tripeptide comprising L-Glutamine, or a salt thereof.

553. The method of any of embodiments 549-552, wherein the NAC is provided as a part of a dipeptide comprising NAC, or a salt thereof, or a tripeptide comprising NAC, or a salt thereof.

554. The method of any of the preceding embodiments, wherein the subject has a disease or disorder selected from the group consisting of non-alcoholic fatty liver (NAFL), non-alcoholic fatty liver disease (NAFLD), non-alcoholic steatohepatitis (NASH), alcoholic fatty liver disease (AFLD), and alcoholic steatohepatitis (ASH).

555. The method of embodiment 554, wherein the subject has pediatric NAFLD.

556. The method of any of the preceding embodiments, wherein the subject has a high BMI, obesity, gut leakiness, gut dysbiosis or gut microbiome disturbance.

557. The method of any of the preceding embodiments, wherein the subject has cirrhosis, hepatocarcinoma, an increased risk of liver failure, an increased risk of death, metabolic syndrome, or type 2 diabetes.

558. The method of any of the preceding embodiments, wherein the subject has increased levels of inflammatory cytokines relative to a normal subject, e.g., the subject has increased levels of TNFα relative to a normal subject e.g., without the one or more symptoms or without the fatty liver disease.

559. The method of any of the preceding embodiments, wherein the patient exhibits muscle atrophy or has a decreased ratio of muscle tissue to adipose tissue relative to a normal subject, e.g., without the one or more symptoms or without a fatty liver disease, e.g., the patient exhibits muscle atrophy without one or both of fibrosis or cirrhosis.

560. The method of any of the preceding embodiments, wherein the subject exhibits reverse lipid transport from adipose tissue to liver tissue.

561. The composition of any of the preceding embodiments, wherein the composition comprises free amino acids, wherein the amino acids comprise arginine, glutamine, N-acetylcysteine, and a branched-chain amino acid chosen from one, two, or all of leucine, isoleucine, and valine.

562. The composition of embodiment 561, wherein the branched-chain amino acid is leucine, isoleucine, and valine.

563. The composition of embodiment 561 or 562, wherein the wt ratio of leucine, isoleucine, valine, arginine, glutamine, N-acetylcysteine is 1:0.5:0.5:1.5:2:0.15.

564. The composition of any of embodiments 561-563, wherein a total weight (wt) of the amino acids is about 2 g to about 60 g.

565. The composition of embodiment 564, wherein the total wt of the amino acids is about 6 g, about 12 g, about 18 g, about 24 g, or about 48 g.

566. The composition of any of embodiments 561-565, wherein the composition comprises about 0.5 g to about 10 g of leucine, about 0.25 g to about 5 g of isoleucine, about 0.25 g to about 5 g of valine, about 1 g to about 20 g of arginine, about 1 g to about 20 g of glutamine, and about 0.1 g to about 5 g of N-acetylcysteine.

567. The composition of embodiment 566, wherein the composition comprises about 1 g of leucine, about 0.5 g of isoleucine, about 0.5 g of valine, about 1.5 g of arginine, about 2 g of glutamine, and about 0.15 g of N-acetylcysteine.

568. The composition of embodiment 566, wherein the composition comprises about 2 g of leucine, about 1 g of isoleucine, about 1 g of valine, about 3.0 g of arginine, about 4 g of glutamine, and about 0.3 g of N-acetylcysteine.

569. The composition of embodiment 566, wherein the composition comprises about 4 g of leucine, about 2 g of isoleucine, about 2 g of valine, about 6.0 g of arginine, about 8 g of glutamine, and about 0.6 g of N-acetylcysteine.

570. The composition of any of embodiments 561-566, wherein the amino acids comprise about 10 wt % to about 30 wt % leucine, about 5 wt % to about 15 wt % isoleucine, about 5 wt % to about 15 wt % valine, about 15 wt % to about 40 wt % arginine, about 20 wt % to about 50 wt % glutamine, and about 1 wt % to about 8 wt % n-acetylcysteine.

571. The composition of embodiment 570, wherein the amino acids comprise about 16 wt % to about 18 wt % leucine, about 7 wt % to about 9 wt % isoleucine, about 7 wt % to about 9 wt % valine, about 28 wt % to about 32 wt % arginine, about 31 wt % to about 34 wt % glutamine, and about 1 wt % to about 5 wt % n-acetylcysteine.

572. The composition of embodiment 571, wherein the amino acids comprise about 16.8 wt % leucine, about 8.4 wt % isoleucine, about 8.4 wt % valine, about 30.4 wt % arginine, about 33.6 wt % glutamine, and about 2.5 wt % n-acetylcysteine.

573. The composition of any of the preceding embodiments, wherein the composition further comprises one or more pharmaceutically acceptable excipients.

574. The composition of embodiment 573, wherein the excipients are selected from the group consisting of citric acid, lecithin, a sweetener, a dispersion enhancer, a flavoring, a bitterness masking agent, and a natural or artificial coloring.

575. The composition of any of the preceding embodiments, wherein the composition is in the form of a solid, powder, solution, or gel.

576. The composition of any of the preceding embodiments, wherein the amino acids consist of leucine, isoleucine, valine, arginine, glutamine and N-acetylcysteine.

577. A method for treating one or more symptoms selected from the group consisting of decreased fat metabolism, hepatocyte apoptosis, hepatocyte ballooning, inflammation of adipose tissue, inflammation of hepatic tissue, fibrosis, and oxidative stress, wherein the method comprises administering to a subject in need thereof an effective amount of the composition of any one of embodiments 561-576.

578. The method of embodiment 577, wherein the subject has non-alcoholic fatty liver disease (NAFLD).

579. The method of embodiment 577 or 578, wherein the subject has pediatric NAFLD.

580. The method of embodiment 578 or 579, wherein the patient has steatosis.

581. The method of embodiment 577, wherein the subject has non-alcoholic steatohepatitis (NASH).

582. The method of embodiment 581, wherein the subject has fibrosis.

583. The method of embodiment 577, wherein the subject has cirrhosis.

584. The method of embodiment 583, wherein the subject has hepatocarcinoma, an increased risk of liver failure, or an increased risk of death.

585. The method of any of embodiments 577-584, wherein the subject has type 2 diabetes.

586. A method for treating non-alcoholic fatty liver disease (NAFLD) comprising administering to a subject in need thereof an effective amount of the composition of any of embodiments 561-576.

587. The method of embodiment 586, wherein the subject has pediatric NAFLD.

588. The method of embodiment 586 or 587, wherein the patient has steatosis.

589. A method for treating non-alcoholic steatohepatitis (NASH) comprising administering to a subject in need thereof an effective amount of the composition of any of embodiments 561-576.

590. The method of embodiment 589, wherein the subject has fibrosis.

591. A method for treating cirrhosis comprising administering to a subject in need thereof an effective amount of the composition of any of embodiments 561-576.

592. The method of embodiment 591, wherein the subject has hepatocarcinoma, an increased risk of liver failure, or an increased risk of death.

593. The method of any of embodiments 577-592, wherein administering the composition results in an improvement in one or more metabolic symptoms in the subject.

594. The method of embodiment 593, wherein the improvement in one or more metabolic symptoms is selected from the following: increased free fatty acid and lipid metabolism, improved mitochondrial function, white adipose tissue (WAT) browning, decreased reactive oxygen species (ROS), increased levels of glutathione (GSH), decreased hepatic inflammation, decreased hepatocyte ballooning, improved gut barrier function, increased insulin secretion, or glucose tolerance.

595. The method of embodiment 594, wherein the increased free fatty acid and lipid metabolism occurs in the liver.

596. The method of embodiment 594 or 595, wherein administration of the composition results in an improvement in one or more metabolic symptoms after a treatment period of 24 hours.

597. The method of any of embodiments 577-596, wherein the method further comprises determining the level of one, two, three, four, five, six, seven, eight, nine, ten, or more (e.g., all) of the following:
 a) alanine aminotransferase (ALT);
 b) aspartate aminotransferase (AST);
 c) adiponectin;
 d) N-terminal fragment of type III collagen (proC3);
 e) caspase-cleaved keratin 18 fragments (M30 and M65);
 f) IL-1 beta;
 g) C-reactive protein;
 h) PIIINP;
 i) TIMP1;
 j) MCP-1; or
 k) FGF-21.

598. The method of embodiment 597, wherein administration of the composition results in an improvement in one or more of a)-k) after a treatment period of 24 hours.

599. The method of any of embodiments 577-598, wherein the composition is administered prior to a meal.

600. The method of any of embodiments 577-598, wherein the composition is administered concurrent with a meal.

601. The method of any of embodiments 577-598, wherein the composition is administered following a meal.

602. The method of any of embodiments 577-601, wherein the composition is administered with a second agent.

603. The method of embodiment 602, wherein the second agent is selected from the group consisting of a farnesoid X receptor (FXR) agonist, a stearoyl CoA desaturase inhibitor, a CCR2 and CCR5 chemokine antagonist, a PPAR alpha and delta agonist, a caspase inhibitor, a galectin-3 inhibitor, an acetyl CoA carboxylase inhibitor, or an ileal sodium bile acid co-transporter inhibitor.

604. A dietary composition comprising the composition of any of embodiments 561-576, e.g., wherein the dietary composition is chosen from a medical food, a functional food, or a supplement.

605. The composition of any of embodiments 561-576 for use as a dietary composition, e.g., wherein the dietary composition is chosen from a medical food, a functional food, or a supplement.

606. The dietary composition of embodiment 605, wherein the subject has type 2 diabetes and/or a relatively high BMI.

607. The dietary composition of any of embodiments 605 or 606, wherein the subject has non-alcoholic fatty liver disease (NAFLD).

608. The dietary composition of any of embodiments 605-607, wherein the subject has pediatric NAFLD.

609. The dietary composition of any of embodiments 605-608, wherein the patient has steatosis.

610. The dietary composition of any of embodiments 605-609, wherein the subject has non-alcoholic steatohepatitis (NASH).

611. The dietary composition of embodiment 610, wherein the subject has fibrosis.

612. The dietary composition of any of embodiments 604-606, wherein the subject has cirrhosis.

613. The dietary composition of embodiment 612, wherein the subject has hepatocarcinoma, an increased risk of liver failure, or an increased risk of death.

614. The dietary composition of any of embodiments 604-613, wherein the subject has type 2 diabetes.

615. The dietary composition of any of embodiments 604-614, wherein the composition promotes weight loss in the subject.

616. The method or dietary composition of any of the preceding embodiments, wherein the composition is administered at a dose of about 15 g/d to about 90 g/d.

617. The method or dietary composition of embodiment 616, wherein the composition is administered at a dose of about 18 g/d, about 24 g/d, about 36/d, about 54 g/d, or about 72 g/d.

618. The method or dietary composition of any of the preceding embodiments, wherein the composition is administered one, two, to three times per day.

619. The method or dietary composition of any of the preceding embodiments, wherein the composition is administered at a dose of about 6 g, about 8 g, about 12 g, about 16 g, about 18 g, or about 24 g three times per day.

620. The composition of any of the preceding embodiments, wherein:
 1) the ratio of the L-amino acid entity to the I-amino acid entity is at least 1.5:1, or at least 1.75:1, and not more than 2.5:1 or not more than 3:1, e.g., the ratio of the L-amino acid entity to the I-amino acid entity is about 2:1;
 2) the ratio of L-amino acid entity to V-amino acid entity is at least 2:1, at least 3:1, at least 3.5:1, at least 4:1, or at least 5:1, and not more than 6:1, e.g., the ratio of L-amino acid entity to V-amino acid entity is about 4:1;
 3) the ratio of the L-amino acid entity to the R-amino acid entity is at least 1:1, at least 3.5:3, at least 4:3, or at least 2:1, and not more than 5:2, e.g., the ratio of the L-amino acid entity to the R-amino acid entity is about 4:3;
 4) the ratio of the L-amino acid entity to the L-glutamine or a salt thereof is at least 0.5:1, or at least 0.75:1, and not more than 1.5 to 1 or not more than 2:1, e.g., the ratio of the L-amino acid entity to the L-glutamine or salt thereof is about 1:1;
 5) the ratio of the L-amino acid entity to the NAC entity or a salt thereof is at least 2:1, at least 3:1, at least 3.5:1, or at least 4:1, and not more than 5 to 1 or not more than 6:1, e.g., the ratio of the L-amino acid entity to the NAC entity or salt thereof is about 4:1 (e.g., 4:0.9);
 6) optionally wherein the ratio of the L-amino acid entity to the S-amino acid entity or a salt thereof is greater than 1:3, greater than 1.5:3, about 2:3, or about 3:5, and not more than 2.5:3 or 1:1, e.g., the ratio of the L-amino acid entity to the S-amino acid entity is about 2:3, or the ratio of the L-amino acid entity to the S-amino acid entity is about 3:5; or
 7) a combination of two, three, four, five, or six of (1)-(6).

621. The composition of embodiment 620, wherein:
 8) the ratio of I-amino acid entity to V-amino acid entity is at least 1:1, at least 1.5:1, or about 2:1, and not more than 2.5:1 or not more than 3:1, e.g., the ratio of I-amino acid entity to V-amino acid entity is about 2:1;
 9) the ratio of the I-amino acid entity to the R-amino acid entity is greater than 1:3, greater than 1.5:3, or about 2:3, and not more than 2.5:3 or not more than 1:1, e.g., the ratio of the I-amino acid entity to the R-amino acid entity is about 2:3;
 10) the ratio of the I-amino acid entity to the L-glutamine or a salt thereof is at least 1:4, at least 1:3, or about 1:2, and not more than 1:1 or not more than 2:1, e.g., the ratio of the I-amino acid entity to the L-glutamine or salt thereof is about 1:2;

11) the ratio of the I-amino acid entity to the NAC entity or a salt thereof is at least 1:1, at least 1.5:1, or about 2:1, and not more than 2.5:1 or not more than 3:1, e.g., the ratio of the I-amino acid entity to the NAC entity or salt thereof is about 2:1 (e.g., 2:0.9);

12) optionally wherein the ratio of the I-amino acid entity to the S-amino acid entity or a salt thereof is greater than 1:4, greater than 1.5:4, about 1:3, or about 3:10, and not more than 1.5:3 or 2:3, e.g., the ratio of the I-amino acid entity to the S-amino acid entity is about 1:3, or the ratio of the I-amino acid entity to the S-amino acid entity is about 3:10; or 13) a combination of two, three, four, or five of (8)-(12).

622. The composition of embodiment 620 or 621, wherein:

14) the ratio of the V-amino acid entity to the R-amino acid entity is greater than 1:4, greater than 1.5:4, or about 1:3, and not more than 1:2 or not more than 1:1, e.g., the ratio of the V-amino acid entity to the R-amino acid entity is about 1:3;

15) the ratio of the V-amino acid entity to the L-glutamine or a salt thereof is greater than 1:5, or greater than 1.5:5, about 1:4, and not more than 1.5:4 or not more than 1:3, e.g., the ratio of the V-amino acid entity to the L-glutamine or salt thereof is about 1:4;

16) the ratio of the V-amino acid entity to the NAC entity or a salt thereof is at least 1:2, at least 1.5:2, or about 1:1, and not more than 1.5:1 or not more than 2:1, e.g., the ratio of the V-amino acid entity to the NAC entity or salt thereof is about 1:1 (e.g., 1:0.9);

17) optionally wherein the ratio of the V-amino acid entity to the S-amino acid entity or a salt thereof is greater than 1:8, greater than 1:7, about 1:6, or about 3:20, and not more than 1.5:6 or 1:3, e.g., the ratio of the V-amino acid entity to the S-amino acid entity is about 1:6, or the ratio of the V-amino acid entity to the S-amino acid entity is about 3:20; or 18) a combination of two, three, or four of (14)-(17).

623. The composition of any of embodiments 620-622, wherein:

19) the ratio of the R-amino acid entity to the L-glutamine or a salt thereof is greater than 1:2, greater than 1.25:2, or about 3:4, and not more than 3.5:4 or not more than 1:1, e.g., the ratio of the R-amino acid entity to the L-glutamine or salt thereof is about 3:4;

20) the ratio of the R-amino acid entity to the NAC entity or a salt thereof is at least 4:1, at least 4:1.5, or about 3:1, and not more than 3:1.5 or not more than 3:2, e.g., the ratio of the R-amino acid entity to the NAC entity or salt thereof is about 3:1 (e.g., 3:0.9);

21) optionally wherein the ratio of the R-amino acid entity to the S-amino acid entity or a salt thereof is greater than 1:4, greater than 1:3, about 1:2, or about 9:20, and not more than 1.5:2 or 1:1, e.g., the ratio of the R-amino acid entity to the S-amino acid entity is about 1:2, or the ratio of the R-amino acid entity to the S-amino acid entity is about 9:20; or 22) a combination of two or three of (19)-(21).

624. The composition of any of embodiments 620-623, wherein:

23) the ratio of the L-glutamine to the NAC entity or a salt thereof is at least 5:1, at least 5:1.5, or about 4:1, and not more than 4:1.5 or not more than 3:1, e.g., the ratio of the L-glutamine to the NAC entity or salt thereof is about 4:1 (e.g., 4:0.9);

24) optionally wherein the ratio of the L-glutamine to the S-amino acid entity or a salt thereof is greater than 1:3, greater than 1.25:3, about 2:3, or about 3:5, and not more than 2.5:3 or 1:1, e.g., the ratio of the L-glutamine to the S-amino acid entity is about 2:3, or the ratio of the L-glutamine to the S-amino acid entity is about 3:5; or 25) a combination of (23) and (24).

625. The composition of any of embodiments 620-624, wherein:

26) the ratio of the NAC entity to the S-amino acid entity or a salt thereof is greater than 1:8, greater than 1:7, or about 1:6, and not more than 1:5 or not more than 1.5:5, e.g., the ratio of the NAC entity to the S-amino acid entity is about 1:6 (e.g., 0.9:6 or 2.7:20).

626. The composition of any of embodiments 620-625, wherein the composition satisfies the properties of (1)-(7) defined above.

627. The composition of any of embodiments 620-626, wherein the composition satisfies the properties of at least 2, 3, 4, 5, 6, or 7 of any of properties (1)-(26) defined above.

628. The composition of any of embodiments 620-627, wherein the ratio of the L-amino acid-entity, the I-amino acid-entity, and the V-amino acid-entity in combination to the R-amino acid entity, L-glutamine or a salt thereof, and NAC or a salt thereof is 12:6:3:9:12:2.7.

629. The composition of any of embodiments 620-628, wherein the ratio of the L-amino acid-entity, the I-amino acid-entity, and the V-amino acid-entity in combination to the R-amino acid entity, L-glutamine or a salt thereof, NAC or a salt thereof, and the S-amino acid entity is 12:6:3:9:12:2.7:18.

630. The composition of any of embodiments 620-629, wherein the ratio of the L-amino acid-entity, the I-amino acid-entity, and the V-amino acid-entity in combination to the R-amino acid entity, L-glutamine or a salt thereof, NAC or a salt thereof, and the S-amino acid entity is 12:6:3:9:12:2.7:20.

631. The composition of any of embodiments 620-630, wherein the ratio of the L-amino acid-entity, the I-amino acid-entity, and the V-amino acid-entity in combination to the R-amino acid entity, L-glutamine or a salt thereof, and NAC or a salt thereof is 12+/−15%:6+/−15%:3+/−15%:9+/−15%:12+/−15%:2.7+/−15%.

632. The composition of any of embodiments 620-631, wherein the ratio of the L-amino acid-entity, the I-amino acid-entity, and the V-amino acid-entity in combination to the R-amino acid entity, L-glutamine or a salt thereof, NAC or a salt thereof, and the S-amino acid entity is 12+/−15%:6+/−15%:3+/−15%:9+/−15%:12+/−15%:2.7+/−15%:18+/−15%.

633. The composition of any of embodiments 620-632, wherein the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12:6:3:9:12:2.7:9:9. In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12:6:3:9:12:2.7:10:10.

634. The composition of any of embodiments 620-633, wherein the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12+/−15%:6+/−15%:3+/−15%:9+/−15%:12+/−15%:

2.7+/−15%:9+/−15%:9+/−15%. In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12+/−15%: 6+/−15%:3+/−15%:9+/−15%:12+/−15%:2.7+/−15%:10+/−15%:10+/−15%.

635. A pharmaceutical composition comprising the composition of any of the preceding embodiments.

636. The composition of any of the preceding embodiments, wherein the L-amino acid entity is chosen from the group consisting of L-leucine, β-hydroxy-β-methybutyrate (HMB), oxo-leucine, isovaleryl-CoA, D-leucine, and n-acetyl-leucine, or a combination thereof.

637. The composition of any of the preceding embodiments, wherein the R-amino acid entity is chosen from the group consisting of L-arginine, ornithine, argininosuccinate, citrulline, aspartate, glutamate, agmatine, creatine, D-arginine, and N-acetyl-arginine, or a combination thereof.

638. The composition of any of the preceding embodiments, wherein the Q-amino acid entity is chosen from the group consisting of L-glutamine, glutamate, carbamoyl-P, glutamate, D-glutamine, and n-acetylglutamine, or a combination thereof.

639. The composition of any of the preceding embodiments, wherein the NAC-amino acid entity is chosen from the group consisting of NAC, serine, acetylserine, cystathionine, glutathione, homocysteine, methionine, D-cysteine, L-cysteine, cystamine, and cystine, or a combination thereof.

640. The composition of any of the preceding embodiments, wherein the S-amino acid entity is chosen from the group consisting of L-serine, phosphoserine, β-hydroxypyruvate, L-glycine, tryptophan, acetylserine, cystathionine, and phosphatidylserine.

641. A dietary composition comprising the composition of any of the preceding embodiments, wherein the dietary compositions is chosen from a medical food, a functional food, or a supplement.

642. A method of providing amino acid entities to a subject comprising administering to the subject an effective amount of the composition of any of the preceding embodiments.

643. A method of manufacturing or making a composition comprising forming a composition comprising the following:
  a) a L-amino acid entity,
  b) an R-amino acid entity,
  c) a Q-amino acid entity;
  d) a NAC entity, e.g., NAC; and
  optionally, e) an S-amino acid entity;
  provided that:
  f) at least one amino acid entity is not provided as a peptide of more than 20 amino acid residues in length, wherein:
  (i) the amino acid entity of (a) is selected from Table 2; and
  (ii) one or both of the R-amino acid entity and the Q-amino acid entity are present at a higher amount (wt. %) than the L-amino acid entity.

644. The method of any of the preceding embodiments, wherein:
1) the ratio of the L-amino acid entity to the I-amino acid entity is at least 1.5:1, or at least 1.75:1, and not more than 2.5:1 or not more than 3:1, e.g., the ratio of the L-amino acid entity to the I-amino acid entity is about 2:1;

2) the ratio of L-amino acid entity to V-amino acid entity is at least 2:1, at least 3:1, at least 3.5:1, at least 4:1, or at least 5:1, and not more than 6:1, e.g., the ratio of L-amino acid entity to V-amino acid entity is about 4:1;

3) the ratio of the L-amino acid entity to the R-amino acid entity is at least 1:1, at least 3.5:3, at least 4:3, or at least 2:1, and not more than 5:2, e.g., the ratio of the L-amino acid entity to the R-amino acid entity is about 4:3;

4) the ratio of the L-amino acid entity to the L-glutamine or a salt thereof is at least 0.5:1, or at least 0.75:1, and not more than 1.5 to 1 or not more than 2:1, e.g., the ratio of the L-amino acid entity to the L-glutamine or salt thereof is about 1:1;

5) the ratio of the L-amino acid entity to the NAC entity or a salt thereof is at least 2:1, at least 3:1, at least 3.5:1, or at least 4:1, and not more than 5 to 1 or not more than 6:1, e.g., the ratio of the L-amino acid entity to the NAC entity or salt thereof is about 4:1 (e.g., 4:0.9);

6) optionally wherein the ratio of the L-amino acid entity to the S-amino acid entity or a salt thereof is greater than 1:3, greater than 1.5:3, about 2:3, or about 3:5, and not more than 2.5:3 or 1:1, e.g., the ratio of the L-amino acid entity to the S-amino acid entity is about 2:3, or the ratio of the L-amino acid entity to the S-amino acid entity is about 3:5; or 7) a combination of two, three, four, five, or six of (1)-(6).

645. The method of embodiment 644, wherein:
8) the ratio of I-amino acid entity to V-amino acid entity is at least 1:1, at least 1.5:1, or about 2:1, and not more than 2.5:1 or not more than 3:1, e.g., the ratio of I-amino acid entity to V-amino acid entity is about 2:1;

9) the ratio of the I-amino acid entity to the R-amino acid entity is greater than 1:3, greater than 1.5:3, or about 2:3, and not more than 2.5:3 or not more than 1:1, e.g., the ratio of the I-amino acid entity to the R-amino acid entity is about 2:3;

10) the ratio of the I-amino acid entity to the L-glutamine or a salt thereof is at least 1:4, at least 1:3, or about 1:2, and not more than 1:1 or not more than 2:1, e.g., the ratio of the I-amino acid entity to the L-glutamine or salt thereof is about 1:2;

11) the ratio of the I-amino acid entity to the NAC entity or a salt thereof is at least 1:1, at least 1.5:1, or about 2:1, and not more than 2.5:1 or not more than 3:1, e.g., the ratio of the I-amino acid entity to the NAC entity or salt thereof is about 2:1 (e.g., 2:0.9);

12) optionally wherein the ratio of the I-amino acid entity to the S-amino acid entity or a salt thereof is greater than 1:4, greater than 1.5:4, about 1:3, or about 3:10, and not more than 1.5:3 or 2:3, e.g., the ratio of the I-amino acid entity to the S-amino acid entity is about 1:3, or the ratio of the I-amino acid entity to the S-amino acid entity is about 3:10; or 13) a combination of two, three, four, or five of (8)-(12).

646. The method of embodiment 644 or 645, wherein:
14) the ratio of the V-amino acid entity to the R-amino acid entity is greater than 1:4, greater than 1.5:4, or about 1:3, and not more than 1:2 or not more than 1:1, e.g., the ratio of the V-amino acid entity to the R-amino acid entity is about 1:3;

15) the ratio of the V-amino acid entity to the L-glutamine or a salt thereof is greater than 1:5, or greater than 1.5:5, about 1:4, and not more than 1.5:4 or not more than 1:3, e.g., the ratio of the V-amino acid entity to the L-glutamine or salt thereof is about 1:4;

16) the ratio of the V-amino acid entity to the NAC entity or a salt thereof is at least 1:2, at least 1.5:2, or about 1:1, and not more than 1.5:1 or not more than 2:1, e.g., the ratio of the V-amino acid entity to the NAC entity or salt thereof is about 1:1 (e.g., 1:0.9);

17) optionally wherein the ratio of the V-amino acid entity to the S-amino acid entity or a salt thereof is greater than 1:8, greater than 1:7, about 1:6, or about 3:20, and not more than 1.5:6 or 1:3, e.g., the ratio of the V-amino acid entity to the S-amino acid entity is about 1:6, or the ratio of the V-amino acid entity to the S-amino acid entity is about 3:20; or 18) a combination of two, three, or four of (14)-(17).

647. The method of any of embodiments 644-646, wherein:

19) the ratio of the R-amino acid entity to the L-glutamine or a salt thereof is greater than 1:2, greater than 1.25:2, or about 3:4, and not more than 3.5:4 or not more than 1:1, e.g., the ratio of the R-amino acid entity to the L-glutamine or salt thereof is about 3:4;

20) the ratio of the R-amino acid entity to the NAC entity or a salt thereof is at least 4:1, at least 4:1.5, or about 3:1, and not more than 3:1.5 or not more than 3:2, e.g., the ratio of the R-amino acid entity to the NAC entity or salt thereof is about 3:1 (e.g., 3:0.9);

21) optionally wherein the ratio of the R-amino acid entity to the S-amino acid entity or a salt thereof is greater than 1:4, greater than 1:3, about 1:2, or about 9:20, and not more than 1.5:2 or 1:1, e.g., the ratio of the R-amino acid entity to the S-amino acid entity is about 1:2, or the ratio of the R-amino acid entity to the S-amino acid entity is about 9:20; or 22) a combination of two or three of (19)-(21).

648. The method of any of embodiments 644-647, wherein:

23) the ratio of the L-glutamine to the NAC entity or a salt thereof is at least 5:1, at least 5:1.5, or about 4:1, and not more than 4:1.5 or not more than 3:1, e.g., the ratio of the L-glutamine to the NAC entity or salt thereof is about 4:1 (e.g., 4:0.9);

24) optionally wherein the ratio of the L-glutamine to the S-amino acid entity or a salt thereof is greater than 1:3, greater than 1.25:3, about 2:3, or about 3:5, and not more than 2.5:3 or 1:1, e.g., the ratio of the L-glutamine to the S-amino acid entity is about 2:3, or the ratio of the L-glutamine to the S-amino acid entity is about 3:5; or 25) a combination of (23) and (24).

649. The method of any of embodiments 644-648, wherein:

26) the ratio of the NAC entity to the S-amino acid entity or a salt thereof is greater than 1:8, greater than 1:7, or about 1:6, and not more than 1:5 or not more than 1.5:5, e.g., the ratio of the NAC entity to the S-amino acid entity is about 1:6 (e.g., 0.9:6 or 2.7:20).

650. The method of any of embodiments 644-649, wherein the composition satisfies the properties of (1)-(7) defined above.

651. The method of any of embodiments 644-650, wherein the composition satisfies the properties of at least 2, 3, 4, 5, 6, or 7 of any of properties (1)-(26) defined above.

652. The method of any of embodiments 644-651, wherein the ratio of the L-amino acid-entity, the I-amino acid-entity, and the V-amino acid-entity in combination to the R-amino acid entity, L-glutamine or a salt thereof, and NAC or a salt thereof is 12:6:3:9:12:2.7.

653. The method of any of embodiments 644-652, wherein the ratio of the L-amino acid-entity, the I-amino acid-entity, and the V-amino acid-entity in combination to the R-amino acid entity, L-glutamine or a salt thereof, NAC or a salt thereof, and the S-amino acid entity is 12:6:3:9:12:2.7:18.

654. The method of any of embodiments 644-653, wherein the ratio of the L-amino acid-entity, the I-amino acid-entity, and the V-amino acid-entity in combination to the R-amino acid entity, L-glutamine or a salt thereof, NAC or a salt thereof, and the S-amino acid entity is 12:6:3:9:12:2.7:20.

655. The method of any of embodiments 644-654, wherein the ratio of the L-amino acid-entity, the I-amino acid-entity, and the V-amino acid-entity in combination to the R-amino acid entity, L-glutamine or a salt thereof, and NAC or a salt thereof is 12+/−15%:6+/−15%:3+/−15%:9+/−15%:12+/−15%:2.7+/−15%.

656. The method of any of embodiments 644-655, wherein the ratio of the L-amino acid-entity, the I-amino acid-entity, and the V-amino acid-entity in combination to the R-amino acid entity, L-glutamine or a salt thereof, NAC or a salt thereof, and the S-amino acid entity is 12+/−15%: 6+/−15%:3+/−15%:9+/−15%:12+/−15%:2.7+/−15%:18+/−15%.

657. The method of any of embodiments 644-656, wherein the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12:6:3:9:12:2.7:9:9. In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12:6:3:9:12: 2.7:10:10.

658. The method of any of embodiments 644-657, wherein the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12+/−15%:6+/−15%:3+/−15%:9+/−15%:12+/−15%: 2.7+/−15%:9+/−15%:9+/−15%. In certain embodiments, the ratio of the L-amino acid-entity, the I-amino acid-entity, and the V-amino acid-entity in combination to the R-amino acid entity, L-glutamine or a salt thereof, NAC or a salt thereof, the S-amino acid entity, and the L-glycine is 12+/−15%: 6+/−15%:3+/−15%:9+/−15%:12+/−15%:2.7+/−15%:10+/−15%:10+/−15%.

659. The composition or method of any of the preceding embodiments, wherein the composition is capable of enhancing fatty acid oxidation, e.g., one or both of reducing levels of unsaturated fatty acids or increasing levels of acylcarnitine (e.g., in a STAM mouse model or a FATZO mouse model). In certain embodiments, the reduction in levels of unsaturated fatty acids is at least 25%, 30%, 35%, 40%, 45%, 50%, 55%, 60%, 65%, 70%, 75%, 80%, 85%, 90%, 95%, or 99% of the level of change shown in Table 53, e.g., measured as described in Example 9. In certain embodiments, the increase in levels of acylcarnitine is at least 25%, 30%, 35%, 40%, 45%, 50%, 55%, 60%, 65%, 70%, 75%, 80%, 85%, 90%, 95%, or 99% of the level of change shown in Table 53, e.g., measured as described in Example 9.

660. The composition or method of any of the preceding embodiments, wherein the composition is capable of reducing, or reduces, liver fibrosis or liver injury by at least 5%, 10%, 15%, 20%, 21%, 22%, 23%, 24%, 25%, 26%, 27%, 28%, 29%, or 30%, as detected using an assay of alanine transaminase (ALT), e.g., an antibody-based detection assay, e.g., an ELISA, e.g., as described in Example 4, e.g., relative to a reference composition (e.g., a vehicle control).

661. The composition or method of any of the preceding embodiments, wherein the composition is capable of reducing, or reduces, liver fibrosis or liver injury by at least 5%, 10%, 15%, 20%, 21%, 22%, 23%, 24%, 25%, 26%, 27%, 28%, 29%, or 30%, as detected using an assay of aspartate transaminase (AST), e.g., an antibody-based detection assay, e.g., an ELISA, e.g., as described in Example 4, e.g., relative to a reference composition (e.g., a vehicle control).

662. The composition or method of any of the preceding embodiments, wherein the composition is capable of reducing, or reduces, alanine transaminase (ALT) by at least 5%, 10%, 15%, 20%, 21%, 22%, 23%, 24%, 25%, 26%, 27%, 28%, 29%, or 30%, as detected using an assay of ALT, e.g., an antibody-based detection assay, e.g., an ELISA, e.g., as described in Example 4, e.g., relative to a reference composition (e.g., a vehicle control).

663. The composition or method of any of the preceding embodiments, wherein the composition is capable of reducing, or reduces, aspartate transaminase (AST) by at least 5%, 10%, 15%, 20%, 21%, 22%, 23%, 24%, 25%, 26%, 27%, 28%, 29%, or 30%, as detected using an assay of AST, e.g., an antibody-based detection assay, e.g., an ELISA, e.g., as described in Example 4, e.g., relative to a reference composition (e.g., a vehicle control).

664. The composition or method of any of the preceding embodiments, wherein the composition is capable of reducing, or reduces, liver fibrosis or liver injury by at least 5%, 10%, 15%, 20%, 21%, 22%, 23%, 24%, 25%, 26%, 27%, 28%, 29%, or 30%, as detected using an assay of hydroxyproline, e.g., an antibody-based detection assay, e.g., an ELISA, e.g., as described in Example 4, e.g., relative to a reference composition (e.g., a vehicle control).

665. The composition or method of any of the preceding embodiments, wherein the composition is capable of reducing, or reduces, hydroxyproline levels by at least 5%, 10%, 15%, 20%, 21%, 22%, 23%, 24%, 25%, 26%, 27%, 28%, 29%, or 30%, as detected using an assay of hydroxyproline, e.g., an antibody-based detection assay, e.g., an ELISA, e.g., as described in Example 4, e.g., relative to a reference composition (e.g., a vehicle control).

666. The composition or method of any of the preceding embodiments, wherein the composition is capable of reducing, or reduces, liver fibrosis or liver injury by at least 5%, 10%, 15%, 20%, 20%, 30%, 40%, 45%, 50%, 55%, 60%, 65%, 70%, 75%, 80%, 85%, or 90% as detected using LX-2 cells, e.g., levels of Col1a1, Acta2, and/or TIMP2 in LX-2 cells, e.g., as assessed using a nucleic acid amplification method, e.g., PCR or qRT-PCR, e.g., as described in Example 7, e.g., relative to a reference composition (e.g., a vehicle control; an amino acid composition comprising L-leucine, L-isoleucine, L-valine; NAC; or an amino acid composition comprising L-arginine, L-glutamine, and NAC).

667. The composition or method of any of the preceding embodiments, wherein the composition is capable of reducing, or reduces, expression of one or more collagen biomarkers (e.g., Col1a1, Acta2, and/or TIMP2) by at least 5%, 10%, 15%, 20%, 20%, 30%, 40%, 45%, 50%, 55%, 60%, 65%, 70%, 75%, 80%, 85%, or 90% as detected using LX-2 cells, e.g., levels of Col1a1, Acta2, and/or TIMP2 in LX-2 cells, e.g., as assessed using a nucleic acid amplification method, e.g., PCR or qRT-PCR, e.g., as described in Example 7, e.g., relative to a reference composition (e.g., a vehicle control; an amino acid composition comprising L-leucine, L-isoleucine, L-valine; an amino acid composition comprising L-arginine, L-glutamine, and NAC; or NAC).

668. The composition or method of any of the preceding embodiments, wherein the composition is capable of reducing, or reduces, expression of one or more collagen biomarkers (e.g., Col1a1) by at least 5%, 10%, 15%, 20%, 20%, 30%, 40%, 45%, 50%, 55%, 60%, 65%, 70%, 75%, 80%, 85%, or 90% as detected using primary hepatic stellate cells, e.g., levels of Col1a1 in primary hepatic stellate cells, e.g., as assessed using an antibody-based detection assay, e.g., an ELISA, e.g., as described in Example 12, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC).

669. The composition or method of any of the preceding embodiments, wherein the composition is capable of increasing, or increases, expression of one or more collagen biomarkers (e.g., procollagen 1α1) by at least 5%, 10%, 15%, 20%, 20%, 30%, 40%, 45%, 50%, 55%, 60%, 65%, 70%, 75%, 80%, 85%, or 90% as detected using primary hepatic stellate cells, e.g., levels of procollagen 1α1 in primary hepatic stellate cells, e.g., as assessed using an antibody-based detection assay, e.g., an ELISA, e.g., as described in Example 12, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-valine, L-arginine, and L-glutamine; valine; glutamine; arginine; isoleucine; leucine; or NAC).

670. The composition or method of any of the preceding embodiments, wherein the composition is capable of reducing, or reduces, hepatocyte inflammation by at least 5%, 10%, 15%, 20%, 20%, 30%, 40%, 45%, 50%, 55%, 60%, 65%, 70%, 75%, 80%, 85%, or 90% as detected using HepG2 cells, e.g., decreased activity, e.g., decreased TNFα-induced activity of NF-kB in a reporter assay in HepG2 cells, as described in Example 8, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

671. The composition or method of any of the preceding embodiments, wherein the composition is capable of reducing, or reduces, TNFα-induced activity of NF-kB in HepG2 cells by at least 5%, 10%, 15%, 20%, 20%, 30%, 40%, 45%, 50%, 55%, 60%, 65%, 70%, 75%, 80%, 85%, or 90% as detected using HepG2 cells, e.g., decreased activity, e.g., decreased TNFα-induced activity of NF-kB in a reporter assay in HepG2 cells, as described in Example 8, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; or NAC).

672. The composition or method of any of the preceding embodiments, wherein the composition is capable of increasing, or increases, glucose tolerance, e.g., in a STAM mouse model or in a FATZO mouse model, by at least 1%, 2%, 3%, 4%, 5%, 6%, 7%, 8%, 9%, or 10%, as detected using an assay of glucose levels, e.g., using glucose oxidase, e.g., using a glucometer, e.g., as described in Example 5, e.g., relative to a reference composition (e.g., a vehicle control or a positive control, e.g., metformin).

673. The composition or method of any of the preceding embodiments, wherein the composition is capable of increasing, or increases, blood glucose metabolism, e.g., in a STAM mouse model or in a FATZO mouse model, by at least 1%, 2%, 3%, 4%, 5%, 6%, 7%, 8%, 9%, or 10%, as detected using an assay of glucose levels, e.g., using glucose oxidase, e.g., using a glucometer, e.g., as described in Example 5, e.g., relative to a reference composition (e.g., a vehicle control or a positive control, e.g., metformin).

674. The composition or method of any of the preceding embodiments, wherein the composition is capable of decreasing, or decreases, steatosis and/or inflammation by at least 1%, 2%, 3%, 4%, 5%, 6%, 7%, 8%, 9%, or 10%, as detected using an assay of MCP1/CCL2, e.g., in primary hepatocytes, e.g., using an antibody-based detection assay, e.g., an ELISA, e.g., as described in Example 10, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC).

675. The composition or method of any of the preceding embodiments, wherein the composition is capable of decreasing, or decreases, MCP1/CCL2 levels by at least 1%, 2%, 3%, 4%, 5%, 6%, 7%, 8%, 9%, or 10%, as detected using an assay of MCP1/CCL2, e.g., in primary hepatocytes, e.g., using an antibody-based detection assay, e.g., an ELISA, e.g., as described in Example 10, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC).

676. The composition or method of any of the preceding embodiments, wherein the composition is capable of decreasing, or decreases, TNFα inflammatory response by at least 1%, 2%, 3%, 4%, 5%, 6%, 7%, 8%, 9%, or 10%, as detected using an assay of MCP1/CCL2 or an assay of IL-6, e.g., in primary hepatic stellate cells, e.g., using an antibody-based detection assay, e.g., an ELISA, e.g., as described in Example 11, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC).

677. The composition or method of any of the preceding embodiments, wherein the composition is capable of decreasing, or decreases, MCP1/CCL2 levels and/or IL-6 levels by at least 1%, 2%, 3%, 4%, 5%, 6%, 7%, 8%, 9%, or 10%, as detected using an assay of MCP1/CCL2 or an assay of IL-6, e.g., in primary hepatic stellate cells, e.g., using an antibody-based detection assay, e.g., an ELISA, e.g., as described in Example 11, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC).

678. The composition of any of the preceding embodiments for use as a medicament.

679. The composition of any of the preceding embodiments for use in a method as disclosed herein.

680. The use of a composition of any of the preceding embodiments in the manufacture of a medicament.

681. The use of a composition of any of the preceding embodiments in the manufacture of a medicament for treating any of the disorders or conditions disclosed herein.

Although many of the above embodiments are shown in dependent form, it is contemplated that any of the embodiments or combinations thereof may be in independent form.

EXAMPLES

The Example below is set forth to aid in the understanding of the inventions, but is not intended to, and should not be construed to, limit its scope in any way.

Example 1: Method of Producing the Amino Acid Compositions

The amino acid compositions of the instant disclosure and formulations thereof may be made according to methods known in the art. They may also be made by the methods described below.

The starting materials (individual amino acids and excipients) are blended and sieved to generate a powder blend, which is filled into stick packs. The contents of the stick packs are dispersed in water at time of use for oral administration. An example of the mixing and reconstitution protocols, and stick pack formulations made thereby, are provided below.

Mixing Protocol
1. Ingredients were weighed into a container.
2. The container was sealed and placed in a Turbula mixer and contents mixed on low setting for 2 minutes.
3. The blended powder was sieved using a No. 14 screen and any clumps not passing through the sieve were broken apart.
4. The blended and sieved powder was transferred back to the container and mixed in a Turbula mixer on low for 10 minutes.

TABLE 13

Stick pack formulations

| Ingredient | Placebo | Formulation of Amino Acid Composition A-1 | Formulation of Amino Acid Composition A-2 |
|---|---|---|---|
| | | Amount per stick pack (g) | |
| FUSI-BCAA ™ Instantized Blend (2:1:1 L:I:V) | 0.00 | 2.00 | 2.00 |
| (contains L-Leucine) | N/A | (1.00) | (1.00) |
| (contains L-Isoleucine) | N/A | (0.50) | (0.50) |
| (contains L-Valine) | N/A | (0.50) | (0.50) |
| L-Arginine HCl | 0.00 | 1.50 | 1.81 |
| L-Glutamine | 0.00 | 2.00 | 2.00 |
| N-Acetylcysteine | 0.00 | 0.25 | 0.15 |
| Citric Acid | 0.98 | 0.67 | 0.67 |
| Lecithin (Alcolec F100) | 0.59 | 0.83 | 0.83 |
| Acesulfame Potassium | 0.04 | 0.05 | 0.05 |
| Sucralose micronized NF | 0.02 | 0.03 | 0.03 |
| Xanthan Gum (Ticaxan Rapid-3) | 0.24 | 0.24 | 0.24 |
| Vanilla Custard #4306 | 0.06 | 0.06 | 0.06 |

TABLE 13-continued

Stick pack formulations

| Ingredient | Placebo | Formulation of Amino Acid Composition A-1 | Formulation of Amino Acid Composition A-2 |
|---|---|---|---|
| | Amount per stick pack (g) | | |
| Maltrin QD M500 maltodextrin NF | 5.75 | 0.00 | 0.00 |
| Nat Orange WONF #1326 | 0.36 | 0.36 | 0.36 |
| Lime 865.0032U | 0.05 | 0.05 | 0.05 |
| Lemon 862.2169U | 0.05 | 0.05 | 0.05 |
| Bitterness Masking 936.2160U | 0.12 | 0.12 | 0.12 |
| FD&C Yellow 6 | 0.01 | 0.01 | 0.01 |
| FD&C Red 40 (1:100 in M500) | 0.0667 | 0.00 | 0.0000 |
| Total (g) | 8.33 | 8.22 | 8.42 |

Reconstitution Protocol

Stick pack formulations were reconstituted according to the following protocol:
1. A total (g) "amount per stick pack" of powder blend was weighed.
2. About 118.3 g (4 oz) of cold filtered water was weighed into a sealable container.
3. The "amount per stick pack" of the powder blend was transferred to the sealable container and the container was sealed.
4. The container was shaken vigorously for 20 to 30 seconds.

Example 2: Analytical Characterization of the Amino Acid Compositions

Described below are methods used to characterize some of the physicochemical properties in formulations of the amino acid compositions prepared according to Example 1.

Identification and Assay. The identification and assay of % label claim of each amino acid present in Formulations of Amino Acid Composition A-1 and Amino Acid Composition A-2 was evaluated by reversed phase HPLC.

Amino Acid Analysis

Briefly, an amino acid analysis method using reversed-phase high pressure liquid chromatography (HPLC) was developed to measure free amino acid content (except for N-acetylcysteine) in formulations of amino acid compositions described herein following resuspension. Column and chromatographic conditions were modified from Agilent Technical Note: "Automated Amino Acid Analysis Using an Agilent Poroshell HPH—C18 Column (Agilent Application Note 5991-5571EN)". Primary amino acids in the sample are derivatized online using the Agilent 1260 or 1290 UPLC well-plate autosampler using o-phthaldialdehyde (OPA). Separation is achieved using an Agilent ZORBAX Eclipse Plus column (4.6 mm ID×100 mm, 3.5 μm). The OPA-derivatives of primary amino acids are detected using fluorescence (FLD) at 340 nm emission/450 nm excitation wavelengths and UV detection at 338 nm. Individual amino acids are expected to elute according to known representative chromatograms of amino acid standards. Concentrations of amino acids in samples are determined by fitting a sample peak area to a standard curve. Alternatively, amino acid analysis may be performed using derivatization with AccQ-Tag chemistry and standards (Waters).

Amino Acid Analysis: N-Acetylcysteine

For N-acetylcysteine (NAC), an HPLC test method was developed based on the United States Pharmacopeia Monograph Chapter 39 (USP <39>) for "Acetylcysteine" to determine the content of N-acetylcysteine of reconstituted powder of formulations described herein. This HPLC method involves the use of a reversed-phase column without any derivatization step. The separation was done using a column of C-18 backbone as the stationary phase, and 0.05 M $KH_2PO_4$ as the mobile phase. UV detection was performed at 214 nm. The column was then flushed with 5% acetonitrile to remove any residual sample components at the end of each injection. At the end of the sequence, a low flow "system flush" procedure involving stronger organic solvents is used to preserve the column for storage. N-Acetylcysteine is expected to elute according to known representative chromatograms of standards. Concentrations of N-acetylcysteine in samples are determined by fitting a sample peak area to a standard curve.

Results for Formulation of Amino Acid Composition A-1 (compared to theoretical g per serving) are shown in Table 14. For glutamine, a mean mass per serving of 1.84 g was observed; compared to 2.00 g theoretical per serving, this gives a % agreement (or % label claim value) of 92%. For arginine, a mean mass per serving of 1.69 g was observed; compared to 1.50 g theoretical per serving, this gives a % agreement (or % label claim value) of 113%. For valine, a mean mass per serving of 0.51 g was observed; compared to 0.50 g theoretical per serving, this gives a % agreement (or % label claim value) of 101%. For isoleucine, a mean mass per serving of 0.52 g was observed; compared to 0.50 g theoretical per serving, this gives a % agreement (or % label claim value) of 104%. For leucine, a mean mass per serving of 1.04 g was observed; compared to 1.00 g theoretical per serving, this gives a % agreement (or % label claim value) of 104%. For N-acetylcysteine (NAC), a mean mass per serving of 0.28 g was observed; compared to 0.25 g theoretical per serving, this gives a % agreement (or % label claim value) of 111%. Overall, the amino acids and amino acid derivatives in the Formulation of Amino Acid Composition A-1 had a Range of % Label Claims of 92-113%.

TABLE 14

% Label Claim Results: Formulation of Amino Acid Composition A-1

| Sample Name | g of Individual Amino Acid/per serving of Amino Acid Composition A-1 | | | | | |
|---|---|---|---|---|---|---|
| | GLN | ARG | VAL | ILE | LEU | NAC |
| AA Comp A-1 | 1.84 | 1.70 | 0.51 | 0.52 | 1.05 | 0.28 |
| AA Comp A-1 | 1.82 | 1.68 | 0.50 | 0.52 | 1.04 | 0.28 |
| AA Comp A-1 | 1.84 | 1.70 | 0.51 | 0.52 | 1.05 | 0.28 |
| Mean | 1.84 | 1.69 | 0.51 | 0.52 | 1.04 | 0.28 |
| Theoretical g/serving for each AA | 2.00 | 1.50 | 0.50 | 0.50 | 1.00 | 0.25 |
| % Agreement Observed/ Theoretical * 100 | 92 | 113 | 101 | 104 | 104 | 111 |

Results for Formulation of Amino Acid Composition A-2 (compared to theoretical g per serving) are shown in Table 15. For glutamine, a mean mass per serving of 2.102 g was observed; compared to 2.00 g theoretical per serving, this gives a % agreement (or % label claim value) of 105.1%. For arginine, a mean mass per serving of 1.922 g was observed; compared to 1.5 g theoretical per serving, this gives a % agreement (or % label claim value) of 107.5%. For valine, a mean mass per serving of 0.536 g was observed; compared to 0.50 g theoretical per serving, this gives a % agreement (or % label claim value) of 107.5%. For isoleucine, a mean mass per serving of 0.531 g was observed; compared to 0.50 g theoretical per serving, this gives a % agreement (or % label claim value) of 106.2%. For leucine, a mean mass per serving of 1.058 g was observed; compared to 1.00 g theoretical per serving, this gives a % agreement (or % label claim value) of 105.8%. For N-acetylcysteine (NAC), a mean mass per serving of 0.153 g was observed; compared to 0.15 g theoretical per serving, this gives a % agreement (or % label claim value) of 101.7%. Overall, the amino acids and amino acid derivatives in the Formulation of Amino Acid Composition A-2 had a range of mean % label claims of 101-107%. Individual samples had a range of % label claims of 98.3-108.8%.

TABLE 15

% Label Claim Results: Formulation of Amino Acid Composition A-2

| Sample Name | g of Individual Amino Acid/per serving of Amino Acid Composition A-2 | | | | | |
|---|---|---|---|---|---|---|
| | GLN | ARG | VAL | ILE | LEU | NAC |
| AA Comp A-2 | 2.09 | 1.92 | 0.54 | 0.53 | 1.05 | 0.16 |
| AA Comp A-2 | 2.10 | 1.90 | 0.53 | 0.53 | 1.06 | 0.15 |
| AA Comp A-2 | 2.11 | 1.96 | 0.54 | 0.53 | 1.06 | 0.15 |
| AA Comp A-2 | 2.11 | 1.90 | 0.54 | 0.53 | 1.06 | 0.15 |
| Mean | 2.102 | 1.922 | 0.536 | 0.531 | 1.058 | 0.153 |
| Theoretical g/serving for each AA | 2.00 | 1.50 | 0.50 | 0.50 | 1.00 | 0.15 |
| % Agreement Observed/ Theoretical * 100 | 105.1 | 106.6 | 107.5 | 106.2 | 105.8 | 101.7 |

Example 3: Pharmacokinetic Characterization of the Amino Acid Compositions

The amino acid compositions of the present disclosure were characterized in rodent and human subjects for their pharmacokinetic effects on amino acid concentrations in response to ingestion of the compositions.

Rat Pharmacokinetics

The pharmacokinetic effects of a formulation of Amino Acid Composition A-1 were tested in rats. After an overnight fast, rats were given the formulation by oral gavage. Portal vein and jugular vein blood was collected just before the dose, and at 5, 15, 30, 60, 120, 240 and 360 minutes thereafter. Plasma concentration of amino acid levels were measured, and maximum concentration ($C_{max}$), time of maximum concentration ($T_{max}$), and half-life ($T_{1/2}$) were determined. Maximum concentration values are corrected for baseline endogenous amino acid levels. Results for rat PK studies are shown below in Tables 16-21.

TABLE 16

Leucine Rat PK-Formulation of Amino Acid Composition A-1

| Dose (mg/kg) | $C_{max}$ (µM) | $T_{max}$ (h) | $T_{1/2}$ (h) |
|---|---|---|---|
| 266 | 421 | 1.0 | 1.2 |

TABLE 17

Isoleucine Rat PK-Formulation of Amino Acid Composition A-1

| Dose (mg/kg) | $C_{max}$ (µM) | $T_{max}$ (h) | $T_{1/2}$ (h) |
|---|---|---|---|
| 133 | 176 | 0.6 | 1.0 |

TABLE 18

Valine Rat PK - Formulation of Amino Acid Composition A-1

| Dose (mg/kg) | $C_{max}$ (µM) | $T_{max}$ (h) | $T_{1/2}$ (h) |
|---|---|---|---|
| 133 | 323 | 0.9 | 1.5 |

TABLE 19

Arginine Rat PK - Formulation of Amino Acid Composition A-1

| Dose (mg/kg) | $C_{max}$ (µM) | $T_{max}$ (h) | $T_{1/2}$ (h) |
|---|---|---|---|
| 399 | 896 | 1.0 | 1.1 |

TABLE 20

Glutamine Rat PK - Formulation of Amino Acid Composition A-1

| Dose (mg/kg) | $C_{max}$ (µM) | $T_{max}$ (h) | $T_{1/2}$ (h) |
|---|---|---|---|
| 531 | 300 | 1.8 | 4.1 |

TABLE 21

N-acetylcysteine Rat PK - Formulation of Amino Acid Composition A-1

| Dose (mg/kg) | $C_{max}$ (µM) | $T_{max}$ (h) | $T_{1/2}$ (h) |
|---|---|---|---|
| 66 | 34 | 0.9 | 0.8 |

Allometric scaling was assumed to convert rat mg/kg doses into human equivalent mg/kg doses. A comparison of these equivalent mg/kg doses and human gram doses gram (assuming bodyweight of 70 kg) is shown in Table 22.

TABLE 22

Amino Acid Doses: Comparison of Rat and Human

| Dose | Leu | Ile | Val | Arg | Gln | NAC |
|---|---|---|---|---|---|---|
| Rat (mg/kg) | 266 | 133 | 133 | 399 | 531 | 66 |
| Human (mg/kg) | 43 | 21 | 21 | 64 | 86 | 11 |
| Human (g) | 3 | 1.5 | 1.5 | 4.5 | 6 | 0.75 |

Human Pharmacokinetics

The impacts of orally administered Formulation of Amino Acid Composition A-1 prepared according to Example 1 on amino acid pharmacokinetics was evaluated in six apparently healthy human subjects between the ages of 18 and 40. Changes in plasma concentrations of amino acids in response to ingestion of the Formulation of Amino Acid Composition A-1 at two doses (High: 3 stick packs, ~18 g of amino acids; vs. Low: 1 stick pack, ~6 g of amino acids) were determined. Blood samples (3 mL) were collected after an initial baseline and in specific intervals thereafter [i.e., 0 (pre-administration), 15, 30, 60, 90, 120, 150, 180, 210, and 240 minutes]. Plasma concentration of amino acid levels were measured, and maximum concentration ($C_{max}$), time of maximum concentration ($T_{max}$), half-life ($T_{1/2}$) and total exposure (area under curve for plasma concentration time-courses of leucine, isoleucine, valine, arginine and glutamine) were determined. Maximum concentration and total exposure values are corrected for baseline endogenous amino acid levels. These results are shown in Table 23-27.

TABLE 23

Leucine Human PK - Formulation of Amino Acid Composition A-1

| Dose | Dose (g) | $C_{max}$ (μM) | $T_{max}$ (h) | $T_{1/2}$ (h) | $AUC_{last}$ (μM-h) |
|---|---|---|---|---|---|
| HIGH | 3.0 | 294 | 0.8 | 1.1 | 471 |
| LOW | 1.0 | 117 | 0.8 | 1.3 | 153 |

TABLE 24

Isoleucine Human PK - Formulation of Amino Acid Composition A-1

| Dose | Dose (g) | $C_{max}$ (μM) | $T_{max}$ (h) | $T_{1/2}$ (h) | $AUC_{last}$ (μM-h) |
|---|---|---|---|---|---|
| HIGH | 1.5 | 141 | 0.7 | 0.8 | 194 |
| LOW | 0.5 | 52 | 0.8 | 0.6 | 54 |

TABLE 25

Valine Human PK - Formulation of Amino Acid Composition A-1

| Dose | Dose (g) | $C_{max}$ (μM) | $T_{max}$ (h) | $T_{1/2}$ (h) | $AUC_{last}$ (μM-h) |
|---|---|---|---|---|---|
| HIGH | 1.5 | 238 | 0.8 | 1.3 | 400 |
| LOW | 0.5 | 89 | 0.8 | 1.7 | 101 |

TABLE 26

Arginine Human PK - Formulation of Amino Acid Composition A-1

| Dose | Dose (g) | $C_{max}$ (μM) | $T_{max}$ (h) | $T_{1/2}$ (h) | $AUC_{last}$ (μM-h) |
|---|---|---|---|---|---|
| HIGH | 4.5 | 177 | 0.8 | 1.6 | 311 |
| LOW | 1.5 | 69 | 0.8 | 1.3 | 111 |

TABLE 27

Glutamine Human PK - Formulation of Amino Acid Composition A-1

| Dose | Dose (g) | $C_{max}$ (μM) | $T_{max}$ (h) | $T_{1/2}$ (h) | $AUC_{last}$ (μM-h) |
|---|---|---|---|---|---|
| HIGH | 6.0 | 190 | 0.9 | 2.9 | 332 |
| LOW | 2.0 | 103 | 1.1 | 3.0 | 186 |

Example 4: Therapeutic Amino Acid Composition A-1 Treatment Improves Liver Fibrosis in an Animal Model of Chemically Induced Fibrosis Amino Acid Composition A-1 was tested for its ability to affect liver fibrosis in a model of chemically induced liver fibrosis. A commonly used model of experimental hepatic fibrosis is induced chemically in mice using carbon tetrachloride; $CCl_4$ (Gideon Smith, Animal Models of Cutaneous and Hepatic Fibrosis; Progress in Molecular Biology and Translational Science, Vol. 105, pp. 371-408). $CCl_4$ causes inflammation, hepatocyte damage, necrosis and fibrosis after 4 weeks of treatment and cirrhosis after 8 weeks. Liver fibrosis induced in mice by carbon tetrachloride ($CCl_4$) resembles important properties of human liver fibrosis including inflammation, regeneration and fiber formation.

Animals

Male BALB/c mice 7 to 8 weeks of age were used for this study. Animals were housed four per cage, kept on a standard 12 hr light cycle and given free access to water and standard mouse chow. Food and water were available ad libitum.

Procedure

Animals were dosed with 5% $CCl_4$ or vehicle intraperitoneally (IP) typically 3 days a week for 4 weeks. $CCl_4$ was formulated weekly. 10 ml/kg of Amino Acid Composition A-1 at 23 mg/ml, 76 mg/ml or 153 mg/ml was dosed by oral gavage twice daily. Animals were weighed twice weekly and blood was collected via retro-orbital sinus once per week for serum. After four weeks, blood was collected for serum isolation and mice were euthanized via cervical dislocation. Two lobes of liver were removed—the left lobe was placed in a tube containing 10% formalin for histopathology, while the right lobe was weighed and placed in a beadbeater tube containing 2.3 mm zirconia beads and 2× volume of 1:100 protease inhibitor (Sigma Aldrich, #P8340). Tissue samples were homogenized for 2 minutes in a beadbeater machine and immediately spun down at 3,000 rpm for 15 minutes at 4° C. Serum was analyzed for ALT/AST levels at weeks 2 and 4. Homogenized liver samples were further evaluated for Hydroxyproline (Hyp) content to identify formation of liver fibrosis.

Hydroxyproline (Week 4)

Hydroxyproline (4-hydroxyproline, Hyp) is a common nonproteinogenic amino acid and is used as an indirect measure of the amount of collagen present, indicative of fibrosis. Hepatic Hyp content levels in $CCl_4$-treated animals were significantly higher than vehicle treated animals. Data are mean±standard deviation (stdev); "Comp A-1": Amino Acid Composition A-1; *p<0.05 compared to vehicle control by unpaired T test. Raw data are shown in Table 28.

TABLE 28

Hepatic Hyp content level results

| | Hydroxyproline | | | | |
|---|---|---|---|---|---|
| | Vehicle/ Sham | Vehicle/ CCL4 | Comp A-1, 23 mg/ml | Comp A-1, 76 mg/ml | Comp A-1, 153 mg/ml |
| mean | 0.160 | 0.263* | 0.280 | 0.228 | 0.201 |
| stdev | 0.067 | 0.107 | 0.104 | 0.124 | 0.057 |

AST Levels and ALT Levels

Aspartate transaminase (AST) and alanine transaminase (ALT) are commonly measured clinical biomarkers of liver health. Both AST and ALT levels were significantly elevated in $CCl_4$ administered animals for the entire duration of the study, suggesting that liver damage has occurred. Data are mean±standard deviation (stdev); "Comp A-1": Amino Acid Composition A-1; p values are compared to vehicle/$CCl_4$ control; by one-tailed T test; n.s. not significant. Raw data are shown in Tables 29 and 30.

TABLE 29

ALT level results

| | Liver ALT | | | | |
|---|---|---|---|---|---|
| | Vehicle/ Sham | Vehicle/ CCL4 | Comp A-1, 23 mg/ml | Comp A-1, 76 mg/ml | Comp A-1, 153 mg/ml |
| mean | 1608.4 | 4153.4 | 3694.9 | 3023.4 | 2992.7 |
| stdev | 1099.5 | 1427.4 | 2106.4 | 1343.8 | 1674.2 |
| | | | n.s. | p < 0.05 | p = 0.0371 |

TABLE 30

AST level results

Liver AST

|  | Vehicle/ Sham | Vehicle/ CCL4 | Comp A-1, 23 mg/ml | Comp A-1, 76 mg/ml | Comp A-1, 153 mg/ml |
|---|---|---|---|---|---|
| mean | 155.8 | 933.6 | 879.2 | 554.7 | 680.4 |
| stdev | 69.7 | 237.0 | 527.3 | 336.6 | 431.2 |
|  |  |  | n.s. | p < 0.01 | p = 0.0394 |

SUMMARY

Treatment with Amino Acid Composition A-1 resulted in reduction of chemically-induced fibrosis as indicated by reduced levels of hydroxyproline, a marker for collagen production, and in improvement of clinical biomarkers of liver damage as indicated by reduction in levels of liver enzymes ALT and AST (Tables 31-33).

TABLE 31

Hepatic Hyp content level results: raw data
Hydroxyproline

| Vehicle/ Sham | Vehicle/ CCL4 | Comp A-1, 23 mg/ml | Comp A-1, 76 mg/ml | Comp A-1, 153 mg/ml |
|---|---|---|---|---|
| 0.122 | 0.241 | 0.246154 | 0.190323 | 0.248649 |
| 0.277 | 0.318 | 0.529578 | 0.174684 | 0.24 |
| 0.152 | 0.298 | 0.234783 | 0.226549 | 0.18 |
| 0.108 | 0.493 | 0.216393 | 0.169128 | 0.174233 |
| 0.123 | 0.2 | 0.294737 | 0.175887 | 0.133333 |
| 0.108 | 0.196 | 0.22439 | 0.107692 | 0.135758 |
| 0.232 | 0.183 | 0.305512 | 0.212389 | 0.210219 |
|  | 0.177 | 0.393064 | 0.316191 | 0.150265 |
|  |  | 0.272897 | 0.612174 | 0.231293 |
|  |  | 0.192683 | 0.18018 | 0.308824 |
|  |  | 0.164341 | 0.218803 |  |
|  |  |  | 0.203279 |  |
|  |  |  | 0.17971 |  |

TABLE 32

ALT level results: raw data
Liver ALT

| Vehicle/ Sham | Vehicle/ CCL4 | Comp A-1, 23 mg/ml | Comp A-1, 76 mg/ml | Comp A-1, 153 mg/ml |
|---|---|---|---|---|
| 685.0737 | 4963.448 | 1299.647 | 4325.237 | 2611.524 |
| 2623.343 | 578.7053 | 5069.816 | 4325.237 | 2150.594 |
| 1606.933 | 5235.278 | 5566.202 | 2304.237 | 1866.945 |
| 3805.214 | 2115.138 | 5188.003 | 1051.454 | 696.8924 |
| 779.6234 | 4384.331 | 3828.851 | 1488.746 | 1725.121 |
| 637.7988 | 4207.05 | 330.5123 | 4313.419 | 3722.483 |
| 1417.834 | 5471.652 | 649.6176 | 4112.501 | 5211.641 |
| 1311.466 | 5105.273 | 1441.471 | 2859.717 | 4797.986 |
|  | 3462.471 | 5495.29 | 2564.249 | 1216.916 |
|  | 4147.957 | 4892.536 | 5318.009 | 1796.033 |
|  | 5436.196 | 5329.828 | 2836.079 | 5069.816 |
|  | 3852.489 | 5247.097 | 2457.881 | 5046.179 |
|  | 5034.36 |  | 1346.922 |  |

TABLE 33

AST level results: raw data
Liver AST

| Vehicle/ Sham | Vehicle/ CCL4 | Comp A-1, 23 mg/ml | Comp A-1, 76 mg/ml | Comp A-1, 153 mg/ml |
|---|---|---|---|---|
| 95.37346 | 908.3081 | 315.7015 | 703.1751 | 508.1721 |
| 57.38585 | 1050.129 | 928.5682 | 720.9027 | 335.9616 |
| 239.7263 | 877.918 | 1389.484 | 371.4167 | 379.0142 |
| 194.1412 | 660.1224 | 1047.596 | 262.5189 | 211.8688 |
| 123.231 | 599.3423 | 589.2123 | 267.5839 | 510.7046 |
| 102.971 | 675.3175 | 181.4787 | 819.6704 | 885.5156 |
| 237.1938 | 1470.525 | 285.3115 | 629.7324 | 1214.742 |
| 196.6737 | 1070.389 | 305.5715 | 414.4693 | 941.2307 |
|  | 733.5651 | 1690.853 | 505.6396 | 252.3889 |
|  | 976.6858 | 1100.779 | 1485.72 | 297.974 |
|  | 1088.116 | 1232.469 | 356.2217 | 1437.602 |
|  | 918.4382 | 1483.187 | 406.8718 | 1189.416 |
|  | 1108.376 |  | 267.5839 |  |

Example 5: Therapeutic Treatment with Amino Acid Composition A-1 Improves Oral Glucose Tolerance in a Pre-Clinical Animal Model Amino Acid Composition A-1 and metformin were tested for their ability to affect glucose tolerance in a genetically obese B6.Cg-Lep$^{ob}$/J (ob/ob) mouse model (Maida A, et al., 2010, PMID: 20972533).

Model Description

B6.Cg-Lep$^{ob}$/J (ob/ob) mice harbor a spontaneous mutation of leptin (Lep) gene. ob/ob mice exhibit hyperphagia, obesity, and metabolic syndrome/T2DM-like symptoms, e.g. hyperglycemia, hyperinsulinemia, and insulin resistance. ob/ob mice have impaired intestinal barrier function, gut microbial translocation, and an inflammatory, fibrogenic phenotype of hepatic stellate cells (Brun P et al., 2004, PMID: 17023554). ob/ob mice develop skeletal muscle hypoplasia in quadriceps femoris, similar to the effect of aging in humans (Hamrick M W et al., 2004, PMID: 15003785). ob/ob mice exhibit intolerance to glucose and insulin. Metformin lowers plasma glucose (Cool B, et al., Cell Metab 2006, PMID: 16753576), liver triglyceride, and reverses NAFLD in ob/ob mice (Lin H Z et al., 2000, PMID: 10973319; Cool B, et al., Cell Metab 2006, PMID: 16753576). A single dose of metformin treatment reduces blood glucose and improves glucose tolerance (OGTT) in C57/BL6.

Experimental Design

Eight-week-old male ob/ob mice were subjected to treatment of test articles (Amino Acid Composition A-1 and metformin) followed by oral glucose tolerance test (OGTT) on Day 3. Mice were randomized by body weight and unfasted blood glucose on Day −1. Body weight was recorded daily in the morning before AM dosing on Day 1, Day 2, and Day 3. Test articles were dosed by oral gavage at 10 ml/kg. Dosage of a test article was calculated based on daily body weight. Treatment schedule and dose are listed in the following section (Table 34). AM doses were administered at 0700, and PM doses were administered at 1800. Oral glucose tolerance test (OGTT) was performed after 6-hour fasting on Day 3.

TABLE 34

Treatment schedule

| Group | Test article | # | Dosing Schedule |
|---|---|---|---|
| Group 1 | Vehicle | N = 5 | Vehicle dosed on Day 1 and Day 2 at 0700 and 1800, and Day 3 at 0700 and 30 min before OGTT for a total of 6 doses. |
| Group 2 | Metformin | N = 5 | Metformin hydrochloride (450 mg/kg, QD PO at the beginning of dark cycle) dosed on Day −1, Day 1, and Day 2 at 1800, and at 30 min before OGTT on Day 3 for a total of 4 doses. |
| Group 3 | Amino Acid Composition A-1 | N = 5 | Amino Acid Composition A-1 (1500 mg/kg, BID PO at 0700 and 1800) dosed on Day 1 and Day 2 at 0700 and 1800, and Day 3 at 0700 and 30 min before OGTT for a total of 6 doses. |
| Group 4 | Amino Acid Composition A-1 | N = 5 | Amino Acid Composition A-1 (3000 mg/kg, BID PO at 0700 and 1800) dosed on Day 1 and Day 2 at 0700 and 1800, and Day 3 at 0700 and 30 min before OGTT for a total of 6 doses. |

Baseline Glucose and Biochemistry (Insulin, Triglyceride and Cholesterol)

Mice were fasted for 6 hours prior to OGTT test. Food was removed at 0700 hours on Day 3; water was provided during fasting. Blood samples were collected from tail snip or facial puncture at −30 min (relative to OGTT) into $K_2$EDTA tubes for baseline glucose and blood biochemistry (insulin, triglyceride, and cholesterol). Blood glucose was measured by a glucometer (SDI StatStrip Xpress or equivalent). Plasma was collected in $K_2$EDTA and saved at −80° C.

Oral Glucose Tolerance Test (OGTT)

Mice were bled for baseline glucose and plasma at −30 min. Test articles were then dosed by oral gavage at −30 min. Glucose was administered per os (P.O.) at a dosage of 2.0 g/kg body weight. Blood glucose levels were measured at 0 min immediately prior to glucose injection and then at 15, 30, 60, 120 and 240 minutes thereafter (shown as 0.25, 0.5, 1, 2, and 4 hours in Table 35 below).

Results are shown in Table 35. Data are mean±standard deviation (stdev). (p values by Dunnett's multiple comparisons: p<0.005 compared to vehicle control; *p<0.001 compared to vehicle control; ****p<0.0005 compared to vehicle control.)

Results

SUMMARY

Treatment with Amino Acid Composition A-1 resulted in improvement of oral glucose tolerance, as indicated by improved blood glucose clearance upon oral glucose loading. In addition, 3-day treatment with Amino Acid Composition A-1 did not alter baseline blood glucose in ob/ob mice (Table 36).

TABLE 36

OGTT results: Blood glucose levels (mg/dl) raw data

| Timepoint (hours) | | | | | |
|---|---|---|---|---|---|
| | Vehicle | | | | |
| −1 | 211 | 141 | 211 | 219 | 427 |
| 0 | 239 | 256 | 273 | 284 | 361 |
| 0.25 | 741 | 676 | 514 | 578 | 766 |
| 0.5 | 551 | 621 | 604 | 630 | 797 |
| 1 | 305 | 317 | 327 | 369 | 572 |
| 2 | 182 | 243 | 230 | 203 | 325 |
| 4 | 146 | 203 | 167 | 188 | 285 |
| | Amino Acid Comp A-1, 1500 mg/kg | | | | |
| −1 | 224 | 220 | 190 | 191 | 403 |
| 0 | 331 | 548 | 347 | 316 | 331 |
| 0.25 | 526 | 702 | 580 | 531 | 539 |
| 0.5 | 532 | 419 | 621 | 587 | 617 |
| 1 | 431 | 365 | 367 | 395 | 375 |

TABLE 35

OGTT results: Mean Blood glucose levels (mg/dl) and standard deviations (stdev)

| Timepoint (hours) | Vehicle | | Amino Acid Comp A-1, 1500 mg/kg | | Amino Acid Comp A-1, 3000 mg/kg | | Metformin | |
|---|---|---|---|---|---|---|---|---|
| | mean blood glucose level (mg/dl) | stdev | mean blood glucose level (mg/dl) | stdev | mean blood glucose level (mg/dl) | stdev | mean blood glucose level (mg/dl) | stdev |
| −1 | 241.8 | 108.3 | 245.6 | 89.4 | 229.6 | 78.2 | 196.4 | 59.8 |
| 0 | 282.6 | 47.0 | 374.6 | 97.6 | 303.0 | 77.1 | 199.4 | 62.6 |
| 0.25 | 655.0 | 107.2 | 575.6 | 73.8 | 456.2** | 36.6 | 353.6**** | 73.6 |
| 0.5 | 640.6 | 92.6 | 555.2 | 84.0 | 513.0 | 47.9 | 390.2*** | 99.5 |
| 1 | 378.0 | 111.1 | 386.6 | 27.5 | 316.4 | 86.1 | 317.6 | 116.9 |
| 2 | 236.6 | 54.8 | 243.5 | 18.4 | 230.0 | 101.1 | 158.2 | 44.0 |
| 4 | 197.8 | 53.3 | 214.8 | 56.8 | 179.8 | 81.3 | 109.4 | 29.0 |

TABLE 36-continued

OGTT results: Blood glucose levels (mg/dl) raw data

| Timepoint (hours) | | | | | |
|---|---|---|---|---|---|
| 2 | 246 | | 243 | 220 | 265 |
| 4 | 192 | | 193 | 175 | 299 |
| Amino Acid Comp A-1, 3000 mg/kg | | | | | |
| −1 | 137 | 294 | 179 | 214 | 324 |
| 0 | 242 | 359 | 203 | 329 | 382 |
| 0.25 | 412 | 490 | 438 | 443 | 498 |
| 0.5 | 513 | 482 | 467 | 512 | 591 |
| 1 | 240 | 351 | 220 | 342 | 429 |
| 2 | 161 | 334 | 148 | 160 | 347 |
| 4 | 120 | 235 | 110 | 139 | 295 |
| Metformin | | | | | |
| −1 | 265 | 248 | 183 | 120 | 166 |
| 0 | 274 | 234 | 220 | 129 | 140 |
| 0.25 | 387 | 397 | 427 | 310 | 247 |
| 0.5 | 462 | 439 | 482 | 307 | 261 |
| 1 | 365 | 399 | 431 | 239 | 154 |
| 2 | 154 | 183 | 219 | 124 | 111 |
| 4 | 118 | 93 | 155 | 101 | 80 |

Example 6: Therapeutic Treatment of NAFLD, NASH, and HCC with Amino Acid Composition A-1 in a Pre-Clinical Animal Model Amino Acid Composition A-1 and Obeticholic acid (6α-ethyl-chenodeoxycholic acid; "OCA") were tested for their ability to treat NASH in the STAM™ model (Stelic Institute & Co., Tokyo, Japan; Saito K. et al., 2015 Sci Rep 5:12466). Two additional groups of normal C57BL/6 mice fed standard chow and vehicle treated STAM™ mice were included as controls. All animals receiving treatment or vehicle were treated starting at 6 weeks until 9 weeks of age. Compounds were administered via oral gavage, with a dose volume of 10 ml/kg. Amino Acid Composition A-1 was administered twice daily at a dose of 1500 mg/kg, and OCA was administered once daily at a dose of 30 mg/kg.

STAM™ Mouse Model Description

STAM™ is a model for non-alcoholic steatohepatitis (NASH) and hepatocellular carcinoma (HCC), developed by SMC Laboratories, Inc. and created by the combination of chemical and dietary interventions using C57BL/6 mice (Saito K. et al., 2015 Sci Rep 5:12466). Mice are treated with a low dose of streptozotocin at birth and fed a high fat diet starting at 4 weeks. Evidence of fatty liver is present by 5 weeks, followed by NASH by 7 weeks and fibrosis by 9 weeks.

Induction of NASH

NASH was induced in 53 male mice by a single subcutaneous injection of 200m streptozotocin (STZ, Sigma-Aldrich, USA) solution 2 days after birth and feeding with high fat diet (HFD, 57 kcal % fat, Cat #HFD32, CLEA Japan, Japan) after 4 weeks of age.

Route of Drug Administration, Preparation of Dosing Solutions and Treatment Doses Amino Acid Composition A-1, OCA and Vehicle (described below) were administered by oral route in a volume of 10 mL/kg. Amino Acid Composition A-1 was solubilized in deionized water to 150 mg/ml (10×). OCA (Advanced ChemBlocks Inc.) was resuspended in 0.5% methylcellulose in water to 3 mg/ml (10×). Amino Acid Composition A-1 was administered at a dose of 1500 mg/kg twice daily (9 am and 7 pm). OCA was administered at a dose of 30 mg/kg once daily (9 am).

Histological Analyses

Liver samples from mice in Group 2 (Vehicle), 3 (Amino Acid Composition A-1) and 4 (OCA) were used for the following assays. For HE staining, sections were cut from paraffin blocks of liver tissue prefixed in Bouin's solution and stained with Lillie-Mayer's Hematoxylin (Muto Pure Chemicals Co., Ltd., Japan) and eosin solution (Wako Pure Chemical Industries). NAFLD Activity score (NAS) was calculated according to the criteria of Kleiner (Kleiner D. E. et al., Hepatology, 2005; 41:1313).

Experimental Design

Study Groups

Group 1: STZ: Ten neonatal STZ-primed mice were fed with a normal diet ad libitum without any treatment until 9 weeks of age.

Group 2: Vehicle: Ten NASH mice were orally administered vehicle (10% phosphate buffered saline, pH 7.2) in a volume of 10 mL/kg twice daily (9 am and 7 pm) from 6 to 9 weeks of age.

Group 3: Amino Acid Composition A-1: Ten NASH mice were orally administered water for irrigation supplemented with Amino Acid Composition A-1 at a dose of 1500 mg/kg twice daily (9 am and 7 pm) from 6 to 9 weeks of age.

Group 4: OCA: Ten NASH mice were orally administered 0.5% methylcellulose supplemented with OCA at a dose of 30 mg/kg once daily (9 am) from 6 to 9 weeks of age.

Group 5: Normal: Ten normal mice were fed with a normal diet ad libitum without any treatment until 9 weeks of age.

Group 6: HFD: Ten normal mice were fed with a high fat diet ad libitum without any treatment until 9 weeks of age.

Histological Analysis Results: HE Staining, NAFLD Activity Score and α-Smooth Muscle Actin Staining Non-Alcoholic Fatty Liver Disease Activity Score Results The non-alcoholic fatty liver disease (NAFLD) activity score was assessed via histological analysis and grading of H&E stained liver sections from each animal. This score is the sum of three individual scores that grade the degree of steatosis (0-3), inflammation (0-2), and hepatocyte ballooning (0-2). All tissues were graded using the scoring criteria of Kleiner et al. (Kleiner et al. Hepatology. 2005; 41(6): 1313-21). Results are shown in Table 37. Data are mean±standard deviation (stdev). Normal C57BL/6 mice fed standard chow had a mean score of 0+/−0. Vehicle treated STAM™ mice had a mean score of 4.7+/−0.67. Amino Acid Composition A-1 treated mice had a mean score of 3.1+/−0.74. OCA treated mice had a mean score of 2.9+/−0.74. Both Amino Acid Composition A-1 and OCA were statistically different from vehicle for NAFLD Activity Score when compared using Dunnett's multiple comparisons test (Amino Acid Composition A-1 p=0.0001, OCA p=0.0001).

Similarly, Amino Acid Composition A-1 treated mice showed a mean ballooning score of 0.4+/−0.52, compared to a mean ballooning score for vehicle treated STAM™ mice of 1.6+/−0.52, and a mean ballooning score for OCA treated mice of 0.3+/−0.48. Both Amino Acid Composition A-1 and OCA were statistically different from vehicle for ballooning score when compared using Dunnett's multiple comparisons test (Amino Acid Composition A-1 p=0.0001, OCA p=0.0001). Raw data are shown in Tables 37-40.

TABLE 37

NAFLD Activity Score
NAFLD Activity Score (NAS)

| Condition | Normal C57BL/6 mice | Vehicle-treated STAM mice | Amino Acid Composition A-1 treated STAM mice | OCA treated STAM mice |
|---|---|---|---|---|
| Mean | 0 | 4.7 | 3.1 | 2.9 |
| stdev | 0 | 0.67 | 0.74 | 0.74 |

TABLE 38

NAFLD Activity: Steatosis Score

Steatosis

| | Normal C57BL/6 mice | Vehicle-treated STAM mice | Amino Acid Composition A-1 treated STAM mice | OCA treated STAM mice |
|---|---|---|---|---|
| Mean | 0 | 1 | 0.9 | 0.8 |
| stdev | 0 | 0.00 | 0.32 | 0.42 |

TABLE 39

NAFLD Activity: Inflammation Score

Inflammation

| | Normal C57BL/6 mice | Vehicle-treated STAM mice | Amino Acid Composition A-1 treated STAM mice | OCA treated STAM mice |
|---|---|---|---|---|
| Mean | 0 | 2.1 | 1.8 | 1.8 |
| stdev | 0 | 0.32 | 0.63 | 0.79 |

TABLE 40

NAFLD Activity: Ballooning Score

Ballooning

| | Normal C57BL/6 mice | Vehicle-treated STAM mice | Amino Acid Composition A-1 treated STAM mice | OCA treated STAM mice |
|---|---|---|---|---|
| Mean | 0 | 1.6 | 0.4 | 0.3 |
| stdev | 0 | 0.52 | 0.52 | 0.48 |

Fibrosis: Sirius Red Staining Results

Fibrosis was assessed by analysis of Sirius red positively stained cell area from stained liver sections from each animal. Images were quantified using the percent of positively stained area was used as a measure of fibrosis. Results of this analysis are shown in Table 39. Data are mean±standard deviation (stdev). Normal C57BL/6 mice fed standard chow had a mean positive area of 0.286+/−0.09. Vehicle treated STAM™ mice had a mean positive area of 1.1+/−0.26. Amino Acid Composition A-1 treated mice had a mean positive area of 0.828+/−0.33. OCA treated mice had a mean score of 0.776+/−0.25. Amino Acid Composition A-1 and OCA were statistically different from vehicle when compared using Dunnett's multiple comparisons test (Amino Acid Composition A-1 p=0.00494, OCA p<0.016). Raw data are shown in Table 41.

TABLE 41

Fibrosis (mean positively stained area, Sirius red)

| Condition | Normal C57BL/6 mice | Vehicle-treated STAM mice | Amino Acid Composition A-1 treated STAM mice | OCA treated STAM mice |
|---|---|---|---|---|
| Mean | 0.286 | 1.1 | 0.828 | 0.776 |
| stdev | 0.09 | 0.26 | 0.33 | 0.25 |

Figure 1B:
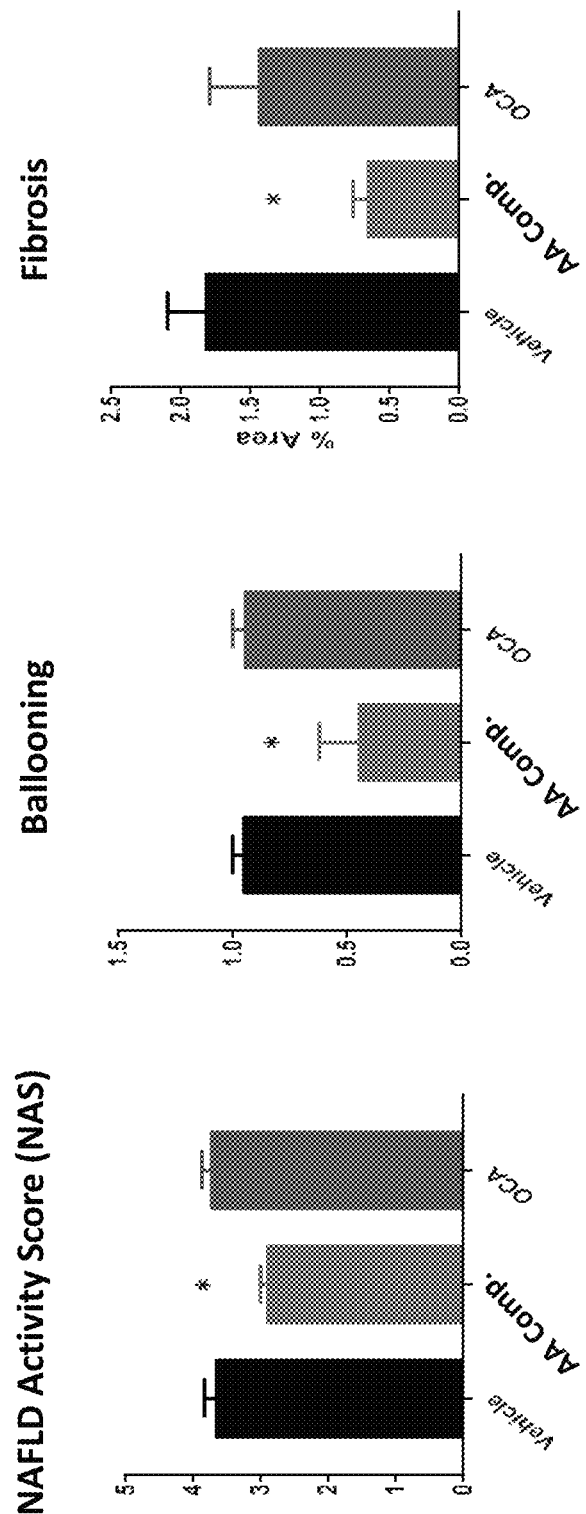

Similarly to the statistically significant improvement in the NAFLD activity score, ballooning, and fibrosis in the STAM mouse model after treatment with Amino Acid Composition A-1 (FIG. 1A), a statistically significant improvement in the NAFLD activity score, ballooning, and fibrosis was determined in the high-fat, high fructose and cholesterol diet (HFFC) mouse model after treatment with Amino Acid Composition A-1 (FIG. 1B).

α-Smooth Muscle Actin (α-SMA) Staining Results

Liver sections of all mice were stained for the marker α-smooth muscle actin (αSMA) to identify activated hepatic stellate cells. Images were quantified using the percent of positively stained area was used as a measure of stellate cell activation. Results are shown in Table 42. Data are mean±standard deviation (stdev); p values are compared to vehicle-treated STAM mice control; by one-tailed T test.

Normal C57BL/6 mice fed standard chow had a mean positive area of 0.682+/−0.26. Vehicle treated STAM™ mice had a mean positive area of 2.128+/−0.50. Amino Acid Composition A-1 treated mice had a mean positive area of 1.657+/−0.84. OCA treated mice had a mean score of 1.562+/−0.31.

TABLE 42

Activated hepatic stellate cells (mean positively stained area, α-smooth muscle actin)

| Condition | Normal C57BL/6 mice | Vehicle-treated STAM mice | Amino Acid Composition A-1 treated STAM mice | OCA treated STAM mice |
|---|---|---|---|---|
| Mean | 0.682 | 2.128 | 1.657 | 1.562 |
| stdev | 0.26 | 0.50 | 0.84 | 0.31 |
| | | | $p = 0.073$ | $p < 0.05$ |

SUMMARY

Treatment with Amino Acid Composition A-1 significantly reduced NASH severity to levels equivalent to Farnesoid X Receptor (FXR) inhibition by OCA (which is currently under clinical investigation by Intercept Pharmaceuticals, Inc. for treatment of NASH), as indicated by significant reduction in NAFLD Activity Score (NAS) (mean NAS: 3.1+/−0.74 for Amino Acid Composition A-1 vs. vehicle treated STAM™ mice mean score of 4.7+/−0.67, compared to OCA treated mice mean score of 2.9+/−0.74), and development of fibrosis as indicated by the downregulation of hepatic stellate cell activation (mean αSMA positively stained area: 1.657+/−0.84 for Amino Acid Composition A-1 vs. vehicle treated STAM™ mice mean area of 2.128+/−0.50, compared to OCA treated mice mean area of 1.562+/−0.31).

TABLE 43

NAFLD Activity Score: raw data

| Normal C57BL/6 mice | Vehicle-treated STAM mice | Amino Acid Composition A-1 treated STAM mice | OCA treated STAM mice |
|---|---|---|---|
| 0 | 6 | 3 | 4 |
| 0 | 5 | 4 | 2 |
| 0 | 5 | 4 | 2 |
| 0 | 4 | 3 | 4 |
| 0 | 5 | 2 | 3 |
| 0 | 5 | 2 | 3 |
| 0 | 4 | 3 | 2 |
| 0 | 4 | 3 | 3 |
| 0 | 4 | 3 | 3 |
| 0 | 5 | 4 | 3 |

TABLE 44

NAFLD Activity: Steatosis Score: raw data
Steatosis

| Normal C57BL/6 mice | Vehicle-treated STAM mice | Amino Acid Composition A-1 treated STAM mice | OCA treated STAM mice |
|---|---|---|---|
| 0 | 1 | 1 | 1 |
| 0 | 1 | 1 | 1 |
| 0 | 1 | 1 | 1 |
| 0 | 1 | 0 | 1 |
| 0 | 1 | 1 | 0 |
| 0 | 1 | 1 | 1 |
| 0 | 1 | 1 | 0 |
| 0 | 1 | 1 | 1 |
| 0 | 1 | 1 | 1 |

TABLE 45

NAFLD Activity: Inflammation Score: raw data
Inflammation

| Normal C57BL/6 mice | Vehicle-treated STAM mice | Amino Acid Composition A-1 treated STAM mice | OCA treated STAM mice |
|---|---|---|---|
| 0 | 3 | 1 | 2 |
| 0 | 2 | 2 | 1 |
| 0 | 2 | 2 | 1 |
| 0 | 2 | 2 | 2 |
| 0 | 2 | 1 | 2 |
| 0 | 2 | 1 | 3 |
| 0 | 2 | 2 | 1 |
| 0 | 2 | 2 | 3 |
| 0 | 2 | 2 | 2 |
| 0 | 2 | 3 | 1 |

TABLE 46

NAFLD Activity: Ballooning Score: raw data
Ballooning

| Normal C57BL/6 mice | Vehicle-treated STAM mice | Amino Acid Composition A-1 treated STAM mice | OCA treated STAM mice |
|---|---|---|---|
| 0 | 2 | 1 | 1 |
| 0 | 2 | 1 | 0 |
| 0 | 2 | 1 | 0 |
| 0 | 1 | 0 | 1 |
| 0 | 2 | 1 | 0 |
| 0 | 2 | 0 | 0 |
| 0 | 1 | 0 | 0 |
| 0 | 1 | 0 | 0 |
| 0 | 1 | 0 | 0 |
| 0 | 2 | 0 | 1 |

TABLE 47

Fibrosis (mean positively stained area, Sirius red): raw data

| Normal C57BL/6 mice | Vehicle-treated STAM mice | Amino Acid Composition A-1 treated STAM mice | OCA treated STAM mice |
|---|---|---|---|
| 0.26 | 0.79 | 1.07 | 0.36 |
| 0.35 | 1.43 | 0.58 | 0.56 |
| 0.19 | 1.44 | 0.48 | 1.1 |
| 0.31 | 1.36 | 0.58 | 1.19 |
| 0.19 | 1.04 | 1.07 | 0.89 |
| 0.36 | 0.75 | 0.34 | 0.91 |
| 0.24 | 1.07 | 0.86 | 0.66 |
| 0.37 | 1.13 | 1.43 | 0.72 |
| 0.18 | 0.83 | 0.96 | 0.68 |
| 0.41 | 1.16 | 0.91 | 0.69 |

TABLE 48

Activated hepatic stellate cells (mean positively stained area, α-smooth muscle actin): raw data

| Normal C57BL/6 mice | Vehicle-treated STAM mice | Amino Acid Composition A-1 treated STAM mice | OCA treated STAM mice |
|---|---|---|---|
| 0.47 | 2.16 | 0.81 | 1.46 |
| 0.59 | 2.77 | 1.35 | 1.51 |
| 1.13 | 2.21 | 1.3 | 1.49 |
| 0.52 | 1.5 | 3.03 | 1.17 |
| 0.75 | 2.87 | 2.04 | 1.49 |
| 0.46 | 1.93 | 0.97 | 1.5 |
| 0.37 | 1.6 | 3.08 | 1.13 |
| 0.85 | 1.46 | 1.91 | 2.03 |
| 0.62 | 2.36 | 1.15 | 1.87 |
| 1.06 | 2.42 | 0.93 | 1.97 |

Example 7: Reduction of Fibrogenic Gene Expression in Hepatic Stellate Cells Treated with an Amino Acid Composition Hepatic stellate cells in a healthy liver are in the space of Disse, between the hepatocytes and liver sinusoidal endothelial cells. In response to liver injury hepatic stellate cells become activated, proliferative and contractile, increase production of αSMA, secretion of type I and III collagens and specific MMP and TIMP proteins. LX-2 cells were selected as a model of activated hepatic stellate cells and used to test whether specific amino acid compositions would reduce fibrogenic gene expression induced with TGFβ1.

LX-2 hepatic stellate cells (Millipore) were seeded on day 0 at 1.67E4 cells per well in collagen I coated 96-well microplates (ThermoFisher) in Dulbecco's Modified Eagle Medium (DMEM, Corning) supplemented with 2% heat inactivated fetal bovine serum (HI-FBS, HyClone) and 0.2% Primocin (InVivoGen) and incubated overnight at 37° C., 5% CO2. On day 1, cells were washed twice with 150 μL per well DPBS (Gibco) and replaced with amino acid free DMEM (US Biologicals) containing a defined custom amino acid concentration based on the mean physiological concentrations in blood based on values published in the Human Metabolome Database (1,2,3), with 25 mM Glucose, 1 mM Sodium Pyruvate and a dose curve of defined amino acid compositions LIVRQ+N-Acetylcysteine, LIVRQ, RQ+N-Acetylcysteine, N-acetylcysteine, LIV at 40× the concentration present in the basal HMDB (Human Metabolome Database (Wishart D S, Tzur D, Knox C, et al., HMDB: the Human Metabolome Database. Nucleic Acids Res. 2007 January; 35(Database issue):D521-6. 17202168)) derived amino acid concentrations or individually with leucine, isoleucine, valine, arginine, glutamine or cysteine at 50× the HMDB derived concentrations. Combinations containing N-acetylcysteine were dosed with 10 mM. Cells were pretreated for 6 hours at 37° C., 5% CO2. After pretreatment, TGFβ1 (R&D Systems) or vehicle was spiked into each well for a final concentration of 5 ng/mL and cells were incubated under this stimulus for a further 12 hours at 37° C., 5% CO2.

After 12 hour incubation, RNA was prepared as described using the FastLane Cell Multiplex Kit (Qiagen) as described in the manufacturers protocol. Two microliters of cell lysate was utilized in subsequent qRT-PCR experiments using the FastLane Cell Multiplex Kit at a reduced final qPCR reaction volume of 20 µL. Quantitative PCR was conducted on lysates to determine collagen-1a1 expression normalized to β-actin housekeeping expression using the ΔΔCt method using TaqMan primer probes (Integrated DNA Technologies: Col1A1, Hs.PT.58.15517795; Actb, Hs.PT.39a.22214847; Acta2, Hs.PT.56a.24853961; Timp2, Hs.PT.58.14780594).

Results:

Table 49 shows the Col1a1, Acta2, and Timp2 gene expression in LX-2 cells treated with amino acid combinations compared to vehicle with or without TGFβ1 stimulus. LIVRQ+N-Acetylcysteine, LIVRQ, RQ+N-Acetylcysteine, and N-acetylcysteine reduced Col1a1 expression and Timp2 expression. LIVRQ+N-acetylcysteine shows the largest reduction of Col1a1, Acta2, and Timp2 gene expression. LIVRQ-N-acetylcysteine reduces Acta2 expression significantly greater than N-Acetylcysteine alone, RQ+N-acetylcysteine, and LIV. LIVRQ+N-acetylcysteine reduces Timp2 expression significantly greater than any of the other combinations (Table 49).

TABLE 49

| | | Col1a1 | | | Acta2 | | | Timp2 | | |
|---|---|---|---|---|---|---|---|---|---|---|
| TGFβ1 | Amino Acid Supplement | Mean | Std. Deviation | Number of values | Mean | Std. Deviation | Number of values | Mean | Std. Deviation | Number of values |
| Yes | Vehicle | 2.861 | 0.3151 | 4 | 0.801 | 0.1149 | 4 | 1.658 | 0.2791 | 4 |
| No | Vehicle | 1.042 | 0.3102 | 4 | 1.006 | 0.1190 | 4 | 1.022 | 0.2400 | 4 |
| Yes | LIVRQNAC | 1.267 | 0.4106 | 4 | 0.292 | 0.0969 | 4 | 0.535 | 0.0306 | 4 |
| Yes | LIVRQ | 1.787 | 0.2926 | 4 | 0.267 | 0.0637 | 4 | 0.975 | 0.2006 | 4 |
| Yes | RQNAC | 1.664 | 0.3320 | 4 | 0.487 | 0.1042 | 4 | 0.897 | 0.1932 | 4 |
| Yes | NAC | 1.659 | 0.4695 | 4 | 0.647 | 0.1097 | 4 | 1.076 | 0.0681 | 4 |
| Yes | LIV | 2.831 | 0.3404 | 3 | 0.793 | 0.0812 | 4 | 1.927 | 0.0944 | 4 |

TABLE 50

| | | Col1a1 | | |
|---|---|---|---|---|
| TGFβ1 | Amino Acid Supplement | Mean | Std. Deviation | Number of values |
| No | Vehicle | 1.015 | 0.1832 | 8 |
| Yes | 1X CYS | 2.491 | 0.1588 | 4 |
| Yes | 50X CYS | 1.695 | 0.3310 | 4 |
| Yes | 1X ILE | 2.020 | 0.1451 | 4 |
| Yes | 50X ILE | 2.028 | 0.3667 | 4 |
| Yes | 1X LEU | 1.901 | 0.3360 | 4 |
| Yes | 50X LEU | 2.372 | 0.4153 | 4 |
| Yes | 1X VAL | 2.093 | 0.2157 | 4 |
| Yes | 50X VAL | 2.203 | 0.5762 | 4 |
| No | Vehicle | 1.010 | 0.1510 | 8 |
| Yes | 1X ARG | 1.620 | 0.6691 | 4 |
| Yes | 50X ARG | 1.970 | 0.7740 | 4 |
| No | Vehicle | 1.012 | 0.1681 | 8 |
| Yes | 1X GLN | 2.340 | 0.7069 | 4 |
| Yes | 50X GLN | 2.194 | 0.3359 | 4 |

Example 8: Reduction in Hepatocyte Inflammation after Treatment with an Amino Acid Composition The ability of amino acids to influence hepatocyte inflammation was assessed using HepG2 Hepatocellular Carcinoma cells stably expressing NF-kB luciferase reporter system (Signosis, Inc.). HepG2 cells were seeded on day 0 in 4.5e4 in a 96-well microplates (ThermoFisher) in Dulbecco's Modified Eagle Medium (DMEM, Corning) supplemented with 0.1% heat inactivated fetal bovine serum (HI-FBS, HyClone) and 0.2% Primocin (InVivoGen) and incubated overnight at 37° C., 5% CO2. On day 1, cells were washed once with 150 µL per well DPBS (Gibco) and replaced with amino acid free DMEM (US Biologicals) containing a defined custom amino acid concentration based on the mean physiological concentrations in blood based on values published in the Human Metabolome Database (Wishart D S, Tzur D, Knox C, et al., HMDB: the Human Metabolome Database. Nucleic Acids Res. 2007 January; 35(Database issue):D521-6. 17202168), with 25 mM Glucose, 1 mM Sodium Pyruvate and a dose curve of defined amino acid compositions (i.e. vehicle, LIVRQ+N-acetylcysteine, LIVRQ, RQ+N-acetylcysteine, N-acetylcysteine alone, LIV or individually with Leucine, Isoleucine, Valine, Arginine, Glutamine, and Cysteine) at 50× (Table 51). Cells were pretreated in the defined media for 12 hours at 37° C., 5% CO2. After pretreatment, TNFα (R&DSystems) or vehicle was spiked into each well for a final concentration of 100 pM and cells were incubated under this stimulus for an additional 6 hours at 37° C., 5% CO2. After 12-hour Table 50 shows the Col1a1 expression of individual amino acids with or without TGFβ1 stimulus at 1× or 50× the HMDB derived amino acid concentration. Individually, only cysteine showed a significant decrease in Col1a1 expression at 50×.

incubation, cells were washed 1× in 150 ul cold PBS and lysed using Passive Lysis Buffer and luciferase assay was performed according to manufacturer's protocol (Signosis). Firefly luciferase activity was assessed using a Bio-Tek SynergyH4 plater reader and luminometer (Sitcheran R*, Comb W C, Cogswell P C, Baldwin A S*. Essential role for epidermal growth factor receptor in glutamate receptor signaling to NF-kappaB. *Mol Cell Biol.* (2008) August; 28(16):5061-70. Epub 2008 Jun. 9).

TNFα-stimulated NF-kB activity was unaffected by treating cells in 50× Leucine, Isoleucine, Valine, Arginine, and Glutamine, relative to the 1× Plasma amino acid baseline media. Pretreating cells in 50× Cysteine did result in a significant blunting of TNFα-induced NF-kB activity. Combinatorial treatments with the single amino acids did have varying effects on the NF-kB reporter activity, but importantly, the combination of all 6 amino acids together (LIVRQNAC) resulted in the most significant inhibition of TNFα induced NF-kB activity in liver cells (Table 51).

TABLE 51

| TNFα | Amino Acid Supplement | NF-kB Reporter Activity | | |
|---|---|---|---|---|
| | | Mean | Std. Deviation | Number of values |
| 100 pM | Vehicle (1× AA) | 8865.50 | 333.05 | 2 |
| 100 pM | LIVRQNAC | 3960.50 | 678.12 | 2 |
| 100 pM | LIVRQ | 5685.00 | 1453.81 | 2 |
| 100 pM | RQNAC | 5618.00 | 926.31 | 2 |
| 100 pM | NAC | 6852.00 | 1023.89 | 2 |
| 100 pM | LIV | 5911.00 | 422.85 | 2 |
| 100 pM | 1× L | 5811.00 | 134.35 | 2 |
| 100 pM | 50× L | 6070.50 | 58.69 | 2 |
| 100 pM | 1× I | 8129.50 | 713.47 | 2 |
| 100 pM | 50× I | 8937.50 | 17.68 | 2 |
| 100 pM | 1× V | 7255.50 | 557.91 | 2 |
| 100 pM | 50× V | 5992.00 | 644.88 | 2 |
| 100 pM | 1× R | 10170.50 | 140.71 | 2 |
| 100 pM | 50× R | 9760.00 | 1083.29 | 2 |
| 100 pM | 1× Glu | 8201.00 | 2091.62 | 2 |
| 100 pM | 50× Glu | 7313.50 | 1054.30 | 2 |
| 100 pM | 1× Cys | 9968.50 | 1614.33 | 2 |
| 100 pM | 50× Cys | 6820.50 | 23.34 | 2 |

Figure 2:
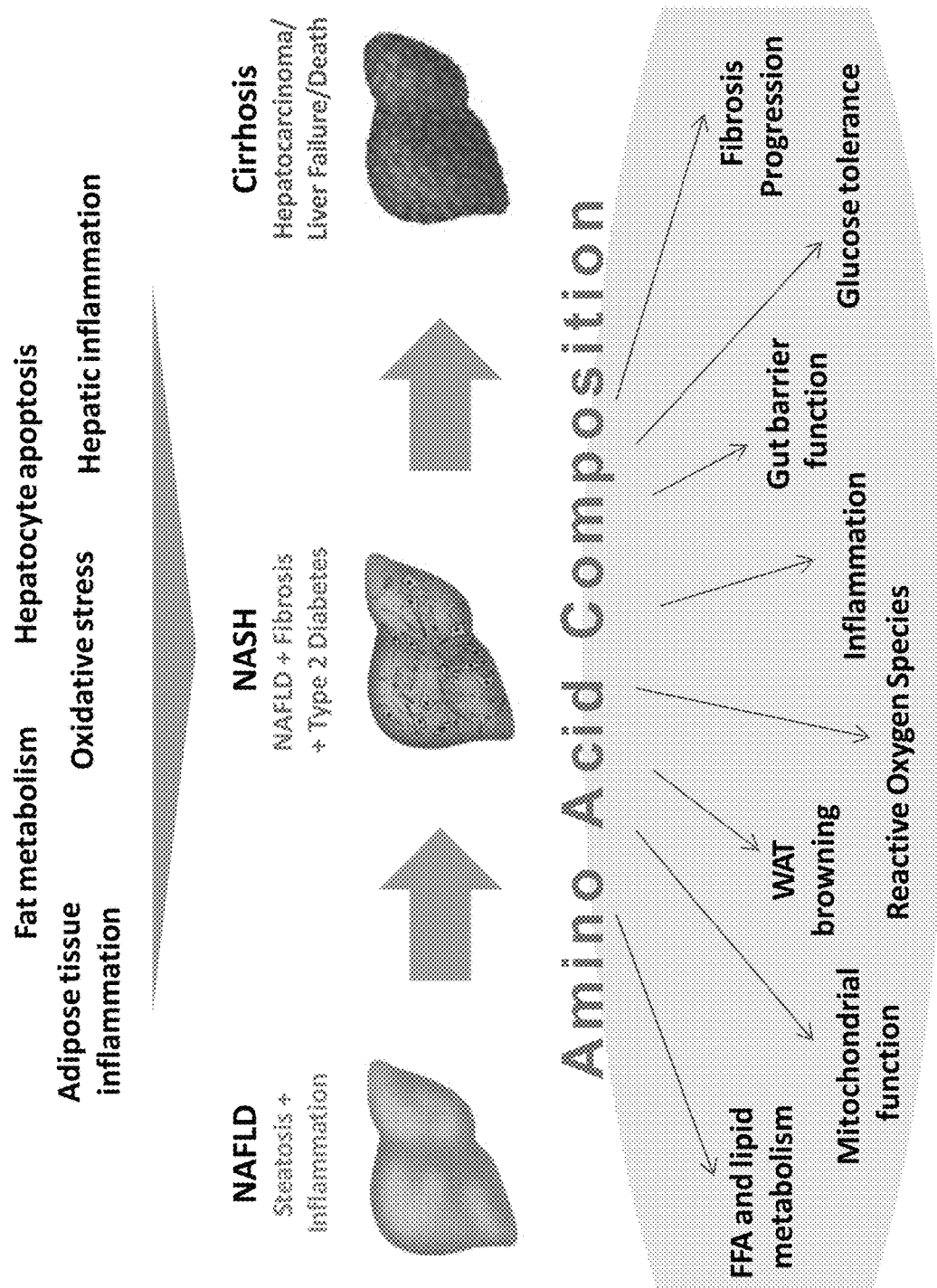
FIG. 2 is a schematic showing the metabolic symptoms of patients with non-alcoholic fatty liver disease (NAFLD), non-alcoholic steatohepatitis (NASH), and cirrhosis prior to administration of a composition comprising amino acid entities described herein (top) and the improvement in patients with NAFLD, NASH, and cirrhosis after administration of the composition (bottom).

Example 9: Treatment with an Amino Acid Composition Ameliorates NASH Progression in Two Rodent Models by Impacting Lipid Metabolism, Inflammation, and Fibrosis The amino acid composition is formulated to simultaneously target multiple mechanisms of disease pathology to safely and effectively treat NASH (Table 52). As described herein, the efficacy of the amino acid composition was studied in two established mouse models of NASH to determine the effect of the amino acid composition on signs and symptoms associated with NASH and related disorders (FIG. 2).

TABLE 52

Exemplary amino acid components of the amino acid composition.

| Amino acid | wt. ratio | wt. % | g/packet | g dose #1 | g dose #2 |
|---|---|---|---|---|---|
| Leucine | 1 | 16.78 | 1.00 g | 2 g | 4 g |
| Isoleucine | 0.5 | 8.39 | 0.50 g | 1 g | 2 g |
| Valine | 0.5 | 8.39 | 0.50 g | 1 g | 2 g |
| Arginine HCl | 1.81 | 30.37 | 1.81 g | 3.62 g | 7.24 g |
| Glutamine | 2 | 33.56 | 2.00 g | 4 g | 8 g |
| N-acetylcysteine | 0.15 | 2.52 | 0.15 g | 0.3 g | 0.6 g |
| Total amino acids | | | 5.96 g | ~12 g | ~24 g |

Animal Studies

Figure 3:
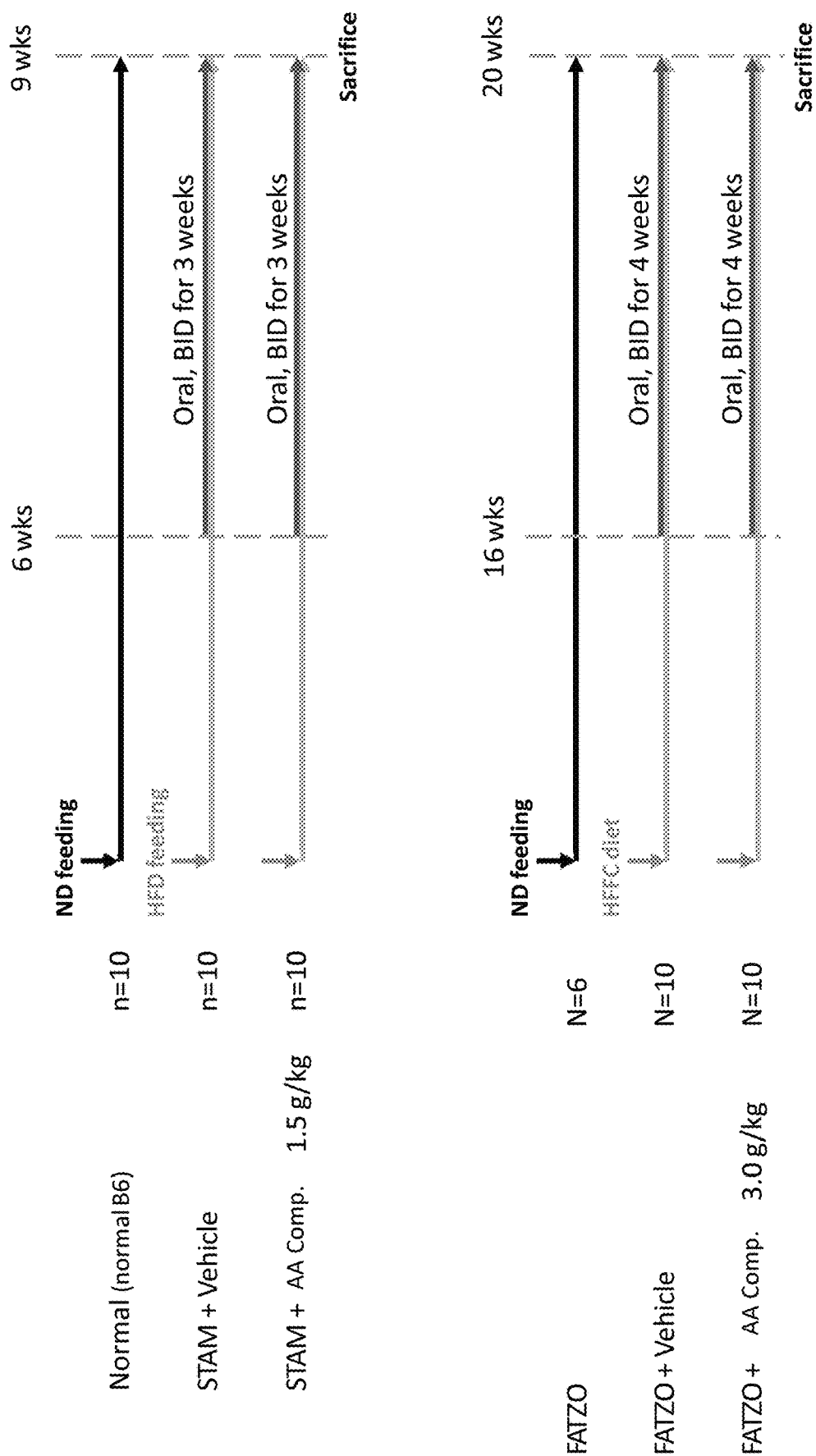
FIG. 3 is a schematic showing treatment regimens for administration of an amino acid composition to STAM and FATZO mice.

The STAM™ mouse is a model for non-alcoholic steatohepatitis (NASH) and hepatocellular carcinoma (HCC), developed by SMC Laboratories, Inc. Evidence of fatty liver is present by 5 weeks of age, followed by NASH by 7 weeks of age, and fibrosis by 9 weeks of age. Male STAM mice were generated in C57BL/6 mice, which received a low dose streptozotocin 2 days after birth and were fed a high fat diet (57% kcal fat, HFD32, CLEA Japan, Inc.) starting at 4 weeks old (Saito K. et al., 2015 Sci Rep 5:12466; hereby incorporated by reference in its entirety). The amino acid composition was administered to STAM mice at a dose of 1.6 m/kg twice daily for 3 weeks starting at 6 weeks of age. One group of vehicle treated STAM mice was included as a control. Unfasted mice were euthanized at 9 weeks old. Plasma and liver samples were harvested for further analysis (FIG. 3).

The FATZO™ mouse is an inbred, polygenic model of obesity, metabolic syndrome, and NASH, developed by Crown Bioscience, Inc (Peterson R G. Et al., 2017 PLoS One; hereby incorporated by reference in its entirety). Male FATZO mice were fed a high fat, fructose, and cholesterol (HFFC) diet (40% kcal fat, D12079B, Research Diets, Inc. and 5% fructose in drinking water) starting at 6 weeks old to induce NAFLD and NASH. Evidence of fatty liver is present by 4 weeks post induction, followed by NASH by 16 weeks post induction and fibrosis by 20 weeks of induction. The designed amino acid composition was administered at a dose of 3.0 g/kg twice daily for 4 weeks starting at 16 weeks post induction (FIG. 3). One group of vehicle treated FATZO mice was included as control. Unfasted mice were euthanized at 20 weeks post-induction. Plasma and liver samples were harvested for further analysis.

Histological Analysis

The Aperio ScanScope CS whole slide digital imaging system (Vista, Calif.) was used for imaging in H&E, Picric Sirius Red, SMA, F4/80. Images were captured from whole slides.

The livers were evaluated by veterinary pathologists blind to sample ID using the NASH Clinical Research Network (CRN) liver histological scoring system (Kleiner D E, et al., 2015, hereby incorporated by reference in its entirety). The NASH CRN Scoring System assesses progression of steatosis, lobular inflammation, hepatocyte ballooning, degeneration, and fibrosis. One cross section of liver for each case was analyzed with the NASH score system. Steatosis, lobular inflammation, and fibrosis progression was assessed on a 0-3 scale. Ballooning degeneration was assessed on a 0-2 scale.

The Positive Pixel Count algorithm of the Aperio Automatic Image Quantitation was used to quantify the percentage of a specific stain present in a scanned slide image. A range of color (range of hues and saturation) and three intensity ranges (weak, positive, and strong) were masked and evaluated. The algorithm counted the number and intensity-sum in each intensity range, along with three additional quantities: average intensity, ratio of strong/total number, and average intensity of weak positive pixels.

A specific positive pixel algorithm was used for imaging the Sirius Red and Oil Red O liver sections. The positive pixel algorithm was modified to distinguish between the orange and blue colors. Alterations from the normal "hue value" (0.1 to 0.96) and "color saturation" (0.04 to 0.29), were made for the Sirius Red evaluation. Vasculature and artifacts were excluded from analysis.

Liver Triglyceride and Cholesterol Measurement Liver total lipid-extracts were obtained by Folch's method (Folch J. et al., J. Biol. Chem. 1957; 226: 497; hereby incorporated by reference in its entirety). Liver samples were homogenized in chloroform-methanol (2:1, v/v) and incubated overnight at room temperature. After washing with chloroform-methanol-water (8:4:3, v/v/v), the extracts were evaporated to dryness, and dissolved in isopropanol. Liver triglyceride and cholesterol contents were measured by the Triglyceride E-test and Cholesterol E-test, respectively.

Gene Expression Analysis

Liver RNA samples were converted into cDNA libraries using the Illumina TruSeq Stranded mRNA sample preparation kit (Illumina #RS-122-2103). Transcriptome were analyzed at Q2 Solutions (Morrisville, N.C.). RNA Seq data were normalized and analyzed using Ingenuity Pathway Analysis (QIAGEN Bioinformatics). Mouse liver gene expression at the pathway level was focused on because it is translatable to human NAFLD (Teufel A, et al., Gastroenterology, 2016, hereby incorporated by reference in its entirety).

Liver Cytokine/Chemokine Measurement

The levels of IL-1b, MCP-1, and MIP-1 protein in liver were quantified using the multiplex ELISA Assay (Meso Scale Discovery, Rockville, Md.).

Figure 4A:
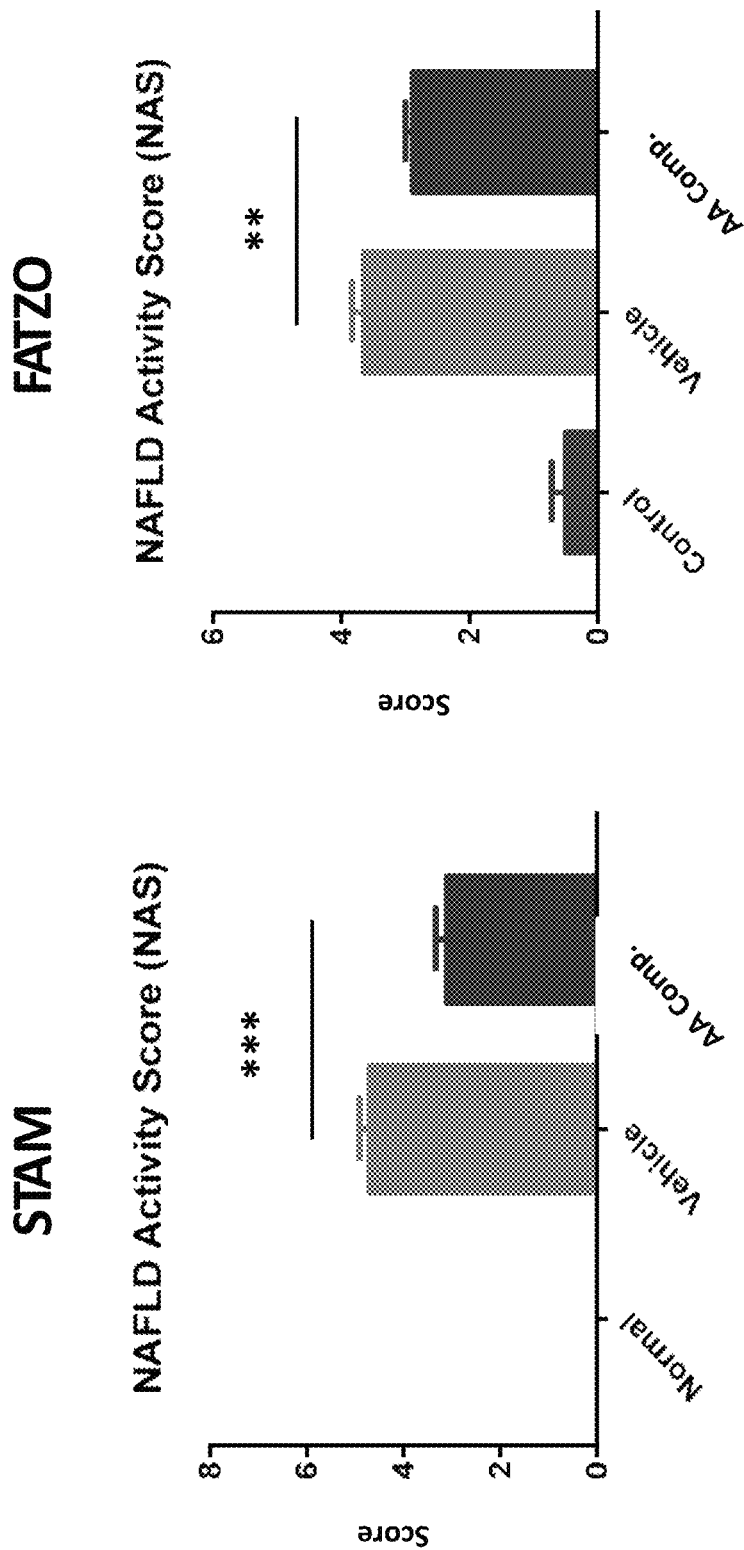
FIGS. 4A-4E are a series of graphs and images showing the effect of treating STAM and FATZO mice with an amino acid composition on the NAFLD activity score (NAS), steatosis, inflammation, and liver fibrosis as determined with histology.
Figure 4B:
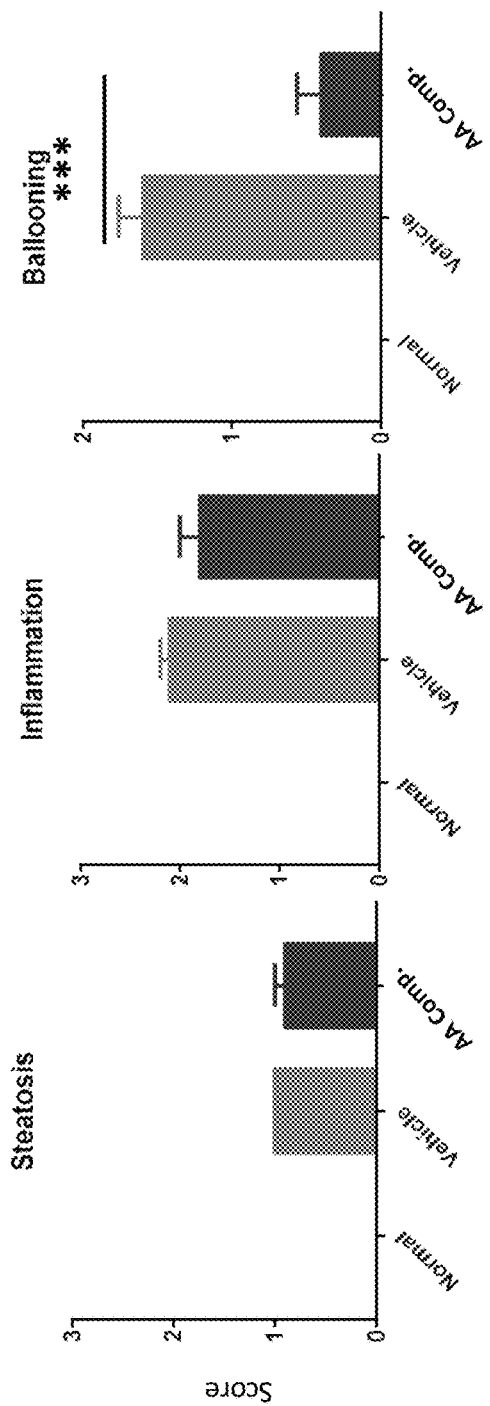
Figure 4C:
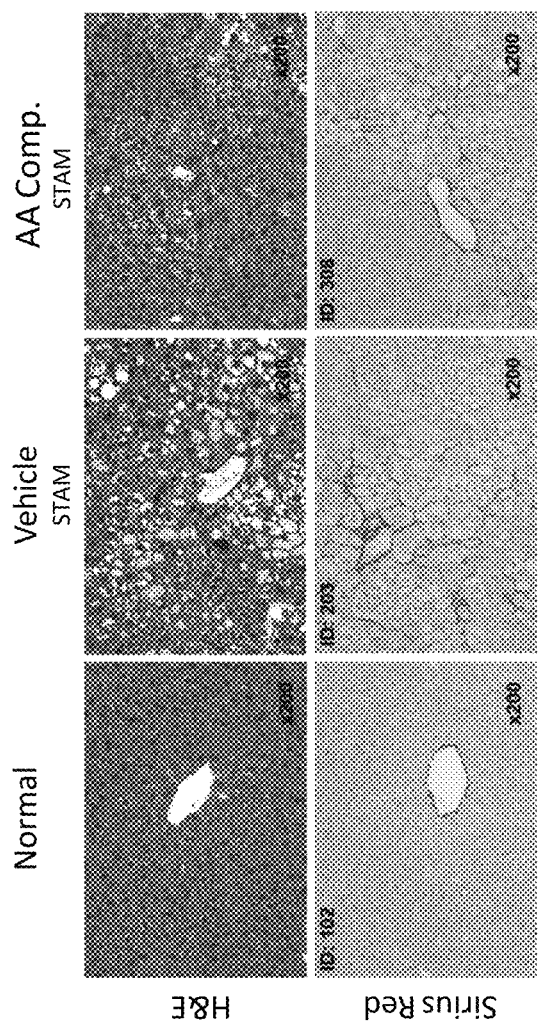

The Amino Acid Composition Improves Ballooning and Fibrosis in Both STAM and FATZO Mice Treatment with the amino acid composition significantly reduced NAFLD activity scores (NAS) in both STAM and FATZO mice (FIG. 4A). Treatment with the amino acid composition also significantly decreased hepatocyte ballooning in STAM mice (FIG. 4B). Scores of steatosis and inflammation were not changed according to histological measures by treatment of STAM mice with the amino acid composition. The Sirius Red-positive, fibrosis area was significantly lowered by treating the STAM mice with the amino acid composition, while the Oil Red O area was not changed by treating the STAM mice with the amino acid composition (FIG. 4C). Liver triglyceride and cholesterol levels were not changed.

Figure 4D:
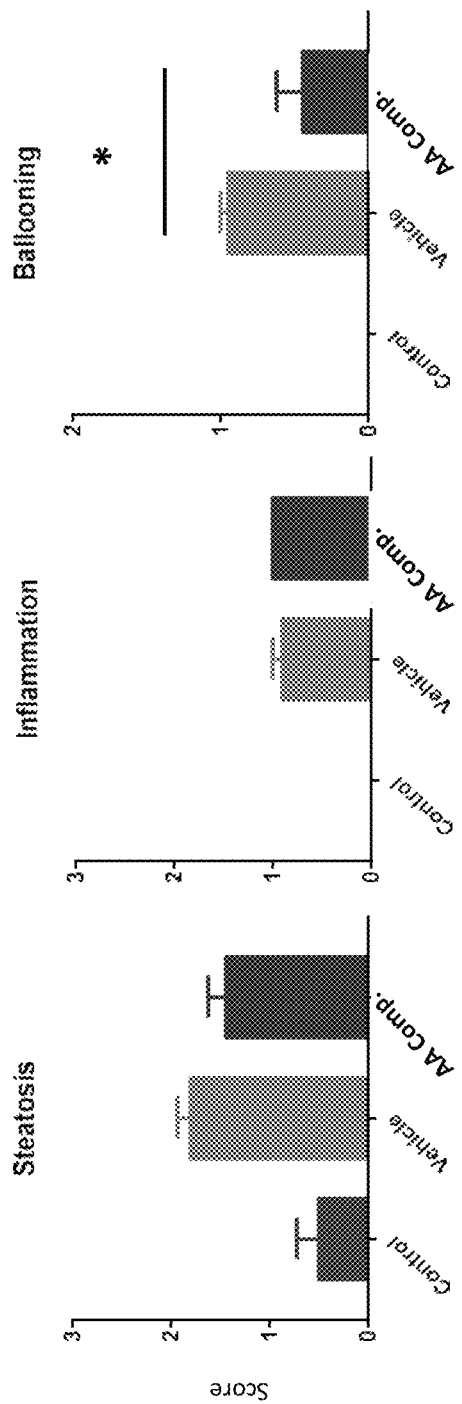
Figure 4E:
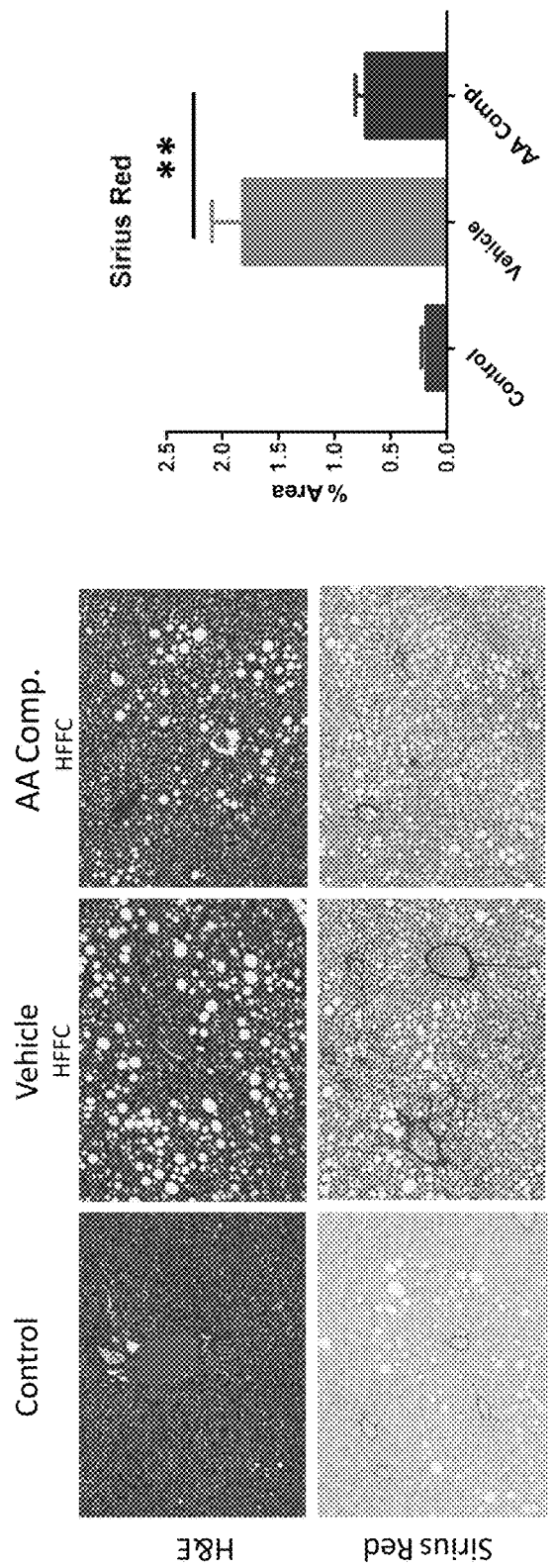

Treatment with the amino acid composition also significantly decreased hepatocyte ballooning in FATZO mice (FIG. 4D). Scores of steatosis and inflammation as well as liver triglyceride and cholesterol levels were not changed in the FATZO mice treated with the amino acid composition treatment. The Sirius Red-positive, fibrosis area was significantly lowered by treatment of the FATZO mice with the amino acid composition, while the Oil Red O area was not changed by treatment of the FATZO mice with the amino acid composition treatment (FIG. 4E).

The Amino Acid Composition Enhances Fatty Acid Oxidation

Figure 5A:
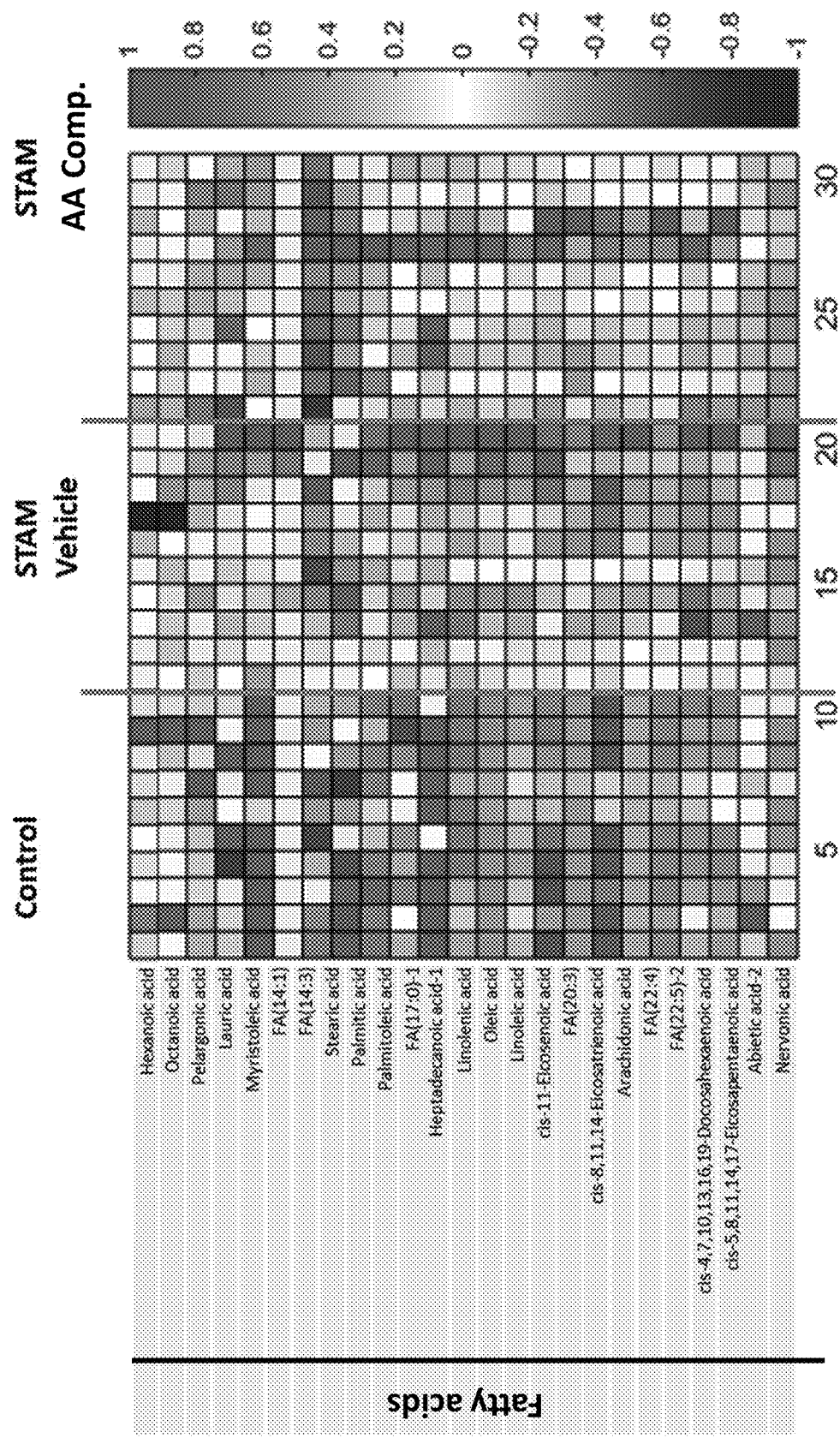
FIGS. 5A-5B are images showing the levels of liver unsaturated fatty acids and acylcarnitines of STAM mice treated with the amino acid composition.
Figure 5B:
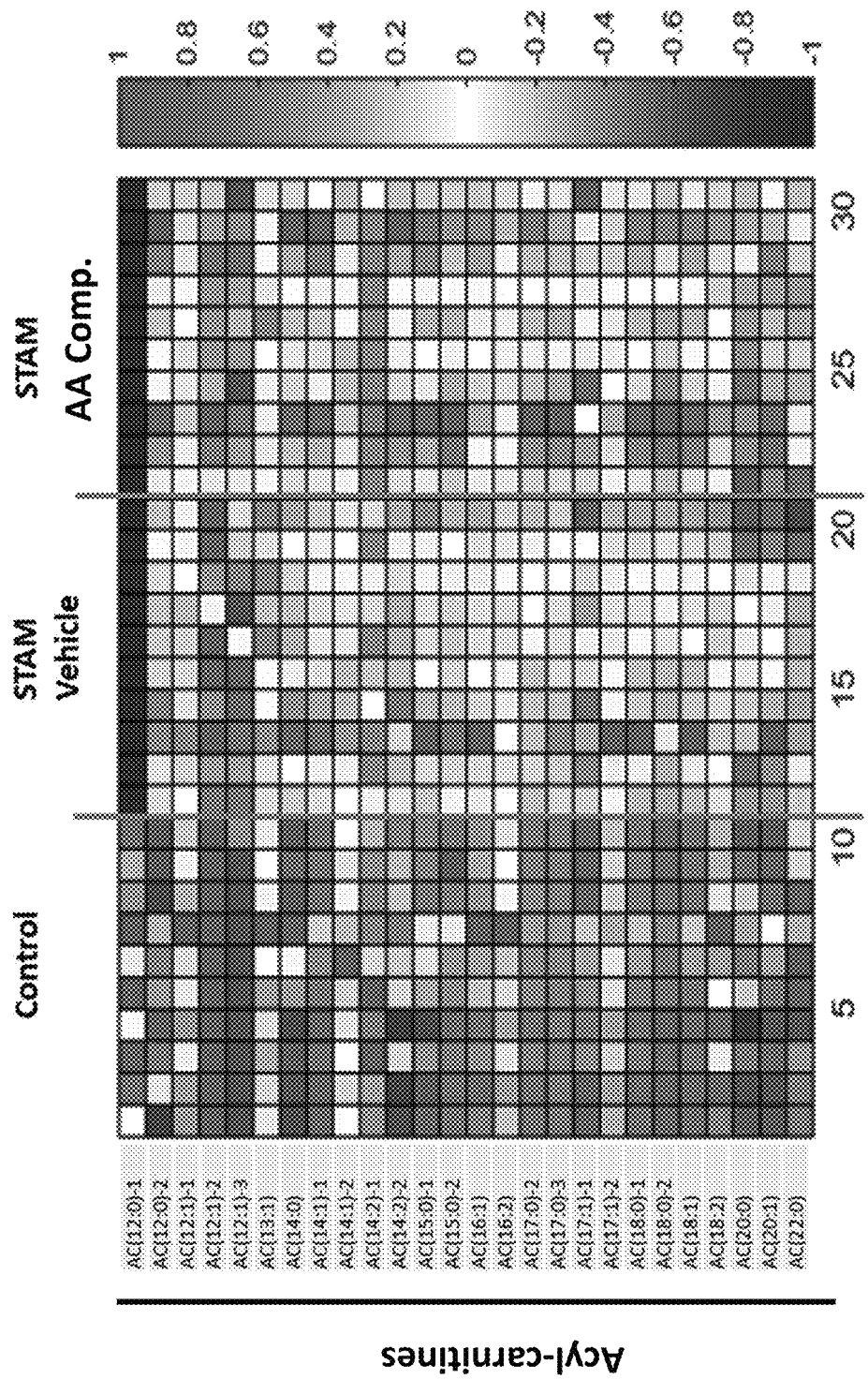

NAFLD is characterized by hepatic lipid accumulation. Liver triglyceride is attributable to a precise balance between acquisition by de novo lipogenesis and uptake of non-esterified fatty acids from the plasma, versus disposal by fatty acid oxidation and by the secretion of triglyceride-rich lipoproteins (Kawano Y, Cohen D E, J Gastroenterol. 2013, hereby incorporated by reference in its entirety). Compared to control mice, STAM mice had higher liver unsaturated fatty acids, which were reduced by treatment with the amino acid composition (FIG. 5A and Table 53). Liver acylcarnitines in STAM mice were increased by treatment with the amino acid composition, suggesting enhanced fatty acid beta-oxidation (FIG. 5B and Table 53).

TABLE 53

P-values and fold changes for liver acylcarnitine and unsaturated fatty acids following treatment of STAM mice with the amino acid composition (treated) compared to control.

| Lipid | KEGG ID | HMDB ID | Control p-val | Control fold change | Treated p-val | Treated fold change |
|---|---|---|---|---|---|---|
| AC(13:1) | No ID | No ID | | −1.61 | 7.94E−02 | 1.32 |
| FA(14:3) | No ID | No ID | 5.17E−03 | 1.69 | 4.83E−01 | −1.24 |
| FA(20:3) | No ID | No ID | 6.97E−06 | 18.29 | 1.35E−01 | −2.17 |
| FA(22:4) | No ID | No ID | 7.12E−07 | 34.79 | 3.15E−01 | −1.79 |
| FA(22:5)-1 | No ID | No ID | 2.39E−02 | 3.31 | 1.19E−01 | −1.80 |
| FA(22:5)-2 | No ID | No ID | 2.11E−04 | 3.03 | 1.69E−02 | −1.92 |
| Linoleic acid | C01595 | HMDB00673 | 9.90E−04 | 3.18 | 1.68E−02 | −1.77 |
| Linolenic acid | C06427 | HMDB01388 | 3.57E−05 | 35.88 | 4.08E−02 | −1.99 |
| Oleic acid | C00712 | HMDB00207 | 1.95E−04 | 18.05 | 3.67E−02 | −1.88 |
| Palmitoleic acid | C08362 | HMDB03229 | 9.84E−05 | 2.69 | 2.70E−02 | −1.48 |

Metabolite Analysis

Metabolic profiling based on both capillary electrophoresis time-of-flight mass spectrometry (CE-TOFMS) and LC-TOFMS platforms was performed at Human Metabolome Technologies (Yamagata, Japan). Metabolites in the samples were identified by comparing the migration time and m/z ratio with authentic standards and quantified by comparing their peak areas with those of authentic standards.

Figure 6:
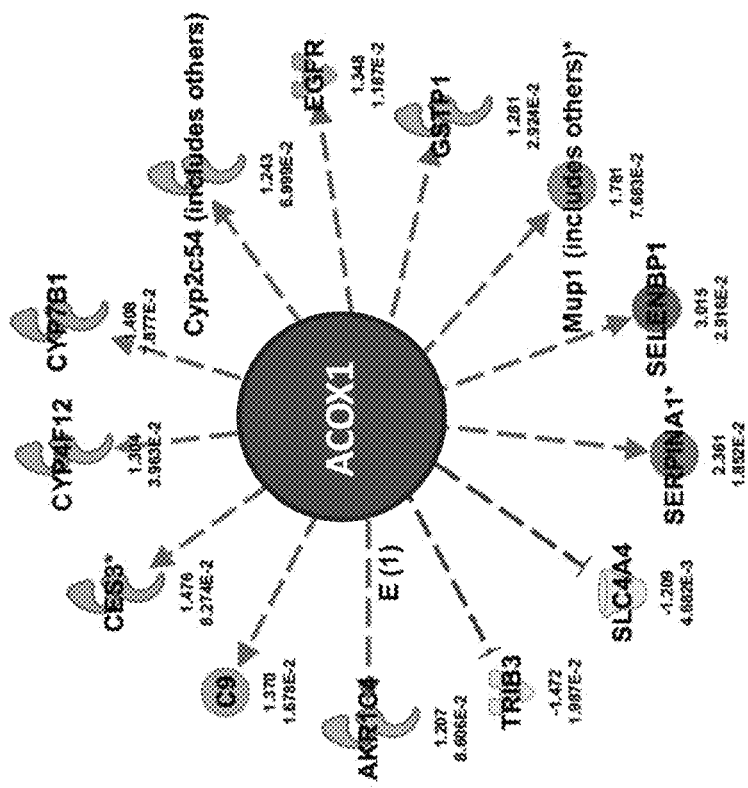
FIG. 6 is an image of a gene map of the liver gene expression pattern following treatment with the amino acid composition in STAM mice showing activation of ACOX1.

Differential gene expression patterns in the liver impacted by treatment with the amino acid composition were interpreted in the context of the upstream regulator systems biology knowledgebase framework developed by Ingenuity Pathway Analysis. Computed z-scores indicated that the gene expression patterns are consistent with activation of ACOX1, which encodes peroxisomal fatty acid oxidation, as an upstream regulator (FIG. 6 and Table 54).

TABLE 54

P-values and fold changes for gene expression associated with the ACOX1
pathway following treatment of STAM mice with the amino acid composition (treated) compared to control.

| gene | IPA_upstream_regulator | ACOX1_path | IPA_gene_name | Control fold change | Control p-val | Treated fold change | Treated p-val |
|---|---|---|---|---|---|---|---|
| Akr1c6 | ACOX1 | ACOX1 | AKR1C4 | −1.68 | 1.88E−06 | 1.207 | 8.606E−02 |
| C9 | ACOX1 | ACOX1 | | −3.10 | 7.81E−07 | 1.370 | 1.678E−02 |
| Ces3a | ACOX1 | ACOX1 | | −2.10 | 2.69E−06 | 1.379 | 3.900E−02 |
| Ces3b | ACOX1 | ACOX1 | | −3.16 | 1.05E−07 | 1.476 | 8.274E−02 |
| Cyp2c50 | ACOX1 | ACOX1 | Cyp2c54 | −1.72 | 1.24E−04 | 1.243 | 6.999E−02 |
| Cyp4a12a | ACOX1 | ACOX1 | | −1.59 | 4.60E−03 | 1.293 | 8.589E−02 |
| Cyp7b1 | ACOX1 | ACOX1 | | −4.45 | 4.29E−04 | 1.408 | 7.877E−02 |
| Egfr | NFKB;ACOX1 | ACOX1 | | −1.98 | 1.31E−04 | 1.348 | 1.187E−02 |
| Gstp1 | ACOX1 | ACOX1 | | −2.31 | 2.56E−06 | 1.281 | 2.924E−02 |
| Mup1 | ACOX1 | ACOX1 | | −7.69 | 1.47E−03 | 1.781 | 7.683E−02 |
| Mup11 | ACOX1 | ACOX1 | | −2.47 | 9.01E−03 | 1.703 | 5.779E−02 |
| Mup14 | ACOX1 | ACOX1 | | −2.05 | 1.27E−02 | 1.395 | 4.890E−02 |
| Mup16 | ACOX1 | ACOX1 | | −6.27 | 4.38E−03 | 1.465 | 7.558E−02 |
| Mup6 | ACOX1 | ACOX1 | | −1.73 | 2.27E−02 | 1.330 | 5.784E−02 |
| Selenbp2 | TGFB;IL10;ACOX1 | ACOX1 | Selenbp1 | −15.77 | 3.73E−05 | 3.015 | 2.916E−02 |
| Serpina1c | TGFB;ACOX1 | ACOX1 | | −2.25 | 7.22E−09 | 1.290 | 5.612E−02 |
| Serpina1e | TGFB;ACOX1 | ACOX1 | | −43.20 | 3.93E−08 | 2.361 | 1.852E−02 |
| S1c4a4 | ACOX1 | ACOX1 | | 1.55 | 7.00E−06 | −1.209 | 4.682E−03 |
| Trib3 | IL2;NFKB;ACOX1 | ACOX1 | | 2.40 | 3.14E−04 | −1.472 | 1.987E−02 |

The Amino Acid Composition Tempers Inflammation Pathways

Figure 7A:
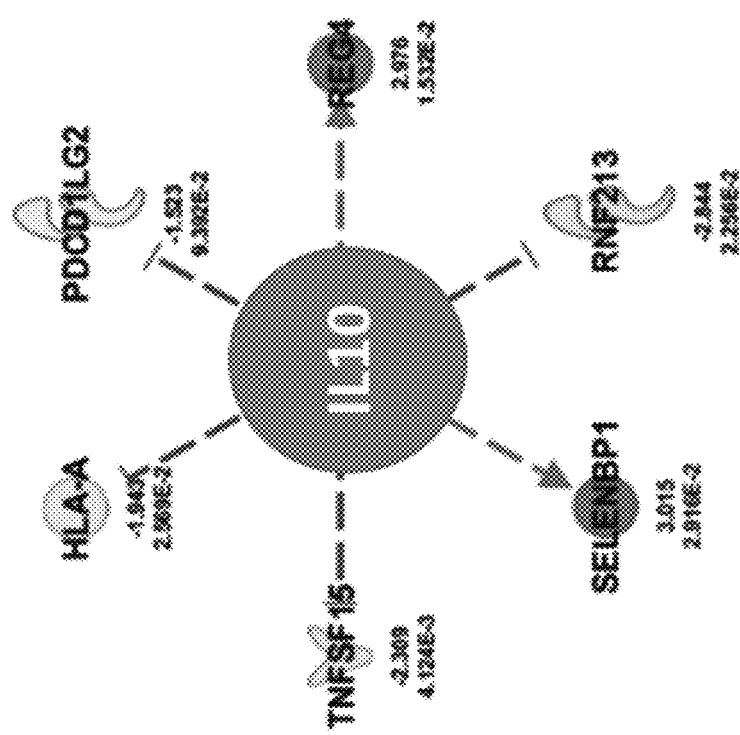
FIGS. 7A-7D are images of gene maps of the liver gene expression pattern following treatment with the amino acid composition in STAM mice showing upstream regulator activation of anti-inflammatory IL-10 (FIG. 7A); inhibition of pro-inflammatory NF-kB (FIG. 7B), interferons, IL-1b, and IL-2 (FIG. 7C); and suppression of the fibrogenic TGF-b signaling pathway.
Figure 7B:
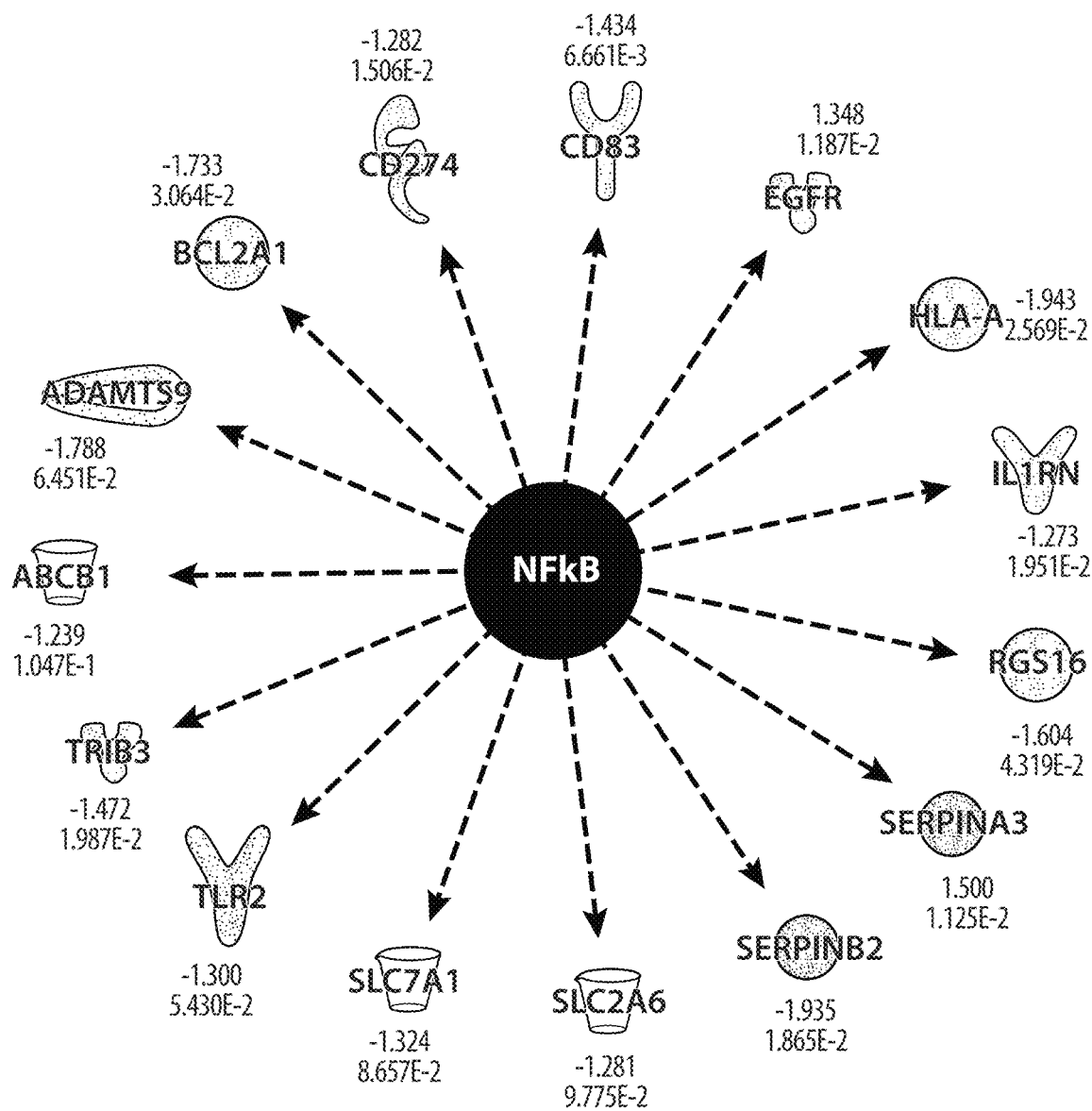
Figure 7C:
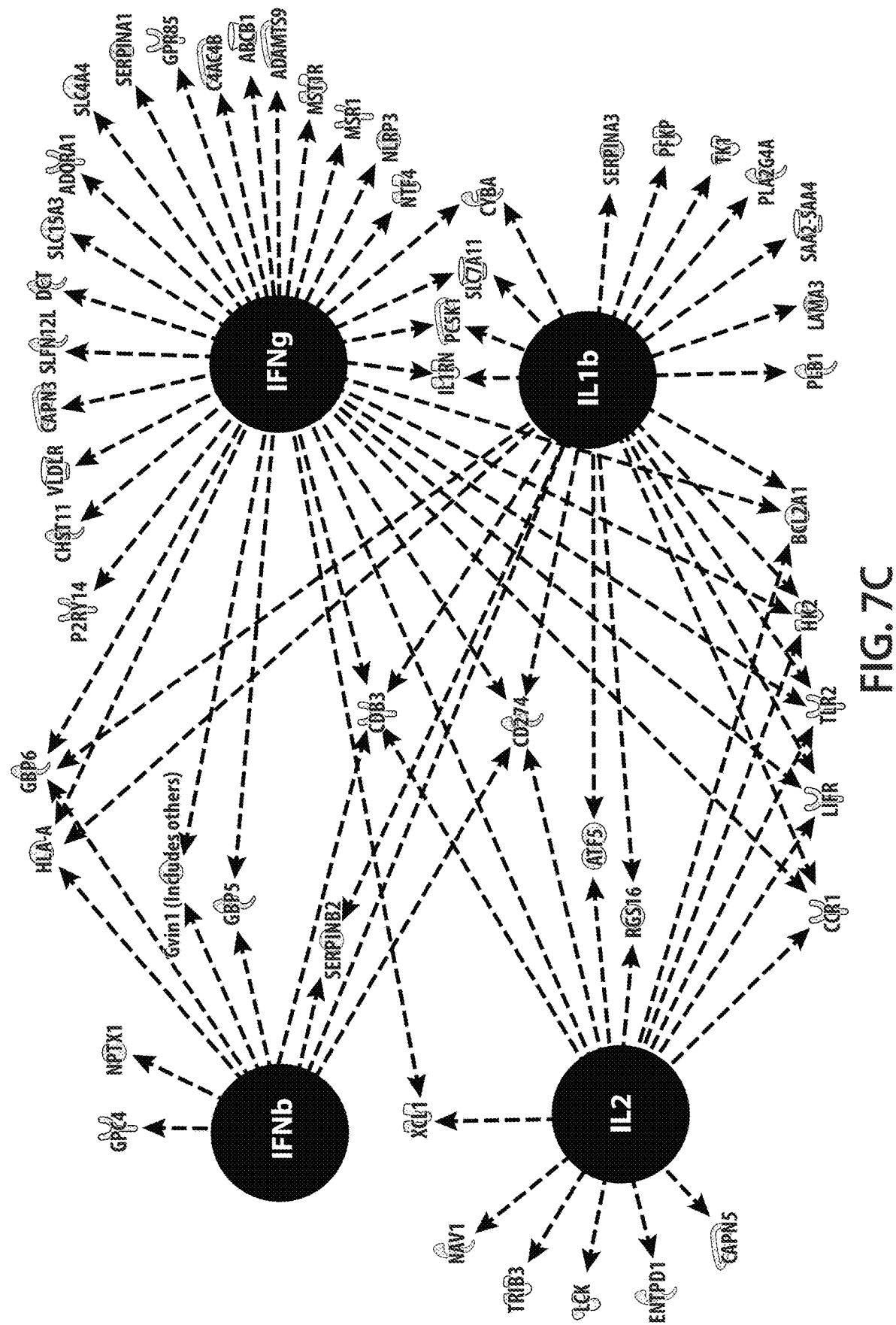
Figure 8:
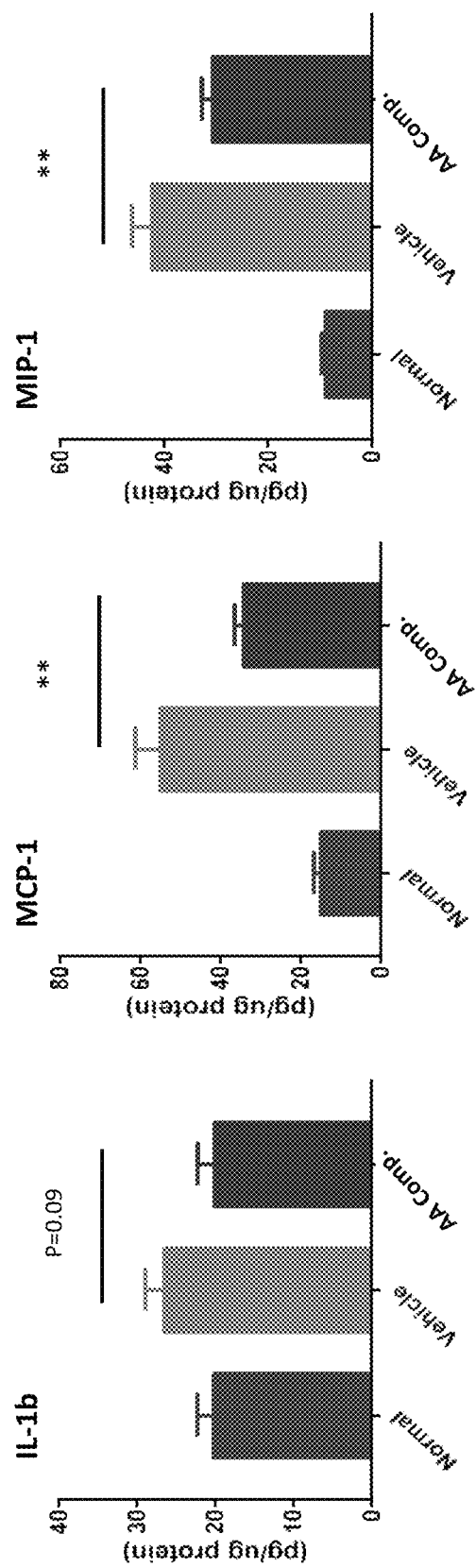
FIG. 8 is a series of graphs showing MCP-1 and MIP-1 protein levels, which are the ligands of C—C chemokine receptor types 2 (CCR2) and 5 (CCR5), following treatment with the amino acid composition.
Figures 9A, 9B, 9C, 9D, 9E, 9F, 9G, 9H, 9I, 9J, 9K, 9L:
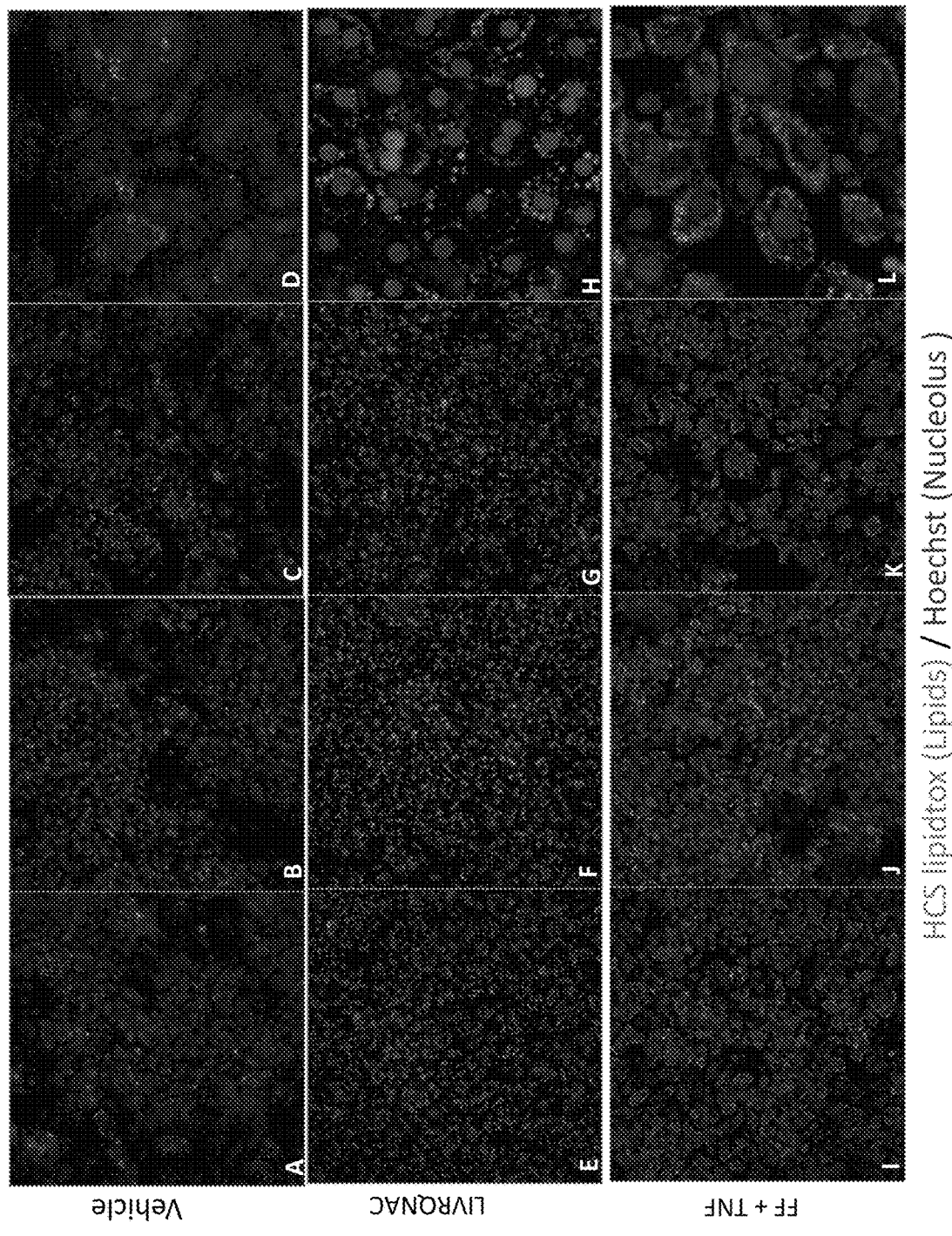
FIGS. 9A-9L are a series of microscopy images shown lipid accumulation in primary human hepatocytes following treatment with vehicle control (FIGS. 9A-9D), a LIVRQNAC amino acid composition (FIGS. 9E-9H), or free fatty acids and TNFα (FF+TNF.

Inflammation is a "second-hit" of NASH. The differential gene expression patterns in the liver as a result of treatment with the amino acid composition yielded z-scores within IPA analysis associated with upstream regulator activation of anti-inflammatory IL-10 (FIG. 7A) and inhibition of pro-inflammatory NF-kB (FIG. 7B and Table 55), interferons, IL-1b, and IL-2 (FIG. 7C and Table 55). At the protein level, treatment with the amino acid composition significantly down-regulated hepatic MCP-1 and MIP-1, which are the ligands of C—C chemokine receptor types 2 (CCR2) and 5 (CCR5), respectively (FIG. 8). Thus, treatment with the amino acid composition tempered the immune system toward an anti-inflammatory state, which may dampen NASH progression.

TABLE 55

P-values and fold changes for gene expression associated with the ACOX1
pathway following treatment of STAM mice with the amino acid composition (treated) compared to control.

| gene | IPA upstream regulator | IPA gene name | IL10_path | IL1b_path | IL2 path | NFKB_path | TGFB_path | Control fold change | Control p-val | Treated fold change | Treated p-val |
|---|---|---|---|---|---|---|---|---|---|---|---|
| Abcb1a | NFKB;IL10 | | IL10 | | | NFKB | | 3.02 | 1.55E−06 | −1.239 | 1.047E−01 |
| Abcb1b | NFKB;IL10 | | IL10 | | | NFKB | | −2.24 | 4.90E−03 | 1.272 | 9.745E−02 |
| Acta1 | TGFB | | | | | | TGFB | 7.96 | 5.87E−03 | −1.849 | 1.044E−01 |
| Adora1 | TGFB | | | | | | TGFB | 1.94 | 1.99E−05 | −1.222 | 3.262E−02 |
| AK007436 | NFKB | ADAMTS9 | | | | NFKB | | 2.32 | 6.38E−03 | −1.788 | 6.451E−02 |
| AK043676 | IL1b | PFKP | | IL1b | | | | 1.68 | 3.12E−03 | −1.462 | 1.586E−02 |
| AK154184 | IL1b; TGFB | CYBA | | IL1b | | | TGFB | 1.99 | 1.02E−03 | −1.222 | 9.247E−02 |
| AK158038 | IL2 | NAV1 | | | IL2 | | | 1.62 | 2.63E−02 | −1.659 | 1.587E−02 |
| Atf5 | IL1b;IL2 | | | IL1b | IL2 | | | 1.71 | 3.00E−04 | −1.223 | 9.622E−02 |
| Bcl2a1d | IL1b;IL2;NFKB | | | IL1b | IL2 | NFKB | | 4.00 | 1.74E−04 | −1.733 | 3.064E−02 |
| Capn5 | IL2 | | | | IL2 | | | 1.51 | 2.05E−05 | −1.235 | 5.908E−03 |
| Ccr1 | IL1b;IL2;TGFB | | | IL1b | IL2 | | TGFB | 2.82 | 1.28E−03 | −1.352 | 7.496E−02 |
| Cd274 | IL1b;IL2;NFKB | | | IL1b | IL2 | NFKB | | 2.37 | 1.71E−07 | −1.282 | 1.506E−02 |
| Cd83 | IL1b;IL2;NFKB;TGFB | | | IL1b | IL2 | NFKB | TGFB | 2.41 | 5.36E−07 | −1.434 | 6.661E−03 |
| Chst11 | TGFB | | | | | | TGFB | 2.91 | 7.87E−06 | −1.308 | 1.881E−02 |
| Clec2i | TGFB | | | | | | TGFB | 1.80 | 1.01E−03 | −1.226 | 5.963E−02 |
| Egfr | NFKB | | | | | NFKB | | −1.98 | 1.31E−04 | 1.348 | 1.187E−02 |
| Entpd1 | IL2 | | | | IL2 | | | 1.87 | 1.84E−04 | −1.218 | 8.413E−02 |
| Fgf21 | TGFB | | | | | | TGFB | 49.56 | 1.03E−03 | −1.478 | 4.472E−02 |
| Gabrd | TGFB | | | | | | TGFB | 5.82 | 1.48E−04 | −1.511 | 5.978E−02 |
| Gbp4 | IL1b;IL10 | Gbp6 | IL10 | IL1b | | | | 1.60 | 1.01E−03 | −1.234 | 5.234E−02 |
| Gbp5 | IL10 | | IL10 | | | | | 1.81 | 7.82E−05 | −1.217 | 6.120E−02 |
| Gm8909 | IL1b;NFKB;IL10 | HLA-A | IL10 | IL1b | | NFKB | | 4.03 | 8.19E−04 | −1.943 | 2.569E−02 |
| Gpr85 | TGFB | | | | | | TGFB | 2.46 | 1.77E−02 | −1.685 | 6.628E−02 |
| Gucy2c | TGFB | | | | | | TGFB | 2.35 | 8.97E−03 | −1.395 | 1.080E−01 |
| Hk2 | IL1b;IL2 | | | IL1b | IL2 | | | 2.00 | 2.01E−04 | −1.301 | 9.834E−02 |
| Hsd17b6 | TGFB | | | | | | TGFB | 2.89 | 4.20E−05 | −1.244 | 1.036E−02 |
| Il1rn | IL1b;NFKB;TGFB;IL10 | | IL10 | IL1b | | NFKB | TGFB | 4.43 | 5.94E−09 | −1.273 | 1.951E−02 |

TABLE 55-continued

P-values and fold changes for gene expression associated with the ACOX1
pathway following treatment of STAM mice with the amino acid composition (treated) compared to control.

| gene | IPA upstream regulator | IPA gene name | IL10_path | IL1b_path | IL2 path | NFKB_path | TGFB_path | Control fold change | Control p-val | Treated fold change | Treated p-val |
|---|---|---|---|---|---|---|---|---|---|---|---|
| Lama3 | IL1b | | | IL1b | | | | −3.09 | 1.90E−05 | 1.650 | 5.542E−02 |
| Lck | IL2 | | | | IL2 | | | 1.92 | 8.87E−04 | −1.246 | 3.027E−02 |
| Lifr | IL1b;IL2;TGFB | | | IL1b | IL2 | | TGFB | −4.43 | 2.43E−05 | 1.406 | 2.099E−02 |
| Msr1 | TGFB | | | | | | TGFB | 1.58 | 1.13E−03 | −1.226 | 5.836E−02 |
| Mst1r | TGFB | | | | | | TGFB | 2.08 | 4.17E−03 | −1.523 | 1.147E−02 |
| Nlrp3 | TGFB | | | | | | TGFB | 1.93 | 1.30E−03 | −1.506 | 2.456E−02 |
| P2ry14 | TGFB | | | | | | TGFB | 3.29 | 4.67E−05 | −1.268 | 4.039E−02 |
| Pcsk1 | IL1b | | | IL1b | | | | 2.07 | 9.00E−03 | −2.070 | 8.150E−02 |
| Pla2g4a | IL1b;TGFB | | | IL1b | | | TGFB | 2.10 | 7.94E−05 | −1.265 | 1.064E−01 |
| Plb1 | IL1b | | | IL1b | | | | 2.01 | 2.09E−02 | −1.696 | 2.324E−02 |
| Rgs16 | IL1b;IL2;NFKB | | | IL1b | IL2 | NFKB | | 7.68 | 2.47E−05 | −1.604 | 4.319E−02 |
| Saa4 | IL1b | | | IL1b | | | | −1.72 | 4.76E−02 | 1.283 | 9.771E−02 |
| Selenbp2 | TGFB;IL10 | Selenbp1 | IL10 | | | | TGFB | −15.77 | 3.73E−05 | 3.015 | 2.916E−02 |
| Sema3b | TGFB | | | | | | TGFB | 4.12 | 4.78E−05 | −1.285 | 9.461E−02 |
| Serpina1c | TGFB | | | | | | TGFB | −2.25 | 7.22E−09 | 1.290 | 5.612E−02 |
| Serpina1e | TGFB | | | | | | TGFB | −43.20 | 3.93E−08 | 2.361 | 1.852E−02 |
| Serpina3k | IL1b;NFKB;TGFB | | | IL1b | | NFKB | TGFB | −2.95 | 1.85E−08 | 1.500 | 1.125E−02 |
| Serpinb2 | IL1b;NFKB | | | IL1b | | NFKB | | 1.94 | 4.98E−02 | −1.935 | 1.865E−02 |
| Slc23a2 | TGFB | | | | | | TGFB | 2.00 | 1.02E−05 | −1.258 | 2.229E−02 |
| Slc2a6 | NFKB;IL10 | | IL10 | | | NFKB | | 1.79 | 2.68E−02 | −1.281 | 9.775E−02 |
| Slc7a1 | NFKB;TGFB | | | | | NFKB | TGFB | 1.64 | 3.96E−03 | −1.324 | 8.657E−02 |
| Slc7a11 | IL1b;IL10 | | IL10 | IL1b | | | | 65.45 | 1.35E−03 | −1.869 | 1.068E−01 |
| Tk1 | IL1b | | | IL1b | | | | −2.40 | 4.99E−06 | 1.295 | 4.036E−02 |
| Tlr11 | IL10 | | IL10 | | | | | 1.66 | 6.11E−03 | −1.368 | 6.005E−02 |
| Tlr2 | IL1b;IL2;NFKB;TGFB;IL10 | | IL10 | IL1b | IL2 | NFKB | TGFB | 2.12 | 5.32E−05 | −1.300 | 5.430E−02 |
| Trib3 | IL2;NFKB | | | | IL2 | NFKB | | 2.40 | 3.14E−04 | −1.472 | 1.987E−02 |
| Xcl1 | IL2 | | | | IL2 | | | 2.52 | 1.22E−03 | −1.796 | 6.279E−02 |

The Amino Acid Composition Prevents Fibrogenesis Pathways

Figure 7D:

Fibrosis is at the nexus of several biologic processes, such as metabolic dysregulation, inflammation, and cell death. Lipid accumulation in hepatocytes and chronic inflammation induce fibrogenic activation of hepatic stellate cells (Wobser H, et al., Cell Res. 2009, which is hereby incorporated by reference in its entirety). The liver gene expression pattern resulting from treatment with the amino acid composition was consistent with the suppression of the fibrogenic TGF-b signaling pathway (FIG. 7D).

Increasing evidence implicates that CCR2/CCR5 and their ligands, including MCP-1/MIP-1, promote macrophage recruitment and hepatic stellate cell activation which contribute to fibrosis following liver tissue damage (Lefebvre E, et al., PLoS One 2016, which is hereby incorporated by reference in its entirety). The amino acid composition displayed a potent antifibrotic activity in the STAM model of NASH via reducing hepatic TGF-b signaling and MCP-1 and MIP-1 proteins (FIG. 8).

Conclusion

The amino acid composition demonstrated consistent disease modifying activity in both STAM and FATZO mouse models of NASH including improvement in NAS and amelioration of ballooning and fibrosis. The activity of the amino acid composition appears to be driven, at least in part, via increase in fatty acid oxidation, reduction in levels of key cytokines and transcription pathways associated with liver inflammation and fibrosis.

Example 10: Hepatocyte Model for Steatosis and Inflammation

Hepatocyte lipotoxicity appears to be a central driver of hepatic cellular injury via oxidative stress and endoplasmic reticulum (ER) stress. The ability of amino acids to influence steatosis (lipid accumulation) and inflammation in hepatocytes was assessed using human primary hepatocytes (Lonza, TRL).

Cell Seeding and Maintenance

Primary hepatocytes lot nos. from two healthy human donors were seeded on day 0 at density of 6e04 cells in 96 well optical microplates (Thermofisher) in hepatocyte plating media (William's E medium (Gibco) supplemented with 10% heat-inactivated FBS (Atlanta Bio), 2 mM Glutamax (Gibco), 1×ITS plus (R&D systems), and 0.2% Primocin (InVivoGen) and incubated for 6 hours at 37° C., 5% CO2. After 6 hours, cells were washed twice with 150 ul William's E medium and incubated overnight at 37° C., 5% CO2 with serum-free hepatocytes culture media (Hepatocytes defined medium (Corning)) supplemented with 5 ug human recombinant EGF (Corning), 2 mM Glutamax (Gibco), and 1× Penicillin/Streptomycin. On day 1, cells were washed twice with 150 µL per well William's E medium (Gibco) and incubated for 24h in the hepatocyte culture media in the same conditions described above.

Amino Acids Pre-Treatment

On day 2, cells were washed twice with 150 ul DPBS 1× (Gibco) and maintained in amino acid-free WEM (US Biologicals) containing a defined custom amino acid concentration based on the mean physiological concentrations in blood. The values are published in the Human Metabolome Database (Wishart D S, Tzur D, Knox C, et al., HMDB: the Human Metabolome Database. Nucleic Acids Res. 2007 January; 35(Database issue):D521-6. 17202168; which is hereby incorporated by reference in its entirety). This custom media is supplemented with 11 mM Glucose, 0.272 mM Sodium Pyruvate, and a dose curve of defined amino acid compositions (i.e., vehicle, LIVRQ+N-acetylcysteine, LIVRQ, RQ+N-acetylcysteine, N-acetylcysteine alone, LIV, or individually with L-Leucine, L-Isoleucine, L-Valine, L-Arginine, L-Glutamine, and L-Cysteine) at various ranges of concentrations. Cells were maintained in this defined media for 24 hours at 37° C., 5% CO2.

Co-Treatment with Free Fatty Acids and Different Amino Acids Combination

After pre-treatment, cells were exposed to free fatty acids (FFA) at 250 uM with a ratio of 2:1 (Oleate:Palmitate) supplemented with TNF-α (Thermofisher) at 1 ng/ml or vehicle. Cells were incubated with the FFAs mixture and the different amino acids combinations for 24 hours at 37° C., 5% CO2. After 24 hours incubation, media was removed for cytokine analysis and replaced by fresh media containing the same stimulus conditions and amino acid concentrations. Cells were incubated for an additional 48 hours for a total of 72 hours of FFA and TNFα stimulation.

Cytokine Analysis after 24h by ELISA

Human CCL2 (MCP-1) was measured by ELISA (Human CCK2/MCP-1 DuoSet ELISA, R&D Systems) at 1/5 or 1/10 dilution in 1× Reagent Diluent (Reagent Ancillary Kit 2, R&D Systems). Data were normalized to the specific per well cell density determined by nuclei count stained by Hoechst 3342 (Life technologies) in the fluorescence microscopy described below.

Intracellular Lipid Accumulation Analysis after 72h by Fluorescence Microscopy

After 72 hours, cells were washed twice in 100 ul PBS 1× (Gibco), fixed with 4% Paraformaldehyde, and washed twice with PBS 1× (100 ul). After fixation, lipids were stained with HCS LipidTOX Red Neutral (Thermofisher Scientific) diluted 1000× and nuclei were stained with Hoechst 3342 (Life Technologies) diluted to 4 ug/ml. The LipidTOX™ neutral lipid stain has an extremely high affinity for neutral lipid droplets that was detected by fluorescence microscopy using a high content imager (Molecular Devices).

Results

Lipid Accumulation and Steatosis Phenotypes

Primary human hepatocytes from healthy donors were found to have low levels of lipid accumulation (FIG. 9A-9D). Treatment of the cells with free fatty acids (FF)+ TNFα induced lipid accumulation (FIG. 9I-9L) with a macro-steatosis phenotype. Treatment with LIVRQNAC changed the hepatocyte phenotypes from macro-steatosis to micro-steatosis (FIG. 9E-9H).

MCP1/CCL2 Secretion

Tables 56-59 show the baseline subtracted secretion of MCP1/CCL2 in primary human hepatocytes cells from two healthy donors (donor 1 for Tables 56 and 57, and donor 2 for Tables 58 and 59). LIVRQNAC, LIVRQNAC+G, LIVRQNAC+S, LIVRQ and RQNAC significantly decreased MCP1/CCL2 secretion in both donors. The combination LIV, however, significantly increased MCP1/CCL2 secretion only in one of the donors. The addition of arginine (R) and glutamine (Q) to a combination of LIV decreased the secretion of MCP1/CCL2 in both donors compared to LIV alone. Individually, N-acetyl cysteine and glutamine are shown to significantly decrease MCP1/CCL2 secretion, while arginine increased MCP1 secretion. Isoleucine, Leucine and Valine did not have an effect on MCP1/CCL2 secretion.

TABLE 56

Changes in MCP1 expression for donor 1 upon administration of amino acid compositions

| | | MCP1 expression relative to Control - Donor 1 | | | | |
|---|---|---|---|---|---|---|
| Amino Acid Supplement | Conc. (X) | Mean | Std. Deviation | Number of values | P-value* | Significance |
| LIVRQNAC | 40 | −24.1616 | 0.032252 | 3 | 0.0001 | **** |
| LIVRQNAC | 30 | −22.2916 | 2.119583 | 3 | 0.0001 | **** |
| LIVRQNAC | 20 | −18.4363 | 0.850597 | 3 | 0.0005 | *** |
| LIVRQNAC | 10 | −14.3383 | 1.854977 | 3 | 0.0074 | ** |
| LIVRQNAC | 1 | 0 | 1.048045 | 3 | | |
| LIVRQNAC + G | 40 | −22.0824 | 0.873105 | 3 | 0.0001 | **** |
| LIVRQNAC + G | 30 | −19.2605 | 1.611788 | 3 | 0.0003 | *** |
| LIVRQNAC + G | 20 | −17.5807 | 2.893835 | 3 | 0.0009 | *** |
| LIVRQNAC + G | 10 | −13.7521 | 3.068991 | 3 | 0.0106 | * |
| LIVRQNAC + G | 1 | 0 | 1.682719 | 3 | | |
| LIVRQNAC + S | 40 | −32.4703 | 0.340537 | 3 | 0.0001 | **** |
| LIVRQNAC + S | 30 | −30.768 | 1.339048 | 3 | 0.0001 | **** |
| LIVRQNAC + S | 20 | −25.5964 | 1.854519 | 3 | 0.0001 | **** |
| LIVRQNAC + S | 10 | −17.8326 | 1.974033 | 3 | 0.0008 | *** |
| LIVRQNAC + S | 1 | 2.37E−15 | 18.41384 | 3 | | |
| LIV | 40 | 15.52052 | 6.323205 | 3 | 0.0094 | ** |
| LIV | 30 | 12.3111 | 10.02706 | 3 | 0.0475 | * |
| LIV | 20 | 12.6686 | 4.109608 | 3 | 0.0401 | * |
| LIV | 10 | −5.18869 | 1.579468 | 3 | 0.6477 | ns |
| LIV | 1 | −1.2E−15 | 8.178943 | 3 | | |
| LIVRQ | 40 | −25.9576 | 0.484283 | 3 | 0.0028 | ** |
| LIVRQ | 30 | −23.6562 | 2.599721 | 3 | 0.0099 | ** |
| LIVRQ | 20 | −13.4723 | 3.427666 | 3 | 0.6401 | ns |
| LIVRQ | 10 | −9.22141 | 7.599407 | 3 | 0.9986 | ns |
| LIVRQ | 1 | −8.23198 | 5.80889 | 3 | | |
| RQNAC | 40 | −21.4681 | 2.903892 | 3 | 0.0003 | *** |
| RQNAC | 30 | −17.1873 | 5.202568 | 3 | 0.0038 | ** |
| RQNAC | 20 | −12.1782 | 2.907484 | 3 | 0.0506 | ns |
| RQNAC | 10 | −8.89378 | 4.748653 | 3 | 0.206 | ns |
| RQNAC | 1 | 1.18E−15 | 10.02527 | 3 | | |
| N-Acetyl Cysteine | 40 | −17.6065 | 1.211739 | 3 | 0.0009 | *** |
| N-Acetyl Cysteine | 20 | −10.8919 | 2.27818 | 3 | 0.0545 | ns |
| N-Acetyl Cysteine | 10 | −2.49755 | 8.795693 | 3 | 0.9424 | ns |

TABLE 56-continued

Changes in MCP1 expression for donor 1 upon administration of amino acid compositions MCP1 expression relative to Control - Donor 1

| Amino Acid Supplement | Conc. (X) | Mean | Std. Deviation | Number of values | P-value* | Significance |
|---|---|---|---|---|---|---|
| N-Acetyl Cysteine | 5 | −0.76286 | 7.457085 | 3 | 0.9991 | ns |
| N-Acetyl Cysteine | 0 | 0 | 6.716428 | 3 | | |

TABLE 57

Changes in MCP1 expression for donor 1 upon administration of single amino acid compositions MCP1 expression relative to Control - Donor 1

| Amino Acid Supplement | Conc. (μM) | Mean | Std. Deviation | Number of values | P-value* | Significance |
|---|---|---|---|---|---|---|
| Valine | 23420 | 14.16805 | 19.23365 | 3 | 0.6777 | ns |
| Valine | 11710 | 77.73396 | 137.82 | 3 | 0.9998 | ns |
| Valine | 4684 | 23.6867 | 46.48697 | 3 | 0.2502 | ns |
| Valine | 234 | −2.4E−15 | 13.86902 | 3 | | |
| Arginine | 5440 | 10.9386 | 4.79774 | 3 | 0.0057 | ** |
| Arginine | 2720 | 6.526801 | 4.266971 | 3 | 0.1517 | ns |
| Arginine | 1088 | 5.114414 | 4.685563 | 3 | 0.3321 | ns |
| Arginine | 109 | 2.37E−15 | 0.666016 | 3 | | |
| Glutamine | 22484 | −21.8392 | 1.113443 | 3 | 0.0004 | *** |
| Glutamine | 11242 | −9.00139 | 1.68951 | 3 | 0.2459 | ns |
| Glutamine | 3747 | −0.89805 | 6.374471 | 3 | 0.9991 | ns |
| Glutamine | 749 | 0 | 9.549143 | 3 | | |
| Isoleucine | 6639 | −0.205 | 2.292188 | 3 | 0.9998 | ns |
| Isoleucine | 3320 | −2.41722 | 2.382379 | 3 | 0.4907 | ns |
| Isoleucine | 1328 | −0.30729 | 2.409691 | 3 | 0.9992 | ns |
| Isoleucine | 66 | −1.2E−15 | 3.163838 | 3 | | |
| Leucine | 15270 | −1.36762 | 3.37035 | 3 | 0.8675 | ns |
| Leucine | 7635 | 1.895506 | 3.757642 | 3 | 0.6872 | ns |
| Leucine | 3054 | 3.340489 | 3.016641 | 3 | 0.2201 | ns |
| Leucine | 153 | 5.92E−16 | 3.132507 | 3 | | |
| N-Acetyl Cysteine | 10000 | −17.6065 | 1.211739 | 3 | 0.0009 | *** |
| N-Acetyl Cysteine | 5000 | −10.8919 | 2.27818 | 3 | 0.0545 | ns |
| N-Acetyl Cysteine | 2500 | −2.49755 | 8.795693 | 3 | 0.9424 | ns |
| N-Acetyl Cysteine | 1000 | −0.76286 | 7.457085 | 3 | 0.9991 | ns |
| N-Acetyl Cysteine | 0 | 0 | 6.716428 | 3 | | |

TABLE 58

Changes in MCP1 expression for donor 2 upon administration of amino acid compositions MCP1 expression relative to Control - Donor 2

| Amino Acid Supplement | Conc. (X) | Mean | Std. Deviation | Number of values | P-value* | Significance |
|---|---|---|---|---|---|---|
| LIVRQNAC | 40 | −24.5376 | 1.632923 | 3 | 0.0001 | **** |
| LIVRQNAC | 30 | −13.6824 | 2.562571 | 3 | 0.0001 | **** |
| LIVRQNAC | 20 | −8.42053 | 1.545343 | 3 | 0.0001 | **** |
| LIVRQNAC | 10 | 2.126223 | 0.453924 | 3 | 0.0007 | *** |
| LIVRQNAC | 1 | −4.7E−15 | 0.412226 | 3 | | |
| LIVRQNAC + G | 40 | −35.3651 | 2.08381 | 3 | 0.0007 | *** |
| LIVRQNAC + G | 30 | −30.3247 | 5.225183 | 3 | 0.001 | *** |
| LIVRQNAC + G | 20 | −17.0719 | 4.522244 | 3 | 0.0119 | * |
| LIVRQNAC + G | 10 | −14.2586 | 2.767898 | 3 | 0.049 | * |
| LIVRQNAC + G | 1 | −7.1E−15 | 7.613666 | 3 | | |
| LIVRQNAC + S | 40 | −35.8381 | 1.404782 | 3 | 0.0001 | **** |
| LIVRQNAC + S | 30 | −30.9946 | 2.372062 | 3 | 0.0001 | **** |
| LIVRQNAC + S | 20 | −16.8831 | 3.223007 | 3 | 0.0004 | *** |
| LIVRQNAC + S | 10 | −5.60595 | 10.2119 | 3 | 0.1887 | |
| LIVRQNAC + S | 1 | 2.37E−15 | 4.4168 | 3 | | |
| LIV | 40 | −46.7898 | 8.664441 | 3 | 0.3692 | ns |
| LIV | 30 | −34.5953 | 16.84743 | 3 | 0.6246 | ns |

TABLE 58-continued

Changes in MCP1 expression for donor 2 upon administration of amino acid compositions

| Amino Acid Supplement | Conc. (X) | Mean | Std. Deviation | Number of values | P-value* | Significance |
|---|---|---|---|---|---|---|
| LIV | 20 | −28.0851 | 31.84348 | 3 | 0.7684 | ns |
| LIV | 10 | −11.0006 | 72.74556 | 3 | 0.9889 | ns |
| LIV | 1 | 9.47E−15 | 60.93638 | 3 | | |
| LIVRQ | 40 | −129.802 | 7.067989 | 3 | 0.0008 | *** |
| LIVRQ | 30 | −110.034 | 4.53852 | 3 | 0.0042 | ** |
| LIVRQ | 20 | −33.3611 | 31.87706 | 3 | 0.6524 | |
| LIVRQ | 10 | −3.30904 | 71.03267 | 3 | 0.9999 | |
| LIVRQ | 1 | −4.7E−15 | 46.12987 | 3 | | |
| RQNAC | 40 | −133.48 | 1.908424 | 3 | 0.0006 | *** |
| RQNAC | 30 | −123.712 | 1.043889 | 3 | 0.0013 | ** |
| RQNAC | 20 | −109.575 | 5.533323 | 3 | 0.0044 | ** |
| RQNAC | 10 | −55.8583 | 22.72309 | 3 | 0.2273 | |
| RQNAC | 1 | 1.42E−14 | 43.79031 | 3 | | |
| N-Acetyl Cysteine | 10000 | −28.4419 | 1.694 | 3 | 0.0001 | *** |
| N-Acetyl Cysteine | 5000 | −10.5725 | 4.362178 | 3 | 0.0012 | ** |
| N-Acetyl Cysteine | 2500 | −4.0591 | 5.600773 | 3 | 0.0572 | ns |
| N-Acetyl Cysteine | 1000 | 1.602474 | 3.423109 | 3 | 0.0001 | **** |
| N-Acetyl Cysteine | 0 | 0 | 2.068861 | 3 | | |

TABLE 59

Changes in MCP1 expression for donor 2 upon administration of single amino acid compositions

| Amino Acid Supplement | Conc. (μM) | Mean | Std. Deviation | Number of values | P-value* | Significance |
|---|---|---|---|---|---|---|
| Valine | 23420 | −30.7921 | 22.55378 | 3 | 0.6118 | ns |
| Valine | 11710 | 38.24762 | 28.44112 | 3 | 0.4268 | ns |
| Valine | 4684 | 10.79011 | 51.87642 | 3 | 0.9835 | ns |
| Valine | 234 | −1.4E−14 | 30.91388 | 3 | | |
| Arginine | 5440 | 8.493664 | 22.98385 | 3 | 0.9913 | ns |
| Arginine | 2720 | 24.06261 | 63.49489 | 3 | 0.7429 | ns |
| Arginine | 1088 | 24.95224 | 52.94171 | 3 | 0.7192 | ns |
| Arginine | 109 | −4.7E−15 | 11.27976 | 3 | | |
| Glutamine | 22484 | −138.873 | 10.74317 | 3 | 0.0001 | **** |
| Glutamine | 11242 | −90.6558 | 15.43989 | 3 | 0.0037 | ** |
| Glutamine | 3747 | −45.0574 | 41.63249 | 3 | 0.2474 | ns |
| Glutamine | 749 | 2.84E−14 | 59.86955 | 3 | 0.7631 | |
| Isoleucine | 6639 | 18.62132 | 26.01824 | 3 | 0.5663 | ns |
| Isoleucine | 3320 | −5.64461 | 7.719105 | 3 | 0.9882 | ns |
| Isoleucine | 1328 | 26.62309 | 5.65413 | 3 | 0.2613 | ns |
| Isoleucine | 66 | 0 | 4.245462 | 3 | | |
| Leucine | 15270 | −26.6436 | 10.08177 | 3 | 0.2607 | ns |
| Leucine | 7635 | −2.98815 | 21.00205 | 3 | 0.9989 | ns |
| Leucine | 3054 | 16.11014 | 8.662188 | 3 | 0.68 | ns |
| Leucine | 153 | −4.7E−15 | 7.63396 | 3 | | |
| N-Acetyl Cysteine | 10000 | −28.4419 | 1.694 | 3 | 0.0001 | *** |
| N-Acetyl Cysteine | 5000 | −10.5725 | 4.362178 | 3 | 0.0012 | ** |
| N-Acetyl Cysteine | 2500 | −4.0591 | 5.600773 | 3 | 0.0572 | ns |
| N-Acetyl Cysteine | 1000 | 1.602474 | 3.423109 | 3 | 0.0001 | **** |
| N-Acetyl Cysteine | 0 | 0 | 2.068861 | 3 | | |

Example 11: Hepatic Stellate Cell—TNFα Inflammatory Response

Methods

Primary human hepatic stellate cells were obtained from Samsara Sciences based on the following criteria for selecting donors: adult age (between 18 and 50 years), normal BMI (>18.5 and <25), and absence of confounding liver disease. Primary human hepatic stellate cells grown in Complete HSC Medium to ~80% confluence in T75 or T150 flasks below passage 10 were seeded into sterile, collagen I coated, 96-well optical plastic microplates (ThermoScientific, 152036) at 4000 cells per well (~1250 cells per cm$^2$) and incubated for 6 hours at 37° C., 5% CO2 in a humidified incubator.

After 6 hours, plates were removed from the incubator and the medium gently pipetted off and washed once with 150 μL per well DPBS. The DPBS was removed and the pretreatment medium (±single amino acid dropout, 1XHMDB DMEM+3% dialyzed FBS+0.2% Primocin, ±supplemental amino acid dose; see experiment for medium composition) was applied to the cells at 150 μL per well. Plates were returned to the incubator overnight, ~14-15 hours.

After overnight pretreatment, the medium was removed from the cells, and the same pretreatment medium, now supplemented with 3 ng/mL TNFα is applied. Each plate contained 3 ng/mL TNFα in 1× human plasma amino acid (HMDB or PAA) concentration medium, 0 ng/mL in 1XHMDB, and 3 ng/mL TNFα+50 nM Bengamide in 1XHMDB to serve as controls. Plates were incubated for 12 hours at 37° C., 5% CO2.

After 12 hour stimulus with TNFα, supernatant was removed and frozen at −80° C. in two separate aliquots. Plates were washed gently once with DPBS and 100 μL per well of 1XHMDB DMEM+3% dialyzed FBS+0.2% Primocin+10% CCK-8 viability reagent (Dojindo). Plates were incubated for 1 hour at 37° C., 5% CO2.

After 1 hour of incubation, viability was measured on the Synergy plate reader (Absorbance at 977 (test), 900 (reference), and 450 (CCK8) nm). Immediately, the medium was removed and the plates were fixed with 70 μL per well 4% paraformaldehyde in PBS at room temperature for 20 minutes, followed by two 150 μL PBS washes, and stored with 100 μL per well PBS at 4° C. until immunofluorescence staining.

Human CCL2/MCP1 and Human IL-6 were measured by ELISA (Human CCK2/MCP-1 DuoSet ELISA, R&D Systems; Human IL-6 DuoSet ELISA, R&D Systems) at 1/5 and 1/20 dilution in 1× Reagent Diluent (Reagent Ancillary Kit 2, R&D Systems). Data were normalized to the specific per well cell density determined by Hoechst stained nuclei count.

Results

Pro-Inflammatory MCP-1 Chemokine Secretion

Tables 60-63 show per-cell normalized MCP-1 chemokine secretion in primary human hepatic stellate cells from two donors as a fold change from the plasma amino acid background. Statistical significance calculated by one-way ANOVA with Dunnett's multiple comparison test within each treatment group. LIVRQNAC+G and RQNAC singificantly decrease MCP-1 secretion in both donors. LIVRQNAC, LIVRQNAC+S reduced MCP1 secretion and was statistically significant in one of two donors. Individually, each of valine, arginine, and leucine had no significant impact on MCP-1 secretion. Glutamine reduced MCP1 secretion in both donors but was only statistically significant in one of two donors. N-acetyl cysteine significantly reduced MCP-1 secretion in both donors.

TABLE 60

Changes in MCP1 secretion for donor 3 upon administration of amino acid compositions

| Amino Acid Supplement | Conc. (X) | Fold Change MCP1 Secretion Normalized Per Cell | | | | |
|---|---|---|---|---|---|---|
| | | Mean | Std. Deviation | Number of values | Significance | P-value |
| LIVRQNAC | 40 | 0.6237 | 0.2500 | 3 | ns | 0.2763 |
| LIVRQNAC | 30 | 0.6180 | 0.2436 | 3 | ns | 0.2657 |
| LIVRQNAC | 20 | 0.5679 | 0.1728 | 3 | ns | 0.1863 |
| LIVRQNAC | 10 | 0.5548 | 0.2139 | 3 | ns | 0.1694 |
| LIVRQNAC | 1 | 1.0000 | 0.3619 | 3 | | |
| LIVRQNAC + G | 40 | 0.6216 | 0.0903 | 3 | ** | 0.0036 |
| LIVRQNAC + G | 30 | 0.6742 | 0.0549 | 3 | ** | 0.0095 |
| LIVRQNAC + G | 20 | 0.6373 | 0.0888 | 3 | ** | 0.0047 |
| LIVRQNAC + G | 10 | 0.7075 | 0.0610 | 3 | * | 0.0179 |
| LIVRQNAC + G | 1 | 1.0000 | 0.1704 | 3 | | |
| LIVRQNAC + S | 40 | 0.5911 | 0.1451 | 3 | ns | 0.2045 |
| LIVRQNAC + S | 30 | 0.5932 | 0.1943 | 3 | ns | 0.2077 |
| LIVRQNAC + S | 20 | 0.5760 | 0.1681 | 3 | ns | 0.1828 |
| LIVRQNAC + S | 10 | 0.6820 | 0.2396 | 3 | ns | 0.3845 |
| LIVRQNAC + S | 1 | 1.0000 | 0.4098 | 3 | | |
| LIV | 40 | 1.2677 | 0.5786 | 3 | ns | 0.7802 |
| LIV | 30 | 1.3632 | 0.5837 | 3 | ns | 0.8368 |
| LIV | 20 | 1.3336 | 0.4754 | 3 | ns | 0.7964 |
| LIV | 10 | 1.3745 | 0.5427 | 3 | ns | 0.9132 |
| LIV | 1 | 1.0000 | 0.3186 | 3 | | |
| LIVRQ | 40 | 1.3042 | 0.4140 | 3 | ns | 0.7695 |
| LIVRQ | 30 | 1.2208 | 0.4403 | 3 | ns | 0.9036 |
| LIVRQ | 20 | 0.9915 | 0.3521 | 3 | ns | 0.9999 |
| LIVRQ | 10 | 0.9968 | 0.3907 | 3 | ns | 0.9999 |
| LIVRQ | 1 | 1.0000 | 0.4257 | 3 | | |
| RQNAC | 40 | 0.3220 | 0.0282 | 3 | **** | 0.0001 |
| RQNAC | 30 | 0.4353 | 0.0941 | 3 | **** | 0.0001 |
| RQNAC | 20 | 0.4629 | 0.0998 | 3 | *** | 0.0001 |
| RQNAC | 10 | 0.6513 | 0.0925 | 3 | ** | 0.0028 |

TABLE 60-continued

Changes in MCP1 secretion for donor 3 upon administration of amino acid compositions

| | | Fold Change MCP1 Secretion Normalized Per Cell | | | | |
|---|---|---|---|---|---|---|
| Amino Acid Supplement | Conc. (X) | Mean | Std. Deviation | Number of values | Significance | P-value |
| RQNAC | 1 | 1.0000 | 0.1132 | 3 | | |
| N-Acetyl Cysteine | 40 | 0.4485 | 0.0587 | 3 | *** | 0.0002 |
| N-Acetyl Cysteine | 20 | 0.5413 | 0.1018 | 3 | *** | 0.0009 |
| N-Acetyl Cysteine | 10 | 0.6565 | 0.0502 | 3 | ** | 0.007 |
| N-Acetyl Cysteine | 5 | 0.8492 | 0.1515 | 3 | ns | 0.2738 |
| N-Acetyl Cysteine | 0 | 1.0000 | 0.1142 | 3 | | |

TABLE 61

Changes in MCP1 secretion for donor 3 upon administration of single amino acid compositions

| | | Fold Change MCP1 Secretion Normalized Per Cell | | | | |
|---|---|---|---|---|---|---|
| Amino Acid Supplement | Conc. (μM) | Mean | Std. Deviation | Number of values | Significance | P-value |
| Valine | 23420 | 1.2651 | 0.1295 | 3 | ns | 0.1126 |
| Valine | 11710 | 1.0204 | 0.1126 | 3 | ns | 0.9956 |
| Valine | 4684 | 1.0630 | 0.0878 | 3 | ns | 0.8999 |
| Valine | 234 | 1.0000 | 0.2008 | 3 | | |
| Arginine | 5440 | 0.7840 | 0.2753 | 3 | ns | 0.7069 |
| Arginine | 2720 | 0.8821 | 0.2249 | 3 | ns | 0.9264 |
| Arginine | 1088 | 0.9435 | 0.3221 | 3 | ns | 0.9903 |
| Arginine | 109 | 1.0000 | 0.3404 | 3 | | |
| Glutamine | 22484 | 0.6212 | 0.1952 | 3 | ns | 0.2465 |
| Glutamine | 11242 | 0.6106 | 0.2085 | 3 | ns | 0.226 |
| Glutamine | 3747 | 0.6036 | 0.2596 | 3 | ns | 0.2135 |
| Glutamine | 749 | 0.7048 | 0.2473 | 3 | ns | 0.4593 |
| Glutamine | 562 | 1.0000 | 0.2185 | 3 | | |
| Isoleucine | 6639 | 1.2084 | 0.1334 | 3 | ns | 0.284 |
| Isoleucine | 3320 | 1.2169 | 0.0589 | 3 | ns | 0.2565 |
| Isoleucine | 1328 | 1.5550 | 0.2070 | 3 | ** | 0.0038 |
| Isoleucine | 66 | 1.0000 | 0.1188 | 3 | | |
| Leucine | 15270 | 1.1808 | 0.2601 | 3 | ns | 0.5156 |
| Leucine | 7635 | 1.3054 | 0.1748 | 3 | ns | 0.1491 |
| Leucine | 3054 | 1.1479 | 0.0605 | 3 | ns | 0.6605 |
| Leucine | 153 | 1.0000 | 0.0784 | 3 | | |
| N-Acetyl Cysteine | 10000 | 0.4485 | 0.0587 | 3 | *** | 0.0002 |
| N-Acetyl Cysteine | 5000 | 0.5413 | 0.1018 | 3 | *** | 0.0009 |
| N-Acetyl Cysteine | 2500 | 0.6565 | 0.0502 | 3 | ** | 0.007 |
| N-Acetyl Cysteine | 1000 | 0.8492 | 0.1515 | 3 | ns | 0.2738 |
| N-Acetyl Cysteine | 0 | 1.0000 | 0.1142 | 3 | | |

TABLE 62

Changes in MCP1 secretion for donor 4 upon administration of amino acid compositions

| | | Fold Change MCP1 Secretion Normalized Per Cell | | | | |
|---|---|---|---|---|---|---|
| Amino Acid Supplement | Conc. (X) | Mean | Std. Deviation | Number of values | Significance | P-value |
| LIVRQNAC | 40 | 0.7791 | 0.0740 | 3 | ns | 0.1328 |
| LIVRQNAC | 30 | 0.6333 | 0.1114 | 3 | * | 0.0116 |
| LIVRQNAC | 20 | 0.6997 | 0.1013 | 3 | * | 0.0352 |
| LIVRQNAC | 10 | 0.8114 | 0.1271 | 3 | ns | 0.2216 |
| LIVRQNAC | 1 | 1.0000 | 0.1607 | 3 | | |
| LIVRQNAC + G | 40 | 0.6738 | 0.0979 | 3 | * | 0.0454 |
| LIVRQNAC + G | 30 | 0.7117 | 0.0783 | 3 | ns | 0.0794 |
| LIVRQNAC + G | 20 | 0.6735 | 0.1127 | 3 | * | 0.0452 |
| LIVRQNAC + G | 10 | 0.7682 | 0.0563 | 3 | ns | 0.1778 |
| LIVRQNAC + G | 1 | 1.0000 | 0.2452 | 3 | | |
| LIVRQNAC + S | 40 | 0.5780 | 0.0781 | 3 | ** | 0.0025 |
| LIVRQNAC + S | 30 | 0.5393 | 0.1185 | 3 | ** | 0.0013 |

TABLE 62-continued

Changes in MCP1 secretion for donor 4 upon administration of amino acid compositions

| Amino Acid Supplement | Conc. (X) | Fold Change MCP1 Secretion Normalized Per Cell | | | | |
|---|---|---|---|---|---|---|
| | | Mean | Std. Deviation | Number of values | Significance | P-value |
| LIVRQNAC + S | 20 | 0.6487 | 0.0732 | 3 | ** | 0.0085 |
| LIVRQNAC + S | 10 | 0.6872 | 0.0118 | 3 | * | 0.017 |
| LIVRQNAC + S | 1 | 1.0000 | 0.1803 | 3 | | |
| LIV | 40 | 0.7010 | 0.1399 | 3 | ** | 0.0059 |
| LIV | 30 | 0.8883 | 0.0530 | 3 | ns | 0.3745 |
| LIV | 20 | 0.9284 | 0.0579 | 3 | ns | 0.7114 |
| LIV | 10 | 0.8663 | 0.0569 | 3 | ns | 0.2428 |
| LIV | 1 | 1.0000 | 0.0928 | 3 | | |
| LIVRQ | 40 | 1.2235 | 0.0592 | 3 | ns | 0.4365 |
| LIVRQ | 30 | 1.1653 | 0.0558 | 3 | ns | 0.6679 |
| LIVRQ | 20 | 0.8845 | 0.2698 | 3 | ns | 0.862 |
| LIVRQ | 10 | 1.0110 | 0.0738 | 3 | ns | 0.9999 |
| LIVRQ | 1 | 1.0000 | 0.3016 | 3 | | |
| RQNAC | 40 | 0.4312 | 0.0994 | 3 | *** | 0.0006 |
| RQNAC | 30 | 0.3910 | 0.0649 | 3 | *** | 0.0003 |
| RQNAC | 20 | 0.5579 | 0.2079 | 3 | ** | 0.0037 |
| RQNAC | 10 | 0.5545 | 0.0663 | 3 | ** | 0.0035 |
| RQNAC | 1 | 1.0000 | 0.0987 | 3 | | |
| N-Acetyl Cysteine | 40 | 0.5011 | 0.0756 | 3 | *** | 0.0001 |
| N-Acetyl Cysteine | 20 | 0.6728 | 0.1024 | 3 | ** | 0.003 |
| N-Acetyl Cysteine | 10 | 0.8033 | 0.1101 | 3 | ns | 0.058 |
| N-Acetyl Cysteine | 5 | 0.6437 | 0.0648 | 3 | ** | 0.0017 |
| N-Acetyl Cysteine | 0 | 1.0000 | 0.0673 | 3 | | |

TABLE 63

Changes in MCP1 secretion for donor 4 upon administration of single amino acid compositions

| Amino Acid Supplement | Conc. (µM) | Fold Change MCP1 Secretion Normalized Per Cell | | | | |
|---|---|---|---|---|---|---|
| | | Mean | Std. Deviation | Number of values | Significance | P-value |
| Valine | 23420 | 1.1525 | 0.0406 | 3 | ns | 0.9999 |
| Valine | 11710 | 1.1544 | 0.1743 | 3 | ns | 0.8877 |
| Valine | 4684 | 1.0942 | 0.0846 | 3 | ns | 0.3545 |
| Valine | 234 | 1.0000 | 0.1464 | 3 | | |
| Arginine | 5440 | 0.9456 | 0.0639 | 3 | ns | 0.9076 |
| Arginine | 2720 | 1.0446 | 0.0741 | 3 | ns | 0.9449 |
| Arginine | 1088 | 1.0453 | 0.1733 | 3 | ns | 0.9423 |
| Arginine | 109 | 1.0000 | 0.1486 | 3 | | |
| Glutamine | 22484 | 0.7039 | 0.0544 | 3 | ** | 0.0065 |
| Glutamine | 11242 | 0.7129 | 0.2237 | 3 | ** | 0.0077 |
| Glutamine | 3747 | 0.6639 | 0.0467 | 3 | ** | 0.0027 |
| Glutamine | 749 | 0.7782 | 0.0860 | 3 | * | 0.0452 |
| Glutamine | 562 | 1.0000 | 0.0709 | 6 | | |
| Isoleucine | 6639 | 0.9103 | 0.0536 | 3 | ns | 0.5597 |
| Isoleucine | 3320 | 0.8830 | 0.0872 | 3 | ns | 0.3538 |
| Isoleucine | 1328 | 1.3338 | 0.1099 | 3 | ** | 0.0044 |
| Isoleucine | 66 | 1.0000 | 0.0853 | 3 | | |
| Leucine | 15270 | 1.5745 | 0.0844 | 3 | ns | 0.1886 |
| Leucine | 7635 | 1.7129 | 0.6026 | 3 | ns | 0.0885 |
| Leucine | 3054 | 1.5342 | 0.1746 | 3 | ns | 0.2332 |
| Leucine | 153 | 1.0000 | 0.2040 | 3 | | |
| N-Acetyl Cysteine | 10000 | 0.5011 | 0.0756 | 3 | *** | 0.0001 |
| N-Acetyl Cysteine | 5000 | 0.6728 | 0.1024 | 3 | ** | 0.003 |
| N-Acetyl Cysteine | 2500 | 0.8033 | 0.1101 | 3 | ns | 0.058 |
| N-Acetyl Cysteine | 1000 | 0.6437 | 0.0648 | 3 | ** | 0.0017 |
| N-Acetyl Cysteine | 0 | 1.0000 | 0.0673 | 3 | | |

IL-6 Cytokine Secretion

Tables 64-67 show per-cell normalized IL-6 cytokine secretion in primary human hepatic stellate cells from two donors as a fold change from the plasma amino acid background. Statistical significance calculated by one-way ANOVA with Dunnett's multiple comparison test within each treatment group. LIVRQNAC, LIVRQNAC+S and RQNAC significantly reduced IL-6 secretion in one of two donors. LIVRQNAC+G, LIVRQNAC+S and RQNAC decreased IL-6 secretion in both donors. LIV and LIVRQ did not have a significant impact on IL-6 secretion in either donor. Individually, valine, arginine, isoleucine, and leucine had no significant effect on IL-6 secretion. N-acetyl cysteine reduced IL-6 secretion in both donors but was only statistically significant in one of two donors. Glutamine significantly reduced IL-6 secretion in both donors.

TABLE 64

Changes in IL-6 cytokine secretion for donor 1 upon administration of amino acid compositions

| Amino Acid Supplement | Conc. (X) | Fold Change IL-6 Secretion Normalized Per Cell | | | | |
|---|---|---|---|---|---|---|
| | | Mean | Std. Deviation | Number of values | Significance | P-value |
| LIVRQNAC | 40 | 0.4857 | 0.0915 | 3 | *** | 0.0004 |
| LIVRQNAC | 30 | 0.5667 | 0.0941 | 3 | ** | 0.0014 |
| LIVRQNAC | 20 | 0.6671 | 0.0431 | 3 | ** | 0.0088 |
| LIVRQNAC | 10 | 0.6579 | 0.1231 | 3 | ** | 0.0074 |
| LIVRQNAC | 1 | 1.0000 | 0.1361 | 3 | | |
| LIVRQNAC + G | 40 | 0.4995 | 0.1427 | 3 | ns | 0.0949 |
| LIVRQNAC + G | 30 | 0.5722 | 0.2185 | 3 | ns | 0.1679 |
| LIVRQNAC + G | 20 | 0.6185 | 0.1769 | 3 | ns | 0.2376 |
| LIVRQNAC + G | 10 | 0.7040 | 0.2809 | 3 | ns | 0.4276 |
| LIVRQNAC + G | 1 | 1.0000 | 0.3513 | 3 | | |
| LIVRQNAC + S | 40 | 0.5397 | 0.1569 | 3 | * | 0.0105 |
| LIVRQNAC + S | 30 | 0.5513 | 0.1190 | 3 | * | 0.0122 |
| LIVRQNAC + S | 20 | 0.6264 | 0.1593 | 3 | * | 0.0338 |

TABLE 64-continued

Changes in IL-6 cytokine secretion for donor 1 upon administration of amino acid compositions

| Amino Acid Supplement | Conc. (X) | Fold Change IL-6 Secretion Normalized Per Cell | | Number of values | Signifi-cance | P-value |
|---|---|---|---|---|---|---|
| | | Mean | Std. Deviation | | | |
| LIVRQNAC + S | 10 | 0.6799 | 0.1218 | 3 | ns | 0.0703 |
| LIVRQNAC + S | 1 | 1.0000 | 0.1671 | 3 | | |
| LIV | 40 | 1.3536 | 0.4767 | 3 | ns | 0.6216 |
| LIV | 30 | 1.2423 | 0.3135 | 3 | ns | 0.8437 |
| LIV | 20 | 1.2321 | 0.4818 | 3 | ns | 0.8611 |
| LIV | 10 | 1.1421 | 0.3489 | 3 | ns | 0.9704 |
| LIV | 1 | 1.0000 | 0.1647 | 3 | | |
| LIVRQ | 40 | 0.8274 | 0.2003 | 3 | ns | 0.7863 |
| LIVRQ | 30 | 0.8880 | 0.2175 | 3 | ns | 0.938 |
| LIVRQ | 20 | 0.8468 | 0.1100 | 3 | ns | 0.8431 |
| LIVRQ | 10 | 0.9247 | 0.2696 | 3 | ns | 0.984 |
| LIVRQ | 1 | 1.0000 | 0.3311 | 3 | | |
| RQNAC | 40 | 0.3958 | 0.0947 | 3 | * | 0.0109 |
| RQNAC | 30 | 0.4433 | 0.1317 | 3 | * | 0.0177 |
| RQNAC | 20 | 0.4936 | 0.1079 | 3 | * | 0.0297 |
| RQNAC | 10 | 0.5729 | 0.1741 | 3 | ns | 0.0674 |
| RQNAC | 1 | 1.0000 | 0.3440 | 3 | | |
| N-Acetyl Cysteine | 40 | 0.5716 | 0.2306 | 3 | ns | 0.2067 |
| N-Acetyl Cysteine | 20 | 0.6121 | 0.1718 | 3 | ns | 0.2729 |
| N-Acetyl Cysteine | 10 | 0.7354 | 0.2816 | 3 | ns | 0.5703 |
| N-Acetyl Cysteine | 5 | 0.7141 | 0.2509 | 3 | ns | 0.5098 |
| N-Acetyl Cysteine | 0 | 1.0000 | 0.3472 | 3 | | |

TABLE 65

Changes in IL-6 cytokine secretion for donor 1 upon administration of single amino acid compositions

| Amino Acid Supplement | Conc. (µM) | Fold Change IL-6 Secretion Normalized Per Cell | | Number of values | Signifi-cance | P-value |
|---|---|---|---|---|---|---|
| | | Mean | Std. Deviation | | | |
| Valine | 23420 | 1.0404 | 0.2175 | 3 | ns | 0.9949 |
| Valine | 11710 | 0.9562 | 0.3332 | 3 | ns | 0.9935 |
| Valine | 4684 | 0.9790 | 0.1777 | 3 | ns | 0.9993 |
| Valine | 234 | 1.0000 | 0.2868 | 3 | | |
| Arginine | 5440 | 0.7776 | 0.1994 | 3 | ns | 0.6927 |
| Arginine | 2720 | 1.0231 | 0.4381 | 3 | ns | 0.9993 |
| Arginine | 1088 | 0.9828 | 0.2957 | 3 | ns | 0.9997 |
| Arginine | 109 | 1.0000 | 0.1728 | 3 | | |
| Glutamine | 22484 | 0.5138 | 0.0818 | 3 | ** | 0.0046 |
| Glutamine | 11242 | 0.5136 | 0.1189 | 3 | ** | 0.0046 |
| Glutamine | 3747 | 0.5460 | 0.0891 | 3 | ** | 0.0072 |
| Glutamine | 749 | 0.6320 | 0.1181 | 3 | * | 0.0249 |
| Glutamine | 562 | 1.0000 | 0.2226 | 3 | | |
| Isoleucine | 6639 | 1.0859 | 0.1489 | 3 | ns | 0.764 |
| Isoleucine | 3320 | 1.1156 | 0.0776 | 3 | ns | 0.5903 |
| Isoleucine | 1328 | 1.0233 | 0.1536 | 3 | ns | 0.9922 |
| Isoleucine | 66 | 1.0000 | 0.1276 | 3 | | |
| Leucine | 15270 | 1.0767 | 0.0246 | 3 | ns | 0.853 |
| Leucine | 7635 | 1.1215 | 0.0872 | 3 | ns | 0.6249 |
| Leucine | 3054 | 1.1762 | 0.2273 | 3 | ns | 0.3655 |
| Leucine | 153 | 1.0000 | 0.1535 | 3 | | |
| N-Acetyl Cysteine | 10000 | 0.5716 | 0.2306 | 3 | ns | 0.2067 |
| N-Acetyl Cysteine | 5000 | 0.6121 | 0.1718 | 3 | ns | 0.2729 |

TABLE 65-continued

Changes in IL-6 cytokine secretion for donor 1 upon administration of single amino acid compositions

| Amino Acid Supplement | Conc. (µM) | Fold Change IL-6 Secretion Normalized Per Cell | | Number of values | Signifi-cance | P-value |
|---|---|---|---|---|---|---|
| | | Mean | Std. Deviation | | | |
| N-Acetyl Cysteine | 2500 | 0.7354 | 0.2816 | 3 | ns | 0.5703 |
| N-Acetyl Cysteine | 1000 | 0.7141 | 0.2509 | 3 | ns | 0.5098 |
| N-Acetyl Cysteine | 0 | 1.0000 | 0.3472 | 3 | | |

TABLE 66

Changes in IL-6 cytokine secretion for donor 2 upon administration of amino acid compositions

| Amino Acid Supplement | Conc. (X) | Fold Change IL-6 Secretion Normalized Per Cell | | Number of values | Signifi-cance | P-value |
|---|---|---|---|---|---|---|
| | | Mean | Std. Deviation | | | |
| LIVRQNAC | 40 | 0.9911 | 0.1150 | 3 | ns | 0.9998 |
| LIVRQNAC | 30 | 0.9560 | 0.0473 | 3 | ns | 0.9404 |
| LIVRQNAC | 20 | 1.0008 | 0.1450 | 3 | ns | 0.9999 |
| LIVRQNAC | 10 | 1.0845 | 0.0707 | 3 | ns | 0.6567 |
| LIVRQNAC | 1 | 1.0000 | 0.0553 | 3 | | |
| LIVRQNAC + G | 40 | 0.8055 | 0.1705 | 3 | ns | 0.4153 |
| LIVRQNAC + G | 30 | 0.8218 | 0.1567 | 3 | ns | 0.4855 |
| LIVRQNAC + G | 20 | 0.9236 | 0.1642 | 3 | ns | 0.9342 |
| LIVRQNAC + G | 10 | 1.1076 | 0.2097 | 3 | ns | 0.8216 |
| LIVRQNAC + G | 1 | 1.0000 | 0.0416 | 3 | | |
| LIVRQNAC + S | 40 | 0.9508 | 0.0933 | 3 | ns | 0.967 |
| LIVRQNAC + S | 30 | 0.8581 | 0.0364 | 3 | ns | 0.4836 |
| LIVRQNAC + S | 20 | 0.8289 | 0.0765 | 3 | ns | 0.3356 |
| LIVRQNAC + S | 10 | 0.8487 | 0.1018 | 3 | ns | 0.432 |
| LIVRQNAC + S | 1 | 1.0000 | 0.2312 | 3 | | |
| LIV | 40 | 0.9122 | 0.0773 | 3 | ns | 0.8233 |
| LIV | 30 | 1.0994 | 0.0987 | 3 | ns | 0.7586 |
| LIV | 20 | 1.0400 | 0.2330 | 3 | ns | 0.9857 |
| LIV | 10 | 0.9579 | 0.1077 | 3 | ns | 0.9828 |
| LIV | 1 | 1.0000 | 0.0540 | 3 | | |
| LIVRQ | 40 | 0.9327 | 0.0639 | 3 | ns | 0.8313 |
| LIVRQ | 30 | 0.8421 | 0.1125 | 3 | ns | 0.2361 |
| LIVRQ | 20 | 0.7871 | 0.0932 | 3 | ns | 0.0841 |
| LIVRQ | 10 | 0.8693 | 0.0750 | 3 | ns | 0.3744 |
| LIVRQ | 1 | 1.0000 | 0.1428 | 3 | | |
| RQNAC | 40 | 0.8711 | 0.0816 | 3 | ns | 0.5267 |
| RQNAC | 30 | 0.7460 | 0.1133 | 3 | ns | 0.0843 |
| RQNAC | 20 | 0.7838 | 0.0708 | 3 | ns | 0.1544 |
| RQNAC | 10 | 0.8781 | 0.1566 | 3 | ns | 0.5705 |
| RQNAC | 1 | 1.0000 | 0.1557 | 3 | | |
| N-Acetyl Cysteine | 40 | 0.7064 | 0.0418 | 3 | ns | 0.0508 |
| N-Acetyl Cysteine | 20 | 0.8111 | 0.1049 | 3 | ns | 0.2549 |
| N-Acetyl Cysteine | 10 | 0.9180 | 0.2230 | 3 | ns | 0.8353 |
| N-Acetyl Cysteine | 5 | 0.9161 | 0.1067 | 3 | ns | 0.8252 |
| N-Acetyl Cysteine | 0 | 1.0000 | 0.0632 | 3 | | |

TABLE 67

Changes in IL-6 cytokine secretion for donor 2 upon administration of single amino acid compositions

| | | Fold Change IL-6 Secretion Normalized Per Cell | | | | |
|---|---|---|---|---|---|---|
| Amino Acid Supplement | Conc. (μM) | Mean | Std. Deviation | Number of values | Signifi-cance | P-value |
| Valine | 23420 | 0.9015 | 0.0930 | 3 | ns | 0.4967 |
| Valine | 11710 | 0.9218 | 0.1179 | 3 | ns | 0.6516 |
| Valine | 4684 | 1.0383 | 0.1014 | 3 | ns | 0.9291 |
| Valine | 234 | 1.0000 | 0.0696 | 3 | | |
| Arginine | 5440 | 0.8895 | 0.0897 | 3 | ns | 0.547 |
| Arginine | 2720 | 0.9401 | 0.1611 | 3 | ns | 0.8654 |
| Arginine | 1088 | 0.9924 | 0.0692 | 3 | ns | 0.9996 |
| Arginine | 109 | 1.0000 | 0.1263 | 3 | | |
| Glutamine | 22484 | 0.5993 | 0.0611 | 3 | **** | 0.0001 |
| Glutamine | 11242 | 0.6478 | 0.0371 | 3 | **** | 0.0001 |
| Glutamine | 3747 | 0.7100 | 0.0356 | 3 | *** | 0.0003 |
| Glutamine | 749 | 0.7673 | 0.0222 | 3 | ** | 0.0017 |
| Glutamine | 562 | 1.0000 | 0.1027 | 6 | | |
| Isoleucine | 6639 | 1.1648 | 0.1125 | 3 | ns | 0.1448 |
| Isoleucine | 3320 | 0.9096 | 0.0916 | 3 | ns | 0.5304 |
| Isoleucine | 1328 | 1.1020 | 0.0987 | 3 | ns | 0.4446 |
| Isoleucine | 66 | 1.0000 | 0.0641 | 3 | | |
| Leucine | 15270 | 1.0183 | 0.1155 | 3 | ns | 0.9795 |
| Leucine | 7635 | 0.9574 | 0.0590 | 3 | ns | 0.8187 |
| Leucine | 3054 | 1.0011 | 0.0618 | 3 | ns | 0.9999 |
| Leucine | 153 | 1.0000 | 0.0277 | 3 | | |
| N-Acetyl Cysteine | 10000 | 0.7064 | 0.0418 | 3 | ns | 0.0508 |
| N-Acetyl Cysteine | 5000 | 0.8111 | 0.1049 | 3 | ns | 0.2549 |
| N-Acetyl Cysteine | 2500 | 0.9180 | 0.2230 | 3 | ns | 0.8353 |
| N-Acetyl Cysteine | 1000 | 0.9161 | 0.1067 | 3 | ns | 0.8252 |
| N-Acetyl Cysteine | 0 | 1.0000 | 0.0632 | 3 | | |

Example 12: TGFβ1 Fibrogenic Gene Expression of Hepatic Stellate Cell

Primary human hepatic stellate cells were obtained from Samsara Sciences based on the following criteria for selecting donors: adult age (between 18 and 50 years), normal BMI (>18.5 and <25), and absence of confounding liver disease. Cells grown in Complete HSC Medium to ~80% confluence in T75 or T150 flasks below passage 10 were seeded into sterile, collagen I coated, 96-well optical plastic microplates (ThermoScientific, 152036) at 6000 cells per well (~1250 cells per cm2) and incubated overnight at 37° C., 5% CO2 in a humidified incubator in DMEM with 2% Fetal Bovine Serum and 1% Antibiotic-Antimycotic.

After the overnight incubation, plates were removed from the incubator and the medium was gently pipetted off and washed twice with 150 μL per well DPBS. The DPBS was removed and the pretreatment medium (±single amino acid dropout, 1XHMDB DMEM+1% Antibiotic-Antimycotic, 10 mM HEPES, ±supplemental amino acid dose; see experiment for medium composition) was applied to the cells at 150 μL per well. Plates were returned to the incubator for 10.5 hours.

After 10.5 hour pretreatment, the medium was removed from the cells, and the same pretreatment medium, now supplemented with 3 ng/mL TGFβ1, was applied. Each plate contained 3 ng/mL TGFβ1 in 1× human plasma amino acid (HMDB or PAA) concentration medium, 0 ng/mL in 1XHMDB, and 3 ng/mL TGFβ1+20 μM Silybin in 1XHMDB to serve as controls. Plates were then incubated for 24 hours at 37° C., 5% CO2.

After 24 hour stimulus, supernatant was removed and frozen at −80° C. in two separate aliquots. The cells were then washed with 125 μL per well Buffer FCW (FastLane Cell Multiplex NR Kit, Qiagen, 216713). The wash buffer was immediately removed and 50 μL of Cell Processing Mix (containing genomic DNA Wipeout buffer) was applied to lyse cells, incubating for 10 minutes at room temperature. RNA lysate was then transferred to 96-well qPCR plates, sealed, and gDNA was digested on thermal cycler at 75° C. for 5 minutes. RNA lysate was frozen at −80° C.

Each 20 μL one-step RT-qPCR reaction contained 4 μL of RNA lysate. Gene expression of Col1a1, Timp2, and Gapdh were multiplexed using the HEX, Cy5, and FAM fluorescent channels, respectively, with commercially available primer-probe mixes (the Human Col1a1 Primer-Probe Set, HEX; the Human Timp2 Primer-Probe Set, Cy5; and the Human Gapdh Primer-Probe Set, FAM from IDT). Gene expression was evaluated using the ΔΔCq method within each single amino acid dropout and supplementation by normalizing to its own 1×HMDB concentration.

Human Procollagen Iα1 was measured from the supernatant by ELISA (Human Pro-Collagen I alpha 1 DuoSet ELISA, R&D Systems) at 1/100 dilution in 1× Reagent Diluent (Reagent Ancillary Kit 2, R&D Systems).

Results

Col1a1 Gene Expression

Tables 68, 69, 69-1, 69-2, 69-3, and 69-4 show the mean fold change in Col1a1 gene expression in primary human hepatic stellate cells from three different healthy donors. LIVRQNAC and LIVRQNAC+S showed significantly decreased Col1a1 gene expression in two of three donors. LIVRQNAC+G and RQNAC showed significantly decreased Col1a1 expression in all three donors. LIVRQ showed a significant change in Col1a1 gene expression in only one donor. LIV alone did not significantly change Col1a1 gene expression.

Each of leucine, isoleucine, valine, and arginine did not significantly change Col1a1 gene expression in any donor when the amino acid was administered alone. Glutamine decreased Col1a1 gene expression in two of three donors. N-acetyl cysteine significantly reduced Col1a1 gene expression in all three donors.

TABLE 68

Fold change of Col1a1 gene expression after administration of an amino acid composition, normalized to Gapdh expression in a first donor

| | | Col1a1 Fold Expression Relative to Control | | | | |
|---|---|---|---|---|---|---|
| Amino Acid Supplement | Conc. (X) | Mean | Std. Deviation | Number of values | P-value* | Signifi-cance |
| LIVRQNAC | 40 | 0.91 | 0.08 | 4 | ns | 0.401 |
| LIVRQNAC | 30 | 0.87 | 0.10 | 4 | ns | 0.1073 |
| LIVRQNAC | 20 | 0.88 | 0.04 | 4 | ns | 0.1483 |
| LIVRQNAC | 10 | 0.90 | 0.08 | 4 | ns | 0.3035 |
| LIVRQNAC | 1 | 1.00 | 0.10 | 4 | | |
| LIVRQNAC + G | 40 | 0.73 | 0.15 | 4 | ** | 0.0053 |
| LIVRQNAC + G | 30 | 0.79 | 0.08 | 4 | * | 0.0252 |
| LIVRQNAC + G | 20 | 0.84 | 0.08 | 4 | ns | 0.1181 |
| LIVRQNAC + G | 10 | 0.79 | 0.11 | 4 | * | 0.0286 |
| LIVRQNAC + G | 1 | 1.00 | 0.03 | 4 | | |
| LIVRQNAC + S | 40 | 0.79 | 0.05 | 4 | * | 0.0325 |
| LIVRQNAC + S | 30 | 0.86 | 0.13 | 4 | ns | 0.1848 |
| LIVRQNAC + S | 20 | 0.96 | 0.10 | 4 | ns | 0.9287 |
| LIVRQNAC + S | 10 | 0.85 | 0.12 | 4 | ns | 0.1566 |
| LIVRQNAC + S | 1 | 1.00 | 0.10 | 4 | | |

TABLE 68-continued

Fold change of Col1a1 gene expression after administration of an amino acid composition, normalized to Gapdh expression in a first donor

| | | Col1a1 Fold Expression Relative to Control | | | | |
|---|---|---|---|---|---|---|
| Amino Acid Supplement | Conc. (X) | Mean | Std. Deviation | Number of values | P-value* | Significance |
| LIV | 40 | 0.93 | 0.03 | 4 | ns | 0.5561 |
| LIV | 30 | 1.04 | 0.07 | 4 | ns | 0.8872 |
| LIV | 20 | 1.04 | 0.09 | 4 | ns | 0.9069 |
| LIV | 10 | 1.05 | 0.10 | 4 | ns | 0.8156 |
| LIV | 1 | 1.00 | 0.07 | 4 | | |
| LIVRQ | 40 | 0.75 | 0.03 | 4 | *** | 0.001 |
| LIVRQ | 30 | 0.73 | 0.05 | 4 | *** | 0.0004 |
| LIVRQ | 20 | 0.80 | 0.03 | 4 | ** | 0.0054 |
| LIVRQ | 10 | 0.84 | 0.08 | 4 | * | 0.0208 |
| LIVRQ | 1 | 1.01 | 0.13 | 4 | | |
| RQNAC | 40 | 0.51 | 0.07 | 4 | **** | 0.0001 |
| RQNAC | 30 | 0.49 | 0.02 | 4 | **** | 0.0001 |
| RQNAC | 20 | 0.59 | 0.04 | 4 | **** | 0.0001 |
| RQNAC | 10 | 0.68 | 0.07 | 4 | **** | 0.0001 |
| RQNAC | 1 | 1.00 | 0.11 | 4 | | |
| N-Acetyl Cysteine | 40 | 0.76 | 0.06 | 4 | ** | 0.0011 |
| N-Acetyl Cysteine | 20 | 1.02 | 0.08 | 4 | ns | 0.9921 |
| N-Acetyl Cysteine | 10 | 1.07 | 0.08 | 4 | ns | 0.5517 |
| N-Acetyl Cysteine | 5 | 1.00 | 0.08 | 4 | ns | 0.9999 |
| N-Acetyl Cysteine | 0 | 1.00 | 0.06 | 4 | | |

TABLE 69

Fold change of Col1a1 gene expression after administration of a single amino acid composition, normalized to Gapdh expression in the first donor

| | | Col1a1 Fold Expression Relative to Control | | | | |
|---|---|---|---|---|---|---|
| Amino Acid Supplement | Conc. (μM) | Mean | Std. Deviation | Number of values | P-value* | Significance |
| Valine | 23420 | 1.00 | 0.05 | 4 | ns | 0.9996 |
| Valine | 11710 | 1.09 | 0.17 | 4 | ns | 0.5528 |
| Valine | 4684 | 1.05 | 0.11 | 4 | ns | 0.8851 |
| Valine | 234 | 1.00 | 0.08 | 4 | | |
| Arginine | 5440 | 1.12 | 0.18 | 4 | ns | 0.2151 |
| Arginine | 2720 | 1.03 | 0.03 | 4 | ns | 0.9625 |
| Arginine | 1088 | 0.99 | 0.06 | 4 | ns | 0.9989 |
| Arginine | 109 | 1.00 | 0.03 | 4 | | |
| Glutamine | 22484 | 0.53 | 0.01 | 4 | **** | 0.0001 |
| Glutamine | 11242 | 0.62 | 0.05 | 4 | **** | 0.0001 |
| Glutamine | 3747 | 0.70 | 0.03 | 3 | **** | 0.0001 |
| Glutamine | 749 | 1.00 | 0.07 | 4 | ns | 0.9999 |
| Glutamine | 562 | 1.00 | 0.07 | 3 | | |
| Isoleucine | 6639 | 1.11 | 0.07 | 4 | ns | 0.7553 |
| Isoleucine | 3320 | 1.10 | 0.14 | 4 | ns | 0.7944 |
| Isoleucine | 1328 | 1.05 | 0.22 | 4 | ns | 0.9831 |
| Isoleucine | 66 | 1.01 | 0.21 | 4 | | |
| Leucine | 15270 | 0.99 | 0.10 | 4 | ns | 0.994 |
| Leucine | 7635 | 1.12 | 0.16 | 4 | ns | 0.5049 |
| Leucine | 3054 | 1.11 | 0.15 | 4 | ns | 0.5499 |
| Leucine | 153 | 1.00 | 0.11 | 4 | | |
| N-Acetyl Cysteine | 10000 | 0.76 | 0.06 | 4 | ** | 0.0011 |
| N-Acetyl Cysteine | 5000 | 1.02 | 0.08 | 4 | ns | 0.9921 |
| N-Acetyl Cysteine | 2500 | 1.07 | 0.08 | 4 | ns | 0.5517 |

TABLE 69-continued

Fold change of Col1a1 gene expression after administration of a single amino acid composition, normalized to Gapdh expression in the first donor

| | | Col1a1 Fold Expression Relative to Control | | | | |
|---|---|---|---|---|---|---|
| Amino Acid Supplement | Conc. (μM) | Mean | Std. Deviation | Number of values | P-value* | Significance |
| N-Acetyl Cysteine | 1000 | 1.00 | 0.08 | 4 | ns | 0.9999 |
| N-Acetyl Cysteine | 0 | 1.00 | 0.06 | 4 | | |

TABLE 69-1

Fold change of Col1a1 gene expression after administration of an amino acid composition, normalized to Gapdh expression in the second donor.

| | | Col1a1 Fold Expression Relative to Control | | | | |
|---|---|---|---|---|---|---|
| Amino Acid Supplement | Conc. (X) | Mean | Std. Deviation | Number of values | P-value* | Significance |
| LIVRQNAC | 40 | 0.72 | 0.05 | 4 | **** | 0.0001 |
| LIVRQNAC | 30 | 0.72 | 0.02 | 4 | **** | 0.0001 |
| LIVRQNAC | 20 | 0.70 | 0.03 | 4 | **** | 0.0001 |
| LIVRQNAC | 10 | 0.71 | 0.08 | 4 | **** | 0.0001 |
| LIVRQNAC | 1 | 1.00 | 0.02 | 4 | | |
| LIVRQNAC + G | 40 | 0.60 | 0.09 | 4 | **** | 0.0001 |
| LIVRQNAC + G | 30 | 0.68 | 0.07 | 4 | *** | 0.0001 |
| LIVRQNAC + G | 20 | 0.71 | 0.09 | 4 | *** | 0.0003 |
| LIVRQNAC + G | 10 | 0.69 | 0.06 | 4 | *** | 0.0002 |
| LIVRQNAC + G | 1 | 1.00 | 0.07 | 4 | | |
| LIVRQNAC + S | 40 | 0.66 | 0.02 | 4 | **** | 0.0001 |
| LIVRQNAC + S | 30 | 0.69 | 0.06 | 4 | **** | 0.0001 |
| LIVRQNAC + S | 20 | 0.76 | 0.05 | 4 | *** | 0.0002 |
| LIVRQNAC + S | 10 | 0.77 | 0.04 | 4 | *** | 0.0003 |
| LIVRQNAC + S | 1 | 1.00 | 0.11 | 4 | | |
| LIV | 40 | 1.20 | 0.21 | 4 | ns | 0.1032 |
| LIV | 30 | 1.10 | 0.09 | 4 | ns | 0.6074 |
| LIV | 20 | 1.10 | 0.04 | 4 | ns | 0.6031 |
| LIV | 10 | 1.02 | 0.08 | 4 | ns | 0.9981 |
| LIV | 1 | 1.00 | 0.11 | 4 | | |
| LIVRQ | 40 | 1.23 | 0.13 | 4 | ns | 0.1945 |
| LIVRQ | 30 | 1.12 | 0.13 | 4 | ns | 0.7176 |
| LIVRQ | 20 | 1.08 | 0.24 | 4 | ns | 0.8874 |
| LIVRQ | 10 | 1.14 | 0.16 | 4 | ns | 0.5632 |
| LIVRQ | 1 | 1.00 | 0.11 | 4 | | |
| RQNAC | 40 | 0.54 | 0.03 | 4 | **** | 0.0001 |
| RQNAC | 30 | 0.55 | 0.06 | 4 | **** | 0.0001 |
| RQNAC | 20 | 0.58 | 0.04 | 4 | **** | 0.0001 |
| RQNAC | 10 | 0.73 | 0.04 | 4 | *** | 0.0007 |
| RQNAC | 1 | 1.01 | 0.16 | 4 | | |
| N-Acetyl Cysteine | 40 | 0.57 | 0.06 | 4 | **** | 0.0001 |
| N-Acetyl Cysteine | 20 | 0.69 | 0.06 | 4 | **** | 0.0001 |
| N-Acetyl Cysteine | 10 | 0.69 | 0.09 | 4 | *** | 0.0001 |
| N-Acetyl Cysteine | 5 | 0.69 | 0.05 | 4 | *** | 0.0001 |
| N-Acetyl Cysteine | 0 | 1.00 | 0.10 | 4 | | |

TABLE 69-2

Fold change of Col1a1 gene expression after administration of a single amino acid composition, normalized to Gapdh expression in second donor.

| | | Col1a1 Fold Expression Relative to Control | | | | |
|---|---|---|---|---|---|---|
| Amino Acid Supplement | Conc. (µM) | Mean | Std. Deviation | Number of values | P-value* | Significance |
| Valine | 23420 | 1.05 | 0.03 | 4 | ns | 0.9194 |
| Valine | 11710 | 0.98 | 0.11 | 4 | ns | 0.9827 |
| Valine | 4684 | 1.05 | 0.18 | 4 | ns | 0.8893 |
| Valine | 234 | 1.00 | 0.11 | 4 | | |
| Arginine | 5440 | 1.15 | 0.10 | 4 | ns | 0.2773 |
| Arginine | 2720 | 1.15 | 0.14 | 4 | ns | 0.2759 |
| Arginine | 1088 | 0.99 | 0.15 | 4 | ns | 0.9938 |
| Arginine | 109 | 1.00 | 0.12 | 4 | | |
| Glutamine | 22484 | 0.86 | 0.07 | 4 | ns | 0.1411 |
| Glutamine | 11242 | 0.91 | 0.09 | 4 | ns | 0.4365 |
| Glutamine | 3747 | 1.04 | 0.14 | 4 | ns | 0.9811 |
| Glutamine | 749 | 1.02 | 0.13 | 4 | ns | 0.9988 |
| Glutamine | 562 | 1.01 | 0.12 | 8 | | |
| Isoleucine | 6639 | 1.03 | 0.07 | 4 | ns | 0.8931 |
| Isoleucine | 3320 | 0.99 | 0.08 | 4 | ns | 0.9841 |
| Isoleucine | 1328 | 0.97 | 0.10 | 4 | ns | 0.9157 |
| Isoleucine | 66 | 1.00 | 0.02 | 4 | | |
| Leucine | 15270 | 1.13 | 0.14 | 4 | ns | 0.0811 |
| Leucine | 7635 | 1.05 | 0.05 | 4 | ns | 0.7277 |
| Leucine | 3054 | 1.06 | 0.03 | 4 | ns | 0.5342 |
| Leucine | 153 | 1.00 | 0.03 | 4 | | |
| N-Acetyl Cysteine | 10000 | 0.57 | 0.06 | 4 | **** | 0.0001 |
| N-Acetyl Cysteine | 5000 | 0.69 | 0.06 | 4 | **** | 0.0001 |
| N-Acetyl Cysteine | 2500 | 0.69 | 0.09 | 4 | *** | 0.0001 |
| N-Acetyl Cysteine | 1000 | 0.69 | 0.05 | 4 | *** | 0.0001 |
| N-Acetyl Cysteine | 0 | 1.00 | 0.10 | 4 | | |

TABLE 69-3

Fold change of Col1a1 gene expression after administration of an amino acid composition, normalized to Gapdh expression in third donor.

| | | Col1a1 Fold Expression Relative to Control | | | | |
|---|---|---|---|---|---|---|
| Amino Acid Supplement | Conc. (X) | Mean | Std. Deviation | Number of values | P-value* | Significance |
| LIVRQNAC | 40 | 0.81 | 0.09 | 4 | ** | 0.008 |
| LIVRQNAC | 30 | 0.70 | 0.06 | 4 | *** | 0.0001 |
| LIVRQNAC | 20 | 0.79 | 0.08 | 4 | ** | 0.0035 |
| LIVRQNAC | 10 | 0.79 | 0.07 | 4 | ** | 0.0039 |
| LIVRQNAC | 1 | 1.00 | 0.06 | 4 | | |
| LIVRQNAC + G | 40 | 0.63 | 0.10 | 4 | *** | 0.0002 |
| LIVRQNAC + G | 30 | 0.64 | 0.02 | 4 | *** | 0.0003 |
| LIVRQNAC + G | 20 | 0.75 | 0.14 | 4 | ** | 0.005 |
| LIVRQNAC + G | 10 | 0.71 | 0.11 | 4 | ** | 0.0017 |
| LIVRQNAC + G | 1 | 1.00 | 0.03 | 4 | | |
| LIVRQNAC + S | 40 | 0.79 | 0.11 | 4 | * | 0.0316 |
| LIVRQNAC + S | 30 | 0.79 | 0.04 | 4 | * | 0.0309 |
| LIVRQNAC + S | 20 | 0.77 | 0.09 | 4 | * | 0.0208 |
| LIVRQNAC + S | 10 | 0.85 | 0.09 | 4 | ns | 0.1434 |
| LIVRQNAC + S | 1 | 1.01 | 0.16 | 4 | | |
| LIV | 40 | 1.00 | 0.16 | 4 | ns | 0.9999 |
| LIV | 30 | 0.94 | 0.16 | 4 | ns | 0.8685 |
| LIV | 20 | 1.08 | 0.08 | 4 | ns | 0.6767 |
| LIV | 10 | 0.93 | 0.04 | 4 | ns | 0.7713 |
| LIV | 1 | 1.00 | 0.05 | 4 | | |
| LIVRQ | 40 | 1.00 | 0.05 | 4 | ns | 0.9999 |
| LIVRQ | 30 | 1.07 | 0.13 | 4 | ns | 0.8753 |
| LIVRQ | 20 | 1.10 | 0.13 | 4 | ns | 0.6983 |
| LIVRQ | 10 | 1.05 | 0.21 | 4 | ns | 0.9641 |
| LIVRQ | 1 | 1.00 | 0.07 | 4 | | |
| RQNAC | 40 | 0.64 | 0.05 | 4 | *** | 0.0003 |
| RQNAC | 30 | 0.70 | 0.13 | 4 | ** | 0.0018 |
| RQNAC | 20 | 0.66 | 0.05 | 4 | *** | 0.0005 |
| RQNAC | 10 | 0.87 | 0.15 | 4 | ns | 0.2175 |
| RQNAC | 1 | 1.00 | 0.04 | 4 | | |
| N-Acetyl Cysteine | 40 | 0.62 | 0.01 | 4 | *** | 0.0005 |
| N-Acetyl Cysteine | 20 | 0.73 | 0.10 | 4 | ** | 0.0083 |
| N-Acetyl Cysteine | 10 | 0.82 | 0.09 | 4 | ns | 0.0909 |
| N-Acetyl Cysteine | 5 | 0.91 | 0.12 | 4 | ns | 0.4954 |
| N-Acetyl Cysteine | 0 | 1.01 | 0.16 | 4 | | |

TABLE 69-4

Fold change of Col1a1 gene expression after administration of a single amino acid composition, normalized to Gapdh expression in second donor.

| | | Col1a1 Fold Expression Relative to Control | | | | |
|---|---|---|---|---|---|---|
| Amino Acid Supplement | Conc. (µM) | Mean | Std. Deviation | Number of values | P-value* | Significance |
| Valine | 23420 | 1.13 | 0.12 | 4 | ns | 0.7199 |
| Valine | 11710 | 1.27 | 0.31 | 4 | ns | 0.1735 |
| Valine | 4684 | 1.22 | 0.16 | 4 | ns | 0.3247 |
| Valine | 234 | 1.01 | 0.13 | 4 | | |
| Arginine | 5440 | 1.02 | 0.09 | 4 | ns | 0.9702 |
| Arginine | 2720 | 0.99 | 0.09 | 4 | ns | 0.9973 |
| Arginine | 1088 | 0.95 | 0.02 | 4 | ns | 0.5384 |
| Arginine | 109 | 1.00 | 0.05 | 4 | | |
| Glutamine | 22484 | 0.81 | 0.11 | 4 | * | 0.0113 |
| Glutamine | 11242 | 0.81 | 0.11 | 4 | ** | 0.0087 |
| Glutamine | 3747 | 1.00 | 0.03 | 4 | ns | 0.9999 |
| Glutamine | 749 | 0.96 | 0.07 | 4 | ns | 0.8697 |
| Glutamine | 562 | 1.00 | 0.10 | 8 | | |
| Isoleucine | 6639 | 1.03 | 0.04 | 4 | ns | 0.9974 |
| Isoleucine | 3320 | 0.94 | 0.13 | 4 | ns | 0.8329 |
| Isoleucine | 1328 | 0.94 | 0.17 | 4 | ns | 0.7947 |
| Isoleucine | 66 | 1.02 | 0.20 | 4 | | |
| Leucine | 15270 | 1.07 | 0.12 | 4 | ns | 0.9535 |
| Leucine | 7635 | 1.00 | 0.16 | 4 | ns | 0.998 |
| Leucine | 3054 | 1.08 | 0.23 | 4 | ns | 0.9185 |
| Leucine | 153 | 1.01 | 0.19 | 4 | | |
| N-Acetyl Cysteine | 10000 | 0.62 | 0.01 | 4 | *** | 0.0005 |
| N-Acetyl Cysteine | 5000 | 0.73 | 0.10 | 4 | ** | 0.0083 |
| N-Acetyl Cysteine | 2500 | 0.82 | 0.09 | 4 | ns | 0.0909 |
| N-Acetyl Cysteine | 1000 | 0.91 | 0.12 | 4 | ns | 0.4954 |
| N-Acetyl Cysteine | 0 | 1.01 | 0.16 | 4 | | |

Procollagen Iα1 Secretion

Tables 70, 71, 71-1, 71-2, 71-3, and 71-4 show the fold change in procollagen Iα1 in primary human hepatic stellate cells from three different healthy donors normalized to their respective baseline amino acid conditions. Statistical significance calculated by one-way ANOVA with Dunnett's multiple comparison test within each treatment group. The combination LIV significantly increased procollagen Iα1 secretion in all three donors. The addition of arginine (R) and glutamine (Q) to a combination of LIV counteracted the profibrogenic effect of LIV alone. LIVRQNAC, LIVRQNAC+G, LIVRQNAC+S and RQNAC significantly decreased procollagen Iα1 secretion in all three donors. Individually, N-acetyl cysteine was shown to significantly decrease procollagen Iα1 secretion in two of the three donors. Valine significantly increased procollagen Iα1 secretion in only one of two donors, while isoleucine and arginine significantly increased procollagen Iα1 secretion in two of three donors. In other words, glutamine administered individually did not have a significant impact on procollagen Iα1 secretion. As such, the reduction of the profibrogenic effect of LIV with arginine and glutamine relative to that of LIV alone would not have been expected based on the effect of individual amino acid treatments.

TABLE 70

Fold change of procollagen 1α1 secretion after administration of an amino acid composition in a first donor

| Amino Acid Supplement | Conc. (X) | Procollagen Iα1 Secretion (Fold Change of 1X) | | | | |
|---|---|---|---|---|---|---|
| | | Mean | Std. Deviation | Number of values | P-value* | Significance |
| LIVRQNAC | 40 | 0.6283 | 0.0585 | 3 | *** | 0.0001 |
| LIVRQNAC | 30 | 0.5975 | 0.0709 | 3 | **** | 0.0001 |
| LIVRQNAC | 20 | 0.6504 | 0.0622 | 4 | *** | 0.0001 |
| LIVRQNAC | 10 | 0.8287 | 0.0936 | 4 | * | 0.0277 |
| LIVRQNAC | 1 | 1.0000 | 0.0908 | 4 | | |
| LIVRQNAC + G | 40 | 0.5288 | 0.0402 | 3 | *** | 0.0006 |
| LIVRQNAC + G | 30 | 0.6297 | 0.0200 | 3 | ** | 0.0042 |
| LIVRQNAC + G | 20 | 0.5926 | 0.0634 | 4 | ** | 0.001 |
| LIVRQNAC + G | 10 | 0.7404 | 0.0920 | 4 | * | 0.0267 |
| LIVRQNAC + G | 1 | 1.0000 | 0.2151 | 4 | | |
| LIVRQNAC + S | 40 | 0.5900 | 0.0450 | 3 | *** | 0.0003 |
| LIVRQNAC + S | 30 | 0.5562 | 0.1242 | 3 | *** | 0.0002 |
| LIVRQNAC + S | 20 | 0.6844 | 0.0638 | 3 | ** | 0.0022 |
| LIVRQNAC + S | 10 | 0.7003 | 0.0946 | 3 | ** | 0.0032 |
| LIVRQNAC + S | 1 | 1.0000 | 0.0311 | 3 | | |
| LIV | 40 | 1.3017 | 0.1474 | 3 | ns | 0.0518 |
| LIV | 30 | 1.3358 | 0.1922 | 3 | * | 0.0305 |
| LIV | 20 | 1.2592 | 0.0747 | 3 | ns | 0.0997 |
| LIV | 10 | 1.0149 | 0.1089 | 3 | ns | 0.9997 |
| LIV | 1 | 1.0000 | 0.0828 | 3 | | |
| LIVRQ | 40 | 1.0070 | 0.1716 | 3 | ns | 0.9999 |
| LIVRQ | 30 | 1.0190 | 0.1103 | 3 | ns | 0.9983 |
| LIVRQ | 20 | 1.1403 | 0.0516 | 3 | ns | 0.3875 |
| LIVRQ | 10 | 1.0454 | 0.0908 | 3 | ns | 0.9609 |
| LIVRQ | 1 | 1.0000 | 0.0935 | 3 | | |
| RQNAC | 40 | 0.3622 | 0.0166 | 3 | **** | 0.0001 |
| RQNAC | 30 | 0.4232 | 0.0819 | 3 | **** | 0.0001 |
| RQNAC | 20 | 0.5819 | 0.0574 | 3 | *** | 0.0001 |
| RQNAC | 10 | 0.8181 | 0.0703 | 3 | * | 0.0313 |
| RQNAC | 1 | 1.0000 | 0.0967 | 3 | | |
| N-Acetyl Cysteine | 40 | 0.5076 | 0.0154 | 3 | **** | 0.0001 |
| N-Acetyl Cysteine | 20 | 0.6593 | 0.0914 | 3 | *** | 0.0003 |
| N-Acetyl Cysteine | 10 | 0.7939 | 0.0715 | 3 | ** | 0.01 |
| N-Acetyl Cysteine | 5 | 0.9175 | 0.0519 | 3 | ns | 0.3855 |
| N-Acetyl Cysteine | 0 | 1.0000 | 0.0686 | 3 | | |

TABLE 71

Fold change of procollagen 1α1 secretion after administration of a single amino acid composition in the first donor

| Amino Acid Supplement | Conc. (μM) | Procollagen Iα1 Secretion (Fold Change of 1X) | | | | |
|---|---|---|---|---|---|---|
| | | Mean | Std. Deviation | Number of values | P-value* | Significance |
| Valine | 23420 | 1.2139 | 0.0544 | 3 | ns | 0.1392 |
| Valine | 11710 | 1.2069 | 0.0881 | 3 | ns | 0.155 |
| Valine | 4684 | 1.1203 | 0.1908 | 3 | ns | 0.5111 |
| Valine | 234 | 1.0000 | 0.1389 | 4 | | |
| Arginine | 5440 | 1.0646 | 0.0939 | 3 | ns | 0.4155 |
| Arginine | 2720 | 1.1757 | 0.0466 | 3 | * | 0.01 |
| Arginine | 1088 | 1.0291 | 0.0615 | 4 | ns | 0.8428 |
| Arginine | 109 | 1.0000 | 0.0389 | 4 | | |
| Glutamine | 22484 | 1.0564 | 0.1293 | 3 | ns | 0.8468 |
| Glutamine | 11242 | 1.0888 | 0.0261 | 3 | ns | 0.5648 |
| Glutamine | 3747 | 1.0757 | 0.1003 | 4 | ns | 0.6356 |
| Glutamine | 749 | 0.9790 | 0.0836 | 4 | ns | 0.993 |
| Glutamine | 562 | 1.0000 | 0.0596 | 3 | | |
| Isoleucine | 6639 | 1.2144 | 0.1129 | 3 | ns | 0.0537 |
| Isoleucine | 3320 | 1.1366 | 0.0938 | 3 | ns | 0.2411 |
| Isoleucine | 1328 | 0.9229 | 0.0614 | 3 | ns | 0.6321 |
| Isoleucine | 66 | 1.0000 | 0.0953 | 3 | | |
| Leucine | 15270 | 1.1710 | 0.1043 | 3 | ns | 0.094 |
| Leucine | 7635 | 1.0915 | 0.0832 | 3 | ns | 0.4736 |
| Leucine | 3054 | 1.1410 | 0.1245 | 4 | ns | 0.1424 |
| Leucine | 153 | 1.0000 | 0.0481 | 4 | | |

TABLE 71-1

Fold change of procollagen 1α1 secretion after administration of an amino acid composition in the second donor

| Amino Acid Supplement | Conc. (X) | Procollagen Iα1 Secretion (Fold Change of 1X) | | | | |
|---|---|---|---|---|---|---|
| | | Mean | Std. Deviation | Number of values | P-value* | Significance |
| LIVRQNAC | 40 | 0.7465 | 0.0551 | 3 | ** | 0.0041 |
| LIVRQNAC | 30 | 0.6829 | 0.0991 | 3 | *** | 0.0007 |
| LIVRQNAC | 20 | 0.6922 | 0.0281 | 4 | *** | 0.0004 |
| LIVRQNAC | 10 | 0.7879 | 0.0748 | 4 | ** | 0.0085 |
| LIVRQNAC | 1 | 1.0000 | 0.1141 | 4 | | |
| LIVRQNAC + G | 40 | 0.6372 | 0.0267 | 3 | **** | 0.0001 |
| LIVRQNAC + G | 30 | 0.7347 | 0.0324 | 3 | **** | 0.0001 |
| LIVRQNAC + G | 20 | 0.6716 | 0.0552 | 4 | **** | 0.0001 |
| LIVRQNAC + G | 10 | 0.7823 | 0.0579 | 4 | *** | 0.0001 |
| LIVRQNAC + G | 1 | 1.0000 | 0.0580 | 4 | | |
| LIVRQNAC + S | 40 | 0.8756 | 0.0372 | 3 | ns | 0.1229 |
| LIVRQNAC + S | 30 | 0.7340 | 0.0432 | 3 | ** | 0.0019 |
| LIVRQNAC + S | 20 | 0.7405 | 0.0491 | 3 | ** | 0.0022 |
| LIVRQNAC + S | 10 | 0.7472 | 0.0710 | 3 | ** | 0.0027 |
| LIVRQNAC + S | 1 | 1.0000 | 0.1031 | 3 | | |
| LIV | 40 | 1.4409 | 0.0697 | 3 | **** | 0.0001 |
| LIV | 30 | 1.3679 | 0.0156 | 3 | *** | 0.0001 |
| LIV | 20 | 1.3418 | 0.1090 | 3 | *** | 0.0002 |
| LIV | 10 | 1.2176 | 0.0343 | 3 | ** | 0.0057 |
| LIV | 1 | 1.0000 | 0.0396 | 3 | | |
| LIVRQ | 40 | 0.9851 | 0.0534 | 3 | ns | 0.9965 |
| LIVRQ | 30 | 1.0185 | 0.0735 | 3 | ns | 0.9921 |
| LIVRQ | 20 | 0.9212 | 0.0215 | 3 | ns | 0.4893 |
| LIVRQ | 10 | 0.9558 | 0.0580 | 3 | ns | 0.8556 |
| LIVRQ | 1 | 1.0000 | 0.1134 | 3 | | |
| RQNAC | 40 | 0.6363 | 0.0432 | 3 | *** | 0.0002 |
| RQNAC | 30 | 0.6154 | 0.0196 | 3 | *** | 0.0001 |
| RQNAC | 20 | 0.7060 | 0.0851 | 3 | *** | 0.0009 |
| RQNAC | 10 | 0.8385 | 0.0248 | 3 | * | 0.041 |
| RQNAC | 1 | 1.0000 | 0.1071 | 3 | | |
| N-Acetyl Cysteine | 40 | 0.8383 | 0.0378 | 3 | ns | 0.4053 |

TABLE 71-1-continued

Fold change of procollagen 1α1 secretion after administration of an amino acid composition in the second donor

| Amino Acid Supplement | Conc. (X) | Mean | Std. Deviation | Number of values | P-value* | Significance |
|---|---|---|---|---|---|---|
| N-Acetyl Cysteine | 20 | 0.7378 | 0.1347 | 3 | ns | 0.1002 |
| N-Acetyl Cysteine | 10 | 0.8877 | 0.2282 | 3 | ns | 0.6842 |
| N-Acetyl Cysteine | 5 | 0.8387 | 0.0832 | 3 | ns | 0.407 |
| N-Acetyl Cysteine | 0 | 1.0000 | 0.0808 | 3 | | |

TABLE 71-2

Fold change of procollagen 1α1 secretion after administration of a single amino acid composition in the second donor

| Amino Acid Supplement | Conc. (μM) | Mean | Std. Deviation | Number of values | P-value* | Significance |
|---|---|---|---|---|---|---|
| Valine | 23420 | 1.3068 | 0.0963 | 3 | ** | 0.0019 |
| Valine | 11710 | 1.2877 | 0.1122 | 3 | ** | 0.0029 |
| Valine | 4684 | 1.2865 | 0.0717 | 4 | ** | 0.0018 |
| Valine | 234 | 1.0000 | 0.0589 | 4 | | |
| Arginine | 5440 | 1.1304 | 0.0187 | 3 | ns | 0.0937 |
| Arginine | 2720 | 1.0722 | 0.0791 | 3 | ns | 0.4483 |
| Arginine | 1088 | 1.0126 | 0.0822 | 4 | ns | 0.989 |
| Arginine | 109 | 1.0000 | 0.0778 | 4 | | |
| Glutamine | 22484 | 0.7143 | 0.0566 | 3 | ** | 0.0058 |
| Glutamine | 11242 | 0.7080 | 0.0246 | 3 | ** | 0.005 |
| Glutamine | 3747 | 0.7541 | 0.0860 | 4 | * | 0.0102 |
| Glutamine | 749 | 0.9191 | 0.1171 | 4 | ns | 0.5776 |
| Glutamine | 562 | 1.0000 | 0.1003 | 3 | | |
| Isoleucine | 6639 | 1.5423 | 0.1489 | 3 | ** | 0.006 |
| Isoleucine | 3320 | 1.4940 | 0.0238 | 3 | * | 0.0102 |
| Isoleucine | 1328 | 1.4811 | 0.2307 | 3 | * | 0.0117 |
| Isoleucine | 66 | 1.0000 | 0.1264 | 3 | | |
| Leucine | 15270 | 0.9518 | 0.0406 | 3 | ns | 0.9292 |
| Leucine | 7635 | 1.2628 | 0.1763 | 3 | ns | 0.0607 |
| Leucine | 3054 | 1.0781 | 0.1735 | 4 | ns | 0.7374 |
| Leucine | 153 | 1.0000 | 0.0681 | 4 | | |

TABLE 71-3

Fold change of procollagen 1α1 secretion after administration of an amino acid composition in the third donor

| Amino Acid Supplement | Conc. (X) | Mean | Std. Deviation | Number of values | P-value* | Significance |
|---|---|---|---|---|---|---|
| LIVRQNAC | 40 | 0.9052 | 0.0344 | 3 | ns | 0.5685 |
| LIVRQNAC | 30 | 0.7456 | 0.0895 | 3 | * | 0.0192 |
| LIVRQNAC | 20 | 0.7817 | 0.0680 | 4 | * | 0.03 |
| LIVRQNAC | 10 | 0.9774 | 0.1451 | 4 | ns | 0.9927 |
| LIVRQNAC | 1 | 1.0000 | 0.1116 | 4 | | |
| LIVRQNAC+G | 40 | 0.7040 | 0.0080 | 3 | ** | 0.002 |
| LIVRQNAC+G | 30 | 0.6249 | 0.0819 | 3 | *** | 0.0003 |
| LIVRQNAC+G | 20 | 0.6863 | 0.1334 | 4 | *** | 0.0006 |
| LIVRQNAC+G | 10 | 1.0068 | 0.0642 | 4 | ns | 0.9998 |
| LIVRQNAC+G | 1 | 1.0000 | 0.0724 | 4 | | |
| LIVRQNAC+S | 40 | 0.9190 | 0.0772 | 3 | ns | 0.3351 |
| LIVRQNAC+S | 30 | 0.8107 | 0.0596 | 3 | * | 0.0101 |

TABLE 71-3-continued

Fold change of procollagen 1α1 secretion after administration of an amino acid composition in the third donor

| Amino Acid Supplement | Conc. (X) | Procollagen Iα1 Secretion (Fold Change of 1X) | | | | |
|---|---|---|---|---|---|---|
| | | Mean | Std. Deviation | Number of values | P-value* | Significance |
| LIVRQNAC+S | 20 | 0.8878 | 0.0129 | 3 | ns | 0.1296 |
| LIVRQNAC+S | 10 | 0.9814 | 0.0458 | 3 | ns | 0.9852 |
| LIVRQNAC+S | 1 | 1.0000 | 0.0780 | 3 | | |
| LIV | 40 | 1.3233 | 0.0667 | 3 | ** | 0.0024 |
| LIV | 30 | 1.2510 | 0.1070 | 3 | * | 0.0125 |
| LIV | 20 | 1.2702 | 0.0639 | 3 | ** | 0.0079 |
| LIV | 10 | 1.1912 | 0.1049 | 3 | ns | 0.0532 |
| LIV | 1 | 1.0000 | 0.0521 | 3 | | |
| LIVRQ | 40 | 1.2020 | 0.1119 | 3 | ns | 0.1081 |
| LIVRQ | 30 | 1.1380 | 0.0955 | 3 | ns | 0.3407 |
| LIVRQ | 20 | 0.9489 | 0.1179 | 3 | ns | 0.9263 |
| LIVRQ | 10 | 1.0786 | 0.0764 | 3 | ns | 0.7564 |
| LIVRQ | 1 | 1.0000 | 0.1056 | 3 | | |
| RQNAC | 40 | 0.6590 | 0.0860 | 3 | ** | 0.0012 |
| RQNAC | 30 | 0.6708 | 0.0407 | 3 | ** | 0.0016 |
| RQNAC | 20 | 0.9135 | 0.1192 | 3 | ns | 0.5063 |
| RQNAC | 10 | 0.8783 | 0.0515 | 3 | ns | 0.245 |
| RQNAC | 1 | 1.0000 | 0.0740 | 3 | | |
| N-Acetyl Cysteine | 40 | 0.6962 | 0.0189 | 3 | * | 0.0125 |
| N-Acetyl Cysteine | 20 | 0.8521 | 0.0709 | 3 | ns | 0.2666 |
| N-Acetyl Cysteine | 10 | 0.9391 | 0.1250 | 3 | ns | 0.8641 |
| N-Acetyl Cysteine | 5 | 1.0897 | 0.1245 | 3 | ns | 0.6511 |
| N-Acetyl Cysteine | 0 | 1.0000 | 0.1133 | 3 | | |

TABLE 71-4

Fold change of procollagen 1α1 secretion after administration of a single amino acid composition in the third donor

| Amino Acid Supplement | Conc. (μM) | Procollagen Iα1 Secretion (Fold Change of 1X) | | | | |
|---|---|---|---|---|---|---|
| | | Mean | Std. Deviation | Number of values | P-value* | Significance |
| Valine | 23420 | 1.1139 | 0.1077 | 3 | ns | 0.5315 |
| Valine | 11710 | 1.0498 | 0.1773 | 3 | ns | 0.918 |
| Valine | 4684 | 1.0428 | 0.1036 | 4 | ns | 0.9323 |
| Valine | 234 | 1.0000 | 0.1203 | 4 | | |
| Arginine | 5440 | 1.2125 | 0.0862 | 3 | * | 0.0112 |
| Arginine | 2720 | 1.1314 | 0.0820 | 3 | ns | 0.1114 |
| Arginine | 1088 | 1.0623 | 0.0629 | 4 | ns | 0.5378 |
| Arginine | 109 | 1.0000 | 0.0760 | 4 | | |
| Glutamine | 22484 | 1.0121 | 0.0730 | 3 | ns | 0.9989 |
| Glutamine | 11242 | 1.1204 | 0.1056 | 3 | ns | 0.2356 |
| Glutamine | 3747 | 0.9734 | 0.0900 | 4 | ns | 0.9747 |
| Glutamine | 749 | 1.0317 | 0.0644 | 4 | ns | 0.9538 |
| Glutamine | 562 | 1.0000 | 0.0447 | 3 | | |
| Isoleucine | 6639 | 1.4465 | 0.0958 | 3 | ** | 0.0014 |
| Isoleucine | 3320 | 1.2703 | 0.0352 | 3 | * | 0.024 |
| Isoleucine | 1328 | 1.2687 | 0.0374 | 3 | * | 0.0247 |
| Isoleucine | 66 | 1.0000 | 0.1629 | 3 | | |
| Leucine | 15270 | 0.9892 | 0.0260 | 3 | ns | 0.9979 |
| Leucine | 7635 | 1.2027 | 0.0693 | 3 | ns | 0.0638 |
| Leucine | 3054 | 1.1399 | 0.1385 | 4 | ns | 0.1844 |
| Leucine | 153 | 1.0000 | 0.1077 | 4 | | |

Example 13: Cytokine Secretion in Primary Human Macrophages

Isolation of Peripheral Blood Mononuclear Cell (PBMC)

Unpurified buffy coats (Research Blood Components) were carefully poured into 50 mL centrifuge tubes and diluted with room temperature Dulbecco's Phosphate Buffered Saline (dPBS) with Calcium and Magnesium (Gibco). Diluted buffy coats were further divided into four total 50 mL centrifuge tubes at 20 mL per tube. Lymphocyte Separation Medium (Corning) was carefully pipetted to the bottom of each centrifuge tube. Mixtures were centrifuged at 850×g for 32 minutes at 20° C. with 0 deceleration and acceleration.

The PBMC layer was separated from other components after centrifugation and added to new 50 mL centrifuge tube containing 25 mL dPBS. Total volume was brought up to 50 mL with dPBS and centrifuged at 600×g for 10 minutes at 20° C. with acceleration of 9, deceleration of 5. Supernatant was carefully removed from cell pellets. The cell pellets were resuspended using 10 mL dPBS. Total volume was then brought up to 50 mL using dPBS and centrifuged at 450×g for 5 min at 20° C. with acceleration of 9, deceleration of 9. The supernatant removal and cell pellet resuspension was repeated again.

The supernatant was then carefully removed from cell pellets. Cell pellets were resuspended in 10 mL dPBS without calcium or magnesium and filtered through a 70 uM cell strainer. The total PBMC number was determined using a Cellometer K2 automated cell counter. A total of 5E6 cells were saved for flow cytometric analysis. Remaining cells were centrifuged at 490×g for 5 minutes at 20° C. with acceleration of 9, deceleration of 9.

CD14+ Cell Selection

CD14+ cells were selected using EasySep™ Human CD14 Positive Selection Kit II (STEMCELL Technologies). Cells were resuspended in cold EasySep™ Buffer (STEMCELL Technologies) at $1\times10^8$ cells/mL. A total of 100 uL/mL EasySep™ Human CD14 Positive Selection Cocktail II was added to the cell suspension, mixed, and incubated at room temperature for 10 minutes. A total of 100 uL/mL RapidSpheres were added to the mixture and incubated at room temperature for 3 minutes after mixing, then RoboSep buffer was added to bring up the total volume to 10 mL. The mixture in a 15 mL tube was placed in magnet and incubated at room temperature for 3 minutes. Supernatant was discarded and 10 mL fresh EasySep™ buffer was added to 15 mL tube. The addition of RoboSep buffer, mixing, and discarding of supernatant was was repeated two more times.

Negative and positive fractions were centrifuged at 490×g for 5 minutes at 20° C. with acceleration of 9, deceleration of 9, and resuspended in DMEM (Gibco) and 10% Heat Inactivated Fetal Bovine Serum (Atlanta Bio) and Penicillin/Streptomycin. Cells were counted and centrifuged again at 490×g for 5 minutes at 20° C. with acceleration of 9, deceleration of 9. After centrifugation, cell were resuspended in DMEM (Gibco) and 10% Heat Inactivated Fetal Bovine Serum (Atlanta Bio) and Penicillin/Streptomycin containing 500 U/mL GM- and plated at $1-2\times10^6$ cells/mL on 10 cm tissue culture plates. Cells were kept in 37° C., 5% CO2 in between feedings/harvest.

CD14+ Cell Feeding

Cells were fed every 3-4 days by removing media and unattached cells, centrifuging at 490×g for 5 minutes at 20 C with acceleration of 9, deceleration of 9, and resuspending in fresh DMEM (Gibco) and 10% Heat Inactivated Fetal Bovine Serum (Atlanta Bio) and Penicillin/Streptomycin-containing 500 U/mL GM-CSF. Resuspended cells were seeded back onto 10 cm tissue culture plates and incubated at 37° C., 5% CO2.

Macrophage Harvest

After complete cell attachment, culture supernatant was removed and cultures were washed 1× with 5 mL PBS. A total of 3 mL room temperature Cellstripper was added and cultures were incubated at 37° C., 5% CO2 for approximately 10 minutes until cells were rounded and beginning to detach. Cell scraper was used to completely detach cells from plate. Collected cell were spun down at 490 g for 5 min at room temperature and resuspended in 10% DMSO in Heat Inactivated Fetal Bovine Serum and immediately frozen in −80 C.

Screen

Primary human PMBC derived macrophages were seeded on day 0 at 3.0E4 cells per well in 96-well microplates (ThermoFisher) in Dulbecco's Modified Eagle Medium (DMEM) (Gibco) supplemented with penicillin-streptomycin (Hyclone) and 10% heat inactivated fetal bovine serum (HI-FBS) (Atlanta Bio) and incubated overnight at 37° C., 5% CO2. On day 1, cells were washed once with 150 uL per well DPBS (Gibco) and treated with 75 uL of:

a. Amino acid free DMEM (US Biologicals) containing a defined custom amino acid concentration based on the mean physiological concentrations in blood based on values published in the Human Metabolome Database (HMDB), with 6 mM glucose, 1 mM sodium pyruvate, 10 mM HEPES, 0.2% primocin (InVivoGen); or b. The same medium described above with one amino acid at various concentrations including complete dropout.

On day 2, cells were treated with 75 uL of the same mediums described above supplemented with 0.30 ng/mL lipopolysaccharide (LPS) (Sigma) for a final concentration of 0.15 ng/mL LPS. Control wells were treated with 1 uM BX-795 (Tocis), 1 uM TAK242 (Sigma), 0.15 ng/mL LPS, or phosphate buffered saline (PBS).

On day 3, the supernatant was collected and immediately frozen in −80° C. freezer. Cells were washed once with 150 uL DPBS and viability was assessed using the WST-8 Cell Proliferation Cytotoxicity Assay (Dojindo). Following the assay, cells were washed twice with 150 uL PBS and fixed with 4% paraformaldehyde for 5 min followed by two additional washes with 150 uL PBS. Protein levels in supernatant samples were analyzed by ELISA for IL-6 and TNFa using commercially available kits (R&D Systems) according to manufacturer-supplied protocols. Results are shown in Tables 71-5 through 71-10 below.

TABLE 71-5

IL-6 Measurements: Donor 1

| Amino Acid Supplement | Conc. (X) | Donor 1 IL-6 Measurements ||||| 
|---|---|---|---|---|---|---|
| | | Mean | Std. Deviation | Number of values | P-value* | Significance |
| LIVRQNAC | 40 | −619.787 | 114.1592 | 3 | 0.0001 | **** |
| LIVRQNAC | 30 | −525.849 | 63.87122 | 3 | 0.0001 | **** |
| LIVRQNAC | 20 | −290.199 | 33.5584 | 3 | 0.0092 | ** |
| LIVRQNAC | 10 | 51.81434 | 183.3933 | 3 | 0.9479 | ns |
| LIVRQNAC | 1 | 0 | 148.7761 | 3 | na | na |
| LIVRQNAC+G | 40 | −1099.11 | 44.1139 | 3 | 0.0001 | **** |
| LIVRQNAC+G | 30 | −903.836 | 107.7113 | 3 | 0.0001 | **** |
| LIVRQNAC+G | 20 | −616.626 | 114.7826 | 3 | 0.0001 | **** |
| LIVRQNAC+G | 10 | −367.918 | 98.44611 | 3 | 0.0007 | *** |
| LIVRQNAC+G | 1 | 0 | 172.9553 | 3 | na | na |
| LIVRQNAC+S | 40 | −968.997 | 90.53282 | 3 | 0.0001 | **** |

TABLE 71-5-continued

| | | | | | |
|---|---|---|---|---|---|
| LIVRQNAC+S | 30 | −798.326 | 52.89122 | 3 | 0.0001 | **** |
| LIVRQNAC+S | 20 | −506.804 | 63.85224 | 3 | 0.0001 | **** |
| LIVRQNAC+S | 10 | −243.259 | 114.742 | 3 | 0.0365 | * |
| LIVRQNAC+S | 1 | 0 | 259.8506 | 3 | na | na |
| LIV | 40 | 4.918642 | 62.7077 | 3 | 0.9999 | ns |
| LIV | 30 | 86.01907 | 128.1151 | 3 | 0.7604 | ns |
| LIV | 20 | 112.1501 | 83.62436 | 3 | 0.564 | ns |
| LIV | 10 | 54.22668 | 63.10515 | 3 | 0.9392 | ns |
| LIV | 1 | 0 | 75.98804 | 3 | na | na |
| LIVRQ | 40 | 322.0706 | 73.87715 | 3 | 0.0033 | ** |
| LIVRQ | 30 | 297.8004 | 34.60168 | 3 | 0.0072 | ** |
| LIVRQ | 20 | 604.021 | 203.8836 | 3 | 0.0001 | **** |
| LIVRQ | 10 | 289.1798 | 57.78952 | 3 | 0.0095 | ** |
| LIVRQ | 1 | 0 | 93.58494 | 3 | na | na |
| RQNAC | 40 | −911.011 | 12.65475 | 3 | 0.0001 | **** |
| RQNAC | 30 | −766.912 | 26.23659 | 3 | 0.0001 | **** |
| RQNAC | 20 | −511.403 | 32.15983 | 3 | 0.0001 | **** |
| RQNAC | 10 | −201.63 | 6.477522 | 3 | 0.1054 | ns |
| RQNAC | 1 | 0 | 174.9658 | 3 | na | na |
| N-Acetyl Cysteine | 40 | −914.194 | 56.77271 | 3 | 0.0001 | **** |
| N-Acetyl Cysteine | 20 | −553.802 | 85.27013 | 3 | 0.0001 | **** |
| N-Acetyl Cysteine | 10 | −121.142 | 53.05191 | 3 | 0.4973 | ns |
| N-Acetyl Cysteine | 5 | 308.1772 | 263.4651 | 3 | 0.0052 | ** |
| N-Acetyl Cysteine | 0 | 0 | 45.08485 | 3 | na | na |

| | | Donor 1 IL-6 Measurements | | | | |
|---|---|---|---|---|---|---|
| Amino Acid Supplement | Conc. (μM) | Mean | Std. Deviation | Number of values | P-value* | Significance |
| Valine | 23420 | −106.268 | 155.3559 | 3 | 0.7885 | ns |
| Valine | 11710 | −97.25 | 77.26313 | 3 | 0.8339 | ns |
| Valine | 4684 | −85.9843 | 74.99317 | 3 | 0.8841 | ns |
| Valine | 234 | 0 | 124.8497 | 3 | na | na |
| Arginine | 5440 | 357.4394 | 154.8508 | 3 | 0.0159 | * |
| Arginine | 2720 | −186.57 | 85.86105 | 3 | 0.3477 | ns |
| Arginine | 1088 | −181.36 | 131.6475 | 3 | 0.3722 | ns |
| Arginine | 109 | 0 | 282.0306 | 3 | na | na |
| Glutamine | 22484 | 440.1437 | 114.443 | 3 | 0.0022 | ** |
| Glutamine | 11242 | 397.1745 | 23.36272 | 3 | 0.0064 | ** |
| Glutamine | 3747 | 291.5443 | 81.30853 | 3 | 0.0623 | ns |
| Glutamine | 749 | 0 | 73.06692 | 3 | na | na |
| Isoleucine | 6639 | −218.332 | 146.5098 | 3 | 0.221 | ns |
| Isoleucine | 3320 | −15.8843 | 89.88616 | 3 | 0.9998 | ns |
| Isoleucine | 1328 | 25.98372 | 323.6109 | 3 | 0.9984 | ns |
| Isoleucine | 66 | 0 | 48.21125 | 3 | na | na |
| Leucine | 15270 | 84.46122 | 68.15253 | 3 | 0.8902 | ns |
| Leucine | 7635 | −69.9873 | 99.00843 | 3 | 0.9398 | ns |
| Leucine | 3054 | 244.9743 | 355.6551 | 3 | 0.1442 | ns |
| Leucine | 153 | 0 | 61.85589 | 3 | na | na |

Treatment with LIVRQNAC, LIVRQNAC+G, LIVRQNAC+S, RQNAC, and NAC significantly reduced LPS-induced IL-6 secretion in primary human monocyte-derived macrophages. Treatment with LIVRQ significantly increased IL-6 secretion, while LIV had no effect. Arginine and glutamine administered alone increased IL-6 secretion while other amino acids alone did not effect IL-6 secretion. Two Way ANOVA Dunnett Multiple Comparisons was performed for statistical analysis. Mean values represented as baseline subtracted values.

TABLE 71-6

IL-6 Measurements: Donor 2

| | | Donor 2 IL-6 Measurements | | | | |
|---|---|---|---|---|---|---|
| Amino Acid Supplement | Conc. (X) | Mean | Std. Deviation | Number of values | P-value* | Significance |
| LIVRQNAC | 40 | −27.1916 | 1.853569 | 3 | 0.0003 | *** |
| LIVRQNAC | 30 | −21.5766 | 1.709414 | 3 | 0.0045 | ** |
| LIVRQNAC | 20 | −8.20655 | 8.458638 | 3 | 0.5143 | ns |
| LIVRQNAC | 10 | −1.71581 | 6.104437 | 3 | 0.9965 | ns |
| LIVRQNAC | 1 | −2.4E-15 | 11.85079 | 3 | | |
| LIVRQNAC+G | 40 | −33.2001 | 3.55425 | 3 | 0.0001 | **** |
| LIVRQNAC+G | 30 | −30.8468 | 0.854995 | 3 | 0.0001 | **** |
| LIVRQNAC+G | 20 | −18.4318 | 4.870421 | 3 | 0.0187 | * |
| LIVRQNAC+G | 10 | 14.63551 | 21.82024 | 3 | 0.0824 | ns |
| LIVRQNAC+G | 1 | 2.37E-15 | 8.607557 | 3 | | |
| LIVRQNAC+S | 40 | −26.5993 | 2.963677 | 3 | 0.0004 | *** |

TABLE 71-6-continued

| | | | | | | |
|---|---|---|---|---|---|---|
| LIVRQNAC+S | 30 | −14.2166 | 1.460268 | 3 | 0.0954 | ns |
| LIVRQNAC+S | 20 | −8.2522 | 2.917345 | 3 | 0.5095 | ns |
| LIVRQNAC+S | 10 | 8.127841 | 1.783214 | 3 | 0.5227 | ns |
| LIVRQNAC+S | 1 | 0 | 6.232673 | 3 | | |
| LIV | 40 | 34.10306 | 1.950493 | 3 | 0.0001 | **** |
| LIV | 30 | 31.10835 | 9.757211 | 3 | 0.0001 | **** |
| LIV | 20 | 20.32684 | 3.17293 | 3 | 0.0081 | ** |
| LIV | 10 | 15.10204 | 9.179111 | 3 | 0.0697 | ns |
| LIV | 1 | −7.1E-15 | 4.738966 | 3 | | |
| LIVRQ | 40 | 49.62156 | 17.37012 | 3 | 0.0001 | **** |
| LIVRQ | 30 | 42.9625 | 7.798872 | 3 | 0.0001 | **** |
| LIVRQ | 20 | 48.38603 | 13.08566 | 3 | 0.0001 | **** |
| LIVRQ | 10 | 45.99191 | 15.19687 | 3 | 0.0001 | **** |
| LIVRQ | 1 | 1.18E-15 | 6.324379 | 3 | | |
| RQNAC | 40 | −36.5521 | 1.877658 | 3 | 0.0001 | **** |
| RQNAC | 30 | −26.3768 | 0.744676 | 3 | 0.0004 | *** |
| RQNAC | 20 | −18.7428 | 1.353649 | 3 | 0.0164 | * |
| RQNAC | 10 | −3.74427 | 4.74578 | 3 | 0.9393 | ns |
| RQNAC | 1 | 2.37E-15 | 12.26314 | 3 | | |
| N-Acetyl Cysteine | 40 | −33.7585 | 0.895842 | 3 | 0.0001 | **** |
| N-Acetyl Cysteine | 20 | −24.9999 | 1.083467 | 3 | 0.0008 | *** |
| N-Acetyl Cysteine | 10 | −9.75111 | 2.381012 | 3 | 0.3617 | ns |
| N-Acetyl Cysteine | 5 | −0.79458 | 5.988677 | 3 | 0.9998 | ns |
| N-Acetyl Cysteine | 0 | −2.4E-15 | 1.900091 | 3 | | |

| | | Donor 2 IL-6 Measurements | | | | |
|---|---|---|---|---|---|---|
| Amino Acid Supplement | Conc. (μM) | Mean | Std. Deviation | Number of values | P-value* | Significance |
| Valine | 23420 | 4.395899 | 10.35903 | 3 | 0.973 | ns |
| Valine | 11710 | −1.19605 | 7.303571 | 3 | 0.9998 | ns |
| Valine | 4684 | −4.52846 | 4.069907 | 3 | 0.97 | ns |
| Valine | 234 | −4.7E-15 | 9.361734 | 3 | | |
| Arginine | 5440 | −12.4164 | 0.292618 | 3 | 0.5017 | ns |
| Arginine | 2720 | −13.6102 | 2.1177 | 3 | 0.4207 | ns |
| Arginine | 1088 | −9.70116 | 9.286942 | 3 | 0.6995 | ns |
| Arginine | 109 | 2.37E-15 | 14.30728 | 3 | | |
| Glutamine | 22484 | 34.38845 | 7.467725 | 3 | 0.0026 | ** |
| Glutamine | 11242 | 63.31441 | 35.02748 | 3 | 0.0001 | **** |
| Glutamine | 3747 | 22.51543 | 9.686139 | 3 | 0.0721 | ns |
| Glutamine | 749 | 2.37E-15 | 2.203881 | 3 | | |
| Isoleucine | 6639 | −1.77438 | 10.22772 | 3 | 0.999 | ns |
| Isoleucine | 3320 | 2.305485 | 1.328015 | 3 | 0.9975 | ns |
| Isoleucine | 1328 | −2.31776 | 9.121049 | 3 | 0.9974 | ns |
| Isoleucine | 66 | 0 | 12.3413 | 3 | | |
| Leucine | 15270 | 47.59735 | 16.64049 | 3 | 0.0001 | **** |
| Leucine | 7635 | 30.46065 | 7.144005 | 3 | 0.0087 | ** |
| Leucine | 3054 | 29.60609 | 13.39676 | 3 | 0.0111 | * |
| Leucine | 153 | 7.11E-15 | 6.308577 | 3 | | |

Treatment with LIVRQNAC, LIVRQNAC+G, LIVRQNAC+S, RQNAC, and NAC significantly reduced LPS-induced IL-6 secretion in primary human monocyte-derived macrophages. Treatment with LIVRQ and LIV significantly increased IL-6 secretion. Glutamine and leucine administered alone increased IL-6 secretion, while the other amino acids alone had no effect. Two Way ANOVA Dunnett Multiple Comparisons was performed for statistical analysis. Mean values represented as baseline subtracted values.

TABLE 71-7

IL-6 Measurements: Donor 3

| | | Donor 3 IL-6 Measurements | | | | |
|---|---|---|---|---|---|---|
| Amino Acid Supplement | Conc. (X) | Mean | Std. Deviation | Number of values | P-value* | Significance |
| LIVRQNAC | 40 | −18.2445 | 4.129349 | 3 | 0.7529 | ns |
| LIVRQNAC | 30 | −16.8219 | 1.366045 | 3 | 0.8001 | ns |
| LIVRQNAC | 20 | −13.4826 | 12.48206 | 3 | 0.8948 | ns |
| LIVRQNAC | 10 | −34.4539 | 37.38053 | 3 | 0.2356 | ns |
| LIVRQNAC | 1 | −1.4E-14 | 14.03982 | 3 | | |
| LIVRQNAC+G | 40 | −54.4799 | 5.467815 | 3 | 0.0228 | * |
| LIVRQNAC+G | 30 | −48.3118 | 1.960574 | 3 | 0.0513 | ns |
| LIVRQNAC+G | 20 | −55.792 | 7.763897 | 3 | 0.019 | * |
| LIVRQNAC+G | 10 | −44.8309 | 14.34972 | 3 | 0.0783 | ns |
| LIVRQNAC+G | 1 | 0 | 26.01471 | 3 | | |
| LIVRQNAC+S | 40 | −14.5337 | 15.82418 | 3 | 0.868 | ns |

TABLE 71-7-continued

| | | | | | | |
|---|---|---|---|---|---|---|
| LIVRQNAC+S | 30 | −25.9127 | 10.00119 | 3 | 0.479 | ns |
| LIVRQNAC+S | 20 | −25.8862 | 21.61536 | 3 | 0.48 | ns |
| LIVRQNAC+S | 10 | −11.9742 | 10.3333 | 3 | 0.9277 | ns |
| LIVRQNAC+S | 1 | −4.3E-14 | 15.34164 | 3 | | |
| LIV | 40 | 10.21257 | 37.58938 | 3 | 0.9576 | ns |
| LIV | 30 | −32.6891 | 24.862 | 3 | 0.2771 | ns |
| LIV | 20 | 27.66715 | 39.40901 | 3 | 0.4207 | ns |
| LIV | 10 | 9.44789 | 71.20002 | 3 | 0.9677 | ns |
| LIV | 1 | −4.7E-14 | 27.50075 | 3 | | |
| LIVRQ | 40 | 74.9145 | 12.55033 | 3 | 0.001 | *** |
| LIVRQ | 30 | 120.1764 | 20.21514 | 3 | 0.0001 | **** |
| LIVRQ | 20 | 77.12007 | 11.45452 | 3 | 0.0007 | *** |
| LIVRQ | 10 | 67.95483 | 43.58345 | 3 | 0.003 | ** |
| LIVRQ | 1 | −2.4E-14 | 27.62048 | 3 | | |
| RQNAC | 40 | −45.9765 | 5.740028 | 3 | 0.0683 | ns |
| RQNAC | 30 | −53.3845 | 16.45009 | 3 | 0.0265 | * |
| RQNAC | 20 | −65.6761 | 3.400465 | 3 | 0.0044 | ** |
| RQNAC | 10 | −32.8776 | 33.99103 | 3 | 0.2724 | ns |
| RQNAC | 1 | −2.8E-14 | 23.14404 | 3 | | |
| N-Acetyl Cysteine | 40 | −140.851 | 4.662272 | 3 | 0.0001 | **** |
| N-Acetyl Cysteine | 20 | −122.656 | 8.219985 | 3 | 0.0001 | **** |
| N-Acetyl Cysteine | 10 | −103.586 | 28.4385 | 3 | 0.0001 | **** |
| N-Acetyl Cysteine | 5 | −70.3269 | 8.563896 | 3 | 0.0021 | ** |
| N-Acetyl Cysteine | 0 | −9.5E-15 | 11.75797 | 3 | | |

| | | Donor 3 IL-6 Measurements | | | | |
|---|---|---|---|---|---|---|
| Amino Acid Supplement | Conc. (μm) | Mean | Std. Deviation | Number of values | P-value* | Significance |
| Valine | 23420 | −29.2004 | 25.98066 | 3 | 0.4329 | ns |
| Valine | 11710 | −43.8022 | 8.331697 | 3 | 0.1239 | ns |
| Valine | 4684 | −30.0609 | 8.478329 | 3 | 0.4072 | ns |
| Valine | 234 | 4.26E-14 | 17.2027 | 3 | | |
| Arginine | 5440 | −6.80983 | 0.643932 | 3 | 0.9922 | ns |
| Arginine | 2720 | −7.50318 | 22.06663 | 3 | 0.9888 | ns |
| Arginine | 1088 | 31.5786 | 70.48311 | 3 | 0.3642 | ns |
| Arginine | 109 | 0 | 17.26952 | 3 | | |
| Glutamine | 22484 | 108.5158 | 55.59202 | 3 | 0.0001 | **** |
| Glutamine | 11242 | 98.4903 | 58.37 | 3 | 0.0001 | **** |
| Glutamine | 3747 | 25.35457 | 16.40416 | 3 | 0.556 | ns |
| Glutamine | 749 | 3.79E-14 | 16.54987 | 3 | | |
| Isoleucine | 6639 | −16.3663 | 8.09174 | 3 | 0.9718 | ns |
| Isoleucine | 3320 | 0 | 19.80362 | 3 | 0.9928 | ns |
| Isoleucine | 1328 | −28.9897 | 13.10903 | 3 | 0.6593 | ns |
| Isoleucine | 66 | −6.69039 | 13.72995 | 3 | | |
| Leucine | 15270 | # | # | 3 | # | # |
| Leucine | 7635 | # | # | 3 | # | # |
| Leucine | 3054 | # | # | 3 | # | # |
| Leucine | 153 | # | # | 3 | # | # |

Leucine was not measured in Exp3 due to technical error

Treatment with LIVRQNAC+G, LIVRQNAC+S, RQNAC, and NAC significantly reduced LPS-induced IL-6 secretion in primary human monocyte-derived macrophages. Treatment with LIVRQ increased IL-6 secretion, while LIV and LIVRQNAC had no statistically significant effects on IL-6 secretion. Glutamine administered alone significantly increased IL-6 secretion, while other amino acids alone had no effect. Two Way ANOVA Dunnett Multiple Comparisons was performed for statistical analysis. Mean values represented as baseline subtracted values.

TABLE 71-8

TNFalpha Measurements: Donor 1

| | | Donor 1 TNFa Measurements | | | | |
|---|---|---|---|---|---|---|
| Amino Acid Supplement | Conc. (X) | Mean | Std. Deviation | Number of values | P-value* | Significance |
| LIVRQNAC | 40 | −422.74 | 4.347575 | 3 | 0.0001 | **** |
| LIVRQNAC | 30 | −389.74 | 1.004633 | 3 | 0.0001 | **** |
| LIVRQNAC | 20 | −336.69 | 3.007435 | 3 | 0.0001 | **** |
| LIVRQNAC | 10 | −246.04 | 27.61929 | 3 | 0.0001 | **** |
| LIVRQNAC | 1 | 0 | 36.31082 | 3 | | |
| LIVRQNAC+G | 40 | −490.92 | 4.427614 | 3 | 0.0001 | **** |
| LIVRQNAC+G | 30 | −447.73 | 9.819865 | 3 | 0.0001 | **** |
| LIVRQNAC+G | 20 | −377.32 | 5.837159 | 3 | 0.0001 | **** |
| LIVRQNAC+G | 10 | −268.29 | 9.642365 | 3 | 0.0001 | **** |
| LIVRQNAC+G | 1 | 0 | 37.44353 | 3 | | |

TABLE 71-8-continued

| | | | | | | |
|---|---|---|---|---|---|---|
| LIVRQNAC+S | 40 | −415.03 | 4.800449 | 3 | 0.0001 | **** |
| LIVRQNAC+S | 30 | −379.44 | 4.694868 | 3 | 0.0001 | **** |
| LIVRQNAC+S | 20 | −323.77 | 7.971135 | 3 | 0.0001 | **** |
| LIVRQNAC+S | 10 | −209.59 | 21.15676 | 3 | 0.0001 | **** |
| LIVRQNAC+S | 1 | 0 | 30.0492 | 3 | | |
| LIV | 40 | 60.37 | 20.26331 | 3 | 0.0065 | ** |
| LIV | 30 | 42.09 | 22.95664 | 3 | 0.0865 | ns |
| LIV | 20 | 63.37 | 37.24144 | 3 | 0.004 | ** |
| LIV | 10 | 45.61 | 44.71078 | 3 | 0.0556 | ns |
| LIV | 1 | 0 | 10.49958 | 3 | | |
| LIVRQ | 40 | 6.38 | 17.1283 | 3 | 0.9909 | ns |
| LIVRQ | 30 | −6.72 | 18.9622 | 3 | 0.989 | ns |
| LIVRQ | 20 | 38.38 | 39.85515 | 3 | 0.1333 | ns |
| LIVRQ | 10 | −18.95 | 10.84371 | 3 | 0.6982 | ns |
| LIVRQ | 1 | 0 | 36.96184 | 3 | | |
| RQNAC | 40 | −408.44 | 1.179877 | 3 | 0.0001 | **** |
| RQNAC | 30 | −390.41 | 1.341282 | 3 | 0.0001 | **** |
| RQNAC | 20 | −338.2 | 3.284307 | 3 | 0.0001 | **** |
| RQNAC | 10 | −251.35 | 4.121085 | 3 | 0.0001 | **** |
| RQNAC | 1 | 0 | 51.06933 | 3 | | |
| N-Acetyl Cysteine | 40 | −644.49 | 2.42197 | 3 | 0.0001 | **** |
| N-Acetyl Cysteine | 20 | −561.33 | 8.435064 | 3 | 0.0001 | **** |
| N-Acetyl Cysteine | 10 | −446.88 | 12.22132 | 3 | 0.0001 | **** |
| N-Acetyl Cysteine | 5 | −326.24 | 11.10173 | 3 | 0.0001 | **** |
| N-Acetyl Cysteine | 0 | 0 | 42.00516 | 3 | | |

Donor 1 TNFa Measurements

| Amino Acid Supplement | Conc. (µM) | Mean | Std. Deviation | Number of values | P-value* | Significance |
|---|---|---|---|---|---|---|
| Valine | 23420 | −14.98 | 20.86784 | 3 | 0.9928 | ns |
| Valine | 11710 | −41.77 | 36.61662 | 3 | 0.7784 | ns |
| Valine | 4684 | −40.37 | 32.31016 | 3 | 0.7974 | ns |
| Valine | 234 | 0 | 24.8661 | 3 | | |
| Arginine | 5440 | 62.06 | 48.80326 | 3 | 0.4786 | ns |
| Arginine | 2720 | 5.12 | 15.47951 | 3 | 0.9998 | ns |
| Arginine | 1088 | −24.33 | 17.74317 | 3 | 0.9577 | ns |
| Arginine | 109 | 0 | 18.5366 | 3 | | |
| Glutamine | 22484 | −103.07 | 27.02483 | 3 | 0.0985 | ns |
| Glutamine | 11242 | −65.24 | 23.02631 | 3 | 0.4346 | ns |
| Glutamine | 3747 | −45.7 | 28.56445 | 3 | 0.7222 | ns |
| Glutamine | 749 | 0 | 30.75138 | 3 | | |
| Isoleucine | 6639 | −40.95 | 78.56369 | 3 | 0.7896 | ns |
| Isoleucine | 3320 | −96.3 | 45.66981 | 3 | 0.1339 | ns |
| Isoleucine | 1328 | −42.68 | 21.07739 | 3 | 0.7657 | ns |
| Isoleucine | 66 | 0 | 115.9559 | 3 | | |
| Leucine | 15270 | −46.21 | 29.00402 | 3 | 0.7148 | ns |
| Leucine | 7635 | −23.04 | 40.08864 | 3 | 0.965 | ns |
| Leucine | 3054 | 42.04 | 77.19161 | 3 | 0.7746 | ns |
| Leucine | 153 | 0 | 157.6578 | 3 | | |

Treatment with LIVRQNAC, LIVRQNAC+G, LIVRQNAC+S, RQNAC, and NAC significantly reduced LPS-induced TNFa secretion in primary human monocyte-derived macrophages. Treatment with LIV increased TNFa secretion, while LIVRQ had no significant effects on TNFa secretion. None of the individually administered amino acids had an effect on TNFa secretion. Two Way ANOVA Dunnett Multiple Comparisons was performed for statistical analysis. Mean values represented as baseline subtracted values.

TABLE 71-9

TNFalpha Measurements: Donor 2

| | | Donor 2 TNFa Measurements | | | | |
|---|---|---|---|---|---|---|
| Amino Acid Supplement | Conc. (X) | Mean | Std. Deviation | Number of values | P-value* | Significance |
| LIVRQNAC | 40 | −98.1341 | 2.118962 | 3 | 0.0001 | **** |
| LIVRQNAC | 30 | −85.1019 | 1.385677 | 3 | 0.0001 | **** |
| LIVRQNAC | 20 | −64.3364 | 10.07525 | 3 | 0.0001 | **** |
| LIVRQNAC | 10 | −38.3512 | 5.120689 | 3 | 0.0001 | **** |
| LIVRQNAC | 1 | 0 | 5.45587 | 3 | | |
| LIVRQNAC+G | 40 | −91.3454 | 5.994009 | 3 | 0.0001 | **** |
| LIVRQNAC+G | 30 | −82.4397 | 4.200763 | 3 | 0.0001 | **** |
| LIVRQNAC+G | 20 | −61.247 | 8.702492 | 3 | 0.0001 | **** |
| LIVRQNAC+G | 10 | −23.9913 | 7.471422 | 3 | 0.008 | ** |
| LIVRQNAC+G | 1 | −4.7E-15 | 4.578295 | 3 | | |

TABLE 71-9-continued

TNFalpha Measurements: Donor 2

Donor 2 TNFa Measurements

| Amino Acid Supplement | Conc. (X) | Mean | Std. Deviation | Number of values | P-value* | Significance |
|---|---|---|---|---|---|---|
| LIVRQNAC+S | 40 | −74.1572 | 4.163823 | 3 | 0.0001 | **** |
| LIVRQNAC+S | 30 | −64.0016 | 5.549308 | 3 | 0.0001 | **** |
| LIVRQNAC+S | 20 | −47.5673 | 3.970363 | 3 | 0.0001 | **** |
| LIVRQNAC+S | 10 | −28.635 | 7.390447 | 3 | 0.0012 | ** |
| LIVRQNAC+S | 1 | −4.7E-15 | 7.564883 | 3 | | |
| LIV | 40 | 49.84155 | 4.092799 | 3 | **** | 0.0001 |
| LIV | 30 | 29.1118 | 14.72509 | 3 | **** | 0.001 |
| LIV | 20 | 30.17595 | 5.797518 | 3 | **** | 0.0006 |
| LIV | 10 | 16.68974 | 10.85983 | 3 | ns | 0.0974 |
| LIV | 1 | 0 | 10.41523 | 3 | | |
| LIVRQ | 40 | 64.1705 | 27.82953 | 3 | **** | 0.0001 |
| LIVRQ | 30 | 50.92104 | 6.955429 | 3 | **** | 0.0001 |
| LIVRQ | 20 | 45.65882 | 19.0128 | 3 | **** | 0.0001 |
| LIVRQ | 10 | 32.37038 | 19.44425 | 3 | **** | 0.0002 |
| LIVRQ | 1 | −4.7E-15 | 5.942707 | 3 | | |
| RQNAC | 40 | −84.147 | 5.821583 | 3 | **** | 0.0001 |
| RQNAC | 30 | −77.9626 | 1.626776 | 3 | **** | 0.0001 |
| RQNAC | 20 | −63.3754 | 3.494595 | 3 | **** | 0.0001 |
| RQNAC | 10 | −37.6072 | 1.88043 | 3 | **** | 0.0001 |
| RQNAC | 1 | −9.5E-15 | 4.727924 | 3 | | |
| N-Acetyl Cysteine | 40 | −103.984 | 0.720962 | 3 | 0.0001 | **** |
| N-Acetyl Cysteine | 20 | −88.6528 | 0.668195 | 3 | 0.0001 | **** |
| N-Acetyl Cysteine | 10 | −70.8382 | 12.08717 | 3 | 0.0001 | **** |
| N-Acetyl Cysteine | 5 | −54.1596 | 11.06287 | 3 | 0.0001 | **** |
| N-Acetyl Cysteine | 0 | 9.47E-15 | 2.926881 | 3 | | |
| Valine | 23420 | −1.25079 | 12.85688 | 3 | 0.9991 | ns |
| Valine | 11710 | −0.83505 | 8.524018 | 3 | 0.9998 | ns |
| Valine | 4684 | −0.00221 | 5.127759 | 3 | 0.9999 | ns |
| Valine | 234 | −4.7E-15 | 8.717375 | 3 | | |
| Arginine | 5440 | −0.57378 | 8.672536 | 3 | 0.9999 | ns |
| Arginine | 2720 | −3.76334 | 2.467885 | 3 | 0.9594 | ns |
| Arginine | 1088 | −12.7222 | 4.764842 | 3 | 0.2488 | ns |
| Arginine | 109 | 1.42E-14 | 3.511446 | 3 | | |
| Glutamine | 22484 | 11.50181 | 6.216029 | 3 | 0.3311 | ns |
| Glutamine | 11242 | 20.03996 | 11.90208 | 3 | 0.0279 | * |
| Glutamine | 3747 | 9.338214 | 9.748253 | 3 | 0.5134 | ns |
| Glutamine | 749 | −9.5E-15 | 7.275868 | 3 | | |
| Isoleucine | 6639 | 19.25756 | 5.097831 | 3 | 0.0365 | * |
| Isoleucine | 3320 | 10.26061 | 7.861148 | 3 | 0.4307 | ns |
| Isoleucine | 1328 | 2.918887 | 1.921961 | 3 | 0.9836 | ns |
| Isoleucine | 66 | 4.74E-15 | 6.264135 | 3 | | |
| Leucine | 15270 | 46.68507 | 11.63209 | 3 | 0.0001 | **** |
| Leucine | 7635 | 41.97528 | 6.512087 | 3 | 0.0001 | **** |
| Leucine | 3054 | 31.74019 | 11.56537 | 3 | 0.0002 | *** |
| Leucine | 153 | 0 | 0.482598 | 3 | | |

Treatment with LIVRQNAC, LIVRQNAC+G, LIVRQNAC+S, RQNAC, and NAC significantly reduced LPS-induced TNFa secretion in primary human monocyte-derived macrophages. Treatment with LIV and LIVRQ increased TNFa secretion. Leucine, isoleucine, and glutamine administered individually increased TNFa secretion, while the other amino acids had no effect. Two Way ANOVA Dunnett Multiple Comparisons was performed for statistical analysis. Mean values represented as baseline subtracted values.

TABLE 71-10

TNFalpha Measurements: Donor 3

Donor 3 TNFa Measurements

| Amino Acid Supplement | Conc. (X) | Mean | Std. Deviation | Number of values | P-value* | Significance |
|---|---|---|---|---|---|---|
| LIVRQNAC | 40 | −18.7507 | 2.487301 | 3 | 0.0001 | **** |
| LIVRQNAC | 30 | −15.5979 | 0.932399 | 3 | 0.0006 | *** |
| LIVRQNAC | 20 | −10.7042 | 3.013527 | 3 | 0.026 | * |
| LIVRQNAC | 10 | −8.49034 | 2.434812 | 3 | 0.1029 | ns |
| LIVRQNAC | 1 | 0 | 4.067982 | 3 | | |
| LIVRQNAC+G | 40 | −14.6552 | 3.149813 | 3 | 0.0013 | ** |
| LIVRQNAC+G | 30 | −11.6973 | 2.026588 | 3 | 0.0129 | * |
| LIVRQNAC+G | 20 | −8.0218 | 0.671662 | 3 | 0.1331 | ns |
| LIVRQNAC+G | 10 | −4.8035 | 1.658348 | 3 | 0.5453 | ns |

TABLE 71-10-continued

| | | | | | |
|---|---|---|---|---|---|
| LIVRQNAC+G | 1 | −2.4E-15 | 5.625453 | 3 | | |
| LIVRQNAC+S | 40 | −14.247 | 1.800575 | 3 | 0.0018 | ** |
| LIVRQNAC+S | 30 | −15.1388 | 1.568817 | 3 | 0.0009 | *** |
| LIVRQNAC+S | 20 | −12.4722 | 3.334857 | 3 | 0.0073 | ** |
| LIVRQNAC+S | 10 | −6.72057 | 1.833554 | 3 | 0.2549 | ns |
| LIVRQNAC+S | 1 | 0 | 4.171555 | 3 | | |
| LIV | 40 | 14.07984 | 11.14252 | 3 | 0.002 | ** |
| LIV | 30 | 1.759786 | 1.102706 | 3 | 0.9748 | ns |
| LIV | 20 | 14.51396 | 10.41503 | 3 | 0.0014 | ** |
| LIV | 10 | 8.560957 | 12.86074 | 3 | 0.0989 | ns |
| LIV | 1 | 2.37E-15 | 3.660423 | 3 | | |
| LIVRQ | 40 | 25.84453 | 0.659584 | 3 | 0.0001 | **** |
| LIVRQ | 30 | 33.74883 | 5.974096 | 3 | 0.0001 | **** |
| LIVRQ | 20 | 20.94481 | 2.163828 | 3 | 0.0001 | **** |
| LIVRQ | 10 | 15.45187 | 3.942596 | 3 | 0.0007 | *** |
| LIVRQ | 1 | 0 | 4.575346 | 3 | | |
| RQNAC | 40 | −21.5102 | 1.191926 | 3 | 0.0001 | **** |
| RQNAC | 30 | −20.8898 | 2.622446 | 3 | 0.0001 | **** |
| RQNAC | 20 | −19.9558 | 3.302225 | 3 | 0.0001 | **** |
| RQNAC | 10 | −9.09425 | 5.483242 | 3 | 0.0725 | ns |
| RQNAC | 1 | 0 | 6.189505 | 3 | | |
| N-Acetyl Cysteine | 40 | −55.3093 | 0.809363 | 3 | 0.0001 | **** |
| N-Acetyl Cysteine | 20 | −48.4373 | 1.563179 | 3 | 0.0001 | **** |
| N-Acetyl Cysteine | 10 | −41.7266 | 3.533914 | 3 | 0.0001 | **** |
| N-Acetyl Cysteine | 5 | −33.6246 | 0.253484 | 3 | 0.0001 | **** |
| N-Acetyl Cysteine | 0 | 4.74E-15 | 8.55997 | 3 | | |

| | | Donor 3 TNFa Measurements | | | | |
|---|---|---|---|---|---|---|
| Amino Acid Supplement | Conc. (μM) | Mean | Std. Deviation | Number of values | P-value* | Significance |
| Valine | 23420 | 3.688279 | 7.532913 | 3 | 0.8962 | ns |
| Valine | 11710 | −2.59866 | 2.586099 | 3 | 0.9674 | ns |
| Valine | 4684 | 0.126 | 0.903014 | 3 | 0.9999 | ns |
| Valine | 234 | −2.4E-15 | 2.731283 | 3 | | |
| Arginine | 5440 | −1.76662 | 4.067694 | 3 | 0.992 | ns |
| Arginine | 2720 | −0.96691 | 4.86075 | 3 | 0.9991 | ns |
| Arginine | 1088 | 3.131153 | 10.346 | 3 | 0.9384 | ns |
| Arginine | 109 | 3.55E-15 | 4.325877 | 3 | | |
| Glutamine | 22484 | 29.14034 | 17.71417 | 3 | 0.0001 | **** |
| Glutamine | 11242 | 18.00238 | 14.58602 | 3 | 0.0061 | ** |
| Glutamine | 3747 | 1.935546 | 2.127977 | 3 | 0.9887 | ns |
| Glutamine | 749 | 0 | 5.196592 | 3 | | |
| Isoleucine | 6639 | −1.66019 | 4.262718 | 3 | 0.9938 | ns |
| Isoleucine | 3320 | 3.308901 | 3.745411 | 3 | 0.9262 | ns |
| Isoleucine | 1328 | −6.22991 | 0.48195 | 3 | 0.5976 | ns |
| Isoleucine | 66 | −2.4E-15 | 3.844593 | 3 | | |
| Leucine | 15270 | # | # | 3 | # | # |
| Leucine | 7635 | # | # | 3 | # | # |
| Leucine | 3054 | # | # | 3 | # | # |
| Leucine | 153 | # | # | 3 | # | # |

Leucine was not measured in Exp3 due to technical error

Treatment with LIVRQNAC, LIVRQNAC+G, LIVRQNAC+S, RQNAC, and NAC significantly reduced LPS-induced TNFa secretion in primary human monocyte-derived macrophages. Treatment with LIV and LIVRQ increased TNFa secretion. Individually administered amino acids had no significant effect on TNFa secretion, except for glutamine which increased TNFa secretion. Two Way ANOVA Dunnett Multiple Comparisons was performed for statistical analysis. Mean values represented as baseline subtracted values.

Example 14: Treatment of NAFLD Patients with an Amino Acid Composition

The study described herein features the administration of a composition including amino acids to treat patients with NAFLD. The composition can include about 2 g of leucine, about 1 g of isoleucine, about 1 g of valine, about 3.62 g of arginine, about 4 g of glutamine, and about 0.3 g of N-acetylcysteine for administration three times per day (e.g., a total of about 36 g per day). The composition can also include about 2 g of leucine, about 1 g of isoleucine, about 1 g of valine, about 3.62 g of arginine, about 4 g of glutamine, and about 0.6 g of N-acetylcysteine for administration three times per day (e.g., a total of about 37 g per day).

Alternatively, the composition can include about 4 g of leucine, about 2 g of isoleucine, about 2 g of valine, about 7.24 g of arginine, about 8 g of glutamine, and about 0.6 g of N-acetylcysteine for administration two or three times per day (e.g., a total of about 48 g or a total of about 72 g per day). The composition can also include about 4 g of leucine, about 2 g of isoleucine, about 2 g of valine, about 7.24 g of arginine, about 8 g of glutamine, and about 1.2 g of N-acetylcysteine for administration two or three times per day (e.g., a total of about 49 g or a total of about 73 g per day).

For each composition, the dose can be administered prior to, concurrently with, or following a meal. Alternatively, the composition is not administered immediately before, with, or after a meal. The amino acid composition can be administered for a period of at least 12 weeks, e.g., for 12 weeks, 13 weeks, 14 weeks, 15 weeks, or 16 weeks. In particular, the amino acid composition is administered for a period of at least 16 weeks, e.g., for 16 weeks. The composition can be administered orally.

Key criteria for selecting NAFLD patients for enrollment in a clinical study of the amino acid composition include: 1) a diagnosis of NAFLD; 2) type 2 diabetes; 3) a relatively high BMI; 4) a NAFLD Fibrosis Score of less than 0.6; 5) a liver biopsy; and 7) a MRI and/or CT assessment of the liver. The patients can have type 2 diabetes in addition to NAFLD.

Fatty liver disease can be document by a prior history of steatosis confirmed within 3 months of screening by at least one of the following methods: liver fat by MRI with a PDFF≥8%; fibroscan with Control Attenuation Parameter≥300 dB/m; or liver biopsy indicating non-NASH NAFLD steatosis>Grade I. If the patient does not have this documented prior history of steatosis within 3 months of screening, then a liver fat score of ≥10% must be documented at the time of screening using the following formula:

Predicted percent liver fat=10^(−0.805+(0.282*metabolic syndrome[yes=1/no=0])+(0.078* type2 diabetes[yes=2/no=0])+(0.525*log 10(insulin mU/L))+(0.521*log 10(AST U/L))−(0.454*log 10(AST/ALT))[34]

Patients can be on stable exercise, diet and lifestyle routine within 3 months prior to screening, with no major body weight fluctuations, e.g., subjects should be within ±3% of their body weight over the last 3 months at the time of screening. Patients can have a body mass index (BMI)≥32 kg/m2 at screening. For sites whose MRI equipment cannot accommodate a patient with a BMI of ≥45 kg/m2, an upper limit between 40 to 45 kg/m2 may be applied.

Patients must be on a stable dose of glucose-lowering medication (which can include metformin, sulfonylureas, dipeptidyl peptidase-4 (DPP-4) inhibitors, sodium-glucose co-transporter 2 (SGLT2) inhibitors, or long-acting basal insulin) for at least 3 months before Screening and plan to remain on the same medication without anticipated dose adjustments of their medications for the duration of the study. Patients may be included in the study if they are concurrently treated with anti-hypertensive medications (e.g., beta blockers, hydrochlorothiazide, ACE inhibitors, angiotensin receptor blockers), medications for dyslipidemia (e.g., statins, fibrates), and medication for hypothyroidism (e.g., levothyroxine), so long as they have been on stable doses and regimen of these medications for at least 3 months before Screening and plan to remain on the same medication without anticipated dose adjustments of their medication for the duration of the study. Patients may be on vitamin supplements (e.g. multivitamins; vitamin E<400 IU/day). However, they must be on stable doses and regimen of these vitamin supplements for at least 3 months before screening without anticipated dose adjustments for the duration of the study.

Primary endpoints in the study include the safety and tolerability of administering the composition including amino acids to patients with NAFLD. Secondary endpoints indicative of an improvement in symptoms of NAFLD include the following: 1) intrahepatic fat reduction by MRI; and 2) assessment of biomarkers involved in liver biochemistry, fibrosis/apoptosis, and metabolism. The following biomarkers can be assessed in a sample (e.g., a plasma or liver sample) from a NAFLD patient: a) alanine aminotransferase (ALT); b) aspartate aminotransferase (AST); c) adiponectin; d) N-terminal fragment of type III collagen (proC3); e) caspase-cleaved keratin 18 fragments (M30 and M65); f) IL-1 beta; g) C-reactive protein; h) PIIINP; i) TIMP1; j) MCP-1; k) FGF-21; or l) gamma glutamyl transferase (GGT). For example, a subject with NAFLD can exhibit a decrease in levels of one, two, or more (e.g., all) of ALT, AST, or GGT after treatment with the composition.

The patient may exhibit a mean change in plasma glucose, insulin, homeostatic model assessment insulin resistance (HOMA IR), lipid profile, hemoglobin A1c (HbA1c) and other metabolic parameters from, e.g., baseline to Weeks 6 and 12, including changes in plasma glucose and insulin levels in the setting of an oral glucose tolerance test (oGTT) from, e.g., baseline to Weeks 6 and 12. The patient may exhibit a mean change in body weight from, e.g., baseline to Weeks 6 and 12.

Administration of the amino acid composition can result in an improvement in the NAFLD activity score, glucose tolerance, hepatocyte inflammation, liver fibrosis or liver injury, steatosis, or hepatocyte ballooning in the patient.

Example 15. Treatment of NASH in a Mouse Model with an Amino Acid Composition

Induction of NASH in Mice

In one example, the effects of LIVRQNAC and related amino acid compositions in the obesity, metabolism-driven non-alcoholic steatohepatitis (NASH) in FATZO mouse model was examined.

Materials and Methods

Induction of NASH in Mice

NASH was induced in 60 male FATZO mice by a western diet (Research Diet #D12079B; fat 40% kcal, protein 17% kcal, carbohydrate 43% kcal) supplemented with 5% fructose in the drinking water (WDF) during a 16 week induction phase. Diets and water were available ad libitum. Littermate control male FATZO mice fed with a control diet (n=6, Purina #5008; fat 17% kcal, protein 27% kcal, carbohydrate 56% kcal) and sterile water were set up for control purpose. Mice were housed in plastic cages with microisolator. Sterilized bedding was replaced once a week. Mice were housed three per cage and maintained on a twelve hour light cycle throughout study duration. Room temperature was monitored daily and maintained at 22-25° C. Body weight was recorded every week during the induction phase.

Study Design

Following 16 weeks diet induction, 6 mice remained on control diet (group 1, Control) while 60 induced mice were randomized on body weight and plasma glucose (fed) for assignment to the following treatments. FATZO mice were administered with test articles starting at 16 weeks post western diet NASH induction for 4 weeks. Test articles were administered by oral gavage. Animals were euthanized at 20 weeks post western diet NASH induction, and tissues were harvested for analysis.

| Group | (n) | Treatment (oral) | Diet |
|---|---|---|---|
| 1 | 6 | Vehicle | 5008 WDF |
| 2 | 10 | Vehicle | D12079B + 5% Fructose |
| 3 | 10 | LIVRQNAC (1500 mg/kg) | D12079B + 5% Fructose |
| 4 | 10 | LIVRQNAC (3000 mg/kg) | D12079B + 5% Fructose |
| 5 | 10 | LIVRQNAC + G (3885 mg/kg) | D12079B + 5% Fructose |
| 6 | 10 | LRQNAC (2469 mg/kg) | D12079B + 5% Fructose |
| 7 | 10 | Obeticholic acid (OCA) 30 mg/kg/day | D12079B + 5% Fructose |

Test Articles

LIVRQNAC, LIVRQNAC+G, LRQNAC, and OCA (Advanced ChemBlocks, Inc.), incipient, and water for irrigation were provided by Axcella Health, Inc. 0.5% Methylcellulosewas provided by CrownBio, Inc. Dosing solutions were prepared according to Appendix 1. TA compounds (amino acid compositions) were amino acid blends formulated fresh daily in water for irrigation (Baxter #27F7114) and the excipients 0.125% Xanthan Gum, 1.5 mM Sodium Lauryl Sulfate and 0.28% Lecithin. Obeticholic acid (OCA) was suspended in 0.5% methylcellulose in water for irrigation. All test articles were stored refrigerated. TA compounds were provided in frozen powder form by the sponsor. Dosing was continued for 4 weeks.

Leucine dosages of LIVRQNAC+G and LRQNAC were matched to that of LIVRQNAC.

Amino Acid Compositions

| Ingredient | Grade | Supplier | Supplier Part Number | Lot Number |
|---|---|---|---|---|
| Fusi-BCAA Unflavored (2:1:1 L-Leu:L-Ile:L-Val) | Instantized (0.3-0.9% Lecithin) | Ajinomoto (AjiPure) | 33555 | OH704 |
| L-Arginine HCl | USP | Sigma (Ajinomoto) | A4599 | CDB0352V |
| L-Arginine HCl | USP | Sigma (Ajinomoto) | A4599 | CDB0352V |
| L-Glutamine | USP | Ajinomoto | 32824 | R014A003 |
| Glycine | USP | Ajinomoto | 30359 | R015T008 |
| Acetylcysteine (NAC) | USP | Spectrum Chemical | AC126 | 1FI0576 |

| Ingredient | LIVRQNAC Daily Dose (g) | LIVRQNAC + G Daily Dose (g) | LRQNAC Daily Dose (g) |
|---|---|---|---|
| Fusi-BCAA Unflavored (2:1:1 L-Leu:L-Ile:L-Val) | 24.0 | 24.0 | |
| Fusil (L-Leucine) | | | 12.0 |
| L-Arginine HCl | 18.0 | 18.0 | 18.0 |
| L-Glutamine | 24.0 | 24.0 | 24.0 |
| Glycine | | 20.0 | |
| Acetylcysteine (NAC) | 1.8 | 1.8 | 1.8 |
| AMINO ACIDS = | 67.8 | 87.8 | 55.8 |

Test Articles Administration

LIVRQNAC, LIVRQNAC+G, LRQNAC, OCA and Vehicle were administered by oral gavage at a volume of 10 mL/kg throughout the study. Dosages were calculated by daily body weight. LIVRQNAC, LIVRQNAC+G, LRQNAC, and Vehicle were administered twice per day (BID), while OCA was administered once a day (QD) in the morning. Mice receiving OCA once per day (QD), and one vehicle QD. Doses were administered by oral gavage at 0700 and 1800 by oral gavage for 4 weeks.

Body Weight and Blood Glucose

The viability, clinical signs and behavior were monitored daily. Body weight was recorded daily during the dosing period. Blood samples were collected weekly in the AM (0700) via tail clip for glucose measurement (StatStrip glucometer).

Necropsy and Sample Harvest

Animals were anesthetized with CO2 inhalation and exsanguinated via cardiac puncture for euthanasia. Terminal blood samples (K2EDTA) were obtained by cardiac puncture in anesthetized animals at termination. Samples were provided frozen to Axcella Health. Organ weights (total liver, gonadal fat pads) were recorded. Pancreas, and small intestine and gonadal fat pads were fixed in 10% Buffered Formalin and prepared as directed in protocol. A section of small intestine, gonadal fat pad and liver were also snap frozen in liquid nitrogen and shipped to the sponsor.

Histological Analyses

The liver tissues were fixed in Bouin's solution at 4° C. for 24 hours followed by baths of standard concentrations of alcohol then xylene to prepare the tissues for paraffin embedding. After being embedded in paraffin and cooled, five-micron sections were cut and stained for routine H&E and Picric Sirius Red. A section of both right and left lobes of the livers were frozen in OCT for analysis of lipid content with Oil-Red-) staining. The Aperio whole slide digital imaging system (Scan Scope CS, Vista, Calif.) was used for imaging. All slides were imaged at 20×. The scan time ranged from 1.5 minutes to a maximum time of 2.25 minutes. The whole images were housed and stored in their Spectrum software system and images were shot from the whole slides.

The livers were evaluated using the NASH liver criteria for scoring. In this mouse study, one cross section of liver for each case was analyzed with the NASH score system. According to the published NASH CRN Scoring System, this scoring system comprises of NAFLD Activity Score (NAS), fibrosis stage and identification of NASH by pattern recognition. The NAS can range from 0 to 8 and is calculated by the sum of scores of steatosis (0-3), lobular inflammation (0-3) and hepatocyte ballooning (0-2) from H&E stained sections. Fibrosis was scored (0-4) from picrosirius red stained slides. The NASH system is used for human liver 18 gauge biopsies. Steatosis, lobular inflammation, hepatocyte. balloon degeneration, fibrosis, NAS and the presence of NASH by pattern recognition were systematically assessed. In this study we evaluated one total cross section of liver per mouse in this study. This is about 15 times the size of an 18 gauge human liver biopsy. The pathology score was determined as 0, +1, +2, or +3. The lesions were scored on location (periportal, centrilobular, and mid zonal) and fat accumulation (focal, periportal, and/or centrilobular). The other part of the score was distribution of the lesions: focal, multifocal and/or diffuse. Also, mild, moderate and severity of the lesions. These parameters made up the total NASH score.

All immunohistochemical staining steps were performed using the Dako FLEX SYSTEM on an automated immunostainer; incubations were done at room temperature and Tris buffered saline plus 0.05% Tween 20, pH 7.4 (TBS—Dako Corp.) was used for all washes and diluents. Thorough washing was performed after each incubation. Primary antibodies included anti-mouse SMA, F4/80, Mac-2, and Picric Sirius Red. Control sections were treated with an isotype control using the same concentration as primary antibodies to verify the staining specificity.

White adipose tissue (WAT) adipocyte size was analyzed from the H&E stained sections. Using the Aperio Image Scope application, 3 localized regions (edge of tissue, tissue not surrounding vascular area, tissue surrounding vascular area) of each tissue specimen were assessed by measuring the area of 10 largest adipocytes of the region. Within each tissue, 10 hot spots of each regions were quantified ($um^2$) and averaged.

Pancreatic beta-islet cells were identified by immunohistochemical staining.

Image Analysis

Aperio Automatic Image Quantitation was employed to quantify positive pixels of immunohistochemical staining, Oil-Red O, and Sirius Red staining. The Positive Pixel Count algorithm was used to quantify the percentage of a specific stain present in a scanned slide image. A range of color (range of hues and saturation) and three intensity ranges (weak, positive, and strong) were masked and evaluated. The algorithm counted the number and intensity-sum in each intensity range, along with three additional quantities: average intensity, ratio of strong/total number, and average intensity of weak positive pixels. The positive pixel algorithm was modified to distinguish between the orange and blue colors. Alterations from the normal "hue value" (0.1 to 0.96) and "color saturation" (0.04 to 0.29), were made for the Sirius Red evaluation. Vasculature and artifacts were excluded from analysis.

Liver Gene Expression Analysis

Liver gene expression of MCP-1 and MIP-1a was measured by quantitative PCR.

Liver Cytokine and Chemokine Measurement

Liver IL-1b, MCP-1, and MIP-1 protein levels were quantified using the multiplex ELISA Assay (Meso Scale Discovery, Rockville, Md.).

Statistical Analysis

Statistical analyses of liver histological scores were performed using Bonferroni Multiple Comparison Test on GraphPad Prism 6 (GraphPad Software Inc., USA). P values<0.05 were considered statistically significant. Results were expressed as mean±SEM. Comparisons were made between Group 2 (Vehicle) and the following groups; Group 3 (LIVRQNAC 1,500 mg/kg), Group 4 (LIVRQNAC 3,000 mg/kg), Group 5 (LIVRQNAC+G, 3,885 mg/kg), and (LRQNAC, 2,469 mg/kg).

Results

Body and Liver Weight

Feeding the western diet supplemented with fructose (WDF) for 16 weeks elicited significant effects on body weight compared to control fed animals. Prior to administration of test agent, animals fed the WDF were significantly heavier (47.6±0.45 vs. 43.9±1.03 g; p<0.01) compared to animals fed the control diet.

Body weight decreased compared to baseline values in all treatment groups; there were no significant differences in weight loss compared to vehicle (−7.6±0.9, −6.9±1.3, −6.8±1.4, −5.7±1.2, −6.4±1.0, −4.7±1.6 and −3.9±1.5% for control, vehicle, LIVRQNAC (1500 mg/kg), LIVRQNAC (3000 mg/kg), LIVRQNAC+G, LRQNAC, and OCA, respectively; p<0.4992).

Liver weight (% body weight) was significantly higher in vehicle treated animals fed WDF compared to control diet (7.22±0.3 vs. 5.05±0.24%; p<0.0001); however, in animals fed WDF, no significant effects compared to vehicle were noted in any treatment group (7.22±03, 7.14±0.3, 7.19±0.26, 6.69±0.18, 7.02±0.5 and 6.81±0.2 for vehicle, LIVRQNAC (1500 mg/kg), LIVRQNAC (3000 mg/kg), LIVRQNAC+G, LRQNAC, and OCA, respectively; p<0.7450).

Blood Glucose

Feeding the western diet supplemented with fructose (WDF) for 16 weeks elicited significant effects on glycemia compared to control fed animals. Prior to administration of test agent, animals fed the WDF had significantly lower glucose (160.0±3.01 vs. 218.3±28.6 mg/dL; p<0.0001) compared to animals fed the control diet.

Blood glucose, although higher in control animals at baseline, remained relatively stable during 4 weeks of compound administration. When averaged over the dosing period, there were no significant differences in average blood glucose compared to vehicle for any treatment group (166.0±9.7, 157.1±4.6, 154.6±2.3, 159.4±3.8, 155.5±3.8, 153.6±3.0 and 169.7±6.3 mg/dL for control, vehicle, LIVRQNAC (1500 mg/kg), LIVRQNAC (3000 mg/kg), LIVRQNAC+G, LRQNAC, and OCA, respectively; p<0.1587).

Liver Triglyceride and Cholesterol

Liver triglyceride and cholesterol content were similarly elevated after WDF feeding compared to vehicle treated animals fed control diet (liver triglyceride p<0.0040; liver cholesterol: p<0.0001). Among animals fed WDF, there were no significant differences in liver triglyceride (p<0.1206) when compared to vehicle for any treatment group. While OCA reduced liver cholesterol content compared to vehicle by 32% (p<0.05), no amino acid composition treatment group affected liver cholesterol as compared to WDF feeding vehicle group.

| Liver | Vehicle | LIVRQNAC 1.5 g/kg | LIVRQNAC 3.0 g/kg | LIVRQNAC+G | LRQNAC | OCA |
|---|---|---|---|---|---|---|
| Triglyceride | 31.49 ± 5.85 | 47.63 ± 1.19 | 47.94 ± 1.37 | 50.57 ± 1.58 | 49.47 ± 1.4 | 49.81 ± 1.63 |
| Cholesterol | 8.37 ± 0.065 | 7.74 ± 0.318 | 7.48 ± 0.697 | 6.42 ± 0.648 | 7.84 ± 0.104 | 5.63 ± 0.495 |

Liver Histology

Figure 10:
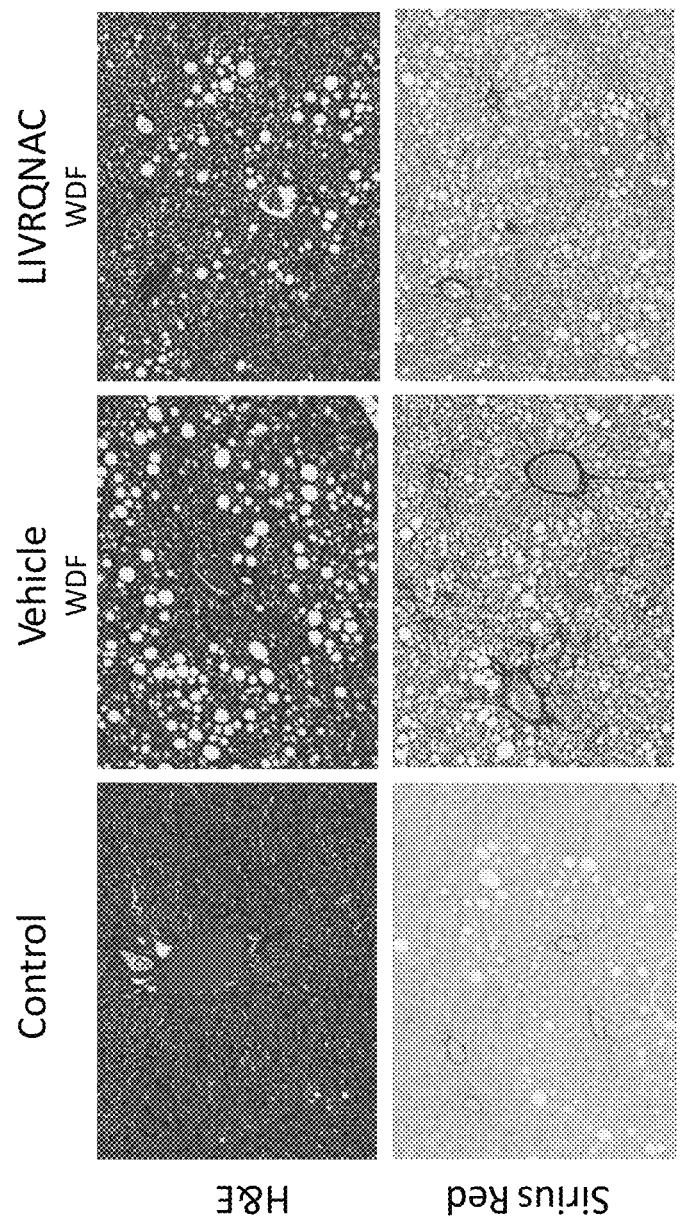
FIG. 10 is a series of microscopy images showing liver histology (H&E stain or Sirius Red stain for collagen deposition) from FATZO mice after administration of the indicated amino acid compositions.
Figure 11:
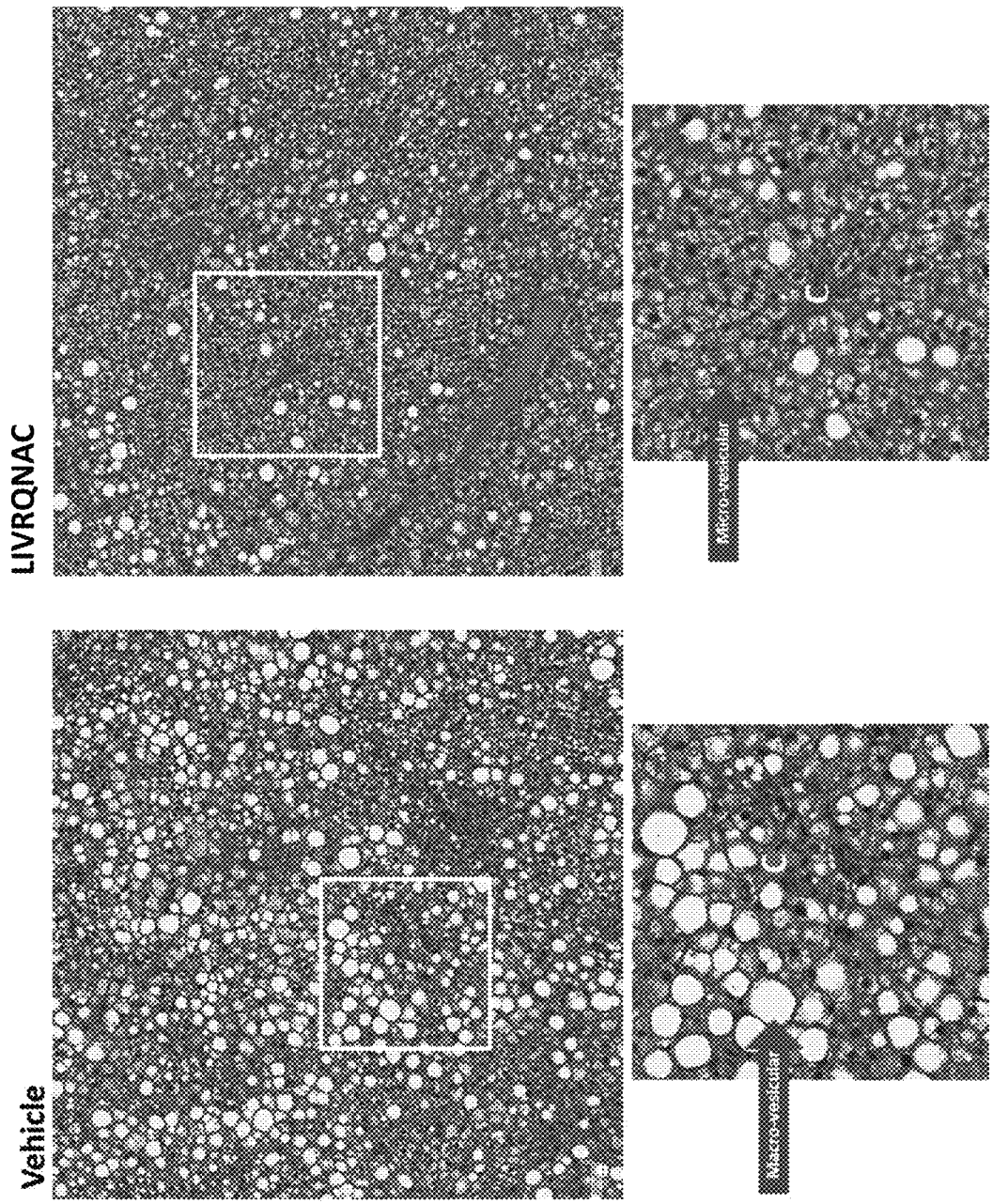
FIG. 11 is a series of microscopy images showing liver histology from FATZO mice after administration of the indicated amino acid compositions.

FATZO mice fed with the control diet developed mild steatosis and no inflammation, ballooning, or fibrosis (FIG. 10). FATZO mice fed with the WDF and treated with vehicle developed significant steatosis, mild inflammation, ballooning, and fibrosis. In contrast to predominantly macrovesicular steatosis in the vehicle groups, a mixture of predominantly microvesicular and diminished macrovesicular steatosis was observed in LIVRQNAC, LIVRQNAC+G and LRQNAC groups, as shown in FIG. 11.

Figure 12:
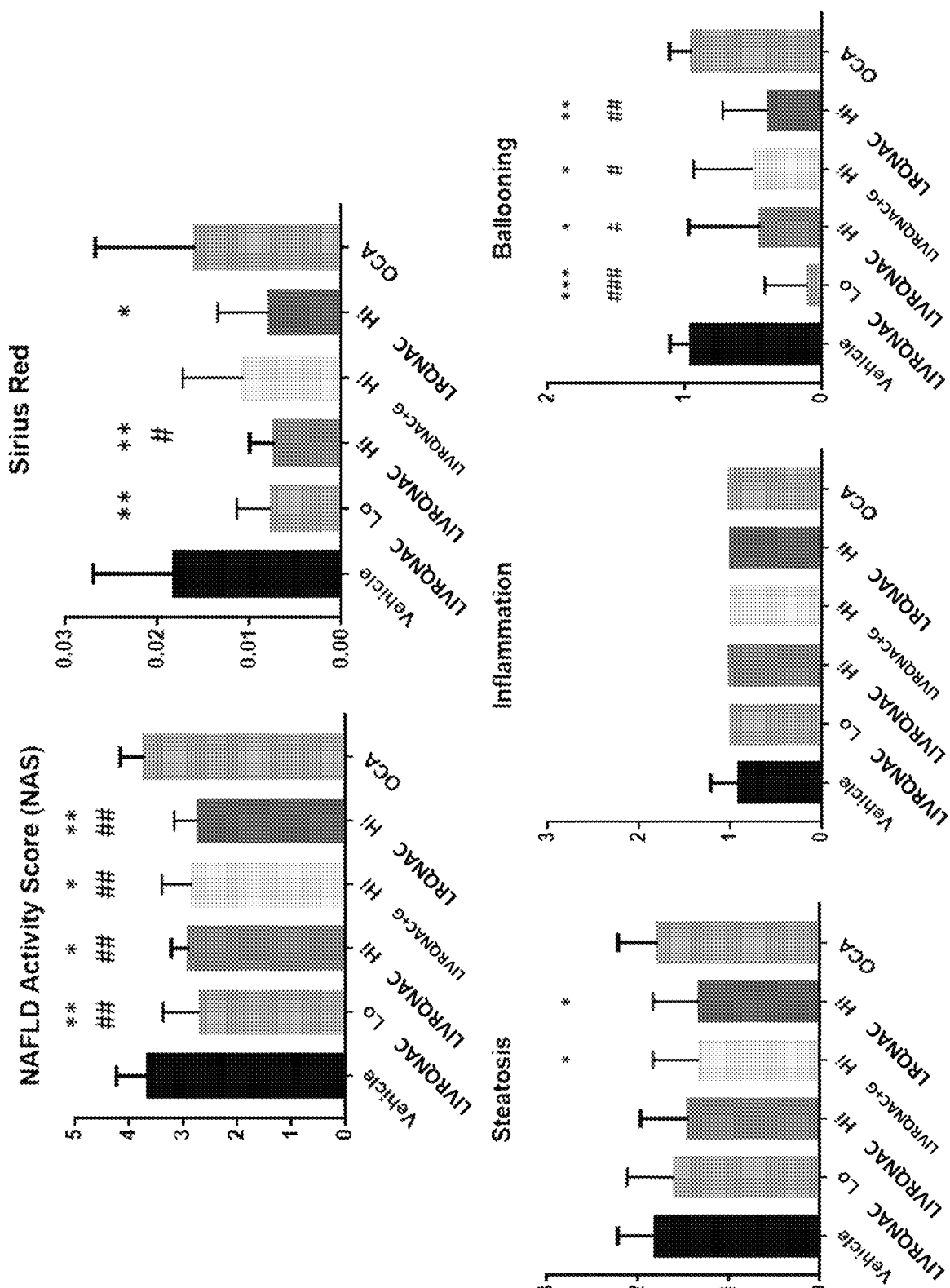
FIG. 12 is a series of graphs showing NAFLD activity scores (top left panel), Sirius Red staining (top right panel), steatosis levels (bottom left panel), inflammation levels (bottom middle panel), and ballooning (bottom right panel)

The NAFLD activity score is calculated from histological scoring of steatosis (0-3), inflammation (0-3), and ballooning (0-2) in fixed liver tissues. In WDF fed animals, all amino acid composition treatments produced a significant reduction in the NAS compared to the vehicle treatment group (FIG. 12). LIVRQNAC and amino acid composition treatments reduced liver steatosis as compared to vehicle, although only LIVRQNAC+G and LRQNAC reached statistical significance (p<0.05), while LIVRQNAC did not (LIVRQNAC 3.0 g/kg, p=0.12). All amino acid composition treatments significantly attenuated hepatocyte ballooning, the biomarker of lipotoxicity and cell death. Amino acid composition treatments did not significantly alter liver inflammation. In conclusion, amino acid composition-associated improvement of liver pathology is mainly attributed to attenuation of hepatocyte ballooning.

There was no significant effect of OCA on the NAS score and NAS components compared to vehicle.

| Liver Pathology | Vehicle | LIVRQNAC 1.5 g/kg | LIVRQNAC 3.0 g/kg | LIVRQNAC+G | LRQNAC | OCA |
|---|---|---|---|---|---|---|
| NAS | 3.65 ± 0.183 | 2.70 ± 0.213 | 2.89 ± 0.111 | 2.83 ± 0.186 | 2.72 ± 0.147 | 3.72 ± 0.147 |
| Steatosis | 1.8 ± 0.133 | 1.6 ± 0.163 | 1.44 ± 0.176 | 1.33 ± 0.167 | 1.33 ± 0.167 | 1.78 ± 0.147 |
| Inflammation | 0.9 ± 0.1 | 1.0 ± 0.0 | 1.0 ± 0.0 | 1.0 ± 0.0 | 1.0 ± 0.0 | 1.0 ± 0.0 |
| Ballooning | 0.95 ± 0.05 | 0.1 ± 0.1 | 0.44 ± 0.176 | 0.50 ± 0.144 | 0.39 ± 0.111 | 0.94 ± 0.056 |

Livers from vehicle treated animals demonstrated a mild fibrosis; score of 0.8±0.1. Only livers from animals treated with LIVRQNAC (1500 mg/kg) demonstrated a significant reduction in fibrosis when compared to the vehicle treated group, (0.2±0.1 versus 0.8±0.1, $p<0.01$), but not with LIVRQNAC (3000 mg/kg), LIVRQNAC+G or LRQNAC. Sirius Red collagen staining demonstrated that all amino acid composition treatments had significantly lower collagen deposition compared to vehicle (LIVRQNAC 1500 mg/kg, $p<0.01$; LIVRQNAC 3000 mg/kg, $p<0.01$; LIVRQNAC+G, $p=0.09$; LRQNAC, $p<0.05$). OCA did not affect liver fibrosis score or Sirius Red collagen staining area.

| Fibrosis | Vehicle | LIVRQNAC 1.5 g/kg | LIVRQNAC 3.0 g/kg | LIVRQNAC+G | LRQNAC | OCA |
|---|---|---|---|---|---|---|
| Fibrosis | 0.8 ± 0.133 | 0.2 ± 0.133 | 0.44 ± 0.176 | 0.44 ± 0.176 | 0.33 ± 0.167 | 0.67 ± 0.167 |
| Sirius Red | 1.82 ± 0.279 | 0.77 ± 0.116 | 0.72 ± 0.092 | 0.107 ± 0.218 | 0.79 ± 0.183 | 1.59 ± 0.36 |

Consistent with liver triglyceride levels, amino acid composition treatments did not alter liver Oil Red O staining area compared to vehicle group. OCA reduced Oil Red O staining area ($p<0.05$).

| Oil Red O | Vehicle | LIVRQNAC 1.5 g/kg | LIVRQNAC 3.0 g/kg | LIVRQNAC+G | LRQNAC | OCA |
|---|---|---|---|---|---|---|
| Oil Red O | 0.32 ± 0.019 | 0.28 ± 0.022 | 0.30 ± 0.022 | 0.26 ± 0.023 | 0.29 ± 0.018 | 0.24 ± 0.021 |
| Triglyceride | 31.49 ± 5.85 | 47.63 ± 1.19 | 47.94 ± 1.37 | 50.57 ± 1.58 | 49.47 ± 1.4 | 49.81 ± 1.63 |

Liver Gene Expression

MCP-1 (CCL2) and MIP-1a (CCL3) are proinflammatory chemokines that mediate liver inflammation via macrophage and neutrophil recruitment. MCP-1 and MIP-1a are the ligands of CCR2 and CCR5, respectively, which serve the promising therapeutic targets to treat liver fibrosis in NASH. MCP-1 and MIP-1a RNA expression levels in the liver were significantly upregulated in the WDF fed mice as compared to control diet-fed mice, as shown in Tables 74 and 75.

TABLE 74

Fold change in MCP-1 mRNA levels after administration of amino acid compositions

| MCP-1 | Ctrl diet | Vehicle | LIVRQNAC (3000 mg/kg) | LIVRQNAC + G (3885 mg/kg) | LRQNAC (2469 mg/kg) |
|---|---|---|---|---|---|
| Mean | 0.1457 | 1.079 | 1.396 | 0.6102 | 0.8777 |
| SEM | 0.0291 | 0.1956 | 0.3414 | 0.09597 | 0.2315 |

TABLE 75

Fold change in MIP-1a mRNA levels after administration of amino acid compositions

| MIP-1a | Ctrl diet | Vehicle | LIVRQNAC (3000 mg/kg) | LIVRQNAC + G (3885 mg/kg) | LRQNAC (2469 mg/kg) |
|---|---|---|---|---|---|
| Mean | 0.08328 | 1.194 | 1.67 | 0.814 | 1.514 |
| SEM | 0.02141 | 0.25 | 0.3366 | 0.1029 | 0.525 |

LIVRQNAC and LRQNAC treatments did not significantly alter liver MCP-1 and MIP-1a RNA expression as compared to vehicle group. LIVRQNAC+G treatment resulted in slightly lower liver MCP-1 RNA expression as compared to vehicle group ($p=0.054$) and LIVRQNAC group ($p<0.05$). Similarly, LIVRQNAC+G treatment resulted in slightly lower liver MCP-1 RNA expression as compared to vehicle group although the difference was not significant ($p=0.19$) and LIVRQNAC group ($p<0.05$).

Liver Chemokines and Cytokines

Consistent with RNA data, liver MCP-1 and MIP-1a protein levels were elevated in the WDF fed mice as compared to control diet-fed mice, as shown in Tables 76 and 77.

TABLE 76

Mean liver MCP-1 protein levels after administration of amino acid compositions

| MCP-1 | Ctrl diet | Vehicle | LIVRQNAC (3000 mg/kg) | LIVRQNAC + G (3885 mg/kg) | LRQNAC (2469 mg/kg) |
|---|---|---|---|---|---|
| Mean | 41.47 | 278.3 | 392 | 221.1 | 247.1 |
| SEM | 7.463 | 61.41 | 83.97 | 36.6 | 75.16 |

TABLE 77

Mean liver MIP-1a protein levels after administration of amino acid compositions

| MIP-1a | Ctrl diet | Vehicle | LIVRQNAC (3000 mg/kg) | LIVRQNAC + G (3885 mg/kg) | LRQNAC (2469 mg/kg) |
|---|---|---|---|---|---|
| Mean | 23.16 | 191.8 | 282.9 | 142.8 | 141.1 |
| SEM | 5.429 | 30.03 | 58.88 | 17.04 | 24.36 |

Liver MCP-1 and MIP-1a protein levels were also positively correlated with RNA expression levels, as shown in Tables 78 and 79.

TABLE 78

Correlations between MCP-1 protein and RNA levels after administration of amino acid compositions

| Ctrl diet | y = 0.0022x + 0.0542 | R2 = 0.3202 |
| Vehicle | y = 0.0029x + 0.3316 | R2 = 0.7986 |
| LIVRQNAC (3000 mg/kg) | y = 0.0036x + 0.0144 | R2 = 0.7831 |
| LIVRQNAC + G (3885 mg/kg) | y = 0.0018x + 0.2542 | R2 = 0.3988 |
| LRQNAC (2469 mg/kg) | y = 0.0027x + 0.2969 | R2 = 0.6857 |

TABLE 79

Correlations between MIP-1a protein and RNA levels after administration of amino acid compositions

| Ctrl diet | y = 0.001x + 0.0593 | R2 = .069 |
| Vehicle | y = 0.0057x + 0.191 | R2 = 0.4202 |
| LIVRQNAC (3000 mg/kg) | y = 0.0051x + 0.2334 | R2 = 0.7887 |
| LIVRQNAC + G (3885 mg/kg) | y = 0.0045x + 0.1817 | R2 = 0.4403 |
| LRQNAC (2469 mg/kg) | y = 0.0064x + 0.1814 | R2 = 0.4875 |

LIVRQNAC and LRQNAC treatments did not significantly alter liver MCP-1 and MIP-1a protein levels as compared to vehicle group. LIVRQNAC+G treatment slightly lowered liver MCP-1 (p=0.095) and MIP-1a (p<0.05) protein levels as compared to LIVRQNAC group. Additionally, liver MCP-1 and MIP-1a protein levels positively correlated, as shown in Table 80.

TABLE 80

Correlations between MCP-1 and MIP-1a protein levels after administration of amino acid compositions

| Ctrl diet | y = 0.6803x − 5.0537 | R2 = 0.8744 |
| Vehicle | y = 0.389x + 83.574 | R2 = 0.6325 |
| LIVRQNAC (3000 mg/kg) | y = 0.6615x + 23.609 | R2 = 0.8903 |
| LIVRQNAC + G (3885 mg/kg) | y = 0.4437x + 44.728 | R2 = 0.9082 |
| LRQNAC (2469 mg/kg) | y = 0.3108x + 75.901 | R2 = 0.9241 |

Proinflammatory cytokines IL-1b, IL-6, TNFa, and CXCL1 protein levels in liver were elevated in the WDF fed mice as compared to control diet-fed mice, as shown in Tables 81-84.

TABLE 81

Mean liver IL-1b protein levels after administration of amino acid compositions

| IL-1b | Ctrl diet | Vehicle | LIVRQNAC (3000 mg/kg) | LIVRQNAC + G (3885 mg/kg) | LRQNAC (2469 mg/kg) |
|---|---|---|---|---|---|
| Mean | 10.53 | 22.31 | 22.11 | 14.42 | 28.85 |
| SEM | 1.248 | 6.063 | 5.739 | 3.299 | 10.41 |

TABLE 82

Mean liver IL-6 protein levels after administration of amino acid compositions

| IL-6 | Ctrl diet | Vehicle | LIVRQNAC (3000 mg/kg) | LIVRQNAC + G (3885 mg/kg) | LRQNAC (2469 mg/kg) |
|---|---|---|---|---|---|
| Mean | 5.838 | 8.452 | 7.298 | 5.77 | 6.71 |
| SEM | 0.3536 | 2.723 | 2.043 | 1.06 | 1.625 |

TABLE 83

Mean liver CXCL1 protein levels after administration of amino acid compositions

| CXCL1 | Ctrl diet | Vehicle | LIVRQNAC (3000 mg/kg) | LIVRQNAC + G (3885 mg/kg) | LRQNAC (2469 mg/kg) |
|---|---|---|---|---|---|
| Mean | 41.42 | 105.9 | 119.6 | 77.77 | 84.9 |
| SEM | 2.487 | 13.26 | 26.15 | 8.023 | 10.49 |

TABLE 84

Mean liver TNFα protein levels after administration of amino acid compositions

| TNFa | Ctrl diet | Vehicle | LIVRQNAC (3000 mg/kg) | LIVRQNAC + G (3885 mg/kg) | LRQNAC (2469 mg/kg) |
|---|---|---|---|---|---|
| Mean | 1.703 | 3.71 | 4.574 | 2.974 | 4.119 |
| SEM | 0.5641 | 0.4647 | 0.5654 | 0.1513 | 0.8341 |

LIVRQNAC, LIVRQNAC+G, and LRQNAC treatments did not significantly alter IL-1b, IL-6, TNFa, and CXCL1 protein levels as compared to vehicle. Liver TNFa levels were lower by LIVRQNAC+G treatment as compared to LIVRQNAC.

SUMMARY

Based on clinical observations, WDF-fed FATZO mice gained more body weight that those fed with a control diet. Fed blood glucose levels were comparable between WDF-fed and control diet-fed mice despite of the difference in body weight change. All treatments were well tolerated in FATZO mice. Both WDF-fed and control diet-fed mice lose body weight during the treatment period, which may be due to the stress associated with administration of test articles or vehicle via oral gavage twice a day.

NAS was significantly attenuated in all amino acid composition treatment groups as compared to vehicle, predominantly attributing to ballooning score. Hepatocyte ballooning was significantly reduced in all the amino acid composition treatment groups. Steatosis was significantly reduced in LIVRQNAC+G and LRQNAC treatment groups. LIVRQNAC also lowered steatosis, although the difference was not significant Inflammation was not affected by amino acid composition treatments. Despite the histological improvement in steatosis score in LIVRQNAC+G and LRQNAC treatment groups, liver triglyceride, cholesterol, and Oil-Red O staining remained unchanged by amino acid composition treatments. Consistent with the histological and biochemical data, de novo lipogenesis enzymes FASN and ACACA RNA levels were not affected by amino acid composition treatment.

Although liver triglyceride levels were not affected by amino acid composition treatments, the characteristics of hepatocyte steatosis were differed by amino acid composition treatments. Liver of the WDF-fed mice (vehicle group) demonstrated predominantly macrovesicular steatosis. In contrast, macrovesicular steatosis was diminished, and a mixture of microvesicular and macrovesicular steatosis in all amino acid composition treatment groups. The biological meaning and mechanism of amino acid compositions on macro- to microvesicular steatosis phenotypes merit further investigation.

Liver fibrosis score in FATZO model of NAFLD was significantly attenuated by LIVRQNAC treatment at low dose but not at high dose. LIVRQNAC+G and LRQNAC had no effect on fibrosis. Nonetheless, Sirius Red collagen staining demonstrated that LIVRQNAC, LIVRQNAC+G and LRQNAC significantly reduced collagen deposition in the liver.

Consistent with liver inflammation scores, liver RNA and protein levels of the proinflammatory chemokine MCP-1 and MIP-1a and cytokines IL-1b, IL-6, TNFa, and CXCL1 were not significantly affected by amino acid composition treatment. It is of interest to note that LIVRQNAC+G (equivalent to LIVRQNAC plus Glycine) treatment had lower liver MCP-1, MIP-1a, and TNFa as compared to LIVRQNAC.

Increased liver oxidative stress associated with inflammation is observed during NAFLD and NASH. Glutathione (GSH) is a pivotal endogenous anti-oxidant which can counteract reactive oxygen species. Glycine and its direct metabolic precursor, serine, are substrates for GSH biosynthesis. Thus, serine and/or glycine supplementation helps replenish GSH and ameliorates NAFLD and NASH. LIVRQNACG treatment had lower inflammation chemokines and cytokines in the liver, supporting that supplementation of glycine or serine is beneficial in NAFLD and NASH.

In conclusion, all three amino acid compositions (LIVRQNAC, LIVRQNAC+G and LRQNAC) tested in FATZO mice attenuate NAFLD activity scores, hepatocyte ballooning, and fibrosis. These amino acid compositions can be used to treat NASH. Glycine-containing amino acid compositions can further reduce liver inflammation which results in reduced liver fibrosis.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A dietary composition comprising:
   (a) L-leucine or a salt thereof, or a dipeptide or salt thereof, or tripeptide or salt thereof, comprising L-leucine;
   (b) an arginine amino acid entity chosen from:
      (i) L-arginine or a salt thereof,
      (ii) a dipeptide or salt thereof, or tripeptide or salt thereof, comprising L-arginine,
      (iii) ornithine or a salt thereof,
      (iv) a dipeptide or salt thereof, or tripeptide or salt thereof, comprising ornithine,
      (v) creatine or a salt thereof, or
      (vi) a dipeptide or salt thereof, or tripeptide or salt thereof, comprising creatine;
   (c) L-glutamine or a salt thereof or a dipeptide or salt thereof, or tripeptide or salt thereof, comprising L-glutamine; and
   (d) N-acetylcysteine (NAC) or a salt thereof or a dipeptide or salt thereof, or tripeptide or salt thereof, comprising NAC;
   wherein when the dietary composition is in powder form, at least 50 wt. % of the total wt. of the dietary composition is one or more amino acid entities in free form,
   wherein the total wt. % of (a)-(d) is greater than the total wt. % of other amino acid entities in the dietary composition,
   wherein the dietary composition is chosen from a nutritional supplement, dietary formulation, functional food, medical food, or beverage.

2. The dietary composition of claim 1, wherein methionine, tryptophan, and cysteine are present at less than 2 wt. % of the dietary composition when the dietary composition is in powder form.

3. The dietary composition of claim 1, wherein methionine, tryptophan, or cysteine are absent in the dietary composition.

4. The dietary composition of claim 1, wherein:
   (1) the wt. % of the L-glutamine or a salt thereof or the dipeptide or salt thereof, or tripeptide or salt thereof, comprising L-glutamine in the dietary composition is greater than the wt. % of the arginine amino acid entity;
   (2) the wt. % of the L-glutamine or a salt thereof or the dipeptide or salt thereof, or tripeptide or salt thereof, comprising L-glutamine in the dietary composition is equal to or greater than the wt. % of the L-leucine or a salt thereof, or a dipeptide or salt thereof, or tripeptide or salt thereof, comprising L-leucine; or
   (3) the wt. % of the arginine amino acid entity in the dietary composition is greater than the wt. % of the L-leucine or a salt thereof, or a dipeptide or salt thereof, or tripeptide or salt thereof, comprising L-leucine.

5. The dietary composition of claim 1, wherein:
   the wt. % of the arginine amino acid entity in (b), the L-glutamine or a salt thereof or the dipeptide or salt thereof, or tripeptide or salt thereof, comprising L-glutamine in (c), and the NAC or a salt thereof or the dipeptide or salt thereof, or tripeptide or salt thereof, comprising NAC in (d) in combination is at least 50% of the dietary composition, when the dietary composition is in powder form, but not more than 90% of the dietary composition, when the dietary composition is in powder form.

6. The dietary composition of claim 1, wherein:
   (1) the ratio of the L-leucine or a salt thereof, or a dipeptide or salt thereof, or tripeptide or salt thereof, comprising L-leucine to the arginine amino acid entity is at least 1:4, and not more than 3:4;
   (2) the ratio of the L-leucine or a salt thereof, or a dipeptide or salt thereof, or tripeptide or salt thereof, comprising L-leucine to the L-glutamine or a salt thereof or the dipeptide or salt thereof, or tripeptide or salt thereof, comprising L-glutamine is at least 1:4, and not more than 3:4; or
   (3) the ratio of the arginine amino acid entity to the L-glutamine or a salt thereof or the dipeptide or salt thereof, or tripeptide or salt thereof, comprising L-glutamine is at least 1:4, and not more than 6:7.

7. The dietary composition of claim 1, wherein the wt. ratio of: (a) L-leucine or a salt thereof, or a dipeptide or salt thereof, or tripeptide or salt thereof, comprising L-leucine, (b) the arginine amino acid entity, (c) the L-glutamine or a salt thereof or the dipeptide or salt thereof, or tripeptide or salt thereof, comprising L-glutamine, and (d) the NAC or salt thereof or the dipeptide or salt thereof, or tripeptide or salt thereof, comprising NAC is:

1+/−15%: 1.5+/−15%: 2+/−15%: 0.15+/−15%;
1+/−15%: 1.5+/−15%: 2+/−15%: 0.3+/−15%;
1+/−15%: 1.81+/−15%: 2+/−15%: 0.15+/−15%; or
1+/−15%: 0.75+/−15%: 1+/−15%: 0.225+/−15%.

8. The dietary composition of claim 1, further comprising one or both of:
   (1) L-isoleucine or a salt thereof or a dipeptide or salt thereof, or tripeptide or salt thereof, comprising L-isoleucine; or
   (2) L-valine or a salt thereof or a dipeptide or salt thereof, or tripeptide or salt thereof, comprising L-valine.

9. The dietary composition of claim 8, wherein the dietary composition comprises:
   (a) L-leucine or a salt thereof;
   (b) L-arginine or a salt thereof;
   (c) L-glutamine or a salt thereof;
   (d) NAC or a salt thereof;
   (e) L-isoleucine or a salt thereof; and
   (f) L-valine or a salt thereof.

10. The dietary composition of claim 9, wherein the dietary composition comprises:
   (a) L-leucine or a salt thereof;
   (b) L-arginine or a salt thereof;
   (c) L-glutamine or a salt thereof;
   (d) NAC or a salt thereof;
   (e) L-isoleucine or a salt thereof; and
   (f) L-valine or a salt thereof;

wherein the wt. ratio of the L-leucine or a salt thereof, the L-isoleucine or a salt thereof, the L-valine or a salt thereof, the L-arginine or a salt thereof, the L-glutamine or a salt thereof, and the NAC or salt thereof is:

1+/−15%: 0.5+/−15%: 0.5+/−15%: 1.5+/−15%: 2+/−15%: 0.15+/−15%;
1+/−15%: 0.5+/−15%: 0.5+/−15%: 1.81+/−15%: 2+/−15%: 0.15+/−15%; or
1+/−15%: 0.5+/−15%: 0.5+/−15%: 1.5+/−15%: 2+/−15%: 0.3+/−15%.

11. The dietary composition of claim 1, wherein at least one of (a)-(d) is a free amino acid.

12. The dietary composition of claim 1, wherein at least one of (a)-(d) is in a salt form.

13. The dietary composition of claim 1, wherein the dietary composition comprises a combination of not more than 15 different amino acid entities.

14. The dietary composition of claim 1, further comprising a serine amino acid entity chosen from L-serine, L-glycine, or a combination thereof.

15. The dietary composition of claim 1, wherein:
the arginine amino acid entity is chosen from:
   i) L-arginine or a salt thereof,
   ii) a dipeptide or salt thereof, or tripeptide or salt thereof, comprising L-arginine,
   iii) ornithine or a salt thereof, or
   iv) a dipeptide or salt thereof, or tripeptide or salt thereof, comprising ornithine.

16. The dietary composition of claim 1, wherein the wt. % of the NAC or a salt thereof or the dipeptide or salt thereof, or tripeptide or salt thereof, comprising NAC is at least 1%, but not more than 10% of the dietary composition, when the dietary composition is in powder form.

17. The dietary composition of claim 1, further comprising L-serine or a salt thereof.

* * * * *